(12) United States Patent
Gonsalves et al.

(10) Patent No.: US 6,638,720 B1
(45) Date of Patent: Oct. 28, 2003

(54) GRAPEVINE LEAFROLL VIRUS PROTEINS AND THEIR USES

(75) Inventors: Dennis Gonsalves, Geneva, NY (US); Kai-Shu Ling, Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/650,324

(22) Filed: Aug. 29, 2000

Related U.S. Application Data

(60) Continuation of application No. 09/579,259, filed on May 25, 2000, now Pat. No. 6,558,953, which is a continuation of application No. 09/224,898, filed on Dec. 31, 1998, now abandoned, which is a division of application No. 08/770,544, filed on Dec. 20, 1996, now Pat. No. 5,907,085.
(60) Provisional application No. 60/009,008, filed on Dec. 21, 1995.

(51) Int. Cl.⁷ .................................................. C12Q 1/68
(52) U.S. Cl. .................................................... 435/6
(58) Field of Search ............................................ 435/6

(56) References Cited

U.S. PATENT DOCUMENTS

| | | | |
|---|---|---|---|
| 4,358,535 A | 11/1982 | Falkow et al. | |
| 4,480,040 A | 10/1984 | Owens et al. | |
| 5,043,272 A | 8/1991 | Hartley | |
| 5,104,792 A | 4/1992 | Silver et al. | |
| 5,106,727 A | 4/1992 | Hartley et al. | |
| 5,196,305 A | 3/1993 | Findlay et al. | |
| 5,288,611 A | 2/1994 | Kohne | |
| 5,322,770 A | 6/1994 | Gelfand | |
| 5,328,825 A | 7/1994 | Warren, III et al. | |
| 5,714,312 A | 2/1998 | Nuno Bardosa Nolasco et al. | |
| 5,872,241 A | 2/1999 | Pyle et al. | |
| 5,907,085 A | 5/1999 | Gonsalves et al. ........... | 800/205 |
| 5,965,355 A | 10/1999 | Monis et al. | |
| 5,990,388 A | 11/1999 | Roth et al. | |
| 6,197,948 B1 | 3/2001 | Zhu et al. .................. | 536/23.72 |

FOREIGN PATENT DOCUMENTS

| | | |
|---|---|---|
| EP | 0 769 696 A2 | 4/1997 |
| WO | WO 97/22700 | 6/1997 |
| WO | WO 98/53055 | 11/1998 |
| WO | WO 99/55880 | 11/1999 |

OTHER PUBLICATIONS

Abou–Ghanem et al., "Some Properties of Grapevine Leafroll–Associated Virus 2 and Molecular Organization of the 3' Region of the Viral Genome," *Journal of Plant Pathology* 80:37–46 (1998).
Abou–Ghanem et al., "Grapevine Leafroll–Associated 2 Genes Encoding RNA Polymerase and Coat Protein, hsp70, hsp90 Gene and ORF2, ORF7 and ORF8," DataBase EMBL Online Accession No. Y14131 (Sep. 2, 1997).
Habili et al., "Identification of a cDNA Clone Specific to Grapevine Leafroll–Associated Virus 1, and Occurrence of the Virus in Australia," *Plant Pathology* 46:516–522 (1997).

Namba et al., "Purification and Properties of Closterovirus–Like Particles Associated with Grapevine Corky Bark Disease," BIOSIS DataBase Accession No. PREV199192116654 (Abstract) (1991).
Namba et al., "Purification and Properties of Closterovirus–Like Particles Associated With Grapevine Corky Bark Disease," *Phytopathology* 81:964–970 (1991).
Zhu et al., "Nucleotide Sequence and Genome Organization of Grapevine Leafroll–Associated Virus–2 are Similar to Beet Yellows Virus, the Closterovirus Type Member," Database EMBL Online Accession No. AF039204 (May 11, 1998).
Agranovsky et al., "Beet Yellows Closterovirus: Complete Genome Structure and Identification of a Leader Papain–Like Thiol Protease," *Virology* 199:311–324 (1994).
Fajardo et al., "Partial Molecular Characterization of an Isolate of Grapevine Leafroll–Associated Virus 3 in Grapes," (Abstract 980) *Fitopatol. Bras.* 26:535 (2001).
GenBank Accession No. CAA51871.
GenBank Accession No. AF037268.
GenBank Accession No. AF283103.
Melzer et al., "Nucleotide Sequence, Genome Organization and Phylogenetic Analysis of Pineapple Mealybug Wilt–Associated Virus–2," *Journal of General Virology* 82:1–7 (2001).
Abou–Ghanem et al., "Physico–Chemical and Molecular Characterization of Grapevine Leafroll–Associated Virus 2," 12$^{th}$ Meeting of the International Council for the Study of Viruses and Virus–Like Diseases of the Grapevine, Sep.–Oct. pp. 15–16 (1997).
Agrios, *Plant Pathology*, Third Ed. Excerpt of Chapter 14, pp. 622–623 and 648–655. Academic Press, San Diego (1988).
Beachy et al., "Coat Protein–Mediated Resistance Against Virus Infection," *Annu. Rev. Plant Pathol.*, 28:451–474 (1990).
Boscia et al., "Nomenclature of Grapevine Leafroll–Associated Putative Closteroviruses," *Vitis* 34:171–175 (1995).
Boscia et al., "Characterization of Grape Leafroll Associated Closterovirus (GLRaV) Serotype II and Comparison with GLRaV Serotype III," *Phytopathology* 80:117 (1990).

(List continued on next page.)

*Primary Examiner*—James Ketter
*Assistant Examiner*—Daniel M. Sullivan
(74) *Attorney, Agent, or Firm*—Clark & Elbing LLP

(57) ABSTRACT

The present invention relates to an isolated protein or polypeptide corresponding to a coat protein or polypeptide of a grapevine leafroll virus. The encoding DNA molecule either alone in isolated form or in an expression system, a host cell, or a transgenic grape plant is also disclosed. Another aspect of the present invention relates to a method of imparting grapevine leafroll resistance to grape plants by transforming them with the DNA molecule of the present invention. A method for imparting tristeza virus resistance in citrus plants using the DNA molecule of the present invention is also disclosed.

2 Claims, 57 Drawing Sheets

OTHER PUBLICATIONS

Figure 1:
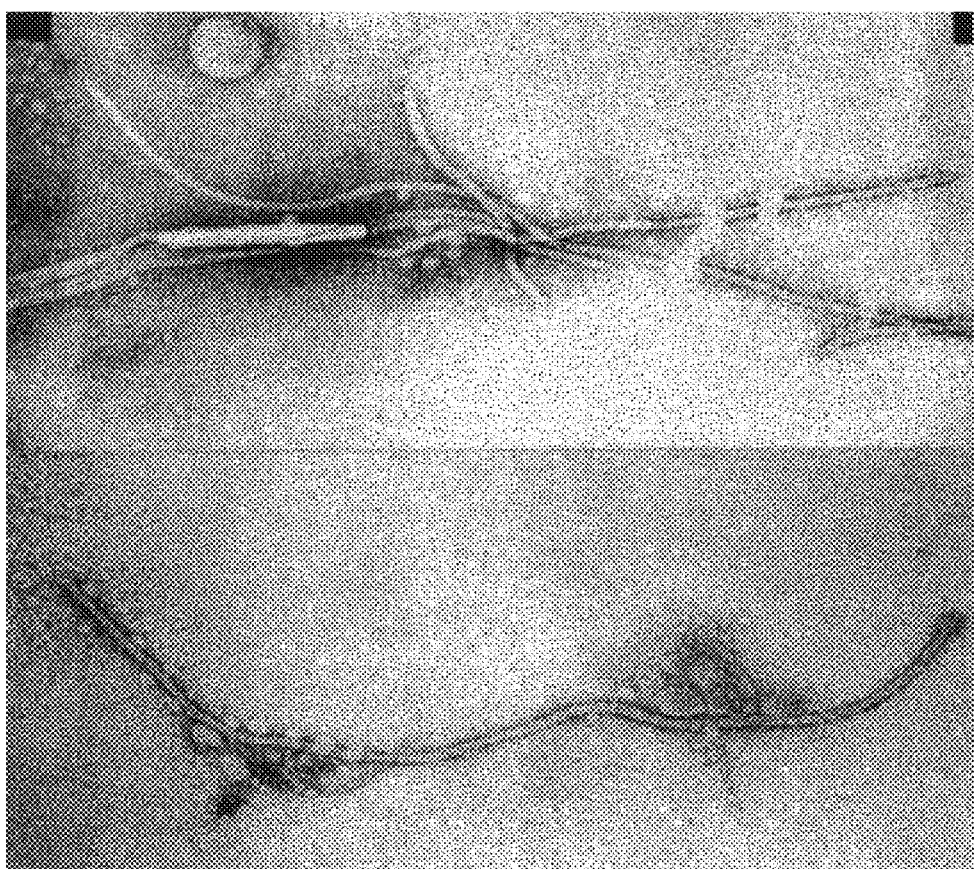

Boston et al., Molecular Chaperones and Protein Folding in Plants, *Plant Mol. Biol.* 32:191–222 (1996).

Candresse et al., "Virus Taxonomy–Classification and Nomenclature. Part II. The Viruses–Closterovirus,"*Archives of Virology* S10:461–464 (1995).

Credi et al., "Grapevine Leafroll–associated Viruses and Grapevine Virus A in Selected *Vitis vinifera* Cultivars in Northern Italy," *Plant Pathology* 45:1110–1116 (1996).

Dolja et al., "Molecular Biology and Evolution of Closteroviruses: Sophisticated Build–Up of Large RNA Genomes," *Annu. Rev. Phytopath.*, 32:261–285 (1994).

Engelbrecht, et al., "Associated of a Closterovirus with Grapevines Indexing Positive for Grapevine Leafroll Disease and Evidence for its Natural Spread in Grapevine," *Phytopath. medit.* 24:101–105 (1985).

Fazeli et al., "Efficient Cloning of cDNA From Grapevine Leafroll–associated Virus 4 and Demonstration of Probe Specificity by the Viral Antibody," *J. Virological Methods* 70:201–211 (1998).

Forsline et al., "Comparative Effectiveness of Symptomatology and ELISA for Detecting Two Isolates of Grapevine Leafroll on Graft–inoculated Cabernet franc," *Am. J. Enol.. Vitic.*, 47:239–243 (1996).

Genbank Sequence accession U22170 for Grapevine Leafroll Associated Virus Type III p20 Protein.

Genbank Sequence accession U22158 for Grapevine Leafroll Associated Virus RNA6 Gene.

Goszczynski et al., "Detection of Two Strains of Grapevine Leafroll–Associated Virus 2," *Vitis* 35:133–135 (1996).

Goszczynski et al., "Production and Use of Antisera Specific to Grapevine Leafroll–Associated Viruses Following Electrophoretic Separation of Their Proteins and Transfer to Nitrocellulose," *African Plant Protection* 1:1–8 (1995).

Goszczynski et al., "Grapevine Leafroll–Associated Virus 2 (GLRaV–2)–Mechanical Transmission, Purificatio, Production and Properties of Antisera, Detection by ELISA," *S. Afr. J. Enol. Vitic.* 17:15–26 (1996).

Gugerli et al., "L'Enroulement de la Vigne: Mise en Évidence de Particules Virales et Développement d'une Méthode Immuno–Enzymatique Pour le Diagnostic Rapide," *Rev. Suisse Vitic. Arboric. Hortic.*, 16:299–304 (1984).

Gugerli et al., "Grapevine Leafroll Associated Virus II Analyzed by Monoclonal Antibodies," 11$^{th}$ Meeting of the International Council for the Study of Viruses and Virus–Like Disease of the Grapevine pp. 23–24 (1993).

Gugerli et al., "Identification Immuno–Chimique du 6$^e$ Virus Associé à la Maladie de L'Enroulement de la Vigne et Amélioration des Techniques de Diagnostic Pour la Sélection Sanitaire en Viticulture," *Rev. Suisse Vitic. Arboric. Hortic.*, 29:137–141 (1997).

Habili et al., "Natural Spread and Molecular Analysis of Grapevine Leafroll–Associated Virus 3 in Australia," *Phytopathology* 85:1418–1422 (1995).

Hu et al., "Use of Monoclonal Antibodies to Characterize Grapevine Leafroll Associated Closteroviruses," *Phytopathology* 80:920–925 (1990).

Hu et al., "Characterization of Closterovirus–like Particles Associated with Grapevine Leafroll Disease," *J. Phytopathology* 128:1–14 (1990).

Karasev et al., "Screening of the Closterovirus Genome by Degenerate Primer–Mediated Polymerase Chain Reaction," *Journal of General Virology* 75:1415–1422 (1994).

Krastanova et al., "Transformation of Grapevine Rootstocks With the Coat Protein Gene of Grapevine Fanleaf Nepovirus," *Plant Cell Reports* , 14:550–554 (1995).

Krustanova et al., *Rastenievud. Nauki.* 29(1–2):90–94 (1992) (Abstract).

Lazar et al., "Occurrence of Grapevine Leafroll Associated Closteroviruses (GLRAV–S) in Hungary," *Med. Fac. Landbouww. Univ. Gen.* 60:307–308 (1995).

Le Gall et al., "Agrobacterium–Mediated Genetic Transformation of Grapevine Somatic Embryos and Regeneration of Transgenic Plants Expressing the Coat Proteins of Grapevine Chrome Mosaic Nepovirus (GCMV)," *Plant Science* 102:161–170 (1994).

Levy et al., "Simple and Rapid Preparation of Infected Plant Tissue Extracts for PCR Amplification of Virus, Viroid, and MLO Nucleic Acids," *J. Virological Methods* 49:295–304 (1994).

Ling et al., "Molecular Cloning and Detection of Grapevine Leafroll Virus By Nucleic Acid Hybridization and Polymerase Chain Reaction," *Phytopathology* 83:245 (1993).

Ling et al., "Identification of Coat Protein Gene and Partial Genome Organization of Grapevine Leafroll–Associated Closterovirus Type III," *Phytopathology* 84:1372 (1994).

Ling et al., "Partial Genome Organization of Grapevine Leafroll–Associated Closterovirus 3," *Phytopathology* 85:1152 (1995).

Ling et al., "Coat Protein Gene Identification, Genome Organization, and PCR Detection of Grapevine Leafroll Associated Closterovirus–3 and Study Towards Transgenic Grapevines", *The American Chemical Society* 125:138016 (Abstract) (1996).

Ling et al., "Coat Protein Gene Identification, Genome Organization, and PCR Detection of Grapevine Leafroll Associated Closterovirus–3 and Study Towards Transgenic Grapevines (Vitis)," *Dissertation Abstracts International* 57(3):1539 (1996).

Ling et al., "The coat protein gene of grapevine leafroll associated closterovirus–3: cloning, nucleotide sequencing and expression in transgenic plants," *Archives of Virology* 142:1101–1116 (1997).

Ling et al., "Nucleotide Sequence of the 3' Terminal Two–thirds of the Grapevine—Leafroll–associated Virus–3 Genome Reveals a Typical Monopartite Closterovirus" *Journal General Virology* 79:1299–1307 (1998).

Maningas et al., "Use of Immunocapture–Polymerase Chain Reaction (IC–PCR) in the Diagnosis of Grapevine Leafroll Virus (GLRV) Disease in Grapevine Field Samples," *Am. J. Enol. Vitic..*, 45:357 (1994).

Minafra et al., "Detection of Grapevine Closterovirus A in Infected Grapevine Tissue by Reverse Transcription–Polymerase Chain Reaction," *Vitis* 31:221–227 (1992).

Minafra et al., "Sensitive Detection of Grapevine Virus A, B or Leafroll–Associated III From Viruliferous Mealybugs and Infected Tissue by cDNA Amplification," *Journal of Virological Methods* 47:175–188 (1994).

Minafra, et al., "Improved PCR Procedures for Multiple Identification of Some Artichoke and Grapevine Viruses," *Bulletin OEPP/EPPO Bulletin* 25:283–287 (1995).

Monis et al., "Detection and Localization of Grapevine Leafroll Associated Closteroviruses in Greenhouse and Tissue Culture Grown Plants," *Am. J. Enol. Vitic.*, 47:199–205 (1996).

Monis et al., "Production of Antibodies Specific to a 37 kD Polypeptide Associated with Grapevine Leafroll Associated Virus," *Am. J. Enol. Vitic.*, 47:351 (1996).

Monis et al., "Relationship Between Grapevine Leafroll Associated Virus–2 Grapevine Corky Bark Associated Virus, and the Rootstock–Scion Incompatibility Syndrome," *Am. J. Enol. Vitic.*, 48:393 (1997).

Monis, et al., "Serological Detection of Grapevine Associated Closteroviruses in Infected Grapevine Cultivars," *Plant Disease*, vol. 81, No. 7, pp. 802–808 (1997).

Nejidat, A. et al., "Engineered Resistance Against Plant Virus Diseases," *Physiologia Plantarum* 80:662–668 (1990).

Rowhani et al., "A Comparison Between ELISA and Bioassay Indexing on Cabernet franc Indicator for Detecting Grapevine Leafroll Associated Viruses," *Am. J. Enol. Vitic.*, 47:349–350 (1996).

Rowhani et al., "A Comparison Between Serological and Biological Assays in Detecting Grapevine Leafroll Associated Viruses," *Plant Disease* 81:799–801 (1997).

Saldarelli et al., "Detection of Grapevine Leafroll–Associated Closterovirus III By Molecular Hybridization," *Plant Pathology* 43:91–96 (1994).

Saldarelli et al., "Use of Degenerate Primers in a RT–PCR Assay for the Identification and Analysis of Some Filamentous Viruses, with Special Reference to Clostero– and Vitiviruses of the Grapevine," *Eur. J. Plant Pathology* 104:945–950 (1998).

Schell et al., "Transformation of 'Nova' Tangelo With the Coat Protein Gene of Citrus Tristeza Closterovirus," *Phytopathology* 84:1076 (1994).

Shlamovitz et al., "Unique and Quick in Vitro Procedure to Detect Grapevine Virus Diseases," *Hortscience* 30:783 (1995).

Stam et al., "The Silence of Genes in Transgenic Plants" *Ann. Bot.*, 79:3–12 (1997).

Teliz, "Field Serological Detection of Viral Antigens Associated with Grapevine Leafroll Disease," *Plant Disease* 71:704–709 (1987).

Wetzel et al., A Highly Sensitive Immunocapture Polymerase Chain Reaction Method for Plum Pox Potyvirus Detection,: *Journal of Virological Methods* 39:27–37 (1992).

Zee et al., "Cytopathology of Leafroll–Diseased Grapevines and the Purification and Serology of Associated Closteroviruslike Particles," *Phytopathology* 77:1427–1434 (1987).

Zhang et al., "A Strategy for Rapid cDNA Cloning From double–stranded RNA Templates Isolated From Plants Infected with RNA Viruses by Using Taq DNA Polymerase," *J. Virol. Methods* 84:59–63 (2000).

Zhu et al., "Nucleotide Sequence and Genome Organization of Grapevine Leafroll Associated Closterovirus 2" $12^{th}$ Meeting of the International Council for the Study of Viruses and Virus–Like Diseases of the Grapevine, Sep.–Oct. (1997).

Zhu et al., "Production and Application of An Antibody to the Grapevine Leafroll Associated Clostervirus 2 Coat Protein Expressed in *Escherichia Coli*," $12^{th}$ Meeting of the International Council for the Study of Viruses and Virus–Like Diseases of the Grapevine, Sep.–Oct. (1997).

Zhu et al., "Nucleotide Sequence and Genome Organization of Grapevine Leafroll–Associated Virus–2 Are Similar to Beet Yellows Virus, The Closterovirus Type Member," *Journal of General Virology* 79:1289–1298 (1998).

Zimmermann et al., "Characterization and Serological Detection of Four Closterovirus–like Particles Associated with Leafroll Disease on Grapevine," *J. Phytopathology* 130:205–218 (1990).

Zimmermann et al., "Production and Characterization of Monoclonal Antibodies Specific to Closterovirus–like Particles Associated with Grapevine Leafroll Disease," *J. Phytopathology* 130:277–288 (1990).

FIG. 2

```
    TGTGGACAGCAATCTTCCAAAGAAAGACAGGGATGACATCATGGAAGCGAGTCGACGACT
1   ----(93-110)--------+---------+---------+---------+---------+  60
    ACACCTGTCGTTAGAAGGTTTCTTTCTGTCCCTACTGTAGTACCTTCGCTCAGCTGCTGA
     V  D  S  N  L  P  K  K  D  R  D  D  I  M  E  A  S  R  R  L  -

ATCGCCATCGGACGCCGCCTTTTGCAGAGCAGTGTCGGTTCAGGTAGGGAAGTATGTGGA
61  ---------+---------+---------+---------+---------+---------+  120
    TAGCGGTAGCCTGCGGCGGAAAACGTCTCGTCACAGCCAAGTCCATCCCTTCATACACCT
     S  P  S  D  A  A  F  C  R  A  V  S  V  Q  V  G  K  Y  V  D  -

CGTAACGCAGAATTTAGAAAGTACGATCGTGCCGTTAAGAGTTATGGAAATAAAGAAAAG
121 ---------+-----(93-25)--------+---------+---------+---------+  180
    GCATTGCGTCTTAAATCTTTCATGCTAGCACGGCAATTCTCAATACCTTTATTTCTTTTC
     V  T  Q  N  L  E  S  T  I  V  P  L  R  V  M  E  I  K  K  R  -

ACGAGGATCAGCACATGTTAGTTTACCGAAGGTGGTATCCGCTTACGTAGATTTTTATAC
181 ---------+---------+---------+---------+---------+---------+  240
    TGCTCCTAGTCGTGTACAATCAAATGGCTTCCACCATAGGCGAATGCATCTAAAAATATG
     R  G  S  A  H  V  S  L  P  K  V  V  S  A  Y  V  D  F  Y  T  -

GAACTTGCAGGAATTGCTGTCGGATGAAGTAACTAGGGCCAGAACCGATACAGTTTCGGC
241 ---------+---------+---------+---------+---------+---------+  300
    CTTGAACGTCCTTAACGACAGCCTACTTCATTGATCCCGGTCTTGGCTATGTCAAAGCCG
     N  L  Q  E  L  L  S  D  E  V  T  R  A  R  T  D  T  V  S  A  -

ATACGCTACCGACTCTATGGCTTTCTTAGTTAAGATGTTACCCCTGACTGCTCGTGAGCA
301 ---------+---------+---------+---------+-------(93-40)----+---------+  360
    TATGCGATGGCTGAGATACCGAAAGAATCAATTCTACAATGGGGACTGACGAGCACTCGT
     Y  A  T  D  S  M  A  F  L  V  K  M  L  P  L  T  A  R  E  Q  -

GTGGTTAAAAGACGTGCTAGGATATCTGCTAGTACGGAGACGACCAGCAAATTTTTCCTA
361 ---------+---------+---------+---------+---------+---------+  420
    CACCAATTTTCTGCACGATCCTATAGACGATCATGCCTCTGCTGGTCGTTTAAAAAGGAT
     W  L  K  D  V  L  G  Y  L  L  V  R  R  R  P  A  N  F  S  Y  -

CGACGTAAGAGTAGCTTGGGTATATGACGTGATCGCTACGCTCAAGCTGGTCATAAGATT
421 ---------+---------+---------+---------+---------+---------+  480
    GCTGCATTCTCATCGAACCCATATACTGCACTAGCGATGCGAGTTCGACCAGTATTCTAA
     D  V  R  V  A  W  V  Y  D  V  I  A  T  L  K  L  V  I  R  L  -

GTTTTTCAACAAGGACACACCCGGGGGTATTAAAGACTTAAAACCGTGTGTGCCTATAGA
481 ---------+---------+---------+---------+---------+---------+  540
    CAAAAAGTTGTTCCTGTGTGGGCCCCCATAATTTCTGAATTTTGGCACACACGGATATCT
     F  F  N  K  D  T  P  G  G  I  K  D  L  K  P  C  V  P  I  E  -

GTCATTCGACCCCTTTCACGAGCTTTCGTCCTATTTCTCTAGGTTAAGTTACGAGATGAC
541 ---------+---------+---------+---------+---------+---------+  600
    CAGTAAGCTGGGGAAAGTGCTCGAAAGCAGGATAAAGAGATCCAATTCAATGCTCTACTG
     S  F  D  P  F  H  E  L  S  S  Y  F  S  R  L  S  Y  E  M  T  -

GACAGGTAAAGGGGGAAAGATATGCCCGGAGATCGCCGAGAAGTTGGT
601 ---------+---------+---------+-------(92-98)----  648
    CTGTCCATTTCCCCCTTTCTATACGGGCCTCTAGCGGCTCTTCAACCA
     T  G  K  G  G  K  I  C  P  E  I  A  E  K  L     -
```

FIG. 3

```
BYV_p64     115_VGCKFNIQSVTEFVKKINGNVAEPSLVEHCWSLSNSCGELINPKDTKRFV
CTV_p61     108_VGCRFTLNDVESYLMSRGEDFADLAAVEHSWCLSNSCSRLLSSTEIDANK
LIYV_P59    131_EGCSFTEQQVVEKYPQVDSLVAKIL.....YRVCNSLGKLLDLKDFENKN
GLRaV3_p55  114_VDSNLPKKDRDDIME..ASRRLSPSDAAFCRAVSVQVGKYVDVTQNLEST

CONSENSUS       vgc-f----v-e---------a--------w--sns-g-l----d-----

BYV_p64         SLIFKGKDLAESTDEAIVS..SSYLDYLSHCLNLYETCNLSSNSGKKSLY
CTV_p61         TLVF.TKNFDSNISG..VT..TKLETYLSYCISLYKKHCM.KDDDYFNLI
LIYV_P59        ISGFEINTAQDSPTVADDN..ES.NDFFRECVNDQRYYSSLSGSKLGKAK
GLRaV3_p55      IVPLRVMEIKKRRGSAHVSLPKVVSAYVDFYTNLQELLSDEVTRARTDTV

CONSENSUS       ---f------------a-v--------yl-.-c-nl--------------

BYV_p64         DEFLKHVIDYL...ENSDLEYRSPSDNPLVAGILYDMCFEYNTLKSTYLK
CTV_p61         LPMFNCLMKVL...ASLGLFYEKHADNPLLTGMLIEFCLENKVYYSTFKV
LIYV_P59        LEANAYIFKILLKSASGEFDIDRLSRNPLAISKFMNLYTNHVTDSETFKS
GLRaV3_p55      SAYATDSMAFLVKMLPLT......AREQWLKDVLGYLLVRRRPANFSYDV

CONSENSUS       -----------L--------l-------npl----l--lc---------t---

BYV_p64         NIESFDCFLSLYLPLLSEVFSMNWERPAPDVRLLFELDAAELLLKVPTIN
CTV_p61         NLDNVRLFKSKVLPVVLTVWDISEPDDPVDERVLIPFDPTDFVLDLPKLN
LIYV_P59        KFEALKSIKTPFASFIKKAFGIR..........LNFEDSKIFYALPKER
GLRaV3_p55      RVAWVYDVIATLKLVIRLFFNKDTPGGIKDLKPCVPIESFDPFHELS...

CONSENSUS       --e------------i---f---------d------f---d-f--lp---

BYV_p64         MHDST...FLYKNKLRYLESYFEDDSNELIKVKVDSLL
CTV_p61         IHDTM...VVVGNQIRQLEYVVESDALDDLSQHVDLRL
LIYV_P59        QSDVLSDDMMVESIVRDAASFTVVSDNNYLPERVDRFV
GLRaV3_p55      ...........SYFSRLSYEMTTGKGGKICPEIAEKL

CONSENSUS       --d------------r-l----------------vd--l
```

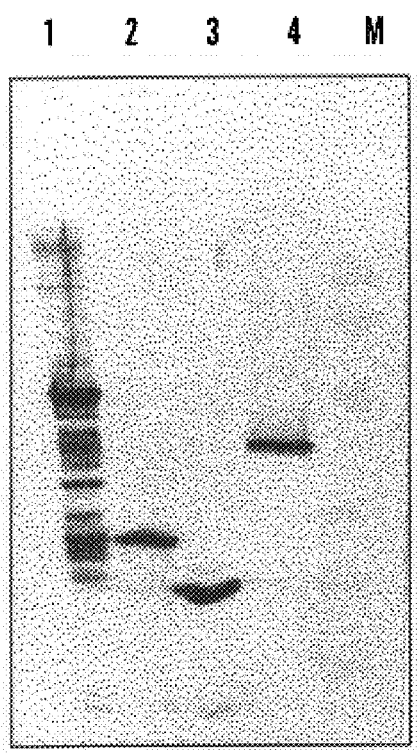 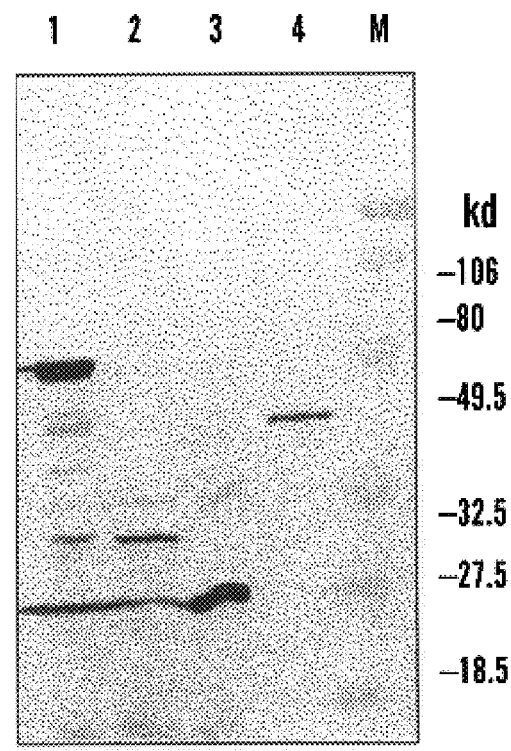
*FIG. 8A*   *FIG. 8B*

FIG. 10

```
    ATGGCATTTGAACTGAAATTAGGGCAGATATATGAAGTCGTCCCCGAAAATAATTTGAGA
  1 ---------+---------+---------+---------+---------+---------+ 60
    M  A  F  E  L  K  L  G  Q  I  Y  E  V  V  P  E  N  N  L  R   -

GTTAGAGTGGGGGATGCGGCACAAGGAAAATTTAGTAAGGCGAGTTTCTTAAAGTACGTT
 61 ---------+---------+---------+---------+---------+---------+ 120
    V  R  V  G  D  A  A  Q  G  K  F  S  K  A  S  F  L  K  Y  V   -

AAGGACGGGACACAGGCGGAATTAACGGGAATCGCCGTAGTGCCCGAAAAATACGTATTC
121 ---------+---------+---------+---------+---------+---------+ 180
    K  D  G  T  Q  A  E  L  T  G  I  A  V  V  P  E  K  Y  V  F   -

GCCACAGCAGCTTTGGCTACAGCGGCGCAGGAGCCACCTAGGCAGCCACCAGCGCAAGTG
181 ---------+---------+---------+---------+---------+---------+ 240
    A  T  A  A  L  A  T  A  A  Q  E  P  P  R  Q  P  P  A  Q  V   -

GCGGAACCACAGGAAACCGATATAGGGGTAGTGCCGGAATCTGAGACTCTCACACCAAAT
241 ---------+---------+---------+---------+---------+---------+ 300
    A  E  P  Q  E  T  D  I  G  V  V  P  E  S  E  T  L  T  P  N   -

AAGTTGGTTTTCGAGAAAGATCCAGACAAGTTCTTGAAGACTATGGGCAAGGGAATAGCT
301 ---------+---------+---------+---------+---------+---------+ 360
    K  L  V  F  E  K  D  P  D  K  F  L  K  T  M  G  K  G  I  A   -

TTGGACTTGGCGGGAGTTACCCACAAACCGAAAGTTATTAACGAGCCAGGGAAAGTATCA
361 ---------+---------+---------+---------+---------+---------+ 420
    L  D  L  A  G  V  T  H  K  P  K  V  I  N  E  P  G  K  V  S   -

GTAGAGGTGGCAATGAAGATTAATGCCGCATTGATGGAGCTGTGTAAGAAGGTTATGGGC
421 ---------+---------+---------+---------+---------+---------+ 480
    V  E  V  A  M  K  I  N  A  A  L  M  E  L  C  K  K  V  M  G   -

GCCGATGACGCAGCAACTAAGACAAAATTCTTCTTGTACGTGATGCAGATTGCTTGCACG
481 ---------+---------+---------+---------+---------+---------+ 540
    A  D  D  A  A  T  K  T  K  F  F  L  Y  V  M  Q  I  A  C  T   -

TTCTTTACATCGTCTTCGACGGAGTTCAAAGAGTTTGACTACATAGAAACCGATGATGGA
541 ---------+---------+---------+---------+---------+---------+ 600
    F  F  T  S  S  S  T  E  F  K  E  F  D  Y  I  E  T  D  D  G   -

AAGAAGATATATGCGGTGTGGGTATATGATTGCATTAAACAAGCTGCTGCTTCGACGGGT
601 ---------+---------+---------+---------+---------+---------+ 660
    K  K  I  Y  A  V  W  V  Y  D  C  I  K  Q  A  A  A  S  T  G   -

TATGAAAACCCGGTAAGGCAGTATCTAGCGTACTTCACACCAACCTTCATCACGGCGACC
661 ---------+---------+---------+---------+---------+---------+ 720
    Y  E  N  P  V  R  Q  Y  L  A  Y  F  T  P  T  F  I  T  A  T   -

CTGAATGGTAAACTAGTGATGAACGAGAAGGTTATGGCACAGCATGGAGTACCACCGAAA
721 ---------+---------+---------+---------+---------+---------+ 780
    L  N  G  K  L  V  M  N  E  K  V  M  A  Q  H  G  V  P  P  K   -

TTCTTTCCGTACACGATAGACTGCGTTCGTCCGACGTACGATCTGTTCAACAACGACGCA
781 ---------+---------+---------+---------+---------+---------+ 840
    F  F  P  Y  T  I  D  C  V  R  P  T  Y  D  L  F  N  N  D  A   -

ATATTAGCATGGAATTTAGCTAGACAGCAGGCGTTTAGAAACAAGACGGTAACGGCCGAT
841 ---------+---------+---------+---------+---------+---------+ 900
    I  L  A  W  N  L  A  R  Q  Q  A  F  R  N  K  T  V  T  A  D   -

AACACCTTACACAACGTCTTCCAACTATTGCAAAAGAAGTAG
901 ---------+---------+---------+---------+-- 942
    N  T  L  H  N  V  F  Q  L  L  Q  K  K  *
```

FIG. 11

```
                    1                                                           50
        BYV_CP      ..........  ..........  ..........  ..........  ..........
        CTV_CP      ..........  ..........  ..........  ..........  ..........
       LIYV_CP      ..........  ..........  ..........  ..........  ..........
     GLRaV3_CP      MAFELKLGQI  YEVVPENNLR  VRVGDAAQGK  FSKASFLKYV  KDGTQAELTG

CONSENSUS      ----------  ----------  ----------  ----------  ----------

51                                                          100
        BYV_CP      ..........  ..........  ..........  ..........  ..........
        CTV_CP      ..........  ..........  ..........  ..........  MDDETKKLKN
       LIYV_CP      ..........  ....MDTDGD  NDVFGSGNDT  RNNDDKKKEE  MKQNISDNSQ
     GLRaV3_CP      IAVVPEKYVF  ATAALATAAQ  EPPRQPPAQV  AEPQETDIGV  VPESETLTPN

CONSENSUS      ----------  ----------  ----------  ----------  ----------

101                                                         150
        BYV_CP      .....MGSAE  PISAIA..TF  ENVSL.AD.Q  TCLHGEDCDK  LRK......N
        CTV_CP      KNKETKEGDD  VVAAES..SF  GSVNLHID.P  TLITMNDVRQ  LSTQQNAALN
       LIYV_CP      IISTRDHEAD  IIGSISKEDL  SKIVVRVDRH  DALSANDVQS  FR...EAMIN
     GLRaV3_CP      KLVFEKDPDK  FLKTMGKGIA  LDLAGVTHKP  KVI...NEPGK VSVEVAMKIN

CONSENSUS      ---------d  -i-------f  --v----d--  -----nd---  l--------N 151                                                         200
        BYV_CP      FEECLKLKG.  ...VPEDNLG  IALGLCLYSC  AT.IGTSNKV  NVQPTS.TFI
        CTV_CP      RDLFLALKGK  YPNLPDKDKD  FHIAMMLYRL  AV.KSSSLQS  DDDTTGITYT
       LIYV_CP      ...FMRDKDP  NRNQPSDKLI  IAMEVGVYQM  VINLGTSAKL  G.NANNLEFT
     GLRaV3_CP      .AALMELCKK  VMGADDAATK  TKFFLYVMQI  ACTFFTS..S  STEFKEFDYI

CONSENSUS      ---f--lk--  ----pd----  ----l--y--  a----tS---  ----------

201                                                         250
        BYV_CP      KASFGGGKEL  YLTHGELNSF  LGSQKLLEGK  PNKLRCFCRT  FQKDYISLRK
        CTV_CP      R....EGVEV  DLSDKLWTDI  VYNSKGIGNR  TNALRVWGRT  NDALYLAFCR
       LIYV_CP      IAYDQETRTY  KVAD..FVNY  MQSR..MRNS  PNVVRQYARA  MEKTINNIRS
     GLRaV3_CP      ET..DDGKKI  Y..AVWVYDC  IKQAAASTGY  ENPVRQYLAY  FTPTFITATL

CONSENSUS      -----eg---  ----------  ----------  -N--R-y-r-  ----y-----

251                                                         300
        BYV_CP      EYRGKLPPIA  RANRHGLPAE  DHYLAADF.I  STSTELTDLQ  QSRLLLAREN
        CTV_CP      QNR.NLSYGG  RPLDAGIPAG  YHYLCADF.L  .TGAGLTDLE  CAVYIQAKEQ
       LIYV_CP      AGIIN.SNGV  LAAKHGVLAS  YRNSYSDFAV  GFGNDTTDAQ  LTSLMLARKQ
     GLRaV3_CP      NGKLVMNEKV  MA.QHGVPPK  FFPYTIDCVR  PTYDLFNNDA  ILAWNLARQQ

CONSENSUS      -----l----  -a--hGvpa-  y-----Df--  -t---ltd--  -----lAr-q 301              328
        BYV_CP      ATH.TEFSSE  SPVTSLKQLG  RGLGTGR*..
        CTV_CP      LLK.KRGADE  VVVTNVRQLG  K.FNTR*...
       LIYV_CP      ALC.KGEGGS  VEHYNTMQLA  NLKHPC*...
     GLRaV3_CP      AFRNKTVTAD  NTLHNVFQLL  QKK*......

CONSENSUS      al--k----e  ----n--QL-  ----------
```

FIG. 18A

ORF1a (HELICASE)

```
         GTGTCTACTTACGCAAGAGTGTGATGAACGACAATTTCAATATCCTTGAGACCCTGGTA
    1    ---------+---------+---------+---------+---------+---------+  60
         CACAGATGAATGCGCTTCTCACACTACTTGCTGTTAAAGTTATAGGAACTCTGGGACCAT
a         V  S  T  Y  A  K  S  V  M  N  D  N  F  N  I  L  E  T  L  V   -

ACTTTGCCCAAGTCCTTTATAGTCAAAGTACCTGGTTCGGTGCTGGTTAGCATAACCACT
   61    ---------+---------+---------+---------+---------+---------+ 120
         TGAAACGGGTTCAGGAAATATCAGTTTCATGGACCAAGCCACGACCAATCGTATTGGTGA
a         T  L  P  K  S  F  I  V  K  V  P  G  S  V  L  V  S  I  T  T   -

TCGGGCATTTCCGACAAACTTGAACTTCGGGGCGCGTTCGACGTTTCTAAAAAGAATTTC
  121    ---------+---------+---------+---------+---------+---------+ 180
         AGCCCGTAAAGGCTGTTTGAACTTGAAGCCCCGCGCAAGCTGCAAAGATTTTTCTTAAAG
a         S  G  I  S  D  K  L  E  L  R  G  A  F  D  V  S  K  K  N  F   -

TCCAGGAGGTTACGTTCGAGTCGTTTGCGCGTATTTTCTAGGGCTATTGTGGAGGATACG
  181    ---------+---------+---------+---------+---------+---------+ 240
         AGGTCCTCCAATGCAAGCTCAGCAAACGCGCATAAAAGATCCCGATAACACCTCCTATGC
a         S  R  R  L  R  S  S  R  L  R  V  F  S  R  A  I  V  E  D  T   -

ATCAAGGTTATGAAGGGCATGAAATCAGAGGATGGTAAACCACTCCCTATAGCCGAGGAT
  241    ---------+---------+---------+---------+---------+---------+ 300
         TAGTTCCAATACTTCCCGTACTTTAGTCTCCTACCATTTGGTGAGGGATATCGGCTCCTA
a         I  K  V  M  K  G  M  K  S  E  D  G  K  P  L  P  I  A  E  D   -

TCCGTGTACGCGTTCATGACAGGCAATATGTCAAACGTTCATTGCACTAGGGCTGGTTTG
  301    ---------+---------+---------+---------+---------+---------+ 360
         AGGCACATGCGCAAGTACTGTCCGTTATACAGTTTGCAAGTAACGTGATCCCGACCAAAC
a         S  V  Y  A  F  M  T  G  N  M  S  N  V  H  C  T  R  A  G  L   -

CTCGGGGGCTCAAAGGCTTGCGCGGCTTCTTTAGCTGTGAAGGGTGCAGCTTCACGCGCT
  361    ---------+---------+---------+---------+---------+---------+ 420
         GAGCCCCCGAGTTTCCGAACGCGCCGAAGAAATCGACACTTCCCACGTCGAAGTGCGCGA
a         L  G  G  S  K  A  C  A  A  S  L  A  V  K  G  A  A  S  R  A   -

ACTGGAACAAAACTCTTTTCAGGTCTCACATCCTTTCTTTCCGCCGGTGGTCTGTTTTAC
  421    ---------+---------+---------+---------+---------+---------+ 480
         TGACCTTGTTTTGAGAAAAGTCCAGAGTGTAGGAAAGAAAGGCGGCCACCAGACAAAATG
a         T  G  T  K  L  F  S  G  L  T  S  F  L  S  A  G  G  L  F  Y   -

GATGAAGGCTTGACGCCCGGAGAGAGGCTTGATGCACTAACGCGCCGTGAACATGCTGTG
  481    ---------+---------+---------+---------+---------+---------+ 540
         CTACTTCCGAACTGCGGGCCTCTCTCCGAACTACGTGATTGCGCGGCACTTGTACGACAC
a         D  E  G  L  T  P  G  E  R  L  D  A  L  T  R  R  E  H  A  V   -

AATTCACCTGTAGGCCTCTTAGAACCTGGAGCTTCGGTTGCGAAGCGGGTCGTTTCCGGA
  541    ---------+---------+---------+---------+---------+---------+ 600
         TTAAGTGGACATCCGGAGAATCTTGGACCTCGAAGCCAACGCTTCGCCCAGCAAAGGCCT
a         N  S  P  V  G  L  L  E  P  G  A  S  V  A  K  R  V  V  S  G   -

ACGAAAGCTTTTCTGTCAGAATTGTCATTGGAGGACTTCACCACTTTCGTCATAAAAAAT
  601    ---------+---------+---------+---------+---------+---------+ 660
         TGCTTTCGAAAAGACAGTCTTAACAGTAACCTCCTGAAGTGGTGAAAGCAGTATTTTTTA
a         T  K  A  F  L  S  E  L  S  L  E  D  F  T  T  F  V  I  K  N   -
```

FIG. 18B

```
           AGGGTGCTTATTGGTGTGTTTTTACTCTTTCCATGGCTCTCACTCCGGTGGTCTGGAAGTAC
       661 ---------+---------+---------+---------+---------+---------+ 720
           TCCCACGAATAACCACAAAAATGAGAAAGGTACCGAGAGTGAGGCCACCAGACCTTCATG
    a       R  V  L  I  G  V  F  T  L  S  M  A  L  T  P  V  V  W  K  Y  -

AGAAGGAATATCGCGCGAACTGGCGTGGATGTTTTCCACCGTGCTCGTTCGGGTACCGCG
       721 ---------+---------+---------+---------+---------+---------+ 780
           TCTTCCTTATAGCGCGCTTGACCGCACCTACAAAAGGTGGCACGAGCAAGCCCATGGCGC
    a       R  R  N  I  A  R  T  G  V  D  V  F  H  R  A  R  S  G  T  A  -

GCCATCGGTTTACAATGTCTTAGTGGAGGAAGGTCGTTAGCTGGTGACGCTGCTCGTGGC
       781 ---------+---------+---------+---------+---------+---------+ 840
           CGGTAGCCAAATGTTACAGAATCACCTCCTTCCAGCAATCGACCACTGCGACGAGCACCG
    a       A  I  G  L  Q  C  L  S  G  G  R  S  L  A  G  D  A  A  R  G  -

GCGTTAACAGTGACTCGAGGAGGGCTATCTTCGGCGGTTGCGGTGACCAGAAATACAGTG
       841 ---------+---------+---------+---------+---------+---------+ 900
           CGCAATTGTCACTGAGCTCCTCCCGATAGAAGCCGCCAACGCCACTGGTCTTTATGTCAC
    a       A  L  T  V  T  R  G  G  L  S  S  A  V  A  V  T  R  N  T  V  -

GCTAGGCGTCAGGTACCATTGGCGTTGCTTTCGTTTTCCACGTCTTACGCAGTCAGTGGT
       901 ---------+---------+---------+---------+---------+---------+ 960
           CGATCCGCAGTCCATGGTAACCGCAACGAAAGCAAAAGGTGCAGAATGCGTCAGTCACCA
    a       A  R  R  Q  V  P  L  A  L  L  S  F  S  T  S  Y  A  V  S  G  -

TGCACTTTGTTAGGTATTTGGGCTCATGCTCTCCCTAGGCATTTGATGTTCTTCTTTGGC
       961 ---------+---------+---------+---------+---------+---------+ 1020
           ACGTGAAACAATCCATAAACCCGAGTACGAGAGGGATCCGTAAACTACAAGAAGAAACCG
    a       C  T  L  L  G  I  W  A  H  A  L  P  R  H  L  M  F  F  F  G  -

CTAGGGACGCTCTTCGGGGTGAGTGCCAGTACCAATTCTTGGTCGCTTGGGGGCTATACG
      1021 ---------+---------+---------+---------+---------+---------+ 1080
           GATCCCTGCGAGAAGCCCCACTCACGGTCATGGTTAAGAACCAGCGAACCCCCGATATGC
    a       L  G  T  L  F  G  V  S  A  S  T  N  S  W  S  L  G  G  Y  T  -

AACAGTCTGTTCACCGTACCGGAATTAACTTGGGAAGGGAGGAGTTACAGATCTTTATTG
      1081 ---------+---------+---------+---------+---------+---------+ 1140
           TTGTCAGACAAGTGGCATGGCCTTAATTGAACCCTTCCCTCCTCAATGTCTAGAAATAAC
    a       N  S  L  F  T  V  P  E  L  T  W  E  G  R  S  Y  R  S  L  L  -

CCCCAAGCAGCTTTAGGTATTTCTCTCGTTGTGCGCGGGTTGTTAAGTGAAACTGTGCCA
      1141 ---------+---------+---------+---------+---------+---------+ 1200
           GGGGTTCGTCGAAATCCATAAAGAGAGCAACACGCGCCCAACAATTCACTTTGACACGGT
    a       P  Q  A  A  L  G  I  S  L  V  V  R  G  L  L  S  E  T  V  P  -

CAACTAACGTACGTACCGCCGATTGAAGGTCGGAATGTTTATGATCAGGCACTAAATTTT
      1201 ---------+---------+---------+---------+---------+---------+ 1260
           GTTGATTGCATGCATGGCGGCTAACTTCCAGCCTTACAAATACTAGTCCGTGATTTAAAA
    a       Q  L  T  Y  V  P  P  I  E  G  R  N  V  Y  D  Q  A  L  N  F  -

TATCGCGACTTTGACTATGACGATGGTGCAGGCCCATCCGGGACGGCTGGTCAAAGCGAT
      1261 ---------+---------+---------+---------+---------+---------+ 1320
           ATAGCGCTGAAACTGATACTGCTACCACGTCCGGGTAGGCCCTGCCGACCAGTTTCGCTA
    a       Y  R  D  F  D  Y  D  D  G  A  G  P  S  G  T  A  G  Q  S  D  -
```

FIG. 18C

```
         CCTGGAACCAATACTTCGGATACTTCTTCGGTTTTCTCTGACGATGGTTTGCCCGCTAGT
    1321 ---------+---------+---------+---------+---------+---------+ 1380
         GGACCTTGGTTATGAAGCCTATGAAGAAGCCAAAAGAGACTGCTACCAAACGGGCGATCA
a         P  G  T  N  T  S  D  T  S  S  V  F  S  D  D  G  L  P  A  S  -

GGCGGTGGCTTCGACGCGCGCGTTGAGGCAGGTCCCAGCCATGCTGTTGATGAATCACCA
    1381 ---------+---------+---------+---------+---------+---------+ 1440
         CCGCCACCGAAGCTGCGCGCGCAACTCCGTCCAGGGTCGGTACGACAACTACTTAGTGGT
a         G  G  G  F  D  A  R  V  E  A  G  P  S  H  A  V  D  E  S  P  -

AGGGGTAGTGTTGAGTTCGTCTACAGAGAACGTGTAGATGAACATCCGGCGTGTGGTGAA
    1441 ---------+---------+---------+---------+---------+---------+ 1500
         TCCCCATCACAACTCAAGCAGATGTCTCTTGCACATCTACTTGTAGGCCGCACACCACTT
a         R  G  S  V  E  F  V  Y  R  E  R  V  D  E  H  P  A  C  G  E  -

GCTGAAGTTGAAAAGGATCTAATAACACCACTTGGTACAGCTGTCTTAGAGTCGCCCCCC
    1501 ---------+---------+---------+---------+---------+---------+ 1560
         CGACTTCAACTTTTCCTAGATTATTGTGGTGAACCATGTCGACAGAATCTCAGCGGGGGG
a         A  E  V  E  K  D  L  I  T  P  L  G  T  A  V  L  E  S  P  P  -

GTAGGTCCTGAAGCTGGGAGCGCGCCCAACGTCGAGGACGGTTGTCCGGAGGTTGAAGCT
    1561 ---------+---------+---------+---------+---------+---------+ 1620
         CATCCAGGACTTCGACCCTCGCGCGGGTTGCAGCTCCTGCCAACAGGCCTCCAACTTCGA
a         V  G  P  E  A  G  S  A  P  N  V  E  D  G  C  P  E  V  E  A  -

GAGAAATGTTCGGAGGTCATCGTTGACGTTCCTAGTTCAGAACCGCCGGTACAAGAAGTC
    1621 ---------+---------+---------+---------+---------+---------+ 1680
         CTCTTTACAAGCCTCCAGTAGCAACTGCAAGGATCAAGTCTTGGCGGCCATGTTCTTCAG
a         E  K  C  S  E  V  I  V  D  V  P  S  S  E  P  P  V  Q  E  V  -

CTTGAATCAACCAATGGTGTCCAAGCTGCAAGAACTGAAGAGGTTGTGCAGGGCGACACA
    1681 ---------+---------+---------+---------+---------+---------+ 1740
         GAACTTAGTTGGTTACCACAGGTTCGACGTTCTTGACTTCTCCAACACGTCCCGCTGTGT
a         L  E  S  T  N  G  V  Q  A  A  R  T  E  E  V  V  Q  G  D  T  -

TGTGGAGCTGGGGTAGCTAAATCAGAAGTGAGTCAACGTGTGTTTCCTGCGCAAGTACCC
    1741 ---------+---------+---------+---------+---------+---------+ 1800
         ACACCTCGACCCCATCGATTTAGTCTTCACTCAGTTGCACACAAAGGACGCGTTCATGGG
a         C  G  A  G  V  A  K  S  E  V  S  Q  R  V  F  P  A  Q  V  P  -

GCACATGAAGCTGGTCTTGAGGCATCTAGTGGCGCGGTCGTGGAGCCATTGCAAGTTTCT
    1801 ---------+---------+---------+---------+---------+---------+ 1860
         CGTGTACTTCGACCAGAACTCCGTAGATCACCGCGCCAGCACCTCGGTAACGTTCAAAGA
a         A  H  E  A  G  L  E  A  S  S  G  A  V  V  E  P  L  Q  V  S  -

GTGCCAGTAGCCGTAGAGAAAACTGTTTTATCTGTCGAGAAGGCGCGTGAGCTAAAGGCG
    1861 ---------+---------+---------+---------+---------+---------+ 1920
         CACGGTCATCGGCATCTCTTTTGACAAAATAGACAGCTCTTCCGCGCACTCGATTTCCGC
a         V  P  V  A  V  E  K  T  V  L  S  V  E  K  A  R  E  L  K  A  -

GTAGATAAGGGCAAGGCGGTCGTGCACGCAAAGGAAGTCAAGAATGTACCGGTTAAGACG
    1921 ---------+---------+---------+---------+---------+---------+ 1980
         CATCTATTCCCGTTCCGCCAGCACGTGCGTTTCCTTCAGTTCTTACATGGCCAATTCTGC
a         V  D  K  G  K  A  V  V  H  A  K  E  V  K  N  V  P  V  K  T  -
```

FIG. 18D

```
              TTACCACGAGGGGCTCTAAAAATTAGTGAGGATACCGTTCGTAAGGAATTGTGCATGTTT
         1981 ------------------------------------------------------------+ 2040
              AATGGTGCTCCCCGAGATTTTTAATCACTCCTATGGCAAGCATTCCTTAACACGTACAAA
    a          L  P  R  G  A  L  K  I  S  E  D  T  V  R  K  E  L  C  M  F  -

AGAACGTGTTCCTGCGGCGTGCAGTTGGACGTGTACAATGAAGCGACCATCGCCACTAGG
         2041 ------------------------------------------------------------+ 2100
              TCTTGCACAAGGACGCCGCACGTCAACCTGCACATGTTACTTCGCTGGTAGCGGTGATCC
    a          R  T  C  S  C  G  V  Q  L  D  V  Y  N  E  A  T  I  A  T  R  -

TTCTCAAATGCGTTTACCTTTGTCGATAGCTTGAAAGGGAGGAGTGCGGTCTTTTTCTCA
         2101 ------------------------------------------------------------+ 2160
              AAGAGTTTACGCAAATGGAAACAGCTATCGAACTTTCCCTCCTCACGCCAGAAAAAGAGT
    a          F  S  N  A  F  T  F  V  D  S  L  K  G  R  S  A  V  F  F  S  -

AAGCTGGGTGAGGGGTATACCTATAATGGTGGTAGCCATGTTTCATCAGGGTGGCCTCGT
         2161 ------------------------------------------------------------+ 2220
              TTCGACCCACTCCCCATATGGATATTACCACCATCGGTACAAAGTAGTCCCACCGGAGCA
    a          K  L  G  E  G  Y  T  Y  N  G  G  S  H  V  S  S  G  W  P  R  -

GCCCTAGAGGATATCTTAACGGCAATTAAGTACCCAAGCGTCTTCGACCACTGTTTAGTG
         2221 ------------------------------------------------------------+ 2280
              CGGGATCTCCTATAGAATTGCCGTTAATTCATGGGTTCGCAGAAGCTGGTGACAAATCAC
    a          A  L  E  D  I  L  T  A  I  K  Y  P  S  V  F  D  H  C  L  V  -

CAGAAGTACAAGATGGGTGGAGGCGTACCATTCCACGCTGATGACGAGGAGTGCTATCCA
         2281 ------------------------------------------------------------+ 2340
              GTCTTCATGTTCTACCCACCTCCGCATGGTAAGGTGCGACTACTGCTCCTCACGATAGGT
    a          Q  K  Y  K  M  G  G  G  V  P  F  H  A  D  D  E  E  C  Y  P  -

TCAGATAACCCTATCTTGACGGTCAATCTCGTGGGGAAGGCAAACTTCTCGACTAAGTGC
         2341 ------------------------------------------------------------+ 2400
              AGTCTATTGGGATAGAACTGCCAGTTAGAGCACCCCTTCCGTTTGAAGAGCTGATTCACG
    a          S  D  N  P  I  L  T  V  N  L  V  G  K  A  N  F  S  T  K  C  -

AGGAAGGGTGGTAAGGTCATGGTCATAAACGTAGCTTCGGGTGACTATTTTCTTATGCCT
         2401 ------------------------------------------------------------+ 2460
              TCCTTCCCACCATTCCAGTACCAGTATTTGCATCGAAGCCCACTGATAAAAGAATACGGA
    a          R  K  G  G  K  V  M  V  I  N  V  A  S  G  D  Y  F  L  M  P  -

TGCGGTTTTCAAAGGACGCACTTGCATTCAGTAAACTCCATCGACGAAGGGCGCATCAGT
         2461 ------------------------------------------------------------+ 2520
              ACGCCAAAAGTTTCCTGCGTGAACGTAAGTCATTTGAGGTAGCTGCTTCCCGCGTAGTCA
    a          C  G  F  Q  R  T  H  L  H  S  V  N  S  I  D  E  G  R  I  S  -

TTGACGTTCAGGGCAACTCGGCGCGTCTTTGGTGTAGGCAGGATGTTGCAGTTAGCCGGC
         2521 ------------------------------------------------------------+ 2580
              AACTGCAAGTCCCGTTGAGCCGCGCAGAAACCACATCCGTCCTACAACGTCAATCGGCCG
    a          L  T  F  R  A  T  R  R  V  F  G  V  G  R  M  L  Q  L  A  G  -

GGCGTGTCGGATGAGAAGTCACCAGGTGTTCCAAACCAGCAACCACAGAGCCAAGGTGCT
         2581 ------------------------------------------------------------+ 2640
              CCGCACAGCCTACTCTTCAGTGGTCCACAAGGTTTGGTCGTTGGTGTCTCGGTTCCACGA
    a          G  V  S  D  E  K  S  P  G  V  P  N  Q  Q  P  Q  S  Q  G  A  -
```

FIG. 18E

```
     ACCAGAACAATCACACCAAAATCGGGGGGCAAGGCTCTATCTGAGGGAAGTGGTAGGGAA
2641 ---------+---------+---------+---------+---------+---------+ 2700
     TGGTCTTGTTAGTGTGGTTTTAGCCCCCCGTTCCGAGATAGACTCCCTTCACCATCCCTT
a    T R T I T P K S G G K A L S E G S G R E  -

GTCAAGGGGAGGTCGACATACTCGATATGGTGCGAACAAGATTACGTTAGGAAGTGTGAG
2701 ---------+---------+---------+---------+---------+---------+ 2760
     CAGTTCCCCTCCAGCTGTATGAGCTATACCACGCTTGTTCTAATGCAATCCTTCACACTC
a    V K G R S T Y S I W C E Q D Y V R K C E  -

TGGCTCAGGGCTGATAATCCAGTGATGGCTCTTRAACCTGGCTACACCCCAATGACATTT
2761 ---------+---------+---------+---------+---------+---------+ 2820
     ACCGAGTCCCGACTATTAGGTCACTACCGAGAAYTTGGACCGATGTGGGGTTACTGTAAA
a    W L R A D N P V M A L ? P G Y T P M T F  -

GAAGTGGTTAAAGCCGGGACCTCTGAAGATGCCGTCGTGGAGTACTTGAAGTATCTGGCT
2821 ---------+---------+---------+---------+---------+---------+ 2880
     CTTCACCAATTTCGGCCCTGGAGACTTCTACGGCAGCACCTCATGAACTTCATAGACCGA
a    E V V K A G T S E D A V V E Y L K Y L A  -

ATAGGCATTGGGAGGACATACAGGGCGTTGCTTATGGCTAGAAATATTGCCGTCACTACC
2881 ---------+---------+---------+---------+---------+---------+ 2940
     TATCCGTAACCCTCCTGTATGTCCCGCAACGAATACCGATCTTTATAACGGCAGTGATGG
a    I G I G R T Y R A L L M A R N I A V T T  -

GCCGAAGGTGTTCTGAAAGTACCTAATCAAGTTTATGAATCACTACCGGGCTTTCACGTT
2941 ---------+---------+---------+---------+---------+---------+ 3000
     CGGCTTCCACAAGACTTTCATGGATTAGTTCAAATACTTAGTGATGGCCCGAAAGTGCAA
a    A E G V L K V P N Q V Y E S L P G F H V  -

TACAAGTCGGGCACAGATCTCATTTTTCATTCAACACAAGACGGCTTGCGTGTGAGAGAC
3001 ---------+---------+---------+---------+---------+---------+ 3060
     ATGTTCAGCCCGTGTCTAGAGTAAAAAGTAAGTTGTGTTCTGCCGAACGCACACTCTCTG
a    Y K S G T D L I F H S T Q D G L R V R D  -

CTACCGTACGTATTCATAGCTGAGAAAGGTATTTTTATCAAGGGCAAAGATGTCGACGCG
3061 ---------+---------+---------+---------+---------+---------+ 3120
     GATGGCATGCATAAGTATCGACTCTTTCCATAAAAATAGTTCCCGTTTCTACAGCTGCGC
a    L P Y V F I A E K G I F I K G K D V D A  -

GTAGTAGCTTTGGGCGACAATCTGTCCGTATGTGATGATATATTGGTTTTCCATGATGCT
3121 ---------+---------+---------+---------+---------+---------+ 3180
     CATCATCGAAACCCGCTGTTAGACAGGCATACACTACTATATAACCAAAAGGTACTACGA
a    V V A L G D N L S V C D D I L V F H D A  -

ATTAATTTGATGGGTGCACTGAAAGTTGCTCGATGTGGTATGGTGGGTGAATCATTTAAG
3181 ---------+---------+---------+---------+---------+---------+ 3240
     TAATTAAACTACCCACGTGACTTTCAACGAGCTACACCATACCACCCACTTAGTAAATTC
a    I N L M G A L K V A R C G M V G E S F K  -

TCGTTCGAATACAAATGCTATAATGCTCCCCCAGGTGGCGGTAAGACGACGATGCTAGTG
3241 ---------+---------+---------+---------+---------+---------+ 3300
     AGCAAGCTTATGTTTACGATATTACGAGGGGGTCCACCGCCATTCTGCTGCTACGATCAC
a    S F E Y K C Y N A P P G G G K T T M L V  -
```

FIG. 18F

```
              GACGAATTTGTCAAGTCACCCAATAGCACGGCCACCATTACGGCTAACGTGGGAAGTTCT
      3301    ---------+---------+---------+---------+---------+---------+ 3360
              CTGCTTAAACAGTTCAGTGGGTTATCGTGCCGGTGGTAATGCCGATTGCACCCTTCAAGA
    a          D  E  F  V  K  S  P  N  S  T  A  T  I  T  A  N  V  G  S  S    -

GAGGACATAAATATGGCGGTGAAGAAGAGAGATCCGAATTTGGAAGGTCTCAACAGTGCT
      3361    ---------+---------+---------+---------+---------+---------+ 3420
              CTCCTGTATTTATACCGCCACTTCTTCTCTCTAGGCTTAAACCTTCCAGAGTTGTCACGA
    a          E  D  I  N  M  A  V  K  K  R  D  P  N  L  E  G  L  N  S  A    -

ACCACAGTTAACTCCAGGGTGGTTAACTTTATTGTCAGGGGAATGTATAAAAGGGTTTTG
      3421    ---------+---------+---------+---------+---------+---------+ 3480
              TGGTGTCAATTGAGGTCCCACCAATTGAAATAACAGTCCCCTTACATATTTTCCCAAAAC
    a          T  T  V  N  S  R  V  V  N  F  I  V  R  G  M  Y  K  R  V  L    -

GTGGATGAGGTGTACATGATGCATCAAGGCTTACTACAACTAGGCGTCTTCGCAACCGGC
      3481    ---------+---------+---------+---------+---------+---------+ 3540
              CACCTACTCCACATGTACTACGTAGTTCCGAATGATGTTGATCCGCAGAAGCGTTGGCCG
    a          V  D  E  V  Y  M  M  H  Q  G  L  L  Q  L  G  V  F  A  T  G    -

GCGTCGGAAGGCCTCTTTTTTGGAGACATAAATCAGATACCATTCATAAACMGGGAGAAG
      3541    ---------+---------+---------+---------+---------+---------+ 3600
              CGCAGCCTTCCGGAGAAAAAACCTCTGTATTTAGTCTATGGTAAGTATTTGKCCCTCTTC
    a          A  S  E  G  L  F  F  G  D  I  N  Q  I  P  F  I  N  R  E  K    -

GTGTTTAGGATGGATTGTGCTGTATTTGTTCCAAAGAAGGAAAGCGTTGTATACACTTCT
      3601    ---------+---------+---------+---------+---------+---------+ 3660
              CACAAATCCTACCTAACACGACATAAACAAGGTTTCTTCCTTTCGCAACATATGTGAAGA
    a          V  F  R  M  D  C  A  V  F  V  P  K  K  E  S  V  V  Y  T  S    -

AAATCATACAGGTGTCCGTTAGATGTTTGCTACTTGTTGTCCTCAATGACCGTAAGGGGA
      3661    ---------+---------+---------+---------+---------+---------+ 3720
              TTTAGTATGTCCACAGGCAATCTACAAACGATGAACAACAGGAGTTACTGGCATTCCCCT
    a          K  S  Y  R  C  P  L  D  V  C  Y  L  L  S  S  M  T  V  R  G    -

ACGGAAAAGTGTTACCCTGAAAAGGTCGTTAGCGGTAAGGACAAACCAGTAGTAAGATCG
      3721    ---------+---------+---------+---------+---------+---------+ 3780
              TGCCTTTTCACAATGGGACTTTTCCAGCAATCGCCATTCCTGTTTGGTCATCATTCTAGC
    a          T  E  K  C  Y  P  E  K  V  V  S  G  K  D  K  P  V  V  R  S    -

CTGTCCAAAAGGCCAATTGGAACCACTGATGACGTAGCTGAAATAAACGCTGACGTGTAC
      3781    ---------+---------+---------+---------+---------+---------+ 3840
              GACAGGTTTTCCGGTTAACCTTGGTGACTACTGCATCGACTTTATTTGCGACTGCACATG
    a          L  S  K  R  P  I  G  T  T  D  D  V  A  E  I  N  A  D  V  Y    -

TTGTGCATGACCCAGTTGGAGAAGTCGGATATGAAGAGGTCGTTGAAGGGAAAAGGAAAA
      3841    ---------+---------+---------+---------+---------+---------+ 3900
              AACACGTACTGGGTCAACCTCTTCAGCCTATACTTCTCCAGCAACTTCCCTTTTCCTTTT
    a          L  C  M  T  Q  L  E  K  S  D  M  K  R  S  L  K  G  K  G  K    -

GAAACACCAGTGATGACAGTGCATGAAGCACAGGGAAAAACATTCAGTGATGTGGTATTG
      3901    ---------+---------+---------+---------+---------+---------+ 3960
              CTTTGTGGTCACTACTGTCACGTACTTCGTGTCCCTTTTTGTAAGTCACTACACCATAAC
    a          E  T  P  V  M  T  V  H  E  A  Q  G  K  T  F  S  D  V  V  L    -
```

FIG. 18G

```
         TTTAGGACGAAGAAAGCCGATGACTCCCTATTCACTAAACAACCGCATATACTTGTTGGT
    3961 ---------+---------+---------+---------+---------+---------+ 4020
         AAATCCTGCTTCTTTCGGCTACTGAGGGATAAGTGATTTGTTGGCGTATATGAACAACCA
a         F  R  T  K  K  A  D  D  S  L  F  T  K  Q  P  H  I  L  V  G  -

TTGTCGAGACACACACGCTCACTGGTTTATGCCGCTCTGAGCTCAGAGTTGGACGATAAG
    4021 ---------+---------+---------+---------+---------+---------+ 4080
         AACAGCTCTGTGTGTGCGAGTGACCAAATACGGCGAGACTCGAGTCTCAACCTGCTATTC
a         L  S  R  H  T  R  S  L  V  Y  A  A  L  S  S  E  L  D  D  K  -
                                            *  A  Q  S  W  T  I  R  -

(FRAMESHIFT)
         GTCGGCACATATATTAGCGACGCGTCGCCTCAATCAGTATCCGACGCTTTGCTTCACACG
    4081 ---------+---------+---------+---------+---------+---------+ 4140
         CAGCCGTGTATATAATCGCTGCGCAGCGGAGTTAGTCATAGGCTGCGAAACGAAGTGTGC
a         V  G  T  Y  I  S  D  A  S  P  Q  S  V  S  D  A  L  L  H  T  -
          S  A  H  I  L  A  T  R  H  L  N  Q  Y  P  T  L  C  F  T  R  -

ORF1b (RdRp)
         TTCGCCCCGGCTGGTTGCTTTCGAGGTATATGAGCGTATGAATTTTGGACCGACCTTCGA
    4141 ---------+---------+---------+---------+---------+---------+ 4200
         AAGCGGGGCCGACCAACGAAAGCTCCATATACTCGCATACTTAAAACCTGGCTGGAAGCT
a         F  A  P  A  G  C  F  R  G  I  *                            -
b         S  P  R  L  V  A  F  E  V  Y  E  R  M  N  F  G  P  T  F  E  -

AGGGGAGTTGGTACGAAGATACCAACAAGTCATTTTGTAGCCGTGAATGGGTTTCTCGA
    4201 ---------+---------+---------+---------+---------+---------+ 4260
         TCCCCTCAACCATGCCTTCTATGGTTGTTCAGTAAAACATCGGCACTTACCCAAAGAGCT
b         G  E  L  V  R  K  I  P  T  S  H  F  V  A  V  N  G  F  L  E  -

GGACTTACTCGACGGTTGTCCGGCTTTCGACTATGACTTCTTTGAGGATGATTTCGAAAC
    4261 ---------+---------+---------+---------+---------+---------+ 4320
         CCTGAATGAGCTGCCAACAGGCCGAAAGCTGATACTGAAGAAACTCCTACTAAAGCTTTG
b         D  L  L  D  G  C  P  A  F  D  Y  D  F  F  E  D  D  F  E  T  -

TTCAGATCAGTCTTTCCTCATAGAAGATGTGCGCATTTCTGAATCTTTTTCTCATTTTGC
    4321 ---------+---------+---------+---------+---------+---------+ 4380
         AAGTCTAGTCAGAAAGGAGTATCTTCTACACGCGTAAAGACTTAGAAAAAGAGTAAAACG
b          S  D  Q  S  F  L  I  E  D  V  R  I  S  E  S  F  S  H  F  A  -

GTCGAAAATAGAGGATAGGTTTTACAGTTTTATTAGGTCTAGCGTAGGTTTACCAAAGCG
    4381 ---------+---------+---------+---------+---------+---------+ 4440
         CAGCTTTTATCTCCTATCCAAAATGTCAAAATAATCCAGATCGCATCCAAATGGTTTCGC
b          S  K  I  E  D  R  F  Y  S  F  I  R  S  S  V  G  L  P  K  R  -

CAACACCTTGAAGTGTAACCTCGTCACGTTTGAAAATAGGAATTCCAACGCCGATCGCGG
    4441 ---------+---------+---------+---------+---------+---------+ 4500
         GTTGTGGAACTTCACATTGGAGCAGTGCAAACTTTTATCCTTAAGGTTGCGGCTAGCGCC
b          N  T  L  K  C  N  L  V  T  F  E  N  R  N  S  N  A  D  R  G  -

TTGTAACGTGGGTTGTGACGACTCTGTGGCGCATGAACTGAAGGAGATTTTCTTCGAGGA
    4501 ---------+---------+---------+---------+---------+---------+ 4560
         AACATTGCACCCAACACTGCTGAGACACCGCGTACTTGACTTCCTCTAAAAGAAGCTCCT
b          C  N  V  G  C  D  D  S  V  A  H  E  L  K  E  I  F  F  E  E  -
```

FIG. 18H

```
             GGTCGTTAACAAAGCTCGTTTAGCAGAGGTGACGGAAAGCCATTTGTCCAGCAACACGAT
      4561   ------------+----------+----------+----------+----------+----------+ 4620
             CCAGCAATTGTTTCGAGCAAATCGTCTCCACTGCCTTTCGGTAAACAGGTCGTTGTGCTA
   b          V  V  N  K  A  R  L  A  E  V  T  E  S  H  L  S  S  N  T  M   -

GTTGTTATCAGATTGGTTGGACAAAAGGGCACCTAACGCTTACAAGTCTCTCAAGCGGGC
      4621   ------------+----------+----------+----------+----------+----------+ 4680
             CAACAATAGTCTAACCAACCTGTTTTCCCGTGGATTGCGAATGTTCAGAGAGTTCGCCCG
   b          L  L  S  D  W  L  D  K  R  A  P  N  A  Y  K  S  L  K  R  A   -

TTTAGGTTCGGTTGTCTTTCATCCGTCTATGTTGACGTCTTATACGCTCATGGTGAAAGC
      4681   ------------+----------+----------+----------+----------+----------+ 4740
             AAATCCAAGCCAACAGAAAGTAGGCAGATACAACTGCAGAATATGCGAGTACCACTTTCG
   b          L  G  S  V  V  F  H  P  S  M  L  T  S  Y  T  L  M  V  K  A   -

AGACGTAAAACCCAAGTTGGACAATACGCCATTGTCGAAGTACGTAACGGGGCAGAATAT
      4741   ------------+----------+----------+----------+----------+----------+ 4800
             TCTGCATTTTGGGTTCAACCTGTTATGCGGTAACAGCTTCATGCATTGCCCCGTCTTATA
   b          D  V  K  P  K  L  D  N  T  P  L  S  K  Y  V  T  G  Q  N  I   -

AGTCTACCACGATAGGTGCGTAACTGCGCTTTTTTCTTGCATTTTTACTGCGTGCGTAGA
      4801   ------------+----------+----------+----------+----------+----------+ 4860
             TCAGATGGTGCTATCCACGCATTGACGCGAAAAAAGAACGTAAAAATGACGCACGCATCT
   b          V  Y  H  D  R  C  V  T  A  L  F  S  C  I  F  T  A  C  V  E   -

GCGCTTAAAATACGTAGTGGACGAAAGGTGGCTCTTCTACCACGGGATGGACACTGCGGA
      4861   ------------+----------+----------+----------+----------+----------+ 4920
             CGCGAATTTTATGCATCACCTGCTTTCCACCGAGAAGATGGTGCCCTACCTGTGACGCCT
   b          R  L  K  Y  V  V  D  E  R  W  L  F  Y  H  G  M  D  T  A  E   -

GTTGGCGGCTGCATTGAGGAACAATTTGGGGGACATCCGGCAATACTACACCTATGAACT
      4921   ------------+----------+----------+----------+----------+----------+ 4980
             CAACCGCCGACGTAACTCCTTGTTAAACCCCCTGTAGGCCGTTATGATGTGGATACTTGA
   b          L  A  A  A  L  R  N  N  L  G  D  I  R  Q  Y  Y  T  Y  E  L   -

GGATATCAGTAAGTACGACAAATCTCAGAGTGCTCTCATGAAGCAGGTGGAGGAGTTGAT
      4981   ------------+----------+----------+----------+----------+----------+ 5040
             CCTATAGTCATTCATGCTGTTTAGAGTCTCACGAGAGTACTTCGTCCACCTCCTCAACTA
   b          D  I  S  K  Y  D  K  S  Q  S  A  L  M  K  Q  V  E  E  L  I   -

ACTCTTGACACTTGGTGTTGATAGAGAAGTTTTGTCTACTTTCTTTTGTGGTGAGTATGA
      5041   ------------+----------+----------+----------+----------+----------+ 5100
             TGAGAACTGTGAACCACAACTATCTCTTCAAAACAGATGAAAGAAAACACCACTCATACT
   b          L  L  T  L  G  V  D  R  E  V  L  S  T  F  F  C  G  E  Y  D   -

TAGCGTCGTGAGAACGATGACGAAGGAATTGGTGTTGTCTGTCGGCTCTCAGAGGCGCAG
      5101   ------------+----------+----------+----------+----------+----------+ 5160
             ATCGCAGCACTCTTGCTACTGCTTCCTTAACCACAACAGACAGCCGAGAGTCTCCGCGTC
   b          S  V  V  R  T  M  T  K  E  L  V  L  S  V  G  S  Q  R  R  S   -

TGGTGGTGCTAACACGTGGTTGGGAAATAGTTTAGTCTTGTGCACCTTGTTGTCCGTAGT
      5161   ------------+----------+----------+----------+----------+----------+ 5220
             ACCACCACGATTGTGCACCAACCCTTTATCAAATCAGAACACGTGGAACAACAGGCATCA
   b          G  G  A  N  T  W  L  G  N  S  L  V  L  C  T  L  L  S  V  V   -
```

FIG. 18I

```
        ACTTAGGGGATTAGATTATAGTTATATTGTAGTTAGCGGTGATGATAGCCTTATATTTAG
   5221 ---------+---------+---------+---------+---------+---------+ 5280
        TGAATCCCCTAATCTAATATCAATATAACATCAATCGCCACTACTATCGGAATATAAATC
b         L  R  G  L  D  Y  S  Y  I  V  V  S  G  D  D  S  L  I  F  S  -

TCGGCAGCCGTTGGATATTGATACGTCGGTTCTGAGCGATAATTTTGGTTTTGACGTAAA
   5281 ---------+---------+---------+---------+---------+---------+ 5340
        AGCCGTCGGCAACCTATAACTATGCAGCCAAGACTCGCTATTAAAACCAAAACTGCATTT
b         R  Q  P  L  D  I  D  T  S  V  L  S  D  N  F  G  F  D  V  K  -

GATTTTTAACCAAGCTGCTCCATATTTTTGTTCTAAGTTTTTAGTTCAAGTCGAGGATAG
   5341 ---------+---------+---------+---------+---------+---------+ 5400
        CTAAAAATTGGTTCGACGAGGTATAAAAACAAGATTCAAAAATCAAGTTCAGCTCCTATC
b          I  F  N  Q  A  A  P  Y  F  C  S  K  F  L  V  Q  V  E  D  S  -

TCTCTTTTTTGTTCCCGATCCACTTAAACTCTTCGTTAAGTTTGGAGCTTCCAAAACTTC
   5401 ---------+---------+---------+---------+---------+---------+ 5460
        AGAGAAAAAACAAGGGCTAGGTGAATTTGAGAAGCAATTCAAACCTCGAAGGTTTTGAAG
b          L  F  F  V  P  D  P  L  K  L  F  V  K  F  G  A  S  K  T  S  -

AGATATCGACCTTTTACATGAGATTTTTCAATCTTTCGTCGATCTTTCGAAGGGTTTCAA
   5461 ---------+---------+---------+---------+---------+---------+ 5520
        TCTATAGCTGGAAAATGTACTCTAAAAAGTTAGAAAGCAGCTAGAAAGCTTCCCAAAGTT
b          D  I  D  L  L  H  E  I  F  Q  S  F  V  D  L  S  K  G  F  N  -

TAGAGAGGACGTCATCCAGGAATTAGCTAAGCTGGTGACGCGGAAATATAAGCATTCGGG
   5521 ---------+---------+---------+---------+---------+---------+ 5580
        ATCTCTCCTGCAGTAGGTCCTTAATCGATTCGACCACTGCGCCTTTATATTCGTAAGCCC
b          R  E  D  V  I  Q  E  L  A  K  L  V  T  R  K  Y  K  H  S  G  -

ATGGACCTACTCGGCTTTGTGTGTCTTGCACGTTTTAAGTGCAAATTTTTCGCAGTTCTG
   5581 ---------+---------+---------+---------+---------+---------+ 5640
        TACCTGGATGAGCCGAAACACACAGAACGTGCAAAATTCACGTTTAAAAAGCGTCAAGAC
b          W  T  Y  S  A  L  C  V  L  H  V  L  S  A  N  F  S  Q  F  C  -

TAGGTTATATTACCACAATAGCGTGAATCTCGATGTGCGCCCTATTCAGAGGACCGAGTC
   5641 ---------+---------+---------+---------+---------+---------+ 5700
        ATCCAATATAATGGTGTTATCGCACTTAGAGCTACACGCGGGATAAGTCTCCTGGCTCAG
b          R  L  Y  Y  H  N  S  V  N  L  D  V  R  P  I  Q  R  T  E  S  -

GCTTTCCTTGCTGGCCTTGAAGGCAAGAATTTTAAGGTGGAAAGCTTCTCGTTTTGCCTT
   5701 ---------+---------+---------+---------+---------+---------+ 5760
        CGAAAGGAACGACCGGAACTTCCGTTCTTAAAATTCCACCTTTCGAAGAGCAAAACGGAA
b          L  S  L  L  A  L  K  A  R  I  L  R  W  K  A  S  R  F  A  F  -

TTCGATAAAGAGGGGTTAATCGCGTTGGCCACGCTATAGTGTTTCTGTGCCTCGGTTCTT
   5761 ---------+---------+---------+---------+---------+---------+ 5820
        AAGCTATTTCTCCCCAATTAGCGCAACCGGTGCGATATCACAAAGACACGGAGCCAAGAA
b          S  I  K  R  G  *                                          -

CGTGAGGTTAATACCGAAGGGTCGTCGTACTTATCTCAGTTATTTATTTTTTCGTCTTCT
   5821 ---------+---------+---------+---------+---------+---------+ 5880
        GCACTCCAATTATGGCTTCCCAGCAGCATGAATAGAGTCAATAAATAAAAAAGCAGAAGA

CTTAGGCGTGCCATCCGTGAAGTTAATACCGGTGGCACTCCTTCTCGAAGTGGGTATTAA
   5881 ---------+---------+---------+---------+---------+---------+ 5940
        GAATCCGCACGGTAGGCACTTCAATTATGGCCACCGTGAGGAAGAGCTTCACCCATAATT
```

FIG. 18J

```
     AGACCAAAATTTTTTATTTGTGTGTACTTTTTGTTTTGTTCACACCGTGAGGACAAGACC
5941 ---------+---------+---------+---------+---------+---------+ 6000
     TCTGGTTTTAAAAAATAAACACACATGAAAAACAAAACAAGTGTGGCACTCCTGTTCTGG

ORF2 (7K)
     GGTGGAACATGTACAGTAGAGGGTCTTTCTTTAAGTCTCGGGTTACCCTTCCTACTCTTG
6001 ---------+---------+---------+---------+---------+---------+ 6060
     CCACCTTGTACATGTCATCTCCCAGAAAGAAATTCAGAGCCCAATGGGAAGGATGAGAAC
c         M  Y  S  R  G  S  F  F  K  S  R  V  T  L  P  T  L  V -

TCGGAGCATACATGTGGGAGTTTGAACTCCCGTATCTTACGGACAAGAGACACATCAGCT
6061 ---------+---------+---------+---------+---------+---------+ 6120
     AGCCTCGTATGTACACCCTCAAACTTGAGGGCATAGAATGCCTGTTCTCTGTGTAGTCGA
c        G  A  Y  M  W  E  F  E  L  P  Y  L  T  D  K  R  H  I  S  Y -

ATAGCGCGCCAAGTGTCGCGACTTTTAGCCTTGTGTCGAGGTAGGATAGGGGCCAACAGG
6121 ---------+---------+---------+---------+---------+---------+ 6180
     TATCGCGCGGTTCACAGCGCTGAAAATCGGAACACAGCTCCATCCTATCCCCGGTTGTCC
c         S  A  P  S  V  A  T  F  S  L  V  S  R  *

TGACCAACAGCCTGCACTTAAGGTGCGCTGGAAGTGTTGGATTTGGTCTCAGTGTGCCAA
6181 ---------+---------+---------+---------+---------+---------+ 6240
     ACTGGTTGTCGGACGTGAATTCCACGCGACCTTCACAACCTAAACCAGAGTCACACGGTT

ATATCCTTTTAGGCGATGTACAGGAGTCTAGTTTAGTGTGTCTTTGGGGGATGACGGGAG
6241 ---------+---------+---------+---------+---------+---------+ 6300
     TATAGGAAAATCCGCTACATGTCCTCAGATCAAATCACACAGAAACCCCCTACTGCCCTC

CGACTAGGTTTAGGACTGTAGCTGCTATGTAAGTCGTGCATGCGGCATTGTGCGTAAGAC
6301 ---------+---------+---------+---------+---------+---------+ 6360
     GCTGATCCAAATCCTGACATCGACGATACATTCAGCACGTACGCCGTAACACGCATTCTG

GTGCATGCATTTGGGCGAGTGCCCTAGGGCAGCGTCGGTCAGGTGACTAGCAGCCGGCTC
6361 ---------+---------+---------+---------+---------+---------+ 6420
     CACGTACGTAAACCCGCTCACGGGATCCCGTCGCAGCCAGTCCACTGATCGTCGGCCGAG

TACGGAGCGCTGAAAGTGCTAGGTCCTGAAGGTACAGTTGGGCTGAGGCAGGACATGGTT
6421 ---------+---------+---------+---------+---------+---------+ 6480
     ATGCCTCGCGACTTTCACGATCCAGGACTTCCATGTCAACCCGACTCCGTCCTGTACCAA

GAACGAGTTGACCGTGGGGACCAGCGGCGGTGACTCGGGCCGTAGCCACGCGCGGGGCGG
6481 ---------+---------+---------+---------+---------+---------+ 6540
     CTTGCTCAACTGGCACCCCTGGTCGCCGCCACTGAGCCCGGCATCGGTGCGCGCCCCGCC

CAGGGCGTCTCGTGGTGTATCTGGGCAAGATACGGCTTTATTAGGCACCATAATATGGAG
6541 ---------+---------+---------+---------+---------+---------+ 6600
     GTCCCGCAGAGCACCACATAGACCCGTTCTATGCCGAAATAATCCGTGGTATTATACCTC

CCCAAAGCGTCGGGGTCGGGAAACATCTCCATAGCTTAGTGGCAGCAGCCTAAGATAGGC
6601 ---------+---------+---------+---------+---------+---------+ 6660
     GGGTTTCGCAGCCCCAGCCCTTTGTAGAGGTATCGAATCACCGTCGTCGGATTCTATCCG

TGGGAGGCCCGTTCCCTGTAGTAGTGGTGGGTTAGCATGCCACTAAGCGGTGCGGCGTGA
6661 ---------+---------+---------+---------+---------+---------+ 6720
     ACCCTCCGGGCAAGGGACATCATCACCACCCAATCGTACGGTGATTCGCCACGCCGCACT
```

FIG. 18K

```
           TAAGGCGCCACCGTCCGTAGTTAGGCGACCCGTGTTTTAATAGGGTCTCTTTAGTTAAGT
    6721   ---------+---------+---------+---------+---------+---------+  6780
           ATTCCGCGGTGGCAGGCATCAATCCGCTGGGCACAAAATTATCCCAGAGAAATCAATTCA

TTAGGCATGTCGTACAGTTAGGATTTCTTTTTAGATATTCTTTTATTTTTTATTGTTTGT
    6781   ---------+---------+---------+---------+---------+---------+  6840
           AATCCGTACAGCATGTCAATCCTAAAGAAAAATCTATAAGAAAATAAAAAATAACAAACA

TAGTTTAGATGTACATTATTACGTAGGTTACTTTGGCGCTACGCCAGAGGTTTTTCCTCT
    6841   ---------+---------+---------+---------+---------+---------+  6900
           ATCAAATCTACATGTAATAATGCATCCAATGAAACCGCGATGCGGTCTCCAAAAAGGAGA

TTGTGTGTAGCCTTTAATGTAGGTTTCTTTGTTTTATTTTTGCCTTTCAGGCGGCGCGTT
    6901   ---------+---------+---------+---------+---------+---------+  6960
           AACACACATCGGAAATTACATCCAAAGAAACAAAATAAAAACGGAAAGTCCGCCGCGCAA

TCTTTTCTTCTATTTAGGTTTATCTTCTTTCCTTAGTGTTGTCGTATATGACGCTACGTC
    6961   ---------+---------+---------+---------+---------+---------+  7020
           AGAAAAGAAGATAAATCCAAATAGAAGAAAGGAATCACAACAGCATATACTGCGATGCAG

CAAATTATGAATTTTCCTTCGTGTAGGCGTCGTTGAGTGCGTTCATCGGCGCTAGACGAG
    7021   ---------+---------+---------+---------+---------+---------+  7080
           GTTTAATACTTAAAAGGAAGCACATCCGCAGCAACTCACGCAAGTAGCCGCGATCTGCTC

GTTTAGTGGCGACATAAATAGGTTTTTGCGCGAGATTGGGATAGAACGAGTTCGCCTTAA
    7081   ---------+---------+---------+---------+---------+---------+  7140
           CAAATCACCGCTGTATTTATCCAAAAACGCGCTCTAACCCTATCTTGCTCAAGCGGAATT

AAGAGAAATCGGGGAAGGCGCCACGCGAATGACCTTCGTGCTGAGCGAAGGTAGTATCGT
    7141   ---------+---------+---------+---------+---------+---------+  7200
           TTCTCTTTAGCCCCTTCCGCGGTGCGCTTACTGGAAGCACGACTCGCTTCCATCATAGCA

ORF3 (5K, Membrane protein)
           GATTTTATATTGAAGTAGGCGTATTTGTTTATGGATGATTTTAAACAGGCAATACTGTTG
    7201   ---------+---------+---------+---------+---------+---------+  7260
           CTAAAATATAACTTCATCCGCATAAACAAATACCTACTAAAATTTGTCCGTTATGACAAC
  a                                         M  D  D  F  K  Q  A  I  L  L  -

CTAGTAGTCGATTTTGTCTTCGTGATAATTCTGCTGCTGGTTCTTACGTTCGTCGTCCCG
    7261   ---------+---------+---------+---------+---------+---------+  7320
           GATCATCAGCTAAAACAGAAGCACTATTAAGACGACGACCAAGAATGCAAGCAGCAGGGC
  a        L  V  V  D  F  V  F  V  I  I  L  L  V  L  T  F  V  V  P  -

AGGTTACAGCAAAGCTCCACCATTAATACAGGTCTTAGGACAGTGTGATTCCTCCTTTAG
    7321   ---------+---------+---------+---------+---------+---------+  7380
           TCCAATGTCGTTTCGAGGTGGTAATTATGTCCAGAATCCTGTCACACTAAGGAGGAAATC
  a        R  L  Q  Q  S  S  T  I  N  T  G  L  R  T  V  *  -

ORF4 (HSP70 Homolog)
           TTAGATATGGAAGTAGGTATAGATTTTGGAACCACTTTCAGCACAATCTGCTTTTCCCCA
    7381   ---------+---------+---------+---------+---------+---------+  7440
           AATCTATACCTTCATCCATATCTAAAACCTTGGTGAAAGTCGTGTTAGACGAAAAGGGGT
  a            M  E  V  G  I  D  F  G  T  T  F  S  T  I  C  F  S  P  -
```

FIG. 18L

```
      TCTGGGGTCAGCGGTTGTACTCCTGTGGCCGGTAGTGTTTACGTTGAAACCCAAATTTTT
 7441 ----------+---------+---------+---------+---------+---------+ 7500
      AGACCCCAGTCGCCAACATGAGGACACCGGCCATCACAAATGCAACTTTGGGTTTAAAAA
a      S  G  V  S  G  C  T  P  V  A  G  S  V  Y  V  E  T  Q  I  F  -

ATACCTGAAGGTAGCAGTACTTACTTAATTGGTAAAGCTGCGGGGAAAGCTTATCGTGAC
 7501 ----------+---------+---------+---------+---------+---------+ 7560
      TATGGACTTCCATCGTCATGAATGAATTAACCATTTCGACGCCCCTTTCGAATAGCACTG
a      I  P  E  G  S  S  T  Y  L  I  G  K  A  A  G  K  A  Y  R  D  -

GGTGTAGAGGGAAGGTTGTATGTTAACCCGAAAAGGTGGGCAGGTGTGACGAGGGATAAC
 7561 ----------+---------+---------+---------+---------+---------+ 7620
      CCACATCTCCCTTCCAACATACAATTGGGCTTTTCCACCCGTCCACACTGCTCCCTATTG
a      G  V  E  G  R  L  Y  V  N  P  K  R  W  A  G  V  T  R  D  N  -

GTCGAACGCTACGTCGAGAAATTAAAACCTACATACACCGTGAAGATAGACAGCGGAGGC
 7621 ----------+---------+---------+---------+---------+---------+ 7680
      CAGCTTGCGATGCAGCTCTTTAATTTTGGATGTATGTGGCACTTCTATCTGTCGCCTCCG
a      V  E  R  Y  V  E  K  L  K  P  T  Y  T  V  K  I  D  S  G  G  -

GCCTTATTAATTGGAGGTTTAGGTTCCGGACCAGACACCTTATTGAGGGTCGTTGACGTA
 7681 ----------+---------+---------+---------+---------+---------+ 7740
      CGGAATAATTAACCTCCAAATCCAAGGCCTGGTCTGTGGAATAACTCCCAGCAACTGCAT
a      A  L  L  I  G  G  L  G  S  G  P  D  T  L  L  R  V  V  D  V  -

ATATGTTTATTCTTGAGAGCCTTGATACTGGAGTGCGAAAGGTATACGTCTACGACGGTT
 7741 ----------+---------+---------+---------+---------+---------+ 7800
      TATACAAATAAGAACTCTCGGAACTATGACCTCACGCTTTCCATATGCAGATGCTGCCAA
a      I  C  L  F  L  R  A  L  I  L  E  C  E  R  Y  T  S  T  T  V  -

ACAGCAGCTGTTGTAACGGTACCGGCTGACTATAACTCCTTTAAACGAAGCTTCGTTGTT
 7801 ----------+---------+---------+---------+---------+---------+ 7860
      TGTCGTCGACAACATTGCCATGGCCGACTGATATTGAGGAAATTTGCTTCGAAGCAACAA
a      T  A  A  V  V  T  V  P  A  D  Y  N  S  F  K  R  S  F  V  V  -

GAGGCGCTAAAAGGTCTTGGTATACCGGTTAGAGGTGTTGTTAACGAACCGACGGCCGCA
 7861 ----------+---------+---------+---------+---------+---------+ 7920
      CTCCGCGATTTTCCAGAACCATATGGCCAATCTCCACAACAATTGCTTGGCTGCCGGCGT
a      E  A  L  K  G  L  G  I  P  V  R  G  V  V  N  E  P  T  A  A  -

GCCCTCTATTCCTTAGCTAAGTCGCGAGTAGAAGACCTATTATTAGCGGTTTTTGATTTT
 7921 ----------+---------+---------+---------+---------+---------+ 7980
      CGGGAGATAAGGAATCGATTCAGCGCTCATCTTCTGGATAATAATCGCCAAAAACTAAAA
a      A  L  Y  S  L  A  K  S  R  V  E  D  L  L  L  A  V  F  D  F  -

GGGGGAGGGACTTTCGACGTCTCATTCGTTAAGAAGAAGGGAAATATACTATGCGTCATC
 7981 ----------+---------+---------+---------+---------+---------+ 8040
      CCCCCTCCCTGAAAGCTGCAGAGTAAGCAATTCTTCTTCCCTTTATATGATACGCAGTAG
a      G  G  G  T  F  D  V  S  F  V  K  K  K  G  N  I  L  C  V  I  -

TTTTCAGTGGGTGATAATTTCTTGGGTGGTAGAGATATTGATAGAGCTATCGTGGAAGTT
 8041 ----------+---------+---------+---------+---------+---------+ 8100
      AAAAGTCACCCACTATTAAAGAACCCACCATCTCTATAACTATCTCGATAGCACCTTCAA
a      F  S  V  G  D  N  F  L  G  G  R  D  I  D  R  A  I  V  E  V  -
```

FIG. 18M

```
          ATCAAACAAAAGATCAAAGGAAAGGCGTCTGATGCCAAGTTAGGGATATTCGTATCCTCG
     8101 ---------+---------+---------+---------+---------+---------+ 8160
          TAGTTTGTTTTCTAGTTTCCTTTCCGCAGACTACGGTTCAATCCCTATAAGCATAGGAGC
   a       I  K  Q  K  I  K  G  K  A  S  D  A  K  L  G  I  F  V  S  S   -

ATGAAGGAAGACTTGTCTAACAATAACGCTATAACGCAACACCTTATCCCCGTAGAAGGG
     8161 ---------+---------+---------+---------+---------+---------+ 8220
          TACTTCCTTCTGAACAGATTGTTATTGCGATATTGCGTTGTGGAATAGGGGCATCTTCCC
   a       M  K  E  D  L  S  N  N  N  A  I  T  Q  H  L  I  P  V  E  G   -

GGTGTGGAGGTTGTGGATTTGACTAGCGACGAACTGGACGCAATCGTTGCACCATTCAGC
     8221 ---------+---------+---------+---------+---------+---------+ 8280
          CCACACCTCCAACACCTAAACTGATCGCTGCTTGACCTGCGTTAGCAACGTGGTAAGTCG
   a       G  V  E  V  V  D  L  T  S  D  E  L  D  A  I  V  A  P  F  S   -

GCTAGGGCTGTGGAAGTATTCAAAACTGGTCTTGACAACTTTTACCCAGACCCGGTTATT
     8281 ---------+---------+---------+---------+---------+---------+ 8340
          CGATCCCGACACCTTCATAAGTTTTGACCAGAACTGTTGAAAATGGGTCTGGGCCAATAA
   a       A  R  A  V  E  V  F  K  T  G  L  D  N  F  Y  P  D  P  V  I   -

GCCGTTATGACTGGGGGGTCAAGTGCTCTAGTTAAGGTCAGGAGTGATGTGGCTAATTTG
     8341 ---------+---------+---------+---------+---------+---------+ 8400
          CGGCAATACTGACCCCCCAGTTCACGAGATCAATTCCAGTCCTCACTACACCGATTAAAC
   a       A  V  M  T  G  G  S  S  A  L  V  K  V  R  S  D  V  A  N  L   -

CCGCAGATATCTAAAGTCGTGTTCGACAGTACCGATTTTAGATGTTCGGTGGCTTGTGGG
     8401 ---------+---------+---------+---------+---------+---------+ 8460
          GGCGTCTATAGATTTCAGCACAAGCTGTCATGGCTAAAATCTACAAGCCACCGAACACCC
   a       P  Q  I  S  K  V  V  F  D  S  T  D  F  R  C  S  V  A  C  G   -

GCTAAGGTTTACTGCGATACTTTGGCAGGTAATAGCGGACTGAGACTGGTGGACACTTTA
     8461 ---------+---------+---------+---------+---------+---------+ 8520
          CGATTCCAAATGACGCTATGAAACCGTCCATTATCGCCTGACTCTGACCACCTGTGAAAT
   a       A  K  V  Y  C  D  T  L  A  G  N  S  G  L  R  L  V  D  T  L   -

ACGAATACGCTAACGGACGAGGTAGTGGGTCTTCAGCCGGTGGTAATTTTCCCGAAAGGT
     8521 ---------+---------+---------+---------+---------+---------+ 8580
          TGCTTATGCGATTGCCTGCTCCATCACCCAGAAGTCGGCCACCATTAAAAGGGCTTTCCA
   a       T  N  T  L  T  D  E  V  V  G  L  Q  P  V  V  I  F  P  K  G   -

AGTCCAATACCCTGTTCATATACTCATAGATACACAGTGGGTGGTGGAGATGTGGTATAC
     8581 ---------+---------+---------+---------+---------+---------+ 8640
          TCAGGTTATGGGACAAGTATATGAGTATCTATGTGTCACCCACCACCTCTACACCATATG
   a       S  P  I  P  C  S  Y  T  H  R  Y  T  V  G  G  G  D  V  V  Y   -

GGTATATTTGAAGGGGAGAATAACAGAGCTTTTCTAAATGAGCCGACGTTCCGGGGCGTA
     8641 ---------+---------+---------+---------+---------+---------+ 8700
          CCATATAAACTTCCCCTCTTATTGTCTCGAAAAGATTTACTCGGCTGCAAGGCCCCGCAT
   a       G  I  F  E  G  E  N  N  R  A  F  L  N  E  P  T  F  R  G  V   -

TCGAAACGTAGGGGAGACCCAGTAGAGACCGACGTGGCGCAGTTTAATCTCTCCACGGAC
     8701 ---------+---------+---------+---------+---------+---------+ 8760
          AGCTTTGCATCCCCTCTGGGTCATCTCTGGCTGCACCGCGTCAAATTAGAGAGGTGCCTG
   a       S  K  R  R  G  D  P  V  E  T  D  V  A  Q  F  N  L  S  T  D   -
```

FIG. 18N

```
             GGAACGGTGTCTGTTATCGTTAATGGTGAGGAAGTAAAGAATGAATATCTGGTACCCGGG
      8761  ----------+---------+---------+---------+---------+---------+  8820
             CCTTGCCACAGACAATAGCAATTACCACTCCTTCATTTCTTACTTATAGACCATGGGCCC
a             G  T  V  S  V  I  V  N  G  E  E  V  K  N  E  Y  L  V  P  G   -

ACAACAAACGTACTGGATTCATTGGTCTATAAATCTGGGAGAGAAGATTTAGAGGCTAAG
      8821  ----------+---------+---------+---------+---------+---------+  8880
             TGTTGTTTGCATGACCTAAGTAACCAGATATTTAGACCCTCTCTTCTAAATCTCCGATTC
a             T  T  N  V  L  D  S  L  V  Y  K  S  G  R  E  D  L  E  A  K   -

GCAATACCAGAGTACTTGACCACACTGAATATTTTGCACGATAAGGCTTTCACGAGGAGA
      8881  ----------+---------+---------+---------+---------+---------+  8940
             CGTTATGGTCTCATGAACTGGTGTGACTTATAAAACGTGCTATTCCGAAAGTGCTCCTCT
a             A  I  P  E  Y  L  T  T  L  N  I  L  H  D  K  A  F  T  R  R   -

AACCTGGGTAACAAAGATAAGGGGTTCTCGGATTTAAGGATAGAAGAAAATTTTTTAAAA
      8941  ----------+---------+---------+---------+---------+---------+  9000
             TTGGACCCATTGTTTCTATTCCCCAAGAGCCTAAATTCCTATCTTCTTTTAAAAAATTTT
a             N  L  G  N  K  D  K  G  F  S  D  L  R  I  E  E  N  F  L  K   -

ORF5 (HSP90 Homolog)
             TCCGCCGTAGATACAGACACGATTTTGAATGGATAAATATATTTATGTAACGGGGATATT
      9001  ----------+---------+---------+---------+---------+---------+  9060
             AGGCGGCATCTATGTCTGTGCTAAAACTTACCTATTTATATAAATACATTGCCCCTATAA
a             S  A  V  D  T  D  T  I  L  N  G  *
b                                    M  D  K  Y  I  Y  V  T  G  I  L   -

AAACCCTAACGAGGCTAGAGACGAGGTATTCTCGGTAGTGAATAAGGGATATATTGGACC
      9061  ----------+---------+---------+---------+---------+---------+  9120
             TTTGGGATTGCTCCGATCTCTGCTCCATAAGAGCCATCACTTATTCCCTATATAACCTGG
b             N  P  N  E  A  R  D  E  V  F  S  V  V  N  K  G  Y  I  G  P   -

GGGAGGGCGCTCCTTTTCGAATCGTGGTAGTAAGTACACCGTCGTCTGGGAAAACTCTGC
      9121  ----------+---------+---------+---------+---------+---------+  9180
             CCCTCCCGCGAGGAAAAGCTTAGCACCATCATTCATGTGGCAGCAGACCCTTTTGAGACG
b             G  G  R  S  F  S  N  R  G  S  K  Y  T  V  V  W  E  N  S  A   -

TGCGAGGATTAGTGGATTTACGTCGACTTCGCAATCTACGATAGATGCTTTCGCGTATTT
      9181  ----------+---------+---------+---------+---------+---------+  9240
             ACGCTCCTAATCACCTAAATGCAGCTGAAGCGTTAGATGCTATCTACGAAAGCGCATAAA
b             A  R  I  S  G  F  T  S  T  S  Q  S  T  I  D  A  F  A  Y  F   -

CTTGTTGAAAGGCGGATTGACTACCACGCTCTCTAACCCAATAAACTGTGAGAATTGGGT
      9241  ----------+---------+---------+---------+---------+---------+  9300
             GAACAACTTTCCGCCTAACTGATGGTGCGAGAGATTGGGTTATTTGACACTCTTAACCCA
b             L  L  K  G  G  L  T  T  T  L  S  N  P  I  N  C  E  N  W  V   -

CAGGTCATCTAAGGATTTAAGCGCGTTTTTCAGGACCCTAATTAAAGGTAAGATTTATGC
      9301  ----------+---------+---------+---------+---------+---------+  9360
             GTCCAGTAGATTCCTAAATTCGCGCAAAAAGTCCTGGGATTAATTTCCATTCTAAATACG
b             R  S  S  K  D  L  S  A  F  F  R  T  L  I  K  G  K  I  Y  A   -

ATCGCGTTCTGTGGACAGCAATCTTCCAAAGAAAGACAGGGATGACATCATGGAAGCGAG
      9361  ----------+---------+---------+---------+---------+---------+  9420
             TAGCGCAAGACACCTGTCGTTAGAAGGTTTCTTTCTGTCCCTACTGTAGTACCTTCGCTC
b             S  R  S  V  D  S  N  L  P  K  K  D  R  D  D  I  M  E  A  S   -
```

FIG. 18O

```
            TCGACGACTATCGCCATCGGACGCCGCCTTTTGCAGAGCAGTGTCGGTTCAGGTAGGGAA
     9421   ---------+---------+---------+---------+---------+---------+  9480
            AGCTGCTGATAGCGGTAGCCTGCGGCGGAAAACGTCTCGTCACAGCCAAGTCCATCCCTT
b            R  R  L  S  P  S  D  A  A  F  C  R  A  V  S  V  Q  V  G  K  -

GTATGTGGACGTAACGCAGAATTTAGAAAGTACGATCGTGCCGTTAAGAGTTATGGAAAT
     9481   ---------+---------+---------+---------+---------+---------+  9540
            CATACACCTGCATTGCGTCTTAAATCTTTCATGCTAGCACGGCAATTCTCAATACCTTTA
b            Y  V  D  V  T  Q  N  L  E  S  T  I  V  P  L  R  V  M  E  I  -

AAAGAAAAGACGAGGATCAGCACATGTTAGTTTACCGAAGGTGGTATCCGCTTACGTAGA
     9541   ---------+---------+---------+---------+---------+---------+  9600
            TTTCTTTTCTGCTCCTAGTCGTGTACAATCAAATGGCTTCCACCATAGGCGAATGCATCT
b            K  K  R  G  S  A  H  V  S  L  P  K  V  V  S  A  Y  V  D  -

TTTTTATACGAACTTGCAGGAATTGCTGTCGGATGAAGTAACTAGGGCCAGAACCGATAC
     9601   ---------+---------+---------+---------+---------+---------+  9660
            AAAAATATGCTTGAACGTCCTTAACGACAGCCTACTTCATTGATCCCGGTCTTGGCTATG
b            F  Y  T  N  L  Q  E  L  L  S  D  E  V  T  R  A  R  T  D  T  -

AGTTTCGGCATACGCTACCGACTCTATGGCTTTCTTAGTTAAGATGTTACCCCTGACTGC
     9661   ---------+---------+---------+---------+---------+---------+  9720
            TCAAAGCCGTATGCGATGGCTGAGATACCGAAAGAATCAATTCTACAATGGGGACTGACG
b            V  S  A  Y  A  T  D  S  M  A  F  L  V  K  M  L  P  L  T  A  -

TCGTGAGCAGTGGTTAAAAGACGTGCTAGGATATCTGCTGGTACGGAGACGACCAGCAAA
     9721   ---------+---------+---------+---------+---------+---------+  9780
            AGCACTCGTCACCAATTTTCTGCACGATCCTATAGACGACCATGCCTCTGCTGGTCGTTT
b            R  E  Q  W  L  K  D  V  L  G  Y  L  L  V  R  R  R  P  A  N  -

TTTTTCCTACGACGTAAGAGTAGCTTGGGTATATGACGTGATCGCTACGCTCAAGCTGGT
     9781   ---------+---------+---------+---------+---------+---------+  9840
            AAAAAGGATGCTGCATTCTCATCGAACCCATATACTGCACTAGCGATGCGAGTTCGACCA
b            F  S  Y  D  V  R  V  A  W  V  Y  D  V  I  A  T  L  K  L  V  -

CATAAGATTGTTTTTCAACAAGGACACACCCGGGGGTATTAAAGACTTAAAACCGTGTGT
     9841   ---------+---------+---------+---------+---------+---------+  9900
            GTATTCTAACAAAAAGTTGTTCCTGTGTGGGCCCCCATAATTTCTGAATTTTGGCACACA
b            I  R  L  F  F  N  K  D  T  P  G  G  I  K  D  L  K  P  C  V  -

GCCTATAGAGTCATTCGACCCCTTTCACGAGCTTTCGTCCTATTTCTCTAGGTTAAGTTA
     9901   ---------+---------+---------+---------+---------+---------+  9960
            CGGATATCTCAGTAAGCTGGGGAAAGTGCTCGAAAGCAGGATAAAGAGATCCAATTCAAT
b            P  I  E  S  F  D  P  F  H  E  L  S  S  Y  F  S  R  L  S  Y  -

CGAGATGACGACAGGTAAAGGGGGAAAGATATGCCCGGAGATCGCCGAGAAGTTGGTGCG
     9961   ---------+---------+---------+---------+---------+---------+ 10020
            GCTCTACTGCTGTCCATTTCCCCCTTTCTATACGGGCCTCTAGCGGCTCTTCAACCACGC
b            E  M  T  T  G  K  G  G  K  I  C  P  E  I  A  E  K  L  V  R  -

CCGTCTAATGGAGGAAAACTATAAGTTAAGATTGACCCCAGTGATGGCCTTAATAATTAT
    10021   ---------+---------+---------+---------+---------+---------+ 10080
            GGCAGATTACCTCCTTTTGATATTCAATTCTAACTGGGGTCACTACCGGAATTATTAATA
b            R  L  M  E  E  N  Y  K  L  R  L  T  P  V  M  A  L  I  I  I  -
```

FIG. 18P

```
            ACTGGTATACTACTCCATTTACGGCACAAACGCTACCAGGATTAAAAGACGCCCGGATTT
     10081  ---------+---------+---------+---------+---------+---------+ 10140
            TGACCATATGATGAGGTAAATGCCGTGTTTGCGATGGTCCTAATTTTCTGCGGGCCTAAA
  b          L  V  Y  Y  S  I  Y  G  T  N  A  T  R  I  K  R  R  P  D  F  -

CCTCAATGTGAGGATAAAGGGAAGAGTCGAGAAGGTTTCGTTACGGGGGGTAGAAGATCG
     10141  ---------+---------+---------+---------+---------+---------+ 10200
            GGAGTTACACTCCTATTTCCCTTCTCAGCTCTTCCAAAGCAATGCCCCCCATCTTCTAGC
  b          L  N  V  R  I  K  G  R  V  E  K  V  S  L  R  G  V  E  D  R  -

TGCCTTTAGAATATCAGAAAAGCGCGGGATAAACGCTCAACGTGTATTATGTAGGTACTA
     10201  ---------+---------+---------+---------+---------+---------+ 10260
            ACGGAAATCTTATAGTCTTTTCGCGCCCTATTTGCGAGTTGCACATAATACATCCATGAT
  b          A  F  R  I  S  E  K  R  G  I  N  A  Q  R  V  L  C  R  Y  Y  -

TAGCGATCTCACATGTCTGGCTAGGCGACATTACGGCATTCGCAGGAACAATTGGAAGAC
     10261  ---------+---------+---------+---------+---------+---------+ 10320
            ATCGCTAGAGTGTACAGACCGATCCGCTGTAATGCCGTAAGCGTCCTTGTTAACCTTCTG
  b          S  D  L  T  C  L  A  R  R  H  Y  G  I  R  R  N  N  W  K  T  -

GCTGAGTTATGTAGACGGGACGTTAGCGTATGACACGGCTGATTGTATAACTTCTAAGGT
     10321  ---------+---------+---------+---------+---------+---------+ 10380
            CGACTCAATACATCTGCCCTGCAATCGCATACTGTGCCGACTAACATATTGAAGATTCCA
  b          L  S  Y  V  D  G  T  L  A  Y  D  T  A  D  C  I  T  S  K  V  -

GAGAAATACGATCAACACCGCAGATCACGCTAGCATTATACACTATATCAAGACGAACGA
     10381  ---------+---------+---------+---------+---------+---------+ 10440
            CTCTTTATGCTAGTTGTGGCGTCTAGTGCGATCGTAATATGTGATATAGTTCTGCTTGCT
  b          R  N  T  I  N  T  A  D  H  A  S  I  I  H  Y  I  K  T  N  E  -

AAACCAGGTTACCGGAACTACTCTACCACACCAGCTTTAAAGCTGCGTGTAGTATGCGAC
     10441  ---------+---------+---------+---------+---------+---------+ 10500
            TTTGGTCCAATGGCCTTGATGAGATGGTGTGGTCGAAATTTCGACGCACATCATACGCTG
  b          N  Q  V  T  G  T  T  L  P  H  Q  L  *                       -

GATGTTTCTCGTATTAGTTTTATAAAAATTTTTAATTGCTCTGTGTGTGGTTTTTGTTGA
     10501  ---------+---------+---------+---------+---------+---------+ 10560
            CTACAAAGAGCATAATCAAAATATTTTTAAAAATTAACGAGACACACACCAAAAACAACT

ORF6 (Coat protein)
            GTGAACGCGATGGCATTTGAACTGAAATTAGGGCAGATATATGAAGTCGTCCCCGAAAAT
     10561  ---------+---------+---------+---------+---------+---------+ 10620
            CACTTGCGCTACCGTAAACTTGACTTTAATCCCGTCTATATACTTCAGCAGGGGCTTTTA
  a                M  A  F  E  L  K  L  G  Q  I  Y  E  V  V  P  E  N  -

AATTTGAGAGTTAGAGTGGGGGATGCGGCACAAGGAAAATTTAGTAAGGCGAGTTTCTTA
     10621  ---------+---------+---------+---------+---------+---------+ 10680
            TTAAACTCTCAATCTCACCCCCTACGCCGTGTTCCTTTTAAATCATTCCGCTCAAAGAAT
  a          N  L  R  V  R  V  G  D  A  A  Q  G  K  F  S  K  A  S  F  L  -

AAGTACGTTAAGGACGGGACACAGGCGGAATTAACGGGAATCGCCGTAGTGCCCGAAAAA
     10681  ---------+---------+---------+---------+---------+---------+ 10740
            TTCATGCAATTCCTGCCCTGTGTCCGCCTTAATTGCCCTTAGCGGCATCACGGGCTTTTT
  a          K  Y  V  K  D  G  T  Q  A  E  L  T  G  I  A  V  V  P  E  K  -
```

FIG. 18Q

```
         TACGTATTCGCCACAGCAGCTTTGGCTACAGCGGCGCAGGAGCCACCTAGGCAGCCACCA
  10741  ------------------------------------------------------------+ 10800
         ATGCATAAGCGGTGTCGTCGAAACCGATGTCGCCGCGTCCTCGGTGGATCCGTCGGTGGT
a         Y  V  F  A  T  A  A  L  A  T  A  A  Q  E  P  P  R  Q  P  P   -

GCGCAAGTGGCGGAACCACAGGAAACCGATATAGGGGTAGTGCCGGAATCTGAGACTCTC
  10801  ------------------------------------------------------------+ 10860
         CGCGTTCACCGCCTTGGTGTCCTTTGGCTATATCCCCATCACGGCCTTAGACTCTGAGAG
a         A  Q  V  A  E  P  Q  E  T  D  I  G  V  V  P  E  S  E  T  L   -

ACACCAAATAAGTTGGTTTTCGAGAAAGATCCAGACAAGTTCTTGAAGACTATGGGCAAG
  10861  ------------------------------------------------------------+ 10920
         TGTGGTTTATTCAACCAAAAGCTCTTTCTAGGTCTGTTCAAGAACTTCTGATACCCGTTC
a         T  P  N  K  L  V  F  E  K  D  P  D  K  F  L  K  T  M  G  K   -

GGAATAGCTTTGGACTTGGCGGGAGTTACCCACAAACCGAAAGTTATTAACGAGCCAGGG
  10921  ------------------------------------------------------------+ 10980
         CCTTATCGAAACCTGAACCGCCCTCAATGGGTGTTTGGCTTTCAATAATTGCTCGGTCCC
a         G  I  A  L  D  L  A  G  V  T  H  K  P  K  V  I  N  E  P  G   -

AAAGTATCAGTAGAGGTGGCAATGAAGATTAATGCCGCATTGATGGAGCTGTGTAAGAAG
  10981  ------------------------------------------------------------+ 11040
         TTTCATAGTCATCTCCACCGTTACTTCTAATTACGGCGTAACTACCTCGACACATTCTTC
a         K  V  S  V  E  V  A  M  K  I  N  A  A  L  M  E  L  C  K  K   -

GTTATGGGCGCCGATGACGCAGCAACTAAGACAGAATTCTTCTTGTACGTGATGCAGATT
  11041  ------------------------------------------------------------+ 11100
         CAATACCCGCGGCTACTGCGTCGTTGATTCTGTCTTAAGAAGAACATGCACTACGTCTAA
a         V  M  G  A  D  D  A  A  T  K  T  E  F  F  L  Y  V  M  Q  I   -

GCTTGCACGTTCTTTACATCGTCTTCGACGGAGTTCAAAGAGTTTGACTACATAGAAACC
  11101  ------------------------------------------------------------+ 11160
         CGAACGTGCAAGAAATGTAGCAGAAGCTGCCTCAAGTTTCTCAAACTGATGTATCTTTGG
a         A  C  T  F  F  T  S  S  S  T  E  F  K  E  F  D  Y  I  E  T   -

GATGATGGAAAGAAGATATATGCGGTGTGGGTATATGATTGCATTAAACAAGCTGCTGCT
  11161  ------------------------------------------------------------+ 11220
         CTACTACCTTTCTTCTATATACGCCACACCCATATACTAACGTAATTTGTTCGACGACGA
a         D  D  G  K  K  I  Y  A  V  W  V  Y  D  C  I  K  Q  A  A  A   -

TCGACGGGTTATGAAAACCCGGTAAGGCAGTATCTAGCGTACTTCACACCAACCTTCATC
  11221  ------------------------------------------------------------+ 11280
         AGCTGCCCAATACTTTTGGGCCATTCCGTCATAGATCGCATGAAGTGTGGTTGGAAGTAG
a         S  T  G  Y  E  N  P  V  R  Q  Y  L  A  Y  F  T  P  T  F  I   -

ACGGCGACCCTGAATGGTAAACTAGTGATGAACGAGAAGGTTATGGCACAGCATGGAGTA
  11281  ------------------------------------------------------------+ 11340
         TGCCGCTGGGACTTACCATTTGATCACTACTTGCTCTTCCAATACCGTGTCGTACCTCAT
a         T  A  T  L  N  G  K  L  V  M  N  E  K  V  M  A  Q  H  G  V   -

CCACCGAAATTCTTTCCGTACACGATAGACTGCGTTCGTCCGACGTACGATCTGTTCAAC
  11341  ------------------------------------------------------------+ 11400
         GGTGGCTTTAAGAAAGGCATGTGCTATCTGACGCAAGCAGGCTGCATGCTAGACAAGTTG
a         P  P  K  F  F  P  Y  T  I  D  C  V  R  P  T  Y  D  L  F  N   -
```

FIG. 18R

```
             AACGACGCAATATTAGCATGGAATTTAGCTAGACAGCAGGCGTTTAGAAACAAGACGGTA
     11401   ---------+---------+---------+---------+---------+---------+ 11460
             TTGCTGCGTTATAATCGTACCTTAAATCGATCTGTCGTCCGCAAATCTTTGTTCTGCCAT
  a          N  D  A  I  L  A  W  N  L  A  R  Q  Q  A  F  R  N  K  T  V  -

ACGGCCGATAACACCTTACACAACGTCTTCCAACTATTGCAAAAGAAGTAGCTACGATCG
     11461   ---------+---------+---------+---------+---------+---------+ 11520
             TGCCGGCTATTGTGGAATGTGTTGCAGAAGGTTGATAACGTTTTCTTCATCGATGCTAGC
  a          T  A  D  N  T  L  H  N  V  F  Q  L  L  Q  K  K  *          -

ORF7 (CPr)
             ATGTCTATAAATTGGTGAAAAATTTAGAAATATTTACCTTTTATTGATAATTCATGGGAG
     11521   ---------+---------+---------+---------+---------+---------+ 11580
             TACAGATATTTAACCACTTTTTAAATCTTTATAAATGGAAAATAACTATTAAGTACCCTC
  a          M  S  I  N  W  *                                            -
  c                                                            M  G  A  -

CTTATACACATGTAGACTTTCATGAGTCGCGGTTGCTGAAAGACAAACAAGACTATCTTT
     11581   ---------+---------+---------+---------+---------+---------+ 11640
             GAATATGTGTACATCTGAAAGTACTCAGCGCCAACGACTTTCTGTTTGTTCTGATAGAAA
  c           Y  T  H  V  D  F  H  E  S  R  L  L  K  D  K  Q  D  Y  L  S -

CTTTCAAGTCAGCGGATGAAGCTCCTCCTGATCCTCCCGGATACGTTCGCCCAGATAGTT
     11641   ---------+---------+---------+---------+---------+---------+ 11700
             GAAAGTTCAGTCGCCTACTTCGAGGAGGACTAGGAGGGCCTATGCAAGCGGGTCTATCAA
  c           F  K  S  A  D  E  A  P  P  D  P  P  G  Y  V  R  P  D  S  Y -

ATGTGAGGGCTTATTTGATACAAAGAGCAGACTTTCCCAATACTCAAAGCTTATCAGTTA
     11701   ---------+---------+---------+---------+---------+---------+ 11760
             TACACTCCCGAATAAACTATGTTTCTCGTCTGAAAGGGTTATGAGTTTCGAATAGTCAAT
  c           V  R  A  Y  L  I  Q  R  A  D  F  P  N  T  Q  S  L  S  V  T -

CGTTATCGATAGCCAGTAATAAGTTAGCTTCAGGTCTTATGGGAAGCGACGCAGTATCAT
     11761   ---------+---------+---------+---------+---------+---------+ 11820
             GCAATAGCTATCGGTCATTATTCAATCGAAGTCCAGAATACCCTTCGCTGCGTCATAGTA
  c           L  S  I  A  S  N  K  L  A  S  G  L  M  G  S  D  A  V  S  S -

CGTCGTTTATGCTGATGAACGACGTGGGAGATTACTTCGAGTGCGGCGTGTGTCACAACA
     11821   ---------+---------+---------+---------+---------+---------+ 11880
             GCAGCAAATACGACTACTTGCTGCACCCTCTAATGAAGCTCACGCCGCACACAGTGTTGT
  c           S  F  M  L  M  N  D  V  G  D  Y  F  E  C  G  V  C  H  N  K -

AACCCTACTTAGGACGGGAAGTTATCTTCTGTAGGAAATACATAGGTGGGAGAGGAGTGG
     11881   ---------+---------+---------+---------+---------+---------+ 11940
             TTGGGATGAATCCTGCCCTTCAATAGAAGACATCCTTTATGTATCCACCCTCTCCTCACC
  c           P  Y  L  G  R  E  V  I  F  C  R  K  Y  I  G  G  R  G  V  E -

AGATCACCACTGGTAAGAACTACACGTCGAACAATTGGAACGAGGCGTCGTACGTAATAC
     11941   ---------+---------+---------+---------+---------+---------+ 12000
             TCTAGTGGTGACCATTCTTGATGTGCAGCTTGTTAACCTTGCTCCGCAGCATGCATTATG
  c            I  T  T  G  K  N  Y  T  S  N  N  W  N  E  A  S  Y  V  I  Q -

AAGTGAACGTAGTCGATGGGTTAGCACAGACCACTGTTAATTCTACTTATACGCAAACGG
     12001   ---------+---------+---------+---------+---------+---------+ 12060
             TTCACTTGCATCAGCTACCCAATCGTGTCTGGTGACAATTAAGATGAATATGCGTTTGCC
  c            V  N  V  V  D  G  L  A  Q  T  T  V  N  S  T  Y  T  Q  T  D -
```

FIG. 18S

```
           ACGTTAGTGGTCTACCCAAAAATTGGACGCGTATCTACAAAATAACAAAGATAGTGTCCG
   12061  ----------+----------+----------+----------+----------+----------+ 12120
           TGCAATCACCAGATGGGTTTTTAACCTGCGCATAGATGTTTTATTGTTTCTATCACAGGC
  c         V  S  G  L  P  K  N  W  T  R  I  Y  K  I  T  K  I  V  S  V -

TAGATCAGAACCTCTACCCTGGTTGTTTCTCAGACTCGAAACTGGGTGTAATGCGTATAA
   12121  ----------+----------+----------+----------+----------+----------+ 12180
           ATCTAGTCTTGGAGATGGGACCAACAAAGAGTCTGAGCTTTGACCCACATTACGCATATT
  c         D  Q  N  L  Y  P  G  C  F  S  D  S  K  L  G  V  M  R  I  R -

GGTCACTGTTAGTTTCCCCAGTGCGCATCTTCTTTAGGGATATCTTATTGAAACCTTTGA
   12181  ----------+----------+----------+----------+----------+----------+ 12240
           CCAGTGACAATCAAAGGGGTCACGCGTAGAAGAAATCCCTATAGAATAACTTTGGAAACT
  c         S  L  L  V  S  P  V  R  I  F  F  R  D  I  L  L  K  P  L  K -

AGAAATCGTTCAACGCAAGAATCGAGGATGTGCTGAATATTGACGACACGTCGTTGTTAG
   12241  ----------+----------+----------+----------+----------+----------+ 12300
           TCTTTAGCAAGTTGCGTTCTTAGCTCCTACACGACTTATAACTGCTGTGCAGCAACAATC
  c         K  S  F  N  A  R  I  E  D  V  L  N  I  D  D  T  S  L  L  V -

TACCGAGTCCTGTCGTACCAGAGTCTACGGGAGGTGTAGGTCCATCAGAGCAGCTGGATG
   12301  ----------+----------+----------+----------+----------+----------+ 12360
           ATGGCTCAGGACAGCATGGTCTCAGATGCCCTCCACATCCAGGTAGTCTCGTCGACCTAC
  c         P  S  P  V  V  P  E  S  T  G  G  V  G  P  S  E  Q  L  D  V -

TAGTGGCTTTAACGTCCGACGTAACGGAATTGATCAACACTAGGGGGCAAGGTAAGATAT
   12361  ----------+----------+----------+----------+----------+----------+ 12420
           ATCACCGAAATTGCAGGCTGCATTGCCTTAACTAGTTGTGATCCCCCGTTCCATTCTATA
  c         V  A  L  T  S  D  V  T  E  L  I  N  T  R  G  Q  G  K  I  C -

GTTTTCCAGACTCAGTGTTATCGATCAATGAAGCGGATATCTACGATGAGCGGTATTTGC
   12421  ----------+----------+----------+----------+----------+----------+ 12480
           CAAAAGGTCTGAGTCACAATAGCTAGTTACTTCGCCTATAGATGCTACTCGCCATAAACG
  c         F  P  D  S  V  L  S  I  N  E  A  D  I  Y  D  E  R  Y  L  P -

CGATAACGGAAGCTCTACAGATAAACGCAAGACTACGCAGACTCGTTCTTTCGAAAGGCG
   12481  ----------+----------+----------+----------+----------+----------+ 12540
           GCTATTGCCTTCGAGATGTCTATTTGCGTTCTGATGCGTCTGAGCAAGAAAGCTTTCCGC
  c         I  T  E  A  L  Q  I  N  A  R  L  R  R  L  V  L  S  K  G  G -

GGAGTCAAACACCACGAGATATGGGGAATATGATAGTGGCCATGATACAACTTTTCGTAC
   12541  ----------+----------+----------+----------+----------+----------+ 12600
           CCTCAGTTTGTGGTGCTCTATACCCCTTATACTATCACCGGTACTATGTTGAAAAGCATG
  c         S  Q  T  P  R  D  M  G  N  M  I  V  A  M  I  Q  L  F  V  L -

TCTACTCTACTGTAAAGAATATAAGCGTCAAAGACGGGTATAGGGTGGAGACCGAATTAG
   12601  ----------+----------+----------+----------+----------+----------+ 12660
           AGATGAGATGACATTTCTTATATTCGCAGTTTCTGCCCATATCCCACCTCTGGCTTAATC
  c         Y  S  T  V  K  N  I  S  V  K  D  G  Y  R  V  E  T  E  L  G -

GTCAAAAGAGAGTCTACTTAAGTTATTCGGAAGTAAGGGAAGCTATATTAGGAGGGAAAT
   12661  ----------+----------+----------+----------+----------+----------+ 12720
           CAGTTTTCTCTCAGATGAATTCAATAAGCCTTCATTCCCTTCGATATAATCCTCCCTTTA
  c         Q  K  R  V  Y  L  S  Y  S  E  V  R  E  A  I  L  G  G  K  Y -
```

FIG. 18T

```
            ACGGTGCGTCTCCAACCAACACTGTGCGATCCTTCATGAGGTATTTTGCTCACACCACTA
   12721    ------------------------------------------------------------ 12780
            TGCCACGCAGAGGTTGGTTGTGACACGCTAGGAAGTACTCCATAAAACGAGTGTGGTGAT
 c           G  A  S  P  T  N  T  V  R  S  F  M  R  Y  F  A  H  T  T  I  -

TTACTCTACTTATAGAGAAGAAAATTCAGCCAGCGTGTACTGCCCTAGCTAAGCACGGCG
   12781    ------------------------------------------------------------ 12840
            AATGAGATGAATATCTCTTCTTTTAAGTCGGTCGCACATGACGGGATCGATTCGTGCCGC
 c           T  L  L  I  E  K  K  I  Q  P  A  C  T  A  L  A  K  H  G  V  -

TCCCGAAGAGGTTCACTCCGTACTGCTTCGACTTCGCACTACTGGATAACAGATATTACC
   12841    ------------------------------------------------------------ 12900
            AGGGCTTCTCCAAGTGAGGCATGACGAAGCTGAAGCGTGATGACCTATTGTCTATAATGG
 c           P  K  R  F  T  P  Y  C  F  D  F  A  L  L  D  N  R  Y  Y  P  -

CGGCGGACGTGTTGAAGGCTAACGCAATGGCTTGCGCTATAGCGATTAAATCAGCTAATT
   12901    ------------------------------------------------------------ 12960
            GCCGCCTGCACAACTTCCGATTGCGTTACCGAACGCGATATCGCTAATTTAGTCGATTAA
 c           A  D  V  L  K  A  N  A  M  A  C  A  I  A  I  K  S  A  N  L  -

ORF8
            TAAGGCGTAAAGGTTCGGAGACGTATAACATCTTAGAAAGCATTTGATTATCTAAAGATG
   12961    ------------------------------------------------------------ 13020
            ATTCCGCATTTCCAAGCCTCTGCATATTGTAGAATCTTTCGTAAACTAATAGATTTCTAC
 a                                                                   M  -
 c           R  R  K  G  S  E  T  Y  N  I  L  E  S  I  *                -

GAATTCAGACCAGTTTTAATTACAGTTCGCCGTGATCCCGGCGTAAACACTGGTAGTTTG
   13021    ------------------------------------------------------------ 13080
            CTTAAGTCTGGTCAAAATTAATGTCAAGCGGCACTAGGGCCGCATTTGTGACCATCAAAC
 a           E  F  R  P  V  L  I  T  V  R  R  D  P  G  V  N  T  G  S  L  -

AAAGTGATAGCTTATGACTTACACTACGACAATATATTCGATAACTGCGCGGTAAAGTCG
   13081    ------------------------------------------------------------ 13140
            TTTCACTATCGAATACTGAATGTGATGCTGTTATATAAGCTATTGACGCGCCATTTCAGC
 a           K  V  I  A  Y  D  L  H  Y  D  N  I  F  D  N  C  A  V  K  S  -

TTTCGAGACACCGACACTGGATTCACTGTTATGAAAGAATACTCGACGAATTCAGCGTTC
   13141    ------------------------------------------------------------ 13200
            AAAGCTCTGTGGCTGTGACCTAAGTGACAATACTTTCTTATGAGCTGCTTAAGTCGCAAG
 a           F  R  D  T  D  T  G  F  T  V  M  K  E  Y  S  T  N  S  A  F  -

ATACTAAGTCCTTATAAACTGTTTTCCGCGGTCTTTAATAAGGAAGGTGAGATGATAAGT
   13201    ------------------------------------------------------------ 13260
            TATGATTCAGGAATATTTGACAAAAGGCGCCAGAAATTATTCCTTCCACTCTACTATTCA
 a           I  L  S  P  Y  K  L  F  S  A  V  F  N  K  E  G  E  M  I  S  -

AACGATGTAGGATCGAGTTTCAGGGTTTACAATATCTTTTCGCAAATGTGTAAAGATATC
   13261    ------------------------------------------------------------ 13320
            TTGCTACATCCTAGCTCAAAGTCCCAAATGTTATAGAAAAGCGTTTACACATTTCTATAG
 a           N  D  V  G  S  S  F  R  V  Y  N  I  F  S  Q  M  C  K  D  I  -

AACGAGATCAGCGAGATACAACGCGCCGGTTACCTAGAAACATATTTAGGAGACGGGCAG
   13321    ------------------------------------------------------------ 13380
            TTGCTCTAGTCGCTCTATGTTGCGCGGCCAATGGATCTTTGTATAAATCCTCTGCCCGTC
 a           N  E  I  S  E  I  Q  R  A  G  Y  L  E  T  Y  L  G  D  G  Q  -
```

FIG. 18U

```
         GCTGACACTGATATATTTTTTGATGTCTTAACCAACAACAAAGCAAAGGTAAGGTGGTTA
   13381 ---------+---------+---------+---------+---------+---------+ 13440
         CGACTGTGACTATATAAAAAACTACAGAATTGGTTGTTGTTTCGTTTCCATTCCACCAAT
a         A D T D I F F D V L T N N K A K V R W L  -

GTTAATAAAGACCATAGCGCGTGGTGTGGGATATTGAATGATTTGAAGTGGGAAGAGAGC
   13441 ---------+---------+---------+---------+---------+---------+ 13500
         CAATTATTTCTGGTATCGCGCACCACACCCTATAACTTACTAAACTTCACCCTTCTCTCG
a         V N K D H S A W C G I L N D L K W E E S  -

AACAAGGAGAAATTTAAGGGGAGAGACATACTAGATACTTACGTTTTATCGTCTGATTAT
   13501 ---------+---------+---------+---------+---------+---------+ 13560
         TTGTTCCTCTTTAAATTCCCCTCTCTGTATGATCTATGAATGCAAAATAGCAGACTAATA
a         N K E K F K G R D I L D T Y V L S S D Y  -

ORF9
         CCAGGGTTTAAATGAAGTTGCTTTCGCTCCGCTATCTTATCTTAAGGTTGTCAAAGTCGC
   13561 ---------+---------+---------+---------+---------+---------+ 13620
         GGTCCCAAATTTACTTCAACGAAAGCGAGGCGATAGAATAGAATTCCAACAGTTTCAGCG
a         P G F K *
c                   M K L L S L R Y L I L R L S K S L -

TTAGAACGAACGATCACTTGGTTTTAATACTTATAAAGGAGGCGCTTATAAACTATTACA
   13621 ---------+---------+---------+---------+---------+---------+ 13680
         AATCTTGCTTGCTAGTGAACCAAAATTATGAATATTTCCTCCGCGAATATTTGATAATGT
c         R T N D H L V L I L I K E A L I N Y Y N  -

ACGCCTCTTTCACCGATGAGGGTGCCGTATTAAGAGACTCTCGCGAAAGTATAGAGAATT
   13681 ---------+---------+---------+---------+---------+---------+ 13740
         TGCGGAGAAAGTGGCTACTCCCACGGCATAATTCTCTGAGAGCGCTTTCATATCTCTTAA
c         A S F T D E G A V L R D S R E S I E N F  -

TTCTCGTAGCCAGGTGCGGTTCGCAAAATTCCTGCCGAGTCATGAAGGCTTTGATCACTA
   13741 ---------+---------+---------+---------+---------+---------+ 13800
         AAGAGCATCGGTCCACGCCAAGCGTTTTAAGGACGGCTCAGTACTTCCGAAACTAGTGAT
c         L V A R C G S Q N S C R V M K A L I T N  -

ACACAGTCTGTAAGATGTCGATAGAAACAGCCAGAAGTTTTATCGGAGACTTAATACTCG
   13801 ---------+---------+---------+---------+---------+---------+ 13860
         TGTGTCAGACATTCTACAGCTATCTTTGTCGGTCTTCAAAATAGCCTCTGAATTATGAGC
c         T V C K M S I E T A R S F I G D L I L V  -

TCGCCGACTCCTCTGTTTCAGCGTTGGAAGAAGCGAAATCAATTAAAGATAATTTCCGCT
   13861 ---------+---------+---------+---------+---------+---------+ 13920
         AGCGGCTGAGGAGACAAAGTCGCAACCTTCTTCGCTTTAGTTAATTTCTATTAAAGGCGA
c         A D S S V S A L E E A K S I K D N F R L  -

TAAGAAAAAGGAGAGGCAAGTATTATTATAGTGGTGATTGTGGATCCGACGTTGCGAAAG
   13921 ---------+---------+---------+---------+---------+---------+ 13980
         ATTCTTTTTCCTCTCCGTTCATAATAATATCACCACTAACACCTAGGCTGCAACGCTTTC
c         R K R R G K Y Y Y S G D C G S D V A K V  -

TTAAGTATATTTTGTCTGGGGAGAATCGAGGATTGGGGTGCGTAGATTCCTTGAAGCTAG
   13981 ---------+---------+---------+---------+---------+---------+ 14040
         AATTCATATAAAACAGACCCCTCTTAGCTCCTAACCCCACGCATCTAAGGAACTTCGATC
c         K Y I L S G E N R G L G C V D S L K L V  -
```

FIG. 18V

```
       TTTGCGTAGGTAGACAAGGAGGTGGAAACGTACTACAGCACCTACTAATCTCATCTCTGG
14041  ---------+---------+---------+---------+---------+---------+ 14100
       AAACGCATCCATCTGTTCCTCCACCTTTGCATGATGTCGTGGATGATTAGAGTAGAGACC
  c      C  V  G  R  Q  G  G  G  N  V  L  Q  H  L  L  I  S  S  L  G -

ORF10
       GTTAAAGCATCATGGACCTATCGTTTATTATTGTGCAGATCCTTTCCGCCTCGTACAATA
14101  ---------+---------+---------+---------+---------+---------+ 14160
       CAATTTCGTAGTACCTGGATAGCAAATAATAACACGTCTAGGAAAGGCGGAGCATGTTAT
  c        *   M  D  L  S  F  I  I  V  Q  I  L  S  A  S  Y  N  N -

ATGACGTGACAGCACTTTACACTTTGATTAACGCGTATAATAGCGTTGATGATACGACGC
14161  ---------+---------+---------+---------+---------+---------+ 14220
       TACTGCACTGTCGTGAAATGTGAAACTAATTGCGCATATTATCGCAACTACTATGCTGCG
  c        D  V  T  A  L  Y  T  L  I  N  A  Y  N  S  V  D  D  T  T  R -

GCTGGGCAGCGATAAACGATCCGCAAGCTGAGGTTAACGTCGTGAAGGCTTACGTAGCTA
14221  ---------+---------+---------+---------+---------+---------+ 14280
       CGACCCGTCGCTATTTGCTAGGCGTTCGACTCCAATTGCAGCACTTCCGAATGCATCGAT
  c        W  A  A  I  N  D  P  Q  A  E  V  N  V  V  K  A  Y  V  A  T -

CTACAGCGACGACTGAGCTGCATAGAACAATTCTCATTGACAGTATAGACTCCGCCTTCG
14281  ---------+---------+---------+---------+---------+---------+ 14340
       GATGTCGCTGCTGACTCGACGTATCTTGTTAAGAGTAACTGTCATATCTGAGGCGGAAGC
  c        T  A  T  T  E  L  H  R  T  I  L  I  D  S  I  D  S  A  F  A -

CTTATGACCAAGTGGGGTGTTTGGTGGGCATAGCTAGAGGTTTGCTTAGACATTCGGAAG
14341  ---------+---------+---------+---------+---------+---------+ 14400
       GAATACTGGTTCACCCCACAAACCACCCGTATCGATCTCCAAACGAATCTGTAAGCCTTC
  c        Y  D  Q  V  G  C  L  V  G  I  A  R  G  L  L  R  H  S  E  D -

ATGTTCTGGAGGTCATCAAGTCGATGGAGTTATTCGAAGTGTGTCGTGGAAAGAGGGGAA
14401  ---------+---------+---------+---------+---------+---------+ 14460
       TACAAGACCTCCAGTAGTTCAGCTACCTCAATAAGCTTCACACAGCACCTTTCTCCCCTT
  c         V  L  E  V  I  K  S  M  E  L  F  E  V  C  R  G  K  R  G  S -

GCAAAAGATATCTTGGATACTTAAGTGATCAATGCACTAACAAATACATGATGCTAACTC
14461  ---------+---------+---------+---------+---------+---------+ 14520
       CGTTTTCTATAGAACCTATGAATTCACTAGTTACGTGATTGTTTATGTACTACGATTGAG
  c         K  R  Y  L  G  Y  L  S  D  Q  C  T  N  K  Y  M  M  L  T  Q -

AGGCCGGACTGGCCGCAGTTGAAGGAGCAGACATACTACGAACGAATCATCTAGTCAGTG
14521  ---------+---------+---------+---------+---------+---------+ 14580
       TCCGGCCTGACCGGCGTCAACTTCCTCGTCTGTATGATGCTTGCTTAGTAGATCAGTCAC
  c         A  G  L  A  A  V  E  G  A  D  I  L  R  T  N  H  L  V  S  G -

GTAATAAGTTCTCTCCAAATTTCGGGATCGCTAGGATGTTGCTCTTGACGCTTTGTTGCG
14581  ---------+---------+---------+---------+---------+---------+ 14640
       CATTATTCAAGAGAGGTTTAAAGCCCTAGCGATCCTACAACGAGAACTGCGAAACAACGC
  c         N  K  F  S  P  N  F  G  I  A  R  M  L  L  L  T  L  C  C  G -

GAGCACTATAAAAATGTTATGTTGTTCAGCCAGTGTCAAATTTTCAAACGGGTTACAATT
14641  ---------+---------+---------+---------+---------+---------+ 14700
       CTCGTGATATTTTTACAATACAACAAGTCGGTCACAGTTTAAAAGTTTGCCCAATGTTAA
  c         A  L  *                                                    -
```

FIG. 18W

```
          ATCGCTACTTATTTGCGCATGTTTGTTAGCGGTGCTAATTGTTAGCTTTTGTAGAAGGCG
   14701  ---------+---------+---------+---------+---------+---------+ 14760
          TAGCGATGAATAAACGCGTACAAACAATCGCCACGATTAACAATCGAAAACATCTTCCGC

ORF11
          ATGAGGCACTTAGAAAAACCCATCAGAGTAGCGGTACACTATTGCGTCGTGCGAAGTGAC
   14761  ---------+---------+---------+---------+---------+---------+ 14820
          TACTCCGTGAATCTTTTTGGGTAGTCTCATCGCCATGTGATAACGCAGCACGCTTCACTG
a          M  R  H  L  E  K  P  I  R  V  A  V  H  Y  C  V  V  R  S  D  -

GTTTGTGACGGGTGGGATGTATTTATAGGCGTAACGTTAATCGGTATGTTTATTAGTTAC
   14821  ---------+---------+---------+---------+---------+---------+ 14880
          CAAACACTGCCCACCCTACATAAATATCCGCATTGCAATTAGCCATACAAATAATCAATG
a          V  C  D  G  W  D  V  F  I  G  V  T  L  I  G  M  F  I  S  Y  -

TATTTATATGCTCTAATTAGCATATGTAGAAAAGGAGAAGGTTTAACAACCAGTAATGGG
   14881  ---------+---------+---------+---------+---------+---------+ 14940
          ATAAATATACGAGATTAATCGTATACATCTTTTCCTCTTCCAAATTGTTGGTCATTACCC
a          Y  L  Y  A  L  I  S  I  C  R  K  G  E  G  L  T  T  S  N  G  -

TAAAAATCCTTCAATAAATTTGAAATAAACAAAAGTAAGAAAAATGAAATAATTAGGCTA
   14941  ---------+---------+---------+---------+---------+---------+ 15000
          ATTTTTAGGAAGTTATTTAAACTTTATTTGTTTTCATTCTTTTTACTTTATTAATCCGAT
a          *                                                            -

GTCTTTTTGTTCGTCTTTCGCTTTTGTAGAATAGGTTTTATTTCGAGGTAAGATGACTAA
   15001  ---------+---------+---------+---------+---------+---------+ 15060
          CAGAAAAACAAGCAGAAAGCGAAAACATCTTATCCAAAATAAAGCTCCATTCTACTGATT

ACTCTACCTCACGGTTTAATACTCTGATATTTGTAAAATTAGTCCGTAAAGTCAGATAGT
   15061  ---------+---------+---------+---------+---------+---------+ 15120
          TGAGATGGAGTGCCAAATTATGAGACTATAAACATTTTAATCAGGCATTTCAGTCTATCA

GATATTATATTAGTATAGTATAATAAACGCCAAAATCCAATCAAAGTTTGGGACCTAGGC
   15121  ---------+---------+---------+---------+---------+---------+ 15180
          CTATAATATAATCATATCATATTATTTGCGGTTTTAGGTTAGTTTCAAACCCTGGATCCG

GGGCCTCTTATGAGGCTAACTTATCGACAATAAGTTAGGTCCGCCAC
   15181  ---------+---------+---------+---------+------- 15227
          CCCGGAGAATACTCCGATTGAATAGCTGTTATTCAATCCAGGCGGTG
```

FIG. 20

```
                     _____I(A)_____                             _____Ia____
BYV_HEL    FTFTNLSANV LLYEAPPGGG KTTTLIKVFC ETFSK.VNSL ILTANKSSRE
CTV_HEL    LTFTNEEHSL IVYEAPPGGG KTHSLVNSYA DYCVK.VSCL VVTANKNSQT
GLRaV3_HEL VGESFKSFEY KCYNAPPGGG KTT....MLV DEFVKSPNST ATITANVGSS
LIYV_HEL   MVRRPDVNGL KFYNKPPGAG KTTTIAKLMS KDLKNKVKCL ALSYTKVGRL

CONSENSUS  ---------- --Y-aPPGaG KTt------- d-f-k-v--l -----k----

___                                            ___II_
BYV_HEL    EILAKVNRIV LD...EGDTP LQTRDRILTI DSYLMNNR.G LTCKVLYLDE
CTV_HEL    EISQRISNEL MGRKLAAKYV TDAASRVFTV DSYLMNHL.R LTTQLLFIDE
GLRaV3_HEL EDINM....A VKKR...DPN LEGLNSATTV NSRVVNFIVR GMYKRVLVDE
LIYV_HEL   ELIDKLKKDG IEKP...EKY VKTYDSFLMN NDNILEIV.. ....NLYCDE

CONSENSUS  E--------- -------d-- -------ltv -s--mn---- -----ly-DE

_                       ___III___
BYV_HEL    CFMVHAGAAV ACIEFTKCDS AILFGDSRQI RYGRCSELDT AVLSDLNRFV
CTV_HEL    CFMVHAGAIG AVVEFTSCKA VVFFGDSKQI HYIHRNDLGV SFVADIDAFI
GLRaV3_HEL VYMMHQG.LL QLGVFQPASE GLFFGDINQI PFINREKVFR MDCA..VXLP
LIYV_HEL   VFMMHAGHFL TLLTKIAYQN GYCYGDVNQI PFINRDPYTP AYLS..REFF

CONSENSUS  -fM-HaG--- ----f--c-- --ffGD--QI --i-r----- --------f-

____IV____
BYV_HEL    DDESRVYGEV SYRCPWDVCA WLSTF..... ...YPKTVAT TNLVSAGQSS
CTV_HEL    QPEHRIYGEV SYRCPWDICE WLSEF..... ...YPRHVAT ANVGSIGKSS
GLRaV3_HEL KKESVVYTSK SYRCPLDVCY LLSSMTVRGT EKCYPEKVVS GKDK.PVVRS
LIYV_HEL   RKQDLNYDTY TYRCPLDTCY LLSNLKDEMG NIIYAGGVKN VNEVYPTIRS

CONSENSUS  --e--vY--- sYRCP-DvC- -LS-f----- ---Yp--V-- -n-------S

BYV_HEL    MQVREIESVD DVEYSSEFVY LTMLQSEKKD LLKSFGK..R SRSSVEKPTV
CTV_HEL    VSIEEEINGCD DVPYDKAAKY IVYTQAEKND LQKHLGRLTV GRNKV.VPIV
GLRaV3_HEL LSKRPIGTTD DVAEINADVY LCMTQLEKSD MKRSLKGKGK .ETP.....V
LIYV_HEL   LNLFGINVVG EVPVEYNAKY LTFTQDEKLN LQRHIDSQGG CRNA.....V

CONSENSUS  l----I---d dV-------Y l--tQ-EK-d l---l----- -r-------V

_____V_____                       _____VI_____
BYV_HEL    LTVHEAQGET YRKVNLVRTK FQEDDPFRSE NHITVALSRH VESLTYSVLS
CTV_HEL    NTVHEVQGET YKRVRLVRFK YQEDTPFSSK NHIVVALTRH VDSLVYSVLT
GLRaV3_HEL MTVHEAQGKT FSDVVLFRTK KADDSLFTKQ PHILVGLSRH TRSLVYAALS
LIYV_HEL   STVNEAQGCT FSEVNLVRLV QFDNPVMSDI NQFVVAISRH TTTFKYFTPH

CONSENSUS  -TVhEaQG-T ---V-LvR-k ---d--f--- nhi-ValsRH --sl-Y--l-

BYV_HEL    SKRDDAIAQA I
CTV_HEL    SRRYDDTATN I
GLRaV3_HEL SELDDKVGTY I
LIYV_HEL   SRLNDRVSNA I

CONSENSUS  S---D-v--- I
```

FIG. 22

```
                 ___I___                          _____II_____
    BYV_RdRp     ITTFKLMVKR  DAKVKLDSSC  LVKHPPAQNI  MFHRKAVNAI  FSPCFDEFKN
    CTV_RdRp     ISNFKLMVKR  DAKVKLDDSS  LSKHPAAQNI  MFHKKFINAI  FSPCFDEFKN
 GLRaV3_RdRp     LTSYTLMVKA  DVKPKLDNTP  LSKYVTGQNI  VYHDRCVTAL  FSCIFTACVE
   LIYV_RdRp     FKTLNLMVKG  ETKPKMDLST  YDSYNAPANI  VYYQQIVNLY  FSPIFLECFA

CONSENSUS     ---f-LMVK-  d-K-KlD-s-  l-k----qNI  --h---vna-  FSp-F-e---

___       _____III____                      _____IV_____
    BYV_RdRp     RVITCTNSNI  VFFTEMTNST  LASIAKEMLG  .SEHVYNVGE  IDFSKFDKSQ
    CTV_RdRp     RVLSSLNDNI  VFFTEMTNAG  LAEIIRRIIG  .DDDNLFVGE  VDFSKFDKSQ
 GLRaV3_RdRp     RLKYVVDERW  LFYHGMDTAE  LAXALRNNLG  .DIRQYYTYE  LDISKYDKSQ
   LIYV_RdRp     RLTYCLSDKI  VLYSGMNTDV  LAELIESKLP  LGLNAYHTLE  IDFSKFDKSQ

CONSENSUS     R------d-i  vf---M----  LA------lg  -----y---E  iDfSKfDKSQ

BYV_RdRp     DAFIKSFERT  LYSAFGFDED  LLD.VWMQGE  YTSNATTLDG  QLSFSVDNQR
    CTV_RdRp     DLFIKEYERT  LYSEFGFDTE  LLD.VWMEGE  YRARATTLDG  QLSFSVDGQR
 GLRaV3_RdRp     SALMKQVEEL  ILLTLGVDRE  VLS.TFFCGE  YDSVVRTMTK  ELVLSVGSQR
   LIYV_RdRp     GTCFKLYEEM  MYKMFGFSPE  LYDRDFKYTE  YFCRAKA.TC  GVDLELGTQR

CONSENSUS     --f-K-yE--  ly--fGfd-e  lld-----gE  Y---a-tl--  -l--sv--QR

V                             VI
    BYV_RdRp     KSGASNTWIG  NSIETLGILS  MFYYTNRFKA  LFVSGDDSLI  FSESPIRNSA
    CTV_RdRp     RSGGSNTWIG  NSLVTLGILS  LYYDVSKFDL  LLVSGDDSLI  YSSEKISNFS
 GLRaV3_RdRp     RSGGANTWLG  NSLVLCTLLS  VVLRGLDYSY  IVVSGDDSLI  FSRQPLDIDT
   LIYV_RdRp     RTGSPNTWLS  NTLVTLGMML  SSYDIDDIDL  LLVSGDDSLI  FSRKHLPNKT

CONSENSUS     rsG--NTW-G  Nslvtlg-ls  --y----f--  llVSGDDSLI  fS-----n--

___VII___                ____VIII____
    BYV_RdRp     DAMCTELGFE  TKFLTPSVPY  FCSKFFVMTG  HDVFFVPDPY  KLLVKLGAS.
    CTV_RdRp     SEICLETGFE  TKFMSPSVPY  FCSKFVVQTG  NKTCFVPDPY  KLLVKLGAP.
 GLRaV3_RdRp     SVLSDNFGFD  VKIFNQAAPY  FCSKFLVQVE  DSLFFVPDPL  KLFVKFGAS.
   LIYV_RdRp     QEINKNFGME  AKYIEKSSPY  FCSKFIVELN  GKLKVIPDPI  RFFEKLSIPI

CONSENSUS     ------fGfe  -Kf---s-PY  FCSKF-V---  ----fvPDP-  kl-vKlga--

BYV_RdRp     ..KDEVDDEF  LFEVFTSFRD  LTKDLVDERV  IELLTHLVHS  KYGYESGDTY
    CTV_RdRp     ..QNKLTDVE  LFELFTSFKD  MTQDFGDQVV  LEKLKLLVEA  KYGFASGTTM
 GLRaV3_RdRp     ..KTSDID.L  LHEIFQSFVD  LSKGFNREDV  IQELAKLVTR  KYK.HSGWTY
   LIYV_RdRp     RQEDFVNGSV  VKERFISFKD  LMKEYDNDVA  VIRIDEAVCY  RYSIPVGCSY

CONSENSUS     -------d--  l-E-F-SF-D  l-kdf--e-v  i--l--lV--  kY---sG-ty

BYV_RdRp     AALCAIHCIR  SNFSSFKKLY
    CTV_RdRp     PALCAIHCVR  SNFLSFERLF
 GLRaV3_RdRp     SALCVLHVLS  ANFSQFCRLY
   LIYV_RdRp     AALCYIHCCM  SNFVSFRRIY

CONSENSUS     -ALC-iHc--  sNF-sF-rly
```

GLRaV-3_HEL S P Q S V S D A L L

GLRaV-3_RdRp T R S P R L V A F E V Y

GLRaV-3 (nt) TCg Cct CAA TCa GTa tcc GAc gcT tTg cTtc Aca cgT tcg ccc ccg ctg gtT GCt TTc GAg GTa TAT LIYV (nt) TCa Cta CAA TCt GTt agt GAt ttT gTt tTga Aag acT atc att tta gac agT GCc TTt GAc GTg TAT

LIYV_HEL S L Q S V S D F V L

LIYV_RdRp K T I I L D S A F D V Y

*FIG. 24*

```
                            transmembrane
           1                                                        54
BYV_p7K    MDCVLRSYLL LAFGFLICLF LFCLVVFIWF VYKQILFRTT AQSNEARHNH STVV*
LIYV_p5K   .......... .......... ..MSILLFFL MSILVWFIFT ILKLLFVNTD SEVNIPNKSR F*....
GLRaV3_p5K .......... .......... .....MDD FKQAILLLVV DFVFVILLLL VLTFVVPRLQ QSSTINTGLR TV*...
CTV_p6K    MDCVIQGFLT FLVGIAVFCA FAGLIIIVIT IYRCTIKPVR SASPYGTHAT V*....

CONSENSUS  ---------- f---il-f-- ---lvi-i-- ---------- ---------s ----
```

FIG. 25

FIG. 26A

```
                        _____A_____
BYV_p65      ..MVVFGLDF GTTFSSVCAY VGEELYLFKQ RDSAYIPTYV FLHSDTQEVA
CTV_p65      ..MVLLGLDF GTTFSTVAMA TPSELVILKQ SNSSYIPTCL LLHAEPNSVS
GLRaV3_p59   ...MEVGIDF GTTFSTICFS PSGVSGCTPV AGSVYVETQI FIPEGSSTYL
LIYV_p62     MRDCKVGLDF GTTFSTVSTL VNNSMYVLRL GDSAYIPTCI AITPGGEAI.

CONSENSUS    ------G1DF GTTFStv--- ----l--l-- --S-YipTci f-------v-

BYV_p65      FGYDAEVLSN DLSVRGGFYR DLKRWIGCDE ENYRDYLEKL KPHYKTELLK
CTV_p65      YGYDAEYLAA S.GESGSFYK DLKRWVGCTA KNYQTYLHKL SPSYKVIVKE
GLRaV3_p59   IG.KAAGKAY RDGVEGRLYV NPKRWVGVTR DNVERYVEKL KPTYTVKM..
LIYV_p62     IGGAAEVLSG DDTPHCFFY. DLKRWVGVDD NTFKFAMNKI RPKYVAELVE

CONSENSUS    -G--Ae-l-- -----g-fY- dlKRWvG--- -ny---yl-Kl -P-Y---l--

BYV_p65      VAQSSKSTVK LDCYSGTVPQ NATLPGLIAT FVKALISTAS EAFKCQCTGV
CTV_p65      FGTKSVPVPY LSPLNNDLGL SVALPSLIAS YAKSILSDAE RVFNVSCTGV
GLRaV3_p59   ...DSGGALL IGGLGSGPDT LLRVVDVICL FLRALILECE RYTSTTVTAA
LIYV_p62     ......GEVY LTGINKGFSI KLSVKQLIKA YIETIVRLLA SSYSLRVIDL

CONSENSUS    ----s----- l--------- ------lI-- -----i---- --f----T--

_____B_____
BYV_p65      ICSVPANYNC LQRSFTESCV NLSGYPCVYM VNEPSAAALS ACSRIKGATS
CTV_p65      ICSVPAGYNT LQRAFTQQSI SMSGYSCVYI INEPSAAAYS TLPKLNSADK
GLRaV3_p59   VVTVPADYNS FKRSFVVEAL KGLGIPVRGV VNEPTAAALY SLAKSRVEDL
LIYV_p62     NQSVPADYKN AQRLAARSVL KALSFPCRRI INEPSAAAVY CVSRYPNYNY

CONSENSUS    i-sVPA-Yn- lqR-f----- ---gypc--i -NEPsAAA-- ----------

___C___                ___D___
BYV_p65      PVLVYDFGGG TFDVSVISAL NNTFVVRASG GDMNLGGRDI DKAFVEHLYN
CTV_p65      YLAVYDFGGG TFDVSIVSVR LPTFAVRSSS GDMNLGGRDI DKKLSDKIYE
GLRaV3_p59   LLAVFDFGGG TFDVSFVKKK GNILCVIFSV GDNFLGGRDI DRAIVEVIKQ
LIYV_p62     FL.VYDFGGG TFDVSLIGKY KSYVTVIDTE GDSFLGGRDI DKSIEDYLVG

CONSENSUS    -l-VyDFGGG TFDVS----- ---f-V---s- GD--LGGRDI Dk--------

BYV_p65      KAQ...LPVN YKIDISFLKE SLSKKVSFLN FPVVSEQGVR VDVLVNVSEL
CTV_p65      MAD...FVPQ KELNVSSLKE ALSLQTDPVK YT.VNHYGMS ETVSIDQTVL
GLRaV3_p59   KIKGKASDAK LGIFVSSMKE DLSNNNAITQ HLIPVEGGVE V.VDLTSDEL
LIYV_p62     KYNIKKVIP. .ATYLALIKE E.CNNTNKSI FTILFDDGSV QVVEFSKSEL

CONSENSUS    k--------- ----vs-lKE -ls------- f-i--e-G-- --V-----eL

___E_____
BYV_p65      AEVAAPFVER TIKIVKEVY. .EKYCSSMRL EPNVKAKLLM VGGSSYLPGL
CTV_p65      REIASVFINR TIDILTQV.. ..KVKSSMPE SQSL..KLVV VGGSSYLPGL
GLRaV3_p59   DAIVAPFSAR AVEVFKTGP. .DNFYPDPVI A......VM TGGSSALVKV
LIYV_p62     EKCVRPFVER SIKLINDVVV RNKLTSGV.. ........IYM VGGSSLLQPV

CONSENSUS    --i---pFv-R -i-i---v-- --k--s---- ---------m vGGSS-L---
```

FIG. 26B

```
                         _____F_____  _____
BYV_p65      LSRLSSIPFV  DEC.L.VLPD  ARAAVAGGCA  LYSACLRNDS  PMLLVDCAAH
CTV_p65      LDALATVPFV  SGI.V.PVED  ARTAVARGCA  LYSECLDGRS  KALLIDCITH
GLRaV3_p59   RSDVANLPQI  SKV.VFDSTD  FRCSVACGAK  VYCDTLAGNS  GLRLVDTLTN
LIYV_p62     QDMVRSYAST  KGLTLVADQD  MRSAVSYGCS  VLHK.LEDNK  EIVYIDCNSH

CONSENSUS    -------p-v  ---------D  -R-aVa-Gc-  -y---L---s  ---l-Dc--h

___G_____
BYV_p65      NLSISSKYCE  SIVCVPAGSP  IPFTGVRTVN  MTGSNASAVY  SAALFEGDFV
CTV_p65      HLSVTTFSAD  SVVVAAAGSP  IPFEGERKLT  LRKCVSTSNY  QARMFEGDYE
GLRaV3_p59   TLTDEVVGLQ  PVVIFPKGSP  IPCSYTHRYT  V....GGGDV  VYGIFEGE..
LIYV_p62     PLSDISFNCD  PEPIIRKPMS  IPYTHTVKMR  HDRPLKT...  IVNIYEGSNL

CONSENSUS    -Ls------d  -vvi---gsp  IPf-------  ----------  ----fEGd--

_____H_____
BYV_p65      KCRLNKRIFF  GDVVLGNVGV  TGSATRTVPL  TLEINVSSVG  TISFSLVGPT
CTV_p65      KVFRNERIYA  ASVSLFTLGV  NWSVPNDVEM  TLVTKVDSMG  KVEFYLKGPS
GLRaV3_p59   ....NNRAFL  NEPTFRGVSK  RRGDPVETDV  A.QFNLSTDG  TVSVIVNGEE
LIYV_p62     FMPENDWLIS  SNINTTDFAK  .....VGEEY  SKVYEYDIDG  IITLKIRNEV

CONSENSUS    ----N-r-f-  --v-l-----  ---------e-  ---------G  ---f---g--

BYV_p65      GVKKLIGGNA  AYDFSSYQLG  ERVVADLHKH  NSDKVKLIHA  LTYQPFQRKK
CTV_p65      GELVNVQGTS  HYDYAGMPHP  TRKLVRLSDY  NVNSAALVLA  LTLTREKREK
GLRaV3_p59   VKNEYLVPGT  TNVLDSL...  ...VYKSGRE  DLEAKAIPEY  LTTLNILHDK
LIYV_p62     TGKMFTLPNS  FTKSDNIKPI  TFKLTQLSNT  D.DLATLTSL  LGYHDKNFER

CONSENSUS    ----------  ----------  ------l---  --d---l---  Lt------ek

BYV_p65      LTDGDKALFL  KRLTADYRRE  ARKFSSY...  ......DDAV  LNSSELLLGR
CTV_p65      FLLRT...LF  DTLLADLRKT  A.SLSEYSKK  YPITRNDIDV  VSSR...MGI
GLRaV3_p59   AFTRRNLGNK  DKGFSDLRIE  ENFLKS....  ...AVDTDTI  LNG*......
LIYV_p62     FYG......L  FNVPTILIKE  IDKLGGFKTL  YRRLKSMNAN  F.........

CONSENSUS    f--------l  -----dlr-e  ---l--y---  ----------v  l---------

BYV_p65      IIPKILRGSR  VEKLDV*
CTV_p65      VVSKVLRGSD  LERIPL.
GLRaV3_p59   ..........  .......
LIYV_p62     ..........  .......

CONSENSUS    ----------  -------
```

FIG. 28A

```
BYV_p61      MTTRFSTPAN YYWGELFRRF FGGQEW.... ....KNLMSE AASVSRPRYS
CTV_p61      ......MSSH HVWGSLFRKF YGEAIW.... ....KEYLSE STRNFDERNV
LIYV_P59     ..MLNDRIAV TCFQTLLKKS NVKHEMEQTN NYIVNNLADI NRNTFPALAG
GLRaV3_p55   .......MDK YIYVTGI..L NPNEARDEVF SVVNKGYIGP GGRSFSNRGS

CONSENSUS    ---------- --w--lf--f -----w---- ----k----- ----f--r--

BYV_p61      S.DFRFSDGV ILSRKTFGES TGES..FVRE FSLLLTFPKT YEVCKLCGVA
CTV_p61      SLDHTLSSGV VVRRQSLLNA PQGT..FENE LALLYNSVVI NDFVELTGMP
LIYV_P59     SVRIDFNSDY YISGGQIVVS PKDSNAYVKL LIVYLKYCYI N.YSAKTKYP
GLRaV3_p55   KYTVVWEN.. ..SAARISGL TSTSQSTIDA FAYFL..... ..LKGGLTTT

CONSENSUS    s----f---- --s------- ---s--fv-- ---ll----- ----------

BYV_p61      MELALNGMN. .RLSDYNVSE FN......IV DVKTVGCKFN IQSVTEFVKK
CTV_p61      LKSLMTGIED RKVPD....E LI......SV DPHEVGCRFT LNDVESYLMS
LIYV_P59     PQSLLAVLDY DSFKAKWVKY LDKSLTDYLD DNKTEGCSFT EQQVVEKYPQ
GLRaV3_p55   LSNPINCENW VRSSKDLSAF FRTLIKGKIY ASRSVDSNLP KKDRDDIME.

CONSENSUS    l---l----- ---------- ---------- d---vgc-f- ---v-e----

BYV_p61      INGNVAEPSL VEHCWSLSNS CGELINPKDT KRFVSLIFKG KDLAESTDEA
CTV_p61      RGEDFADLAA VEHSWCLSNS CSRLLSSTEI DANKTLVF.T KNFDSNISG.
LIYV_P59     VDSLVAKIL. ....YRVCNS LGKLLDLKDF ENKNISGFEI NTAQDSPTVA
GLRaV3_p55   .ASRRLSPSD AAFCRAVSVQ VGKYVDVTQN LESTIVPLRV MEIKKRRGSA

CONSENSUS    -----a---- ----w--sns -g-l----d- -------f-- ---------a

BYV_p61      IVS..SSYLD YLSHCLNLYE TCNLSSNSGK KSLYDEFLKH VIDYL...EN
CTV_p61      .VT..TKLET YLSYCISLYK KHCM.KDDDY FNLILPMFNC LMKVL...AS
LIYV_P59     DDN..ES.ND FFRECVNDQR YYSSLSGSKL GKAKLEANAY IFKILLKSAS
GLRaV3_p55   HVSLPKVVSA YVDFYTNLQE LLSDEVTRAR TDTVSAYATD SMAFLVKMLP

CONSENSUS    -v-------- yl--c-nl-- ---------- ---------- ----L-----

BYV_p61      SDLEYRSPSD NPLVAGILYD MCFEYNTLKS TYLKNIESFD CFLSLYLPLL
CTV_p61      LGLFYEKHAD NPLLTGMLIE FCLENKVYYS TFKVNLDNVR LFKSKVLPVV
LIYV_P59     GEFDIDRLSR NPLAISKFMN LYTNHVTDSE TFKSKFEALK SIKTPFASFI
GLRaV3_p55   LT......AR EQWLKDVLGY LLVRRRPANF SYDVRVAWVY DVIATLKLVI

CONSENSUS    --l------- npl----l-- lc-------- t-----e--- ---------i

I
BYV_p61      SEVFSMNWER PAPDVRLLFE LDAAELLLKV PTINMHDST. ..FLYKNKLR
CTV_p61      LTVWDISEPD DPVDERVLIP FDPTDFVLDL PKLNIHDTM. ..VVVGNQIR
LIYV_P59     KKAFGIR... ........LN FEDSKIFYAL PKERQSDVLS DDMMVESIVR
GLRaV3_p55   RLFFNKDTPG GIKDLKPCVP IESFDPFHEL S......... ......SYFS
```

FIG. 28B

```
BYV_p61     YLESYFEDDS  NELIKVKVDS  LLTRDNPEL.  .KLAQRWV..  ...GFHCYYG
CTV_p61     QLEYVVESDA  LDDLSQHVDL  RLAADNPDL.  .RVGLRWA..  ...GMFVYYG
LIYV_P59    DAASFTVVSD  NNYLPERVDR  FVTQLLLELF  PKTKASFPNK  IMFGFLHYFA
GLRaV3_p55  RLSYEMTTGK  GGKICPEIAE  KLVRRLMEEN  YKLRLT.PVM  ALIIILVYYS

CONSENSUS   -l--------  -------vd-  -l-----el-  -k----w---  ---g-l-Yy-

II
BYV_p61     VFRTAQTRKV  KRDAEYKLPP  AL......GE  FVINMSGVEE  FF.EELQKKM
CTV_p61     VYRCVVDRAV  ERPTLFRLPQ  KLLSQDDGES  CSLHMGSVEA  LF.NLVQKVN
LIYV_P59    LSTTNSKR..  .....FNDTQ  ESTIEIEGET  LKISLKFITS  YLRNAIQSQH
GLRaV3_p55  IYGTNATRIK  RRPDFLNVRI  KGRVE.....  .KVSLRGVED  ..RAFRISEK

CONSENSUS   vy-t---R--  -r---f----  ----------  --i----ve-  -f----q---

BYV_p61     PSI...SVRR  RFCGSLSHEA  FSVFKRFGVG  FPPITRLNVP  VKYSYLNVDY
CTV_p61     KDI...NVRR  QFMGRHSEVA  LRLYRNLGLR  FPPISSVRLP  AHHGYLYVDF
LIYV_P59    PDYADSNIVR  LWCNKRSNLA  LGYFKSRNIQ  LYLYS..KYP  RLLNYMRFDY
GLRaV3_p56  RGINAQRVLC  RYYSDLTCLA  RRHYGIRRNN  WKTLSYVD..  GTLAYDTADC

CONSENSUS   --i----v-r  -fc---s--A  l---------  f---s----p  ----Yl--Dy

BYV_p61     YRHVKRVGLT  QDELTILSNI  EFDVAEMCCE  REVALQARRA  QR....GEKP
CTV_p61     YKRVPDGAVT  ADELESLRQL  RSSVDVMCKD  R.VSITPPPF  NRLRRGSSRT
LIYV_P59    FKGLDMGKLT  DEERLSIQTL  RCITEDRS.E  GTLATHNDLN  SWILRP....
GLRaV3_p55  ITSKVRNTIN  TADHASIIHY  IKTNENQVTG  TTLPHQL*..  ..........

CONSENSUS   y-------t  -de--s----  ----e----e  ----------  -r--------

BYV_p61     FQGWKGTKNE  ISPHARSSIR  VKKNNDSLLN  ILWKDVGARS  QRRLNPLHRK
CTV_p61     FRGR.GARGA  SSRHMSRDVA  TSGFNLPYHG  RLYSTS*...  ..........
LIYV_P59    ..........  ..........  ..........  ..........  ..........
GLRaV3_p55  ..........  ..........  ..........  ..........  ..........

CONSENSUS   ----------  ----------  ----------  ----------  ----------

BYV_p61     H*
CTV_p61     ..
LIYV_P59    ..
GLRaV3_p55  ..

CONSENSUS   --
```

FIG. 29A

```
(5' primer, 93-224)
                     NcoI
tacttatctagaacc
              ─────┐
   ┌──────────────┘
   └──ATGGAAGCGAGTCGACGACTA
      ATGGAAGCGAGTCGACGACTATCGCCATCGGACGCCGCCTTTTGCAGAGCAGTGTCGGTT
9404------+---------+---------+---------+---------+---------+---
          M E A S R R L S P S D A A F C R A V S V  -

CAGGTAGGGAAGTATGTGGACGTAACGCAGAATTTAGAAAGTACGATCGTGCCGTTAAGA
      ------+---------+---------+---------+---------+---------+---
          Q V G K Y V D V T Q N L E S T I V P L R  -

GTTATGGAAATAAAGAAAAGACGAGGATCAGCACATGTTAGTTTACCGAAGGTGGTATCC
      ------+---------+---------+---------+---------+---------+---
          V M E I K K R R G S A H V S L P K V V S  -

GCTTACGTAGATTTTTATACGAACTTGCAGGAATTGCTGTCGGATGAAGTAACTAGGGCC
      ------+---------+---------+---------+---------+---------+---
          A Y V D F Y T N L Q E L L S D E V T R A  -

AGAACCGATACAGTTTCGGCATACGCTACCGACTCTATGGCTTTCTTAGTTAAGATGTTA
      ------+---------+---------+---------+---------+---------+---
          R T D T V S A Y A T D S M A F L V K M L  -

CCCCTGACTGCTCGTGAGCAGTGGTTAAAAGACGTGCTAGGATATCTGCTGGTACGGAGA
      ------+---------+---------+---------+---------+---------+---
          P L T A R E Q W L K D V L G Y L L V R R  -

CGACCAGCAAATTTTTCCTACGACGTAAGAGTAGCTTGGGTATATGACGTGATCGCTACG
      ------+---------+---------+---------+---------+---------+---
          R P A N F S Y D V R V A W V Y D V I A T

CTCAAGCTGGTCATAAGATTGTTTTTCAACAAGGACACACCCGGGGGTATTAAAGACTTA
      ------+---------+---------+---------+---------+---------+---
          L K L V I R L F F N K D T P G G I K D L  -

AAACCGTGTGTGCCTATAGAGTCATTCGACCCCTTTCACGAGCTTTCGTCCTATTTCTCT
      ------+---------+---------+---------+---------+---------+---
          K P C V P I E S F D P F H E L S S Y F S  -

AGGTTAAGTTACGAGATGACGACAGGTAAAGGGGGAAAGATATGCCCGGAGATCGCCGAG
      ------+---------+---------+---------+---------+---------+---
          R L S Y E M T T G K G G K I C P E I A E  -

AAGTTGGTGCGCCGTCTAATGGAGGAAAACTATAAGTTAAGATTGACCCCAGTGATGGCC
      ------+---------+---------+---------+---------+---------+---
          K L V R R L M E E N Y K L R L T P V M A  -
```

FIG. 29B

```
TTAATAATTATACTGGTATACTACTCCATTTACGGCACAAACGCTACCAGGATTAAAAGA
------+---------+---------+---------+---------+---------+---
  L  I  I  I  L  V  Y  Y  S  I  Y  G  T  N  A  T  R  I  K  R   -

CGCCCGGATTTCCTCAATGTGAGGATAAAGGGAAGAGTCGAGAAGGTTTCGTTACGGGGG
------+---------+---------+---------+---------+---------+---
  R  P  D  F  L  N  V  R  I  K  G  R  V  E  K  V  S  L  R  G   -

GTAGAAGATCGTGCCTTTAGAATATCAGAAAAGCGCGGGATAAACGCTCAACGTGTATTA
------+---------+---------+---------+---------+---------+---
  V  E  D  R  A  F  R  I  S  E  K  R  G  I  N  A  Q  R  V  L   -

TGTAGGTACTATAGCGATCTCACATGTCTGGCTAGGCGACATTACGGCATTCGCAGGAAC
------+---------+---------+---------+---------+---------+---
  C  R  Y  Y  S  D  L  T  C  L  A  R  R  H  Y  G  I  R  R  N   -

AATTGGAAGACGCTGAGTTATGTAGACGGGACGTTAGCGTATGACACGGCTGATTGTATA
------+---------+---------+---------+---------+---------+---
  N  W  K  T  L  S  Y  V  D  G  T  L  A  Y  D  T  A  D  C  I   -

ACTTCTAAGGTGAGAAATACGATCAACACCGCAGATCACGCTAGCATTATACACTATATC
------+---------+---------+---------+---------+---------+---
  T  S  K  V  R  N  T  I  N  T  A  D  H  A  S  I  I  H  Y  I   -

AAGACGAACGAAAACCAGGTTACCGGAACTACTCTACCACACCAGCTTTAAAGCTGCGTG
------+---------+---------+---------+---------+---------+---
  K  T  N  E  N  Q  V  T  G  T  T  L  P  H  Q  L  *

TAGTATGCGACGATGTTTCT
------+---------+---   10503
ATCATACGCTGCTACAAAGA
                    ggtacctaggagttct
                         NcoI
                    (3' primer, 93-225)
```

GRAPEVINE LEAFROLL VIRUS PROTEINS AND THEIR USES

This application is a continuation of and claims priority to U.S. Ser. No. 09/579,259, filed on May 25, 2000, now U.S. Pat. No. 6,558,953 which is a continuation of U.S. Ser. No. 09/224,898, filed on Dec. 31, 1998, now abandoned, which is a divisional of U.S. Ser. No. 08/770,544, filed on Dec. 20, 1996, now U.S. Pat. No. 5,907,085, which claims benefit of U.S. provisional application serial No. 60/009,008, filed on Dec. 21, 1995, now abandoned.

FIELD OF THE INVENTION

The present invention relates to grapevine leafroll virus proteins, DNA molecules encoding these proteins, and their uses.

BACKGROUND OF THE INVENTION

The world's most widely grown fruit crop, the grape (*Vitis* sp.), is cultivated on all continents except Antarctica. However, major grape production centers are in European countries (including Italy, Spain, and France), which constitute about 70% of the world grape production (Mullins et al., *Biology of the Grapevine*, Cambridge, U.K.:University Press (1992)). The United States, with 300,000 hectares of grapevines, is the eighth largest grape grower in the world. Although grapes have many uses, a major portion of grape production (~80%) is used for wine production. Unlike cereal crops, most of the world's vineyards are planted with traditional grapevine cultivars, which have been perpetuated for centuries by vegetative propagation. Several important grapevine virus and virus-like diseases, such as grapevine leafroll, corky bark, and Rupestris stem pitting, are transmitted and spread through the use of infected vegetatively propagated materials. Thus, propagation of certified, virus-free materials is one of the most important disease control measures. Traditional breeding for disease resistance is difficult due to the highly heterozygous nature and outcrossing behavior of grapevines, and due to polygenic patterns of inheritance. Moreover, introduction of a new cultivar may be prohibited by custom or law. Recent biotechnology developments have made possible the introduction of special traits, such as disease resistance, into an established cultivar without altering its horticultural characteristics.

Many plant pathogens, such as fungi, bacteria, phytoplasmas, viruses, and nematodes can infect grapes, and the resultant diseases can cause substantial losses in production (Pearson et al., *Compendium of Grape Diseases*, American Phytopathological Society Press (1988)). Among these, viral diseases constitute a major hindrance to profitable growing of grapevines. About 34 viruses have been isolated and characterized from grapevines. The major virus diseases are grouped into: (1) the grapevine degeneration caused by the fanleaf nepovirus, other European nepoviruses, and American nepoviruses, (2) the leafroll complex, and (3) the rugose wood complex (Martelli, ed., *Graft Transmissible Diseases of Grapevines, Handbook for Detection and Diagnosis*, FAO, UN, Rome, Italy (1993)).

Of the major virus diseases, the grapevine leafroll complex is the most widely distributed throughout the world. According to Goheen (Goheen, "Grape Leafroll," in Frazier et al., eds., *Virus Diseases of Small Fruits and Grapevines (A Handbook)*, University of California, Division of Agricultural Sciences, Berkeley, Calif., USA, pp. 209–212 (1970) ("Goheen (1970)"), grapevine leafroll-like disease was described as early as the 1850s in German and French literature. However, the virus nature of the disease was first demonstrated by Scheu (Scheu, "Die Rollkrankheit des Rebstockes (Leafroll of grapevine)," *D. D. Weinbau* 14:222–358 (1935) ("Scheu (1935)")). In 1946, Harmon and Snyder (Harmon et al., "Investigations on the Occurrence, Transmission, Spread and Effect of 'White' Fruit Colour in the Emperor Grape," *Proc. Am. Soc. Hort. Sci.* 74:190–194 (1946)) determined the virus nature of White Emperor disease in California. It was later proven by Goheen et al. (Goheen et al., "Leafroll (White Emperor Disease) of Grapes in California, *Phytopathology*, 48:51–54 (1958) ("Goheen (1958)")) that both leafroll and "White Emperor" diseases were the same, and only the name "leafroll" was retained.

Leafroll is a serious virus disease of grapes and occurs wherever grapes are grown. This wide distribution of the disease has come about through the propagation of diseased vines. It affects almost all cultivated and rootstock varieties of Vitis. Although the disease is not lethal, it causes yield losses and reduction of sugar content. Scheu estimated in 1936 that 80 percent of all grapevines planted in Germany were infected (Scheu, *Mein Winzerbuch*, Berlin:Reichsnahrstand-Verlags (1936)). In many California wine grape vineyards, the incidence of leafroll (based on a survey of field symptoms conducted in 1959) agrees with Scheu's initial observation in German vineyards (Goheen et al., "Studies of Grape Leafroll in California," *Amer. J. Enol. Vitic.*, 10:78–84 (1959)). The current situation on leafroll disease does not seem to be any better (Goheen, "Diseases Caused by Viruses and Viruslike Agents," *The American Phytopathological Society*, St. Paul, Minn.:APS Press, 1:47–54 (1988) ("Goheen (1988)"). Goheen also estimated that the disease causes an annual loss of about 5–20 percent of the total grape production (Goheen (1970) and Goheen (1988)). The amount of sugar in individual berries of infected vines is only about ½ to ⅔ that of berries from noninfected vines (Goheen (1958)).

Symptoms of leafroll disease vary considerably depending upon the cultivar, environment, and time of the year. On red or dark-colored fruit varieties, the typical downward rolling and interveinal reddening of basal, mature leaves is the most prevalent in autumn; but not in spring or early summer. On light-colored fruit varieties however, symptoms are less conspicuous, usually with downward rolling accompanied by interveinal chlorosis. Moreover, many infected rootstock cultivars do not develop symptoms. In these cases, the disease is usually diagnosed with a woody indicator indexing assay using *Vitis vivifera* cv. Carbernet Franc (Goheen (1988)).

Ever since Scheu demonstrated that leafroll was graft transmissible, a virus etiology has been suspected (Scheu (1935)). Several virus particle types have been isolated from leafroll diseased vines. These include potyvirus-like (Tanne et al., "Purification and Characterization of a Virus Associated with the Grapevine Leafroll Disease," *Phytopathology*, 67:442–447 (1977)), isometric virus-like (Castellano et al., "Virus-like Particles and Ultrastructural Modifications in the Phloem of Leafroll-affected Grapevines," *Vitis*, 22:23–39 (1983) ("Castellano (1983)") and Namba et.al., "A Small Spherical Virus Associated with the Ajinashika Disease of Koshu Grapevine, *Ann. Phytopathol. Soc. Japan*, 45:70–73 (1979)), and closterovirus-like (Namba, "Grapevine Leafroll Virus, a Possible Member of Closteroviruses, *Ann. Phytopathol. Soc. Japan*, 45:497–502 (1979)) particles. In recent years, however, long flexuous closteroviruses ranging from 1,400 to 2,200 nm have been most consistently associated with leafroll disease (FIG. 1) (Castellano (1983), Faoro et al., "Association of a Possible Closterovirus with Grapevine Leafroll in Northern Italy," *Riv. Patol. Veg., Ser IV*, 17:183–189 (1981), Gugerli et al., "L'enroulement de la vigne: mise en évidence de particules virales et developpement d'une méthode immuno-enzymatique pour le diagnostic rapide (Grapevine Leafroll: Presence of Virus Particles and Development of an Immuno-enzyme method for Diagnosis and Detection)," *Rev. Suisse Viticult. Arboricult. Hort.*, 16:299–304 (1984) ("Gugerli (1984)"), Hu et al., "Characterization of Closterovirus-like Particles Associated with Grapevine Leafroll Disease," *J. Phytopathol.*, 128:1–14 (1990) ("Hu (1990)"), Milne et al., "Closterovirus-like Particles of Two Types Associated with Diseased Grapevines," *Phytopathol. Z.*, 110:360–368 (1984), Zee et al., "Cytopathology of Leafroll-diseased Grapevines and the Purification and Serology of Associated Closteroviruslike Particles," *Phytopathology*, 77:1427–1434 (1987) ("Zee (1987)"), and Zimmermann et al., "Characterization and Serological Detection of Four Closterovirus-like Particles Associated with Leafroll Disease on Grapevine," *J. Phytopathol.*, 130:205–218 (1990) ("Zimmermann (1990)")). These closteroviruses are referred to as grapevine leafroll associated viruses ("GLRaV"). At least six serologically distinct types of GLRaV's (GLRaV-1 to -6) have been detected from leafroll diseased vines (Table 1) (Boscia et al., "Nomenclature of Grapevine Leafroll-associated Putative Closteroviruses, *Vitis*, 34:171–175 (1995) ("Boscia (1995)") and (Martelli, "Leafroll," pp. 37–44 in Martelli, ed., *Graft Transmissible Diseases of Grapevines, Handbook for Detection and Diagnosis*, FAO, Rome Italy, (1993) ("Martelli I")). The first five of these were confirmed in the 10th Meeting of the International Council for the Study of Virus and Virus Diseases of the Grapevine ("ICVG") (Volos, Greece, 1990).

TABLE 1

| Type | Particle length (nm) | Coat protein Mr ($\times 10^3$) | Reference |
| --- | --- | --- | --- |
| GLRaV-1 | 1,400–2,200 | 39 | Gugerli (1984) |
| GLRaV-2 | 1,400–1,800 | 26 | Gugerli (1984) Zimmermann (1990) |
| GLRaV-3 | 1,400–2,200 | 43 | Zee (1987) |
| GLRaV-4 | 1,400–2,200 | 36 | Hu (1990) |
| GLRaV-5 | 1,400–2,200 | 36 | Zimmermann (1990) |
| GLRaV-6 | 1,400–2,200 | 36 | Gugerli (1993) |

Through the use of monoclonal antibodies, however, the original GLRaV II described in Gugerli (1984) has been shown to be an apparent mixture of at least two components, IIa and IIb (Gugerli et al., "Grapevine Leafroll Associated Virus II Analyzed by Monoclonal Antibodies," 11*th Meeting of the International Council for the Study of Viruses and Virus Diseases of the Grapevine*, Montreux, Switzerland, pp. 23–24 (1993) ("Gugerli (1993)")). Recent investigation with comparative serological assays (Boscia (1995)) demonstrated that the IIb component of cv. Chasselas 8/22 is the same as the GLRaV-2 isolate from France (Zimmermann (1990)) which also include the isolates of grapevine corky bark associated closteroviruses from Italy (GCBaV-BA) (Boscia (1995)) and from the United States (GCBaV-NY) (Namba et al., "Purification and Properties of Closterovirus-like Particles Associated with Grapevine Corky Bark Disease," *Phytopathology*, 81:964–970 (1991) ("Namba (1991)")). The IIa component of cv. Chasselas 8/22 was given the provisional name of grapevine leafroll associated virus 6 (GLRaV-6). Furthermore, the antiserum to the CA-5 isolate of GLRaV-2 produced by Boscia et al. (Boscia et al., "Characterization of Grape Leafroll Associated Closterovirus (GLRaV) Serotype II and Comparison with GLRaV Serotype III," *Phytopathology*, 80:117 (1990)) was shown to contain antibodies to both GLRaV-2 and GLRaV-1, with a prevalence of the latter (Boscia (1995)).

Several shorter closteroviruses (particle length 800 nm long) have also been isolated from grapevines. One of these, called grapevine virus A ("GVA") has also been found associated, though inconsistently, with the leafroll disease (Agran et al., "Occurrence of Grapevine Virus A (GVA) and Other Closteroviruses in Tunisian Grapevines Affected by Leafroll Disease," *Vitis*, 29:43–48 (1990), Conti, et al., "Closterovirus Associated with Leafroll and Stem Pitting in Grapevine," *Phytopathol. Mediterr.*, 24:110–113 (1985), and Conti et al., "A Closterovirus from a Stem-pitting-diseased Grapevine," *Phytopathology*, 70:394–399 (1980)). The etiology of GVA is not really known; however, it appears to be more consistently associated with rugose wood sensu lato (Rosciglione at al., "Maladies de l'enroulement et du bois strié de la vigne: analyse microscopique et sérologique (Leafroll and Stem Pitting of Grapevine: Microscopical and Serological Analysis)," *Rev. Suisse Vitic Arboric. Hortic.*, 18:207–211 (1986) ("Rosciglione (1986)"), and Zimmermann (1990)). Moreover, another short closterovirus (800 nm long) named grapevine virus B ("GVB") has been isolated and characterized from corky bark-affected vines (Boscia et al., "Properties of a Filamentous Virus Isolated from Grapevines Affected by Corky Bark, *Arch. Virol.*, 130:109–120 (1993) and Namba (1991)).

As suggested by Martelli I, leafroll symptoms may be induced by more than one virus or they may be simply a general plant physiological response to invasion by an array of phloem-inhabiting viruses. Evidence accumulated in the last 15 years strongly favors the idea that grapevine leafroll is induced by one (or a complex) of long closteroviruses (particle length 1,400 to 2,200 nm).

Grapevine leafroll is transmitted primarily by contaminated scions and rootstocks. However, under field conditions, several species of mealybugs have been shown to be the vector of leafroll (Engelbrecht et al., "Transmission of Grapevine Leafroll Disease and Associated Closteroviruses by the Vine Mealybug *Planococcus-ficus*," *Phytophylactica*, 22:341–346 (1990), Rosciglione, et al., "Transmission of Grapevine Leafroll Disease and an Associated Closterovirus to Healthy Grapevine by the Mealybug Planococcus ficus," (Abstract), *Phytoparasitica*, 17:63–63 (1989), and Tanne, "Evidence for the Transmission by Mealybugs to Healthy Grapevines of a Closter-like Particle Associated with Grapevine Leafroll Disease," *Phytoparasitica*, 16:288 (1988)). Natural spread of leafroll by insect vectors is rapid in various parts of the world. In New Zealand, observations of three vineyards showed that the number of infected vines nearly doubled in a single year (Jordan et al., "Spread of Grapevine Leafroll and its Associated Virus in New Zealand Vineyards," 11*th Meeting of the International Council for the Study of Viruses and Virus Diseases of the Grapevine*, Montreux, Switzerland, pp. 113–114 (1993)). One vineyard became 90% infected 5 years after GLRaV-3 was first observed. Prevalence of leafroll worldwide may increase as chemical control of mealybugs becomes more difficult due to the unavailability of effective insecticides.

In view of the serious risk grapevine leafroll virus poses to vineyards and the absence of an effective treatment of it, the need to prevent this affliction continues to exist. The present invention is directed to overcoming this deficiency in the art.

SUMMARY OF INVENTION

The present invention relates to an isolated protein or polypeptide corresponding to a protein or polypeptide of a grapevine leafroll virus. The encoding RNA and DNA molecules, in either isolated form or incorporated in an expression system, a host cell, or a transgenic Vitis or citrus scion or rootstock cultivar, are also disclosed.

Another aspect of the present invention relates to a method of imparting grapevine leafroll virus resistance to Vitis scion or rootstock cultivars by transforming them with a DNA molecule encoding the protein or polypeptide corresponding to a protein or polypeptide of a grapevine leafroll virus. These DNA molecules can also be used in transformation of citrus scion or rootstock cultivar to impart tristeza virus resistance to such cultivars.

The present invention also relates to an antibody or binding portion thereof or probe which recognizes the protein or polypeptide.

Figure 13:
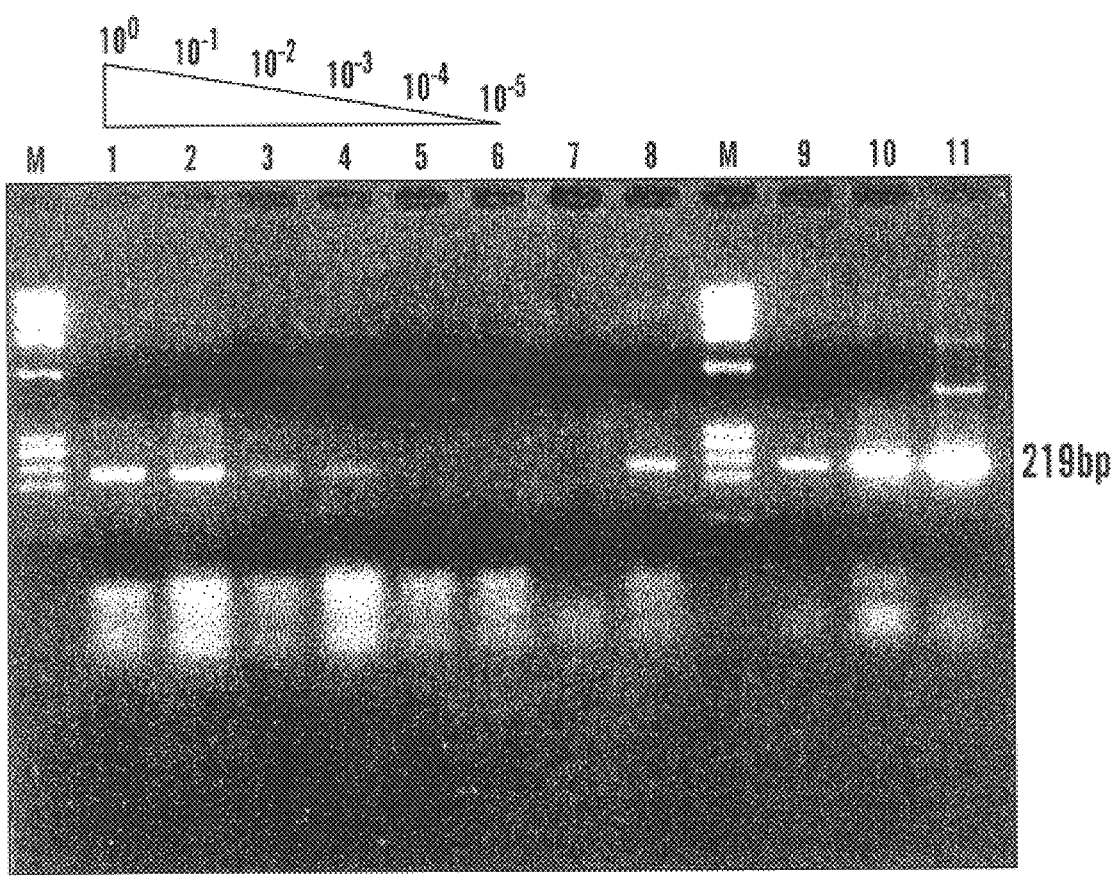

Grapevine leafroll virus resistant transgenic variants of the current commercial grape cultivars and rootstocks allows for more complete control of the virus while retaining the varietal characteristics of specific cultivars. Furthermore, these variants permit control of GLRaV transmitted either by contaminated scions or rootstocks or by GLRaV-carrying mealy bugs. With respect to the latter mode of transmission, the present invention circumvents increased restriction of pesticide use which has made chemical control of mealy bug infestations increasingly difficult. In this manner, as well as others, the interests of the environment and the economics of grape cultivation and wine making are all benefited by the present invention.

BRIEF DESCRIPTION OF THE DRAWINGS

FIG. 1 is electron micrographs of GLRaV-3 particles of the NY1 isolate after negative staining with 1% uranyl acetate of a purified virus preparation (magnification 80,000×).

FIG. 2 shows the nucleotide (SEQ ID NO:7) and amino acid (SEQ ID NO:8) sequences of a PCR amplified fragment of the GLRaV-3 genome. The external and internal primers used for PCR are underlined and their orientations are indicated by arrows.

FIG. 3 compares the alignment of the amino acid sequence deduced from the PCR fragment of GLRaV-3 (SEQ ID NO:8) with respective regions of HSP90 homologues of beet yellow virus ("BYV") (p64) (SEQ ID NO:33), citrus tristeza virus ("CTV") (p61) (SEQ ID NO:34), and lettuce infectious yellow virus ("LIYV") (p59) (SEQ ID NO:35). Consensus amino acid residues are shown. Uppercase letters indicate identical amino acids, lowercase letters indicate at least three identical or functionally similar amino acids.

FIG. 4, panel B, is a Northern blot hybridization. Probe made from a clone insert gave positive reaction to itself (lane 3) as well as dsRNA from leafroll infected tissues (lane 1), but not to nucleic acids extracted from healthy grapevines (lane 2). Lane M contains a molecular weight marker (the Hind III digested fragments of lambda DNA). Panel A of FIG. 4 depicts an ethidium bromide stained agarose gel before transfer to a membrane.

FIG. 5 presents an analysis of GLRaV-3 dsRNA by electrophoresis on an ethidium bromide stained agarose gel. A dsRNA of ca. 16 kb was readily isolated from diseased grapevine (lane 6), but not from the healthy control (lane 5). Other samples that were used for control were tobacco mosaic virus dsRNA (lane 1); cucumber mosaic virus dsRNA (lane 2); pBluescript vector (lane 3) and an insert of clone pC4. λ Hind III digested fragment of lambda DNA was used as the molecular weight marker (lane M).

FIG. 6 is a secondary immunoscreening of plaques derived from three mother plaques that reacted to GLRaV-3 specific polyclonal antibody. Two filters each represent plaques from clones pCP5 (left), pCP8-4 (middle), and pCP10-1 (right).

FIG. 7 is a PCR analysis of immuno-positive clones with flanking vector primer (KS and SK). A similar size (1.0–1.1 kb) PCR product was produced in all three mother clones.

FIG. 8 is a Western blot of antibodies to GLRaV-3 that reacted to proteins produced by cDNA clones after IPTG induction in *E. coli*. Similar banding patterns were observed whether a polyclonal (panel A) or a monoclonal antibody (panel B) was used. Lane 1 shows clone pCP10-1; lane 2, pCP5; lane 3, pCP8-4; and lane 4, the native coat protein from GLRaV-3 infected tissue. Lane M is a prestained protein molecular weight marker.

FIG. 9 shows the cDNA clones containing the coding region for the coat protein of the NY1 isolate of GLRaV-3. Three clones (pCP8-4, pCP5, pCP10-1) were identified by immunoscreening of a cDNA library prepared in lambda ZAP II. Two other clones were aligned after plaque hybridization and nucleotide sequencing. An ORF encoding the coat protein is shown by an arrow in an open rectangle.

FIG. 10 shows the nucleotide (SEQ ID NO:9) and amino acid (SEQ ID NO:10) sequences of the coat protein of grapevine leafroll associated closterovirus-3, isolate NY1. Nucleotide sequencing was conducted by the procedure described in Example 1. The translated amino acid sequence is shown below the nucleotide sequence.

FIG. 11 compares the alignment of the coat protein of GLRaV-3 (SEQ ID NO:10) with respect to BYV (SEQ ID NO:36), CTV (SEQ ID NO:37), and LIYV (SEQ ID NO:38). Consensus amino acid residues are shown. Uppercase letters indicate identical amino acids, and lowercase letters indicate at least three identical or functionally similar amino acids. The three conserved amino acid residues (S, R, and D) identified in all filamentous plant virus coat proteins are in bold (Dolja et al., "Phylogeny of Capsid Proteins of Rod-shaped and Filamentous RNA Plant Viruses: Two Families with Distinct Patterns of Sequence and Probably Structure Conservation," *Virology*, 184:79–86 (1991)).

FIG. 12 is a phylogenetic tree generated by the Clustal Method of MegAlign program in DNASTAR for the coat protein of GLRaV-3 with respect to that of other filamentous plant viruses. The coat protein of GLRaV-3 was incorporated into a previously described alignment (Dolja et al., "Molecular Biology and Evolution of Closteroviruses: Sophisticated Build-up of Large RNA Genomes," *Annual Review of Phytopathology*, 32:261–285 (1994) ("Dolja (1994)")) for comparison. The other virus sequences were obtained from current databases: apple chlorotic leafspot virus ("ACLSV"); apple stem grooving virus ("ASGV"); apple stem pitting virus ("ASPV"); barley yellow mosaic virus ("BaMV"); beet yellows closterovirus ("BYV"); diverged copies of BYV and CTV coat proteins ("BYV p24" and "CTV p27", respectively); citrus tristeza virus ("CTV"); grapevine virus A ("GVA"); grapevine virus B ("GVB"); lily symptomless virus ("LSV"); lily virus X ("LVX"); narcissus mosaic virus ("NMV"); pepper mottle virus ("PeMV"); papaya mosaic virus ("PMV"); potato virus T ("PVT"); potato virus S ("PVS"); potato virus M ("PVM"); potato virus X ("PVX"); tobacco etch virus ("TEV"); tobacco vein mottle virus ("TVMV"); and white clover mosaic virus ("WcMV").

FIG. 13 depicts an analysis of reverse transcription polymerase chain reaction ("RT-PCR") to detect GLRaV-3 in a partially purified virus preparation. The original sample concentration is equivalent to 50 mg/μl of phloem tissue (lane 1) which was diluted by 10-fold series as $10^{-1}$ (lane 2), $10^{-2}$ (lane 3), $10^{-3}$ (lane 4), $10^{-4}$ (lane 5), and $10^{-5}$ (lane 6), respectively. The expected size of 219 bp PCR product was clearly observed up to lane 4 which is equivalent to a detection limit of 10 μg of phloem tissue. Lane 7 was a healthy control. Lane 8 was dsRNA for positive control. Lanes 9–11 were also used for positive controls of purified viral RNA (lane 9), dsRNA (lane 10), and plasmid DNA (pC4) (lane 11) as templates, respectively. Lane M contains a molecular weight marker of Hae III digested fX 174 DNA.

Figure 14:
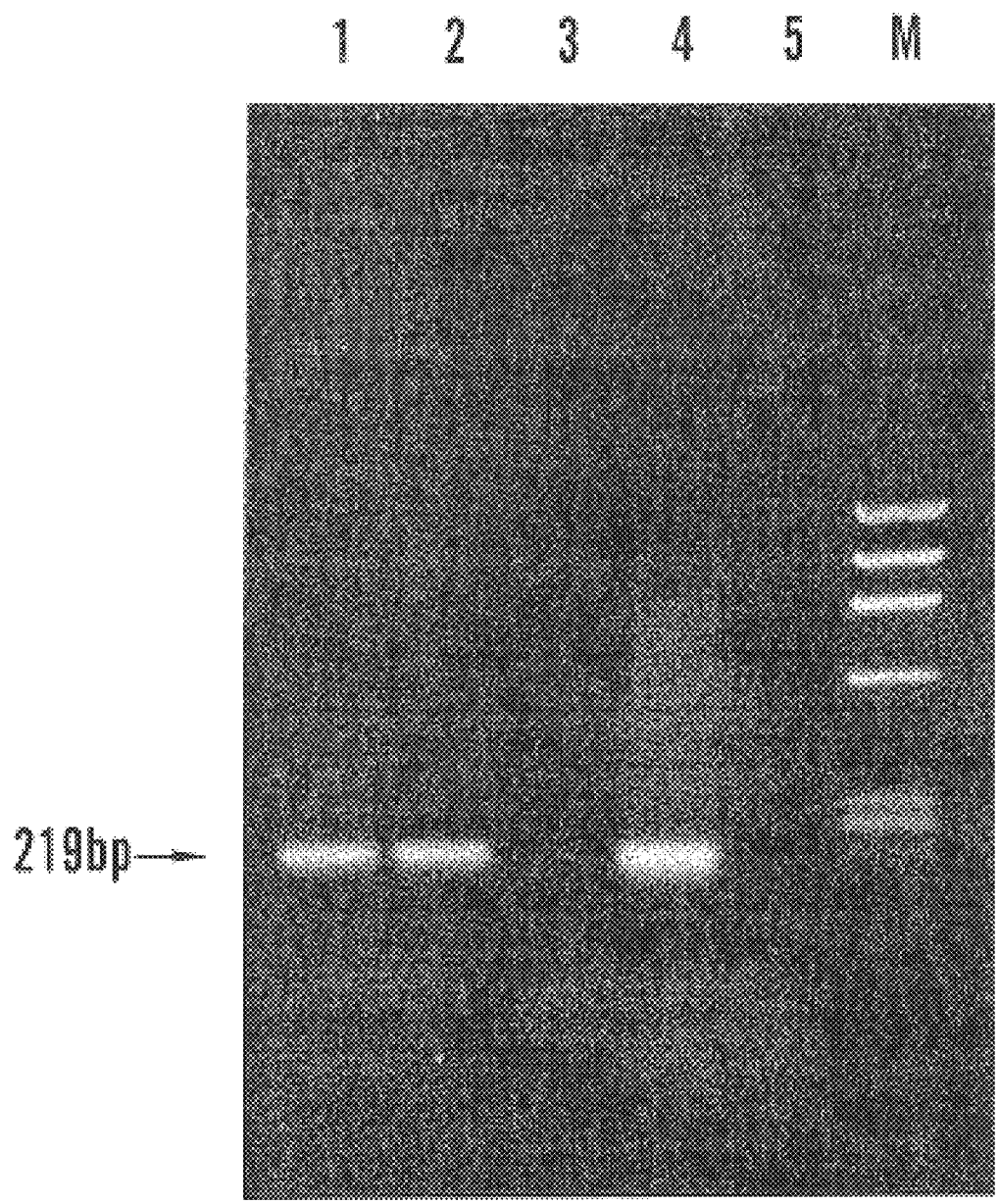

FIG. 14 shows the. enzymatic inhibition in RT-PCR with proteinase K treated samples. By increasing amount of proteinase K treated sample in each 100 μl PCR reaction from 0.1 μl (lane 1) to 1 μl (lane 2) and to 10 μl (lane 3), an expected PCR product of 219 bp was readily observed in lane 1 (0.1 μl) and lane 2 (1 μl), but not in lane 3 (10 μl). The expected size of PCR product (219 bp) was also observed in GLRaV-3 dsRNA as positive control (lane 4), but not from proteinase K treated healthy grapevine tissue as negative control (lane 5). Lane M was the molecular weight standard of Hae III digested fX 174 DNA.

Figure 15:
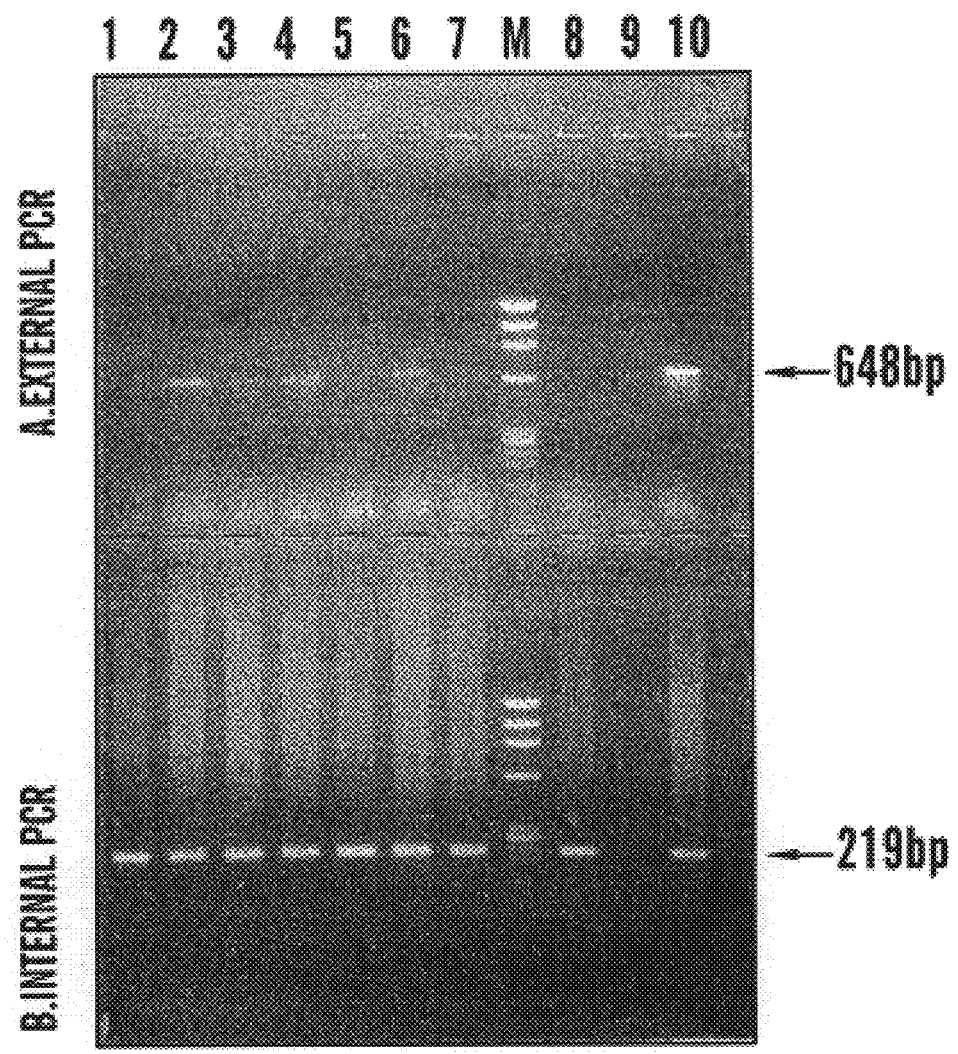

FIG. 15 depicts a comparative analysis of Nested PCR with immuno-capture preparations on field collected samples. Using a polyclonal antibody to GLRaV-3 for immuno-capture, the expected PCR product of 648 bp was not consistently observable in the first round of PCR amplification with external primers over a range of samples (lanes 1–7, panel A). However, the expected PCR product of 219 bp amplified by internal primers was consistently observed over all seven samples (lanes 1–7, panel B). A similar inconsistency is also shown in a sample prepared by proteinase K-treated crude extract (compare panels A to B on lane 8). With dsRNA as template, the expected PCR products were readily observable in both reactions (compare panels A to B on lane 10). No such products were observed on a healthy sample (lane 9). Lane M was a molecular weight marker of Hae III digested fX 174 DNA.

Figure 16A:
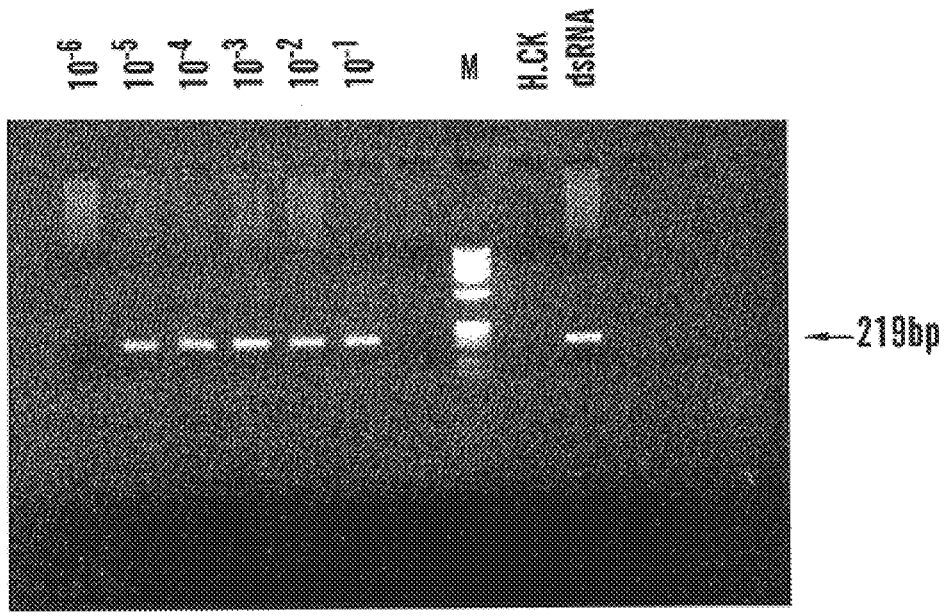

FIG. 16 depicts comparative studies on the sensitivity of Nested PCR with samples prepared by proteinase K-treated crude extract (panel A, PK Nested PCR) and by immuno-capture preparation (panel B, IC Nested PCR). Nested PCR was performed on samples with serial 10-fold dilutions of up to $10^{-6}$ in a proteinase K-treated (panel A) and $10^{-8}$ in an immuno-capture preparation (panel B). The expected PCR product of 219 bp was observable up to $10^{-5}$ in PK Nested PCR and over $10^{-8}$ (the highest dilution used in this test) in IC Nested PCR. A similar PCR product was also observed with dsRNA template but not from healthy grape tissues (H. CK). Lane M was a molecular weight marker of Hae III digested fX 174 DNA.

Figure 17:
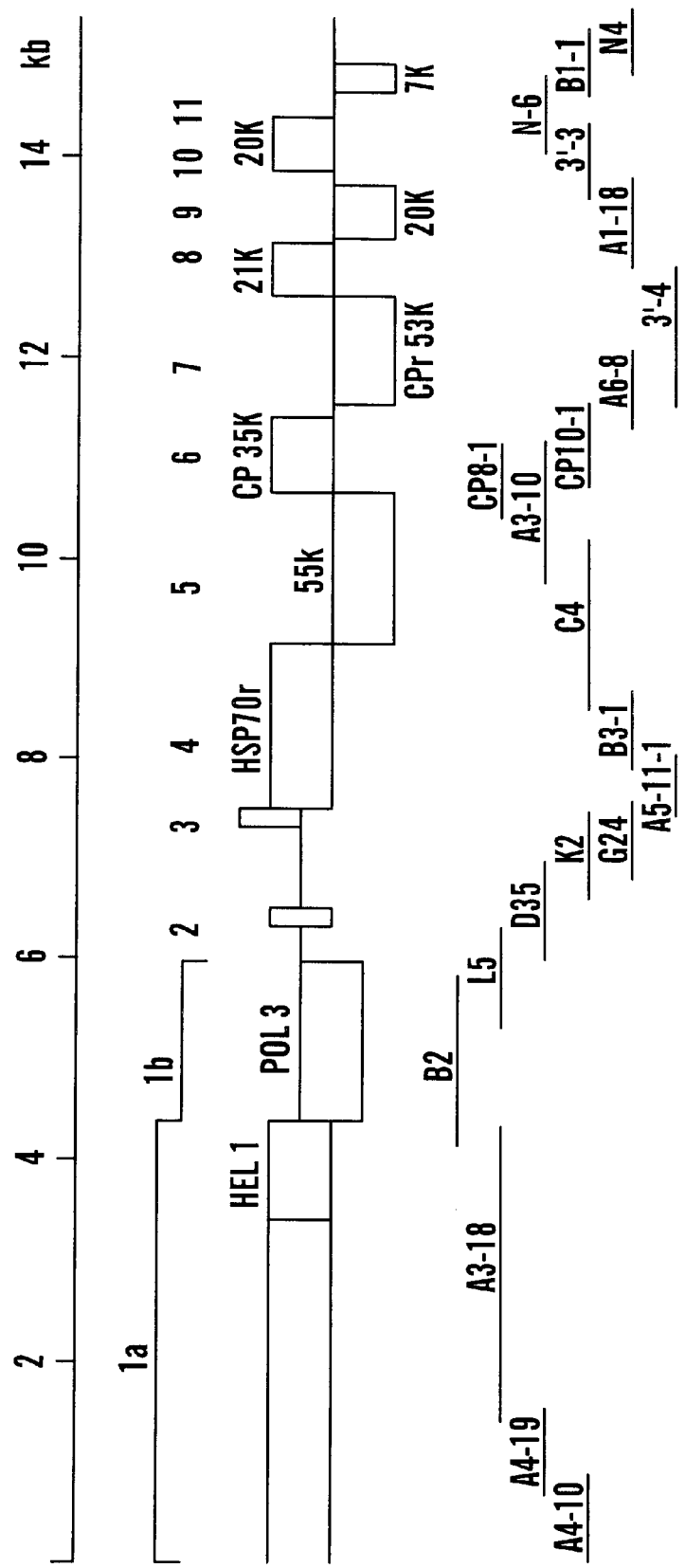

FIG. 17 shows the partial genome organization of GLRaV-3 and the cDNA clones used to determine the nucleotide sequences. Numbered lines represent nucleotide coordinates in kilobases(kb).

FIGS. 18A to W show the nucleotide sequence and partial genome organization of GLRaV-3 (SEQ ID NOS:1–24 and 39–48).

Figure 19:
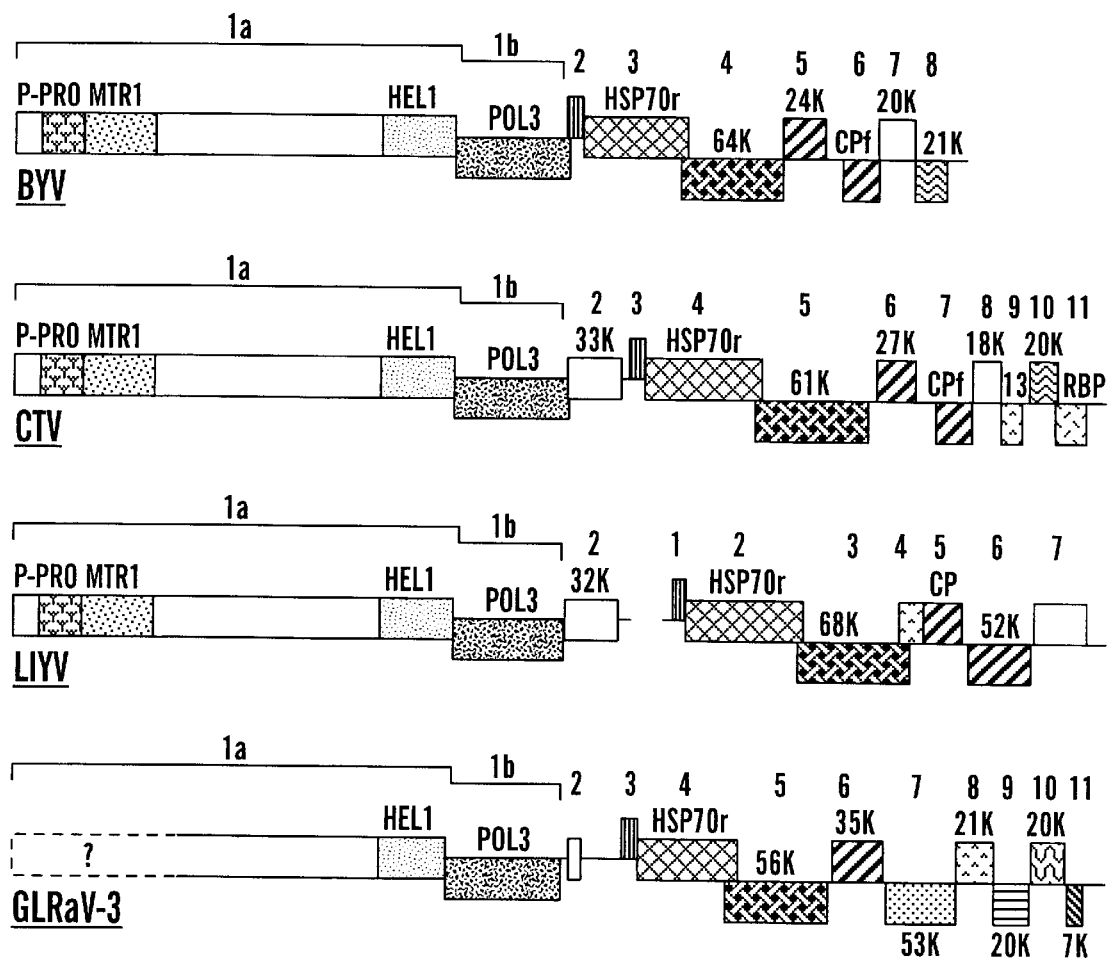

FIG. 19 depicts the proposed genome organization of the GLRaV-3 in comparison with three other closterovirus genomes, BYV, CTV, and LIYV (Dolja (1994)). Homologous proteins are shown by identical patterns. Papain-like proteinase ("P-PRO"); methyltransferase of type 1 ("MTR1"); RNA helicase of superfamily 1 ("HEL1"); RNA polymerase of supergroup 3 ("PTOL"); HSP70-related protein ("HSP70r"); and capsid protein forming filamentous virus particle ("CPf").

FIG. 20 compares the amino acid sequence alignment of the helicase of GLRaV-3 (SEQ ID NO:2) with respect to BYV (SEQ ID NO:49), CTV (SEQ ID NO:50), and LIYV (SEQ ID NO:51). Consensus amino acid residues are shown. Uppercase letters indicate identical amino acids, lowercase letters indicate at least three identical or functionally similar amino acids. Six conserved motifs (I to VI) that are conserved among the Superfamily 1 helicase (Koonin et al., "Evolution and Taxonomy of Positive-strand RNA Viruses: Implications of Comparative Analysis of Amino Acid Sequences," *Critical Reviews in Biochemistry and Molecular Biology*, 28:375–430 (1993)) of the positive-strand RNA viruses are overlined.

Figure 21:
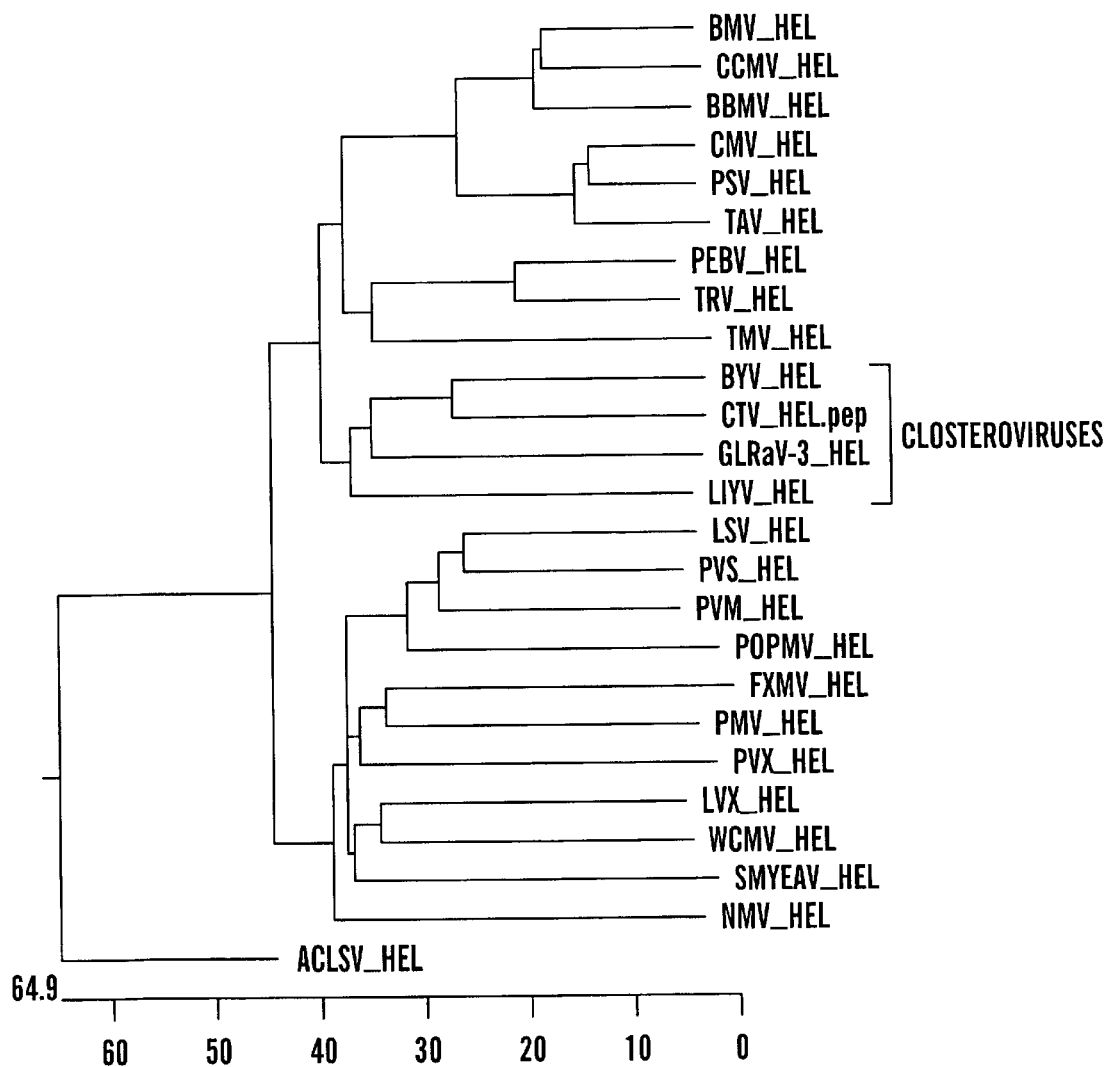

FIG. 21 is a phylogenetic tree showing the amino acid sequence relationship of helicase of alphaviruses. The helicase domain of GLRaV-3 (291 aa) from the present study is used. The other virus sequences were obtained from current databases (Swiss-Prot and GenBank, release 84.0). Apple chlorotic leafspot virus ("ACLSV"); broad bean mottle virus ("BbMV"); brome mosaic virus ("BMV"); beet yellow closterovirus ("BYV"); cowpea chlorotic mottle virus ("CcMV"); cucumber mosaic virus ("CMV"); fox mosaic virus ("FxMV"); lily symptomless virus ("LSV"); lily virus X ("LXV"); narcissus mosaic virus ("NMV"); pea early browning virus ("PeBV"); papaya mosaic virus ("PMV"); poplar mosaic virus ("PopMV"); peanut stunt virus ("PSV"); potato virus S ("PVS"); potato virus M ("PVM"); potato virus X ("PVX"); strawberry mild yellow edge-associated virus ("Sm Yea V"); tomato aspermy virus ("TAV"); tobacco mosaic virus ("TMV"); tobacco rattle virus ("TRV"); and white clover mosaic virus ("WcMV").

FIG. 22 compares the amino acid sequence alignment of the RNA dependent RNA polymerase (RdRp) of GLRaV-3 (SEQ ID NO:4) with respect to BYV (SEQ ID NO:52), CTV (SEQ ID NO:53), and LIYV (SEQ ID NO:54). Consensus amino acid residues are shown. Uppercase letters indicate identical amino acids, and lower case letters indicate at least three identical or functionally similar amino acids. The motifs (I to VIII) that are conserved among Supergroup 3 RNA polymerase of positive-strand RNA viruses are overlined.

Figure 23:
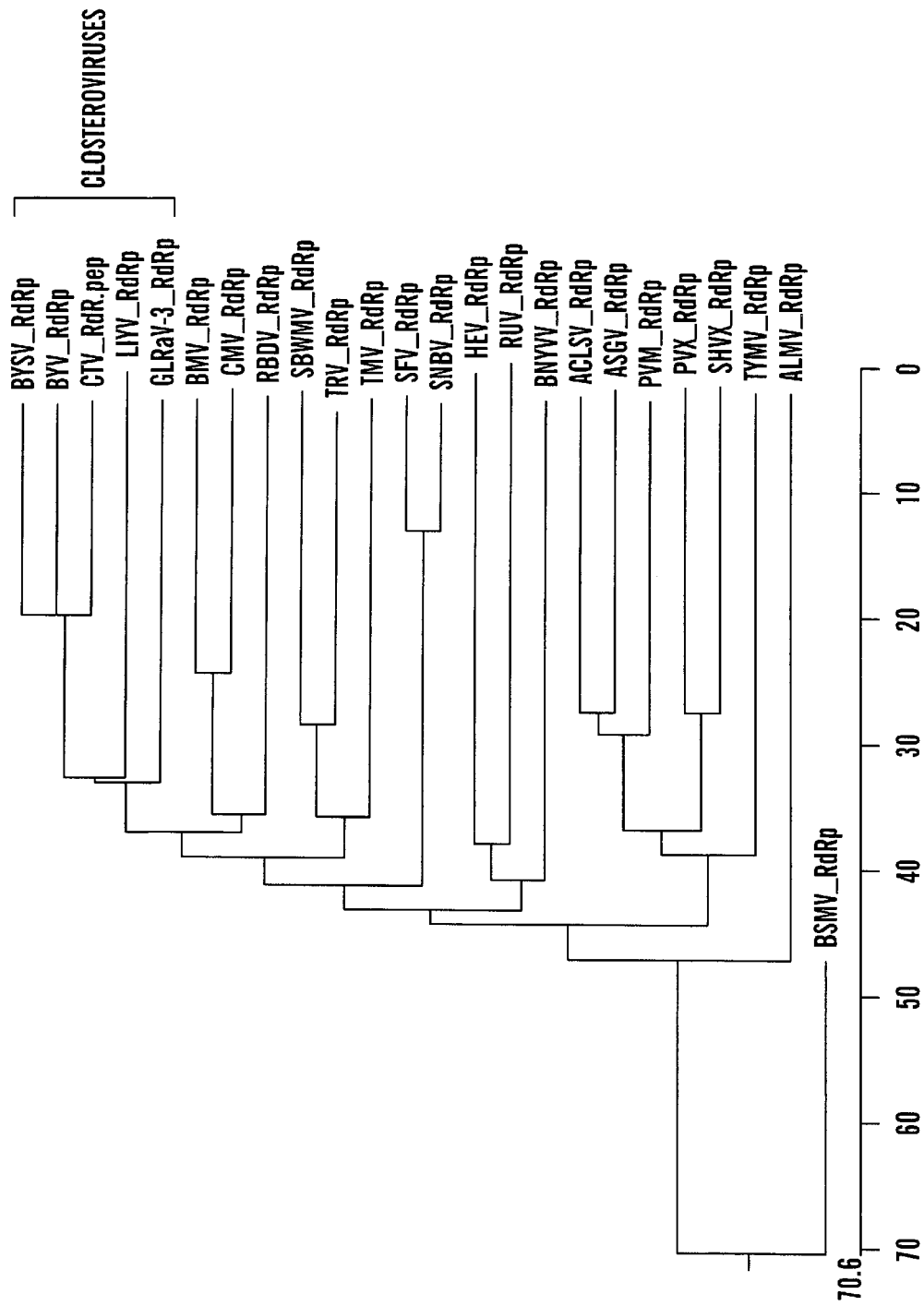

FIG. 23 shows the phylogenetic tree for the RNA dependent RNA polymerases (RdRp) of the alpha-like supergroup of positive strand RNA viruses. RdRp of GLRaV-3 was incorporated into a previously described alignment (Dolja (1994)) for comparison. The other virus sequences were obtained from current databases: Apple chlorotic leaf spot virus ("ACLSV"); alfalfa mosaic virus ("AlMV"); apple stem grooving virus ("ASGV"); brome mosaic virus ("BMV"); beet necrotic yellow vein virus ("BNYVV"); beet yellow virus ("BYV"); barley stripe mosaic virus ("BSMV"); beet yellow stunt virus ("BYSV"); cucumber mosaic virus ("CMV"); citrus tristeza virus ("CTV"); hepatitis E virus ("HEV"); potato virus M ("PVM"); potato virus X ("PVX"); raspberry bushy dwarf virus ("RBDV"); shallot virus X ("SHVX"); Sinbis virus ("SNBV"); tobacco mosaic virus ("TMV"); tobacco rattle virus ("TRV"); and turnip yellow mosaic virus ("TYMV").

FIG. 24 compares the alignment of the GLRaV-3 and LIYV nucleotide sequences (presented as DNA) in the vicinity of the proposed frameshift, nt 4,099–4,165 in GLRaV-3 (SEQ ID NO:1) and nt 5,649–5,715 in LIYV (SEQ ID NO:64). Identical nucleotides are typed in uppercase letters. LIYV +1 frameshift region (aAAG) and the corresponding GLRaV-3 (cACA) are bold and italic. The encoded C-terminus of the HEL and N-terminus of RdRp are presented above (GLRaV-3) (SEQ ID NOS:2 and 4) and below (LIYV) (SEQ ID NOS:65 and 66) the nucleotide alignment. Repeat sequences are underlined.

FIG. 25 compares the amino acid alignment of the small hydrophobic transmembrane protein of GLRaV-3 p5K (SEQ ID NO:14) with respect to BYV (p6K) (SEQ ID NO:55), CTV (p6K) (SEQ ID NO:57), and LIYV (p5K) (SEQ ID NO:56). Consensus amino acid residues are shown. Lowercase letters indicate at least three identical or functionally similar amino acids. The transmembrane domain that has been identified in several other closteroviruses, BYV, CTV, and LIYV (Karasev et al., Complete Sequence of the Citrus Tristeza Virus RNA Genome," Virology, 208:511–520 (1995)), is overlined.

FIGS. 26A to B present the amino acid sequence alignment of the HSP70-related protein of GLRaV-3 (p59K) (SEQ ID NO:6) with respect to BYV (p65K) (SEQ ID NO:58), CTV (p65K) (SEQ ID NO:59), and LIYV (p62K) (SEQ ID NO:60). The eight conserved motifs (A to H) of cellular HSP70 are overlined. Consensus amino acid residues are shown. Uppercase letters indicate identical amino acids, and lowercase letters indicate at least three identical or functionally similar amino acids.

Figure 27:
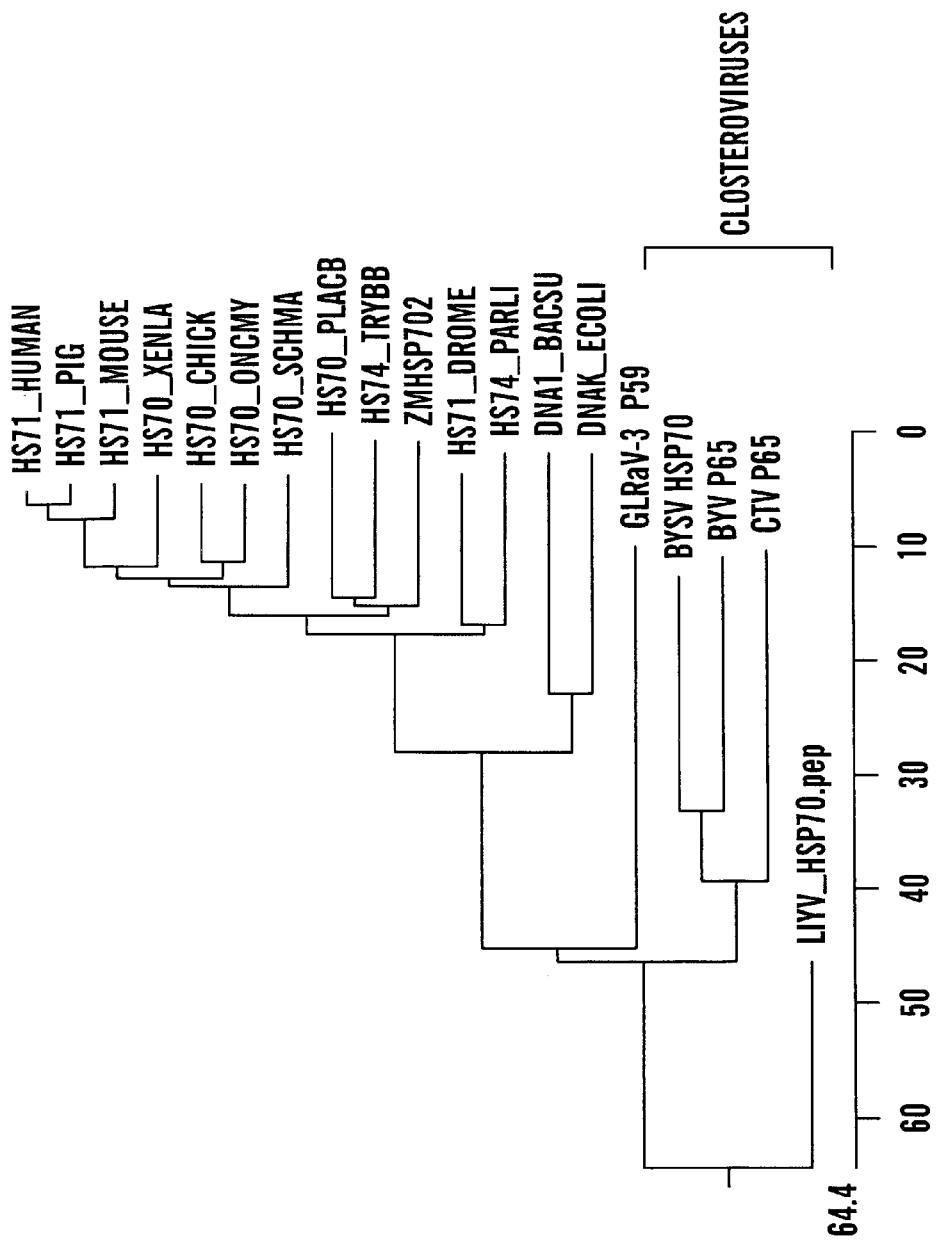

FIG. 27 is a phylogenetic relationship for viral and cellular HSP70 proteins. HSP70-related protein of GLRaV-3 (p59) was incorporated into a previously described alignment (Dolja (1994)) for comparison. The sequences of BYV, CTV, and LIYV proteins were from Agranovsky et al., "Putative 65-kDa protein of Beet Yellows Closterovirus is a Homologue of HSP70 Heat Shock Proteins," Journal of General Virology, 217:603–610 (1991), Pappu et al., "Nucleotide Sequence and Organization of Eight 3' Open Reading Frames of the Citrus Tristeza Closterovirus Genome," Virology, 199:35–46 (1994), and Klaassen et al., "Genome Structure and Phylogenetic Analysis of Lettuce Infectious Yellows Virus, a Whitefly-transmitted, Bipartite Closterovirus," Virology, 208:99–110 (1995), respectively. Only N-terminal half of beet yellow stunt virus HSP70-related protein (Karasev et al., "Screening of the Closterovirus Genome by Degenerate Primer-mediated Polymerase Chain Reaction," Journal of General Virology, 75:1415–1422 (1994)) is used. Other sequences were obtained from the Swiss-Prot database; their accession numbers are as follows: DNA1_BACSU, Bacillus subtilis (P13343); DNAK_ECOLI, Escherichia coli (P04475); HS70_CHICK (P08106); HS70_ONCMY, Oncorhynchus mykiss (P08108); HS70_PLACB, Plasmodium cynomolgi (Q05746); HS70_SCHMA, Schistosoma mansoni (P08418); HS70_XENLA, Xenopus laevis (P02827); HS71_DROME, Drosophila melanogaster (P02825); HS71_HUMAN (P08107); HS71_MOUSE (P17879); HS71_PIG (P34930); HS74_PARLI, Paracentrotus lividus (Q06248); HS74_TRYBB, Trypanosoma brucei (P11145); and ZMHSP702, maize gene for heat shock protein 70 exon 2 (X03697).

FIGS. 28A to B compare the amino acid sequence alignment of the HSP90-related proteins of GLRaV-3 (p55K) (SEQ ID NO:8) with respect to BYV (p64K) (SEQ ID NO:61), CTV (p61K) (SEQ ID NO:62), and LIYV (p59K) (SEQ ID NO:63). Two domains, I and II, which have been identified on CTV (p61K) are overlined. Consensus amino acid residues are shown. Uppercase letters indicate identical amino acids; lowercase letters indicate at least three identical or functionally similar amino acids.

FIGS. 29A to B show a nucleotide sequence fragment (SEQ ID NOS:1, 7, 29, and 67) containing the 43 kDa open reading frame (SEQ ID NO:8) that was used to engineer a plant expression cassette, pBI525GLRaV-3hsp90. This sequence fragment (from nucleotides 9,404 to 10,503 of the partial GLRaV-3 genome sequence, FIG. 18) was later proven to be located in the 3' portion of GLRaV-3 HSP90-related gene. Nucleotides in the lower case were designed to facilitate engineering by addition of NcoI restriction sites.

Figure 30:
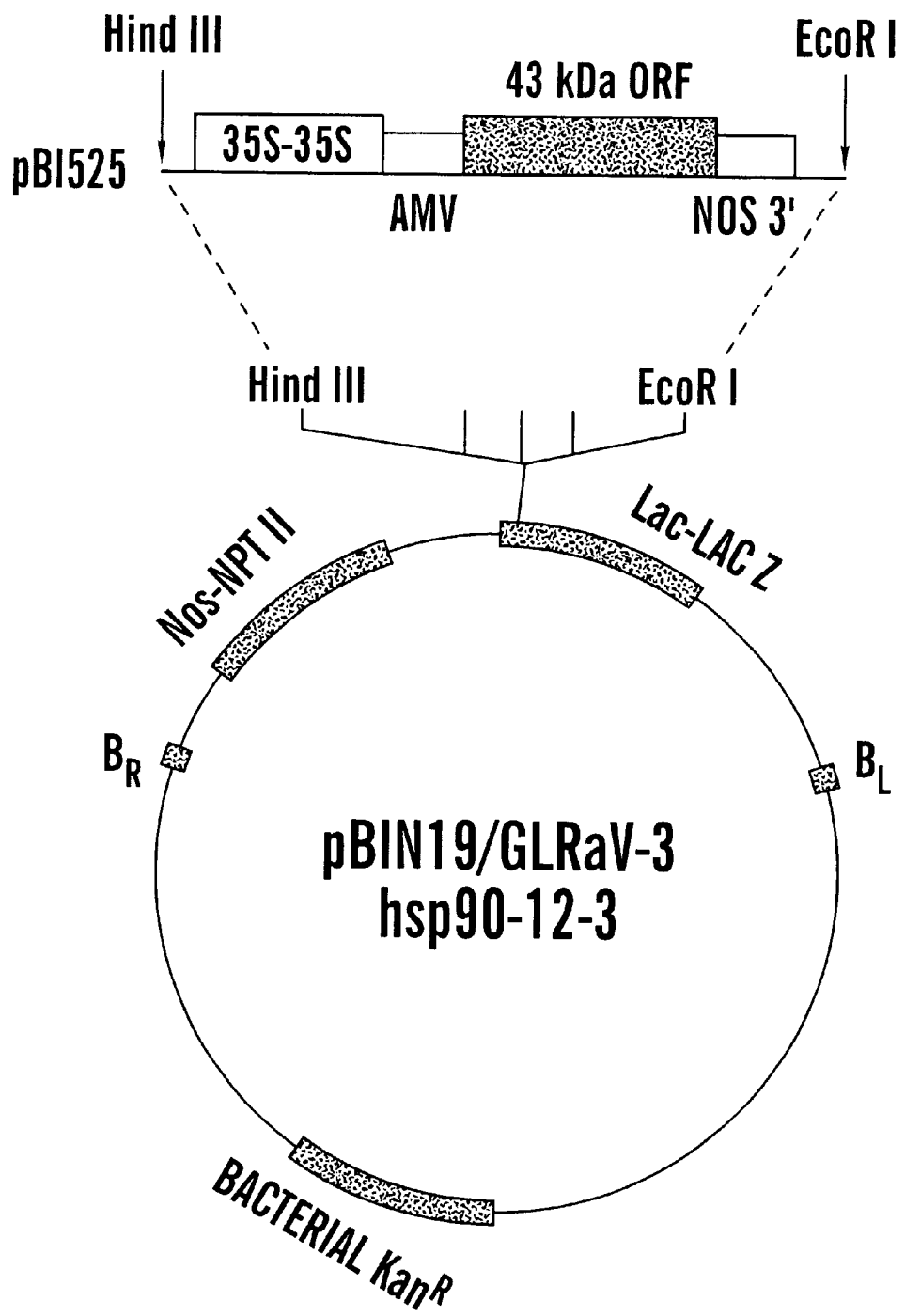

FIG. 30 is a diagram summarizing the strategies employed in the construction of the plant transformation vector pBin19GLRaV-3hsp90-12-3. A plant expression cassette, in the Hind III-EcoR I fragment containing CaMV 35S-35S promoters-AMV 5' untranslated sequence-43K ORF-Nos 3' untranslated region, was excised from pBI525GLRaV-3hsp90 and cloned into the similar restriction enzyme treated plant transformation vector pBin19. The resulting clone, pBin19GLRaV-3hsp90-12-3, is shown. Locations of important genetic elements within the binary plasmid are indicated: BR, right border; BL, left border; Nos-NPT II, plant expressible neomycin phosphotransferase gene; Lac-LAC Z, plant expressible Lac Z gene; and Bacterial Kan, bacterial kanamycin resistant gene.

Figure 31:
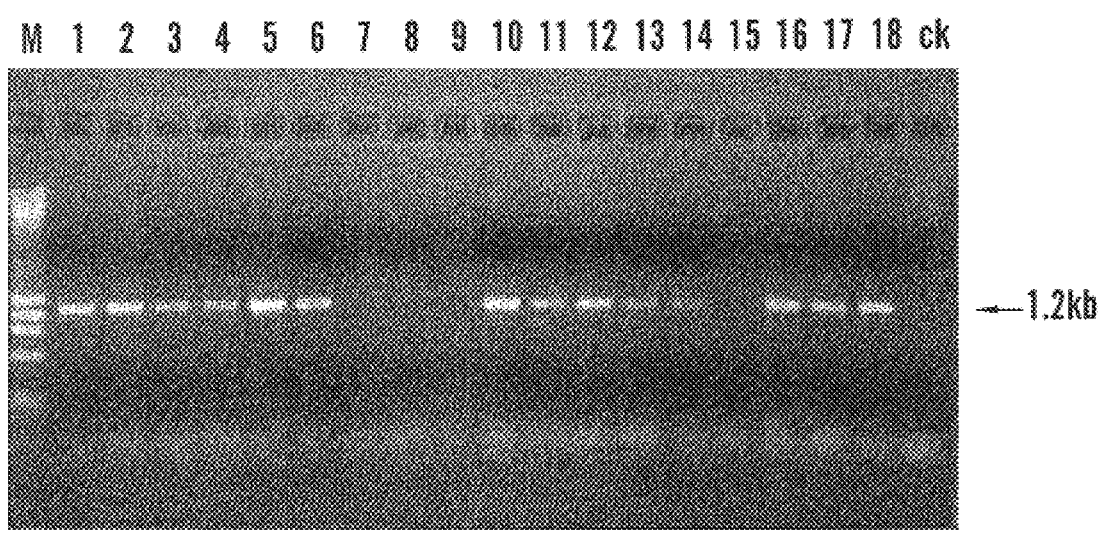

FIG. 31 presents an analysis of transgenic tobacco plants with PCR. Using primers flanking the 43K ORF, the proper size of PCR product (1.2 kb) was readily observed from 14 of the 18 kanamycin resistant plants. Lane ck shows a healthy control of nontransformed tobacco. Lane M shows a Mr marker of λ Hind III and fx174 Hae III.

Figure 32:
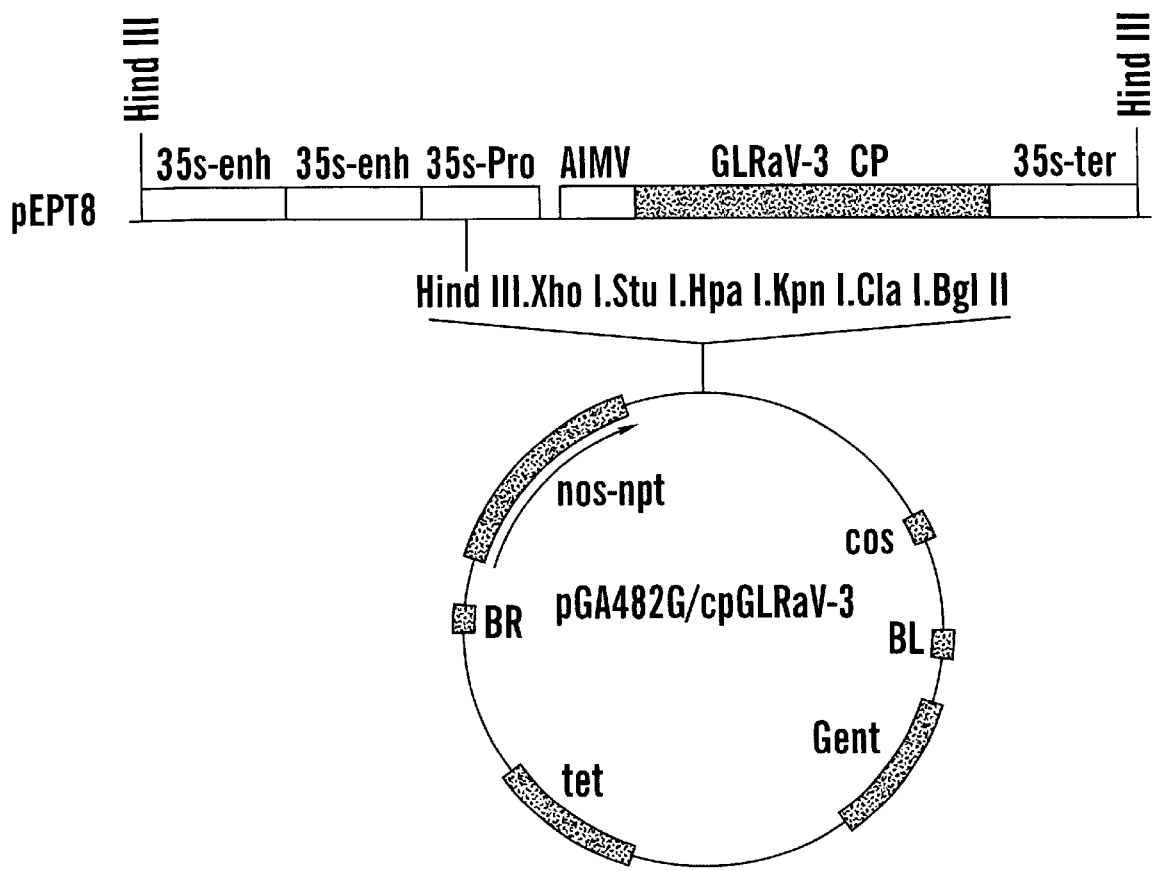

FIG. 32 shows the Agrobacterium-binary vector pGA482G/cpGLRaV-3, which was constructed by cloning the HindIII fragment of pEPT8cpGLRaV-3 into a derivative of pGA482 and used for transformation via Agrobacterium or Biolistic approach.

DETAILED DESCRIPTION OF THE INVENTION

The present invention relates to isolated DNA molecules encoding for the proteins or polypeptides of a grapevine leafroll virus. Applicants have sequenced a substantial portion of the grapevine leafroll virus genome within which are a plurality of open reading frames, each containing DNA molecules in accordance with the present invention. One such DNA molecule constitutes an open reading frame which codes for a grapevine leafroll virus helicase and comprises the nucleotide sequence corresponding to SEQ. ID. NO: 1 as follows:

```
GTGTCTACTT ACGCGAAGAG TGTGATGAAC GACAATTTCA
ATATCCTTGA

GACCCTGGTA ACTTTGCCCA AGTCCTTTAT AGTCAAAGTA
CCTGGTTCGG

TGCTGGTTAG CATAACCACT TCGGGCATTT CCGACAAACT
TGAACTTCGG

GGCGCGTTCG ACGTTTCTAA AAAGAATTTC TCCAGGAGGT
TACGTTCGAG

TCGTTTGCGC GTATTTTCTA GGGCTATTGT GGAGGATACG
ATCAAGGTTA

TGAAGGGCAT GAAATCAGAG GATGGTAAAC CACTCCCTAT
AGCCGAGGAT
```

-continued

```
TCCGTGTACG CGTTCATGAC AGGCAATATG TCAAACGTTC
ATTGCACTAG

GGCTGGTTTG CTCGGGGCT CAAAGGCTTG CGCGGCTTCT
TTAGCTGTGA

AGGGTGCAGC TTCACGCGCT ACTGGAACAA AACTCTTTTC
AGGTCTCACA

TCCTTTCTTT CCGCCGGTGG TCTGTTTTAC GATGAAGGCT
TGACGCCCGG

AGAGAGGCTT GATGCACTAA CGCGCCGTGA ACATGCTGTG
AATTCACCTG

TAGGCCTCTT AGAACCTGGA GCTTCGGTTG CGAAGCGGGT
CGTTTCCGGA

ACGAAAGCTT TTCTGTCAGA ATTGTCATTG GAGGACTTCA
CCACTTTCGT

CATAAAAAAT AGGGTGCTTA TTGGTGTTTT TACTCTTTCC
ATGGCTCTCA

CTCCGGTGGT CTGGAAGTAC AGAAGGAATA TCGCGCGAAC
TGGCGTGGAT

GTTTTCCACC GTGCTCGTTC GGGTACCGCG GCCATCGGTT
TACAATGTCT

TAGTGGAGGA AGGTCGTTAG CTGGTGACGT TGCTCGTGGC
GCGTTAACAG

TGACTCGAGG AGGGCTATCT TCGGCGGTTG CGGTGACCAG
AAATACAGTG

GCTAGGCGTC AGGTACCATT GGCGTTGCTT TCGTTTTCCA
CGTCTTACGC

AGTCAGTGGT TGCACTTTGT TAGGTATTTG GGCTCATGCT
CTCCCTAGGC

ATTTGATGTT CTTCTTTGGC CTAGGGACGC TCTTCGGGGT
GAGTGCCAGT

ACCAATTCTT GGTCGCTTGG GGGCTATACG AACAGTCTGT
TCACCGTACC

GGAATTAACT TGGGAAGGGA GGAGTTACAG ATCTTTATTG
CCCCAAGCAG

CTTTAGGTAT TTCTCTCGTT GTGCGCGGGT TGTTAAGTGA
AACTGTGCCA

CAACTAACGT ACGTACCGCC GATTGAAGGT CGGAATGTTT
ATGATCAGGC

ACTAAATTTT TATCGCGACT TTGACTATGA CGATGGTGCA
GGCCCATCCG

GGACGGCTGG TCAAAGCGAT CCTGGAACCA ATACTTCGGA
TACTTCTTCG

GTTTTCTCTG ACGATGGTTT GCCCGCTAGT GGCGGTGGCT
TCGACGCGCG

CGTTGAGGCA GGTCCCAGCC ATGCTGTTGA TGAATCACCA
AGGGGTAGTG

TTGAGTTCGT CTACAGAGAA CGTGTAGATG AACATCCGGC
GTGTGGTGAA

GCTGAAGTTG AAAAGGATCT AATAACACCA CTTGGTACAG
CTGTCTTAGA

GTCGCCCCCC GTAGGTCCTG AAGCTGGGAG CGCGCCCAAC
GTCGAGGACG

GTTGTCCGGA GGTTGAAGCT GAGAAATGTT CGGAGGTCAT
CGTTGACGTT
```

-continued

```
CCTAGTTCAG AACCGCCGGT ACAAGAAGTC CTTGAATCAA
CCAATGGTGT

CCAAGCTGCA AGAACTGAAG AGGTTGTGCA GGGCGACACA
TGTGGAGCTG

GGGTAGCTAA ATCAGAAGTG AGTCAACGTG TGTTTCCTGC
GCAAGTACCC

GCACATGAAG CTGGTCTTGA GGCATCTAGT GGCGCGGTCG
TGGAGCCATT

GCAAGTTTCT GTGCCAGTAG CCGTAGAGAA AACTGTTTTA
TCTGTCGAGA

AGGCGCGTGA GCTAAAGGCG GTAGATAAGG GCAAGGCGGT
CGTGCACGCA

AAGGAAGTCA AGAATGTACC GGTTAAGACG TTACCACGAG
GGGCTCTAAA

AATTAGTGAG GATACCGTTC GTAAGGAATT GTGCATGTTT
AGAACGTGTT

CCTGCGGCGT GCAGTTGGAC GTGTACAATG AAGCGACCAT
CGCCACTAGG

TTCTCAAATG CGTTTACCTT TGTCGATAGC TTGAAAGGGA
GGAGTGCGGT

TTTCATCAGG GTGGCCTCGT GCCCTAGAGG ATATCTTAAC
GGCAATTAAG

TACCCAAGCG TCTTCGACCA CTGTTTAGTG CAGAAGTACA
AGATGGGTGG

AGGCGTACCA TTCCACGCTG ATGACGAGGA GTGCTATCCA
TCAGATAACC

CTATCTTGAC GGTCAATCTC GTGGGGAAGG CAAACTTCTC
GACTAAGTGC

AGGAAGGGTG GTAAGGTCAT GGTCATAAAC GTAGCTTCGG
GTGACTATTT

TCTTATGCCT TGCGGTTTTC AAAGGACGCA CTTGCATTCA
GTAAACTCCA

TCGACGAAGG GCGCATCAGT TTGACGTTCA GGGCAACTCG
GCGCGTCTTT

GGTGTAGGCA GGATGTTGCA GTTAGCCGGC GGCGTGTCGG
ATGAGAAGTC

ACCAGGTGTT CCAAACCAGC AACCACAGAG CCAAGGTGCT
ACCAGAACAA

TCACACCAAA ATCGGGGGC AAGGCTCTAT CTGAGGGAAG
TGGTAGGGAA

GTCAAGGGGA GGTCGACATA CTCGATATGG TGCGAACAAG
ATTACGTTAG

GAAGTGTGAG TGGCTCAGGG CTGATAATCC AGTGATGGCT
CTTAAACCTG

GCTACACCCC AATGACATTT GAAGTGGTTA AAGCCGGGAC
CTCTGAAGAT

GCCGTCGTGG AGTACTTGAA GTATCTGGCT ATAGGCATTG
GGAGGACATA

CAGGGCGTTG CTTATGGCTA GAAATATTGC CGTCACTACC
GCCGAAGGTG

TTCTGAAAGT ACCTAATCAA GTTTATGAAT CACTACCGGG
CTTTCACGTT
```

-continued

```
TACAAGTCGG GCACAGATCT CATTTTTCAT TCAACACAAG
ACGGCTTGCG

TGTGAGAGAC CTACCGTACG TATTCATAGC TGAGAAAGGT
ATTTTTATCA

AGGGCAAAGA TGTCGACGCG GTAGTAGCTT TGGGCGACAA
TCTGTCCGTA

TGTGATGATA TATTGGTTTT CCATGATGCT ATTAATTTGA
TGGGTGCACT

GAAAGTTGCT CGATGTGGTA TGGTGGGTGA ATCATTTAAG
TCGTTCGAAT

ACAAATGCTA TAATGCTCCC CCAGGTGGCG GTAAGACGAC
GATGCTAGTG

GACGAATTTG TCAAGTCACC CAATAGCACG GCCACCATTA
CGGCTAACGT

GGGAAGTTCT GAGGACATAA ATATGGCGGT GAAGAAGAGA
GATCCGAATT

TGGAAGGTCT CAACAGTGCT ACCACAGTTA ACTCCAGGGT
GGTTAACTTT

ATTGTCAGGG GAATGTATAA AAGGGTTTTG GTGGATGAGG
TGTACATGAT

GCATCAAGGC TTACTACAAC TAGGCGTCTT CGCAACCGGC
GCGTCGGAAG

GCCTCTTTTT TGGAGACATA AATCAGATAC CATTCATAAA
CCGGGAGAAG

GTGTTTAGGA TGGATTGTGC TGTATTTGTT CCAAAGAAGG
AAAGCGTTGT

ATACACTTCT AAATCATACA GGTGTCCGTT AGATGTTTGC
TACTTGTTGT

CCTCAATGAC CGTAAGGGGA ACGGAAAAGT GTTACCCTGA
AAAGGTCGTT

AGCGGTAAGG ACAAACCAGT AGTAAGATCG CTGTCCAAAA
GGCCAATTGG

AACCACTGAT GACGTAGCTG AAATAAACGC TGACGTGTAC
TTGTGCATGA

CCCAGTTGGA GAAGTCGGAT ATGAAGAGGT CGTTGAAGGG
AAAAGGAAAA

GAAACACCAG TGATGACAGT GCATGAAGCA CAGGGAAAAA
CATTCAGTGA

TGTGGTATTG TTTAGGACGA AGAAAGCCGA TGACTCCCTA
TTCACTAAAC

AACCGCATAT ACTTGTTGGT TTGTCGAGAC ACACACGCTC
ACTGGTTTAT

GCCGCTCTGA GCTCAGAGTT GGACGATAAG GTCGGCACAT
ATATTAGCGA

CGCGTCGCCT CAATCAGTAT CCGACGCTTT GCTTCACACG
TTCGCCCCGG

CTGGTTGCTT TCGAGGTATA TGA.
```

The helicase has an amino acid sequence corresponding to SEQ. ID. NO: 2 as follows:

```
VSTYAKSVMN DNFNILETLV TLPKSFIVKV PGSVLVSITT
SGISDKLELR
```

-continued

```
GAFDVSKKNF SRRLRSSRLR VFSRAIVEDT IKVMKGMKSE
DGKPLPIAED

SVYAFMTGNM SNVHCTRAGL LGGSKACAAS LAVKGAASRA
TGTKLFSGLT

SFLSAGGLFY DEGLTPGERL DALTRREHAV NSPVGLLEPG
ASVAKRVVSG

TKAFLSELSL EDFTTFVIKN RVLIGVFTLS MALTPVVWKY
RRNIARTGVD

VFHRARSGTA AIGLQCLSGG RSLAGDAARG ALTVTRGGLS
SAVAVTRNTV

ARRQVPLALL SFSTSYAVSG CTLLGIWAHA LPRHLMFFFG
LGTLFGVSAS

TNSWSLGGYT NSLFTCPELT WEGRSYRSLL PQAALGISLV
VRGLLSETVP

QLTYVPPIEG RNVYDQALNF YRDFDYDDGA GPSGTAGQSD
PGTNTSDTSS

VFSDDGLPAS GGGFDARVEA GPSHAVDESP TGSVEGVYRE
RVDEHPACGE

AEVEKSLITP LGTAVLESPP VGPEAGSAPN VEDGCPEVEA
EKCSEVIVDV

PSSEPPVQEV LESTNGVQAA RTEEVVQGDT CGAGVAKSEV
SQRVFPAQVP

AHEAGLEASS GAVVEPLQVS VPVAVEKTVL SVEKARELKA
VDKGKAVVHA

KEVKNVPVKT LPRGALKISE DTVRKELCMF RTCSCGVQLD
VYNEATIATR

FSNAFTFVDS LKGRSAVFFS KLGEGYTYNG GSHVSSGWPR
ALEDILTAIK

YPSVFDHCLV QKYKMGGGVP FHADDEECYP SDNPILTVNL
VGKANFSTKC

RKGGKVMVIN VASGDYFLMP CGFQRTHLHS VNSIDEGRIS
LTFRATRRVF

GVGRMLQLAG GVSDEKSPGV PNQQPQSQGA TRTITPKSGG
KALSEGSGRE

VKGRSTYSIW CEQDYVRKCE WLRADNPVMA LKPGYTPMTF
EVVKAGTSED

AVVEYLKYLA IGIGRTYRAL LMARNIAVTT AEGVLKVPNQ
VYESLPGFHV

YKSGTDLIFH STQDGLRVRD LPYVFIAEKG IFIKGKDVDA
VVALGDNLSV

CDDILVFHDA INLMGALKVA RCGMVGESFK SFEYKCYNAP
PGGGKTTMLV

DEFVKSPNST ATITANVGSS EDINMAVKKR DPNLEGLNSA
TTVNSRVVNF

IVRGMYKRVL VDEVYMMHQG LLQLGVFATG ASEGLFFGDI
NQIPFINREK

VFRMDCAVFV PKKESVVYTS KSYRCPLDVC YLLSSMTVRG
TEKCYPEKVV

SGKDKPVVRS LSKRPIGTTD DVAEINADVY LCMTQLEKSD
MKRSLKGKGK

ETPVMTVHEA QGKTFSDVVL FRTKKADDSL FTKQPHILVG
LSRHTRSLVY

AALSSELDDK VGTYISDASP QSVSDALLHT FAPAGCFRGI
``` and a molecular weight from about 146 to about 151 kDa, preferably about 148.5 kDa.

Another such DNA molecule constitutes an open reading frame which codes for a grapevine leafroll virus RNA-dependent RNA polymerase and comprises the nucleotide sequence corresponding to SEQ. ID. NO: 3 as follows:

```
ATGAATTTTG GACCGACCTT CGAAGGGGAG TTGGTACGGA
AGATACCAAC

AAGTCATTTT GTAGCCGTGA ATGGGTTTCT CGAGGACTTA
CTCGACGGTT

GTCCGGCTTT CGACTATGAC TTCTTTGAGG ATGATTTCGA
AACTTCAGAT

CAGTCTTTCC TCATAGAAGA TGTGCGCATT TCTGAATCTT
TTTCTCATTT

TGCGTCGAAA ATAGAGGATA GGTTTTACAG TTTTATTAGG
TCTAGCGTAG

GTTTACCAAA GCGCAACACC TTGAAGTGTA ACCTCGTCAC
GTTTGAAAAT

AGGAATTCCA ACGCCGATCG CGGTTGTAAC GTGGGTTGTG
ACGACTCTGT

GGCGCATGAA CTGAAGGAGA TTTTCTTCGA GGAGGTCGTT
AACAAAGCTC

GTTAGCAGA GGTGACGGAA AGCCATTTGT CCAGCAACAC
GATGTTGTTA

TCAGATTGGT TGGACAAAAG GGCACCTAAC GCTTACAAGT
CTCTCAAGCG

GGCTTTAGGT TCGGTTGTCT TTCATCCGTC TATGTTGACG
TCTTATACGC

TCATGGTGAA AGCAGACGTA AAACCCAAGT TGGACAATAC
GCCATTGTCG

AAGTACGTAA CGGGGCAGAA TATAGTCTAC CACGATAGGT
GCGTAACTGC

GCTTTTTTCT TGCATTTTTA CTGCGTGCGT AGAGCGCTTA
AAATACGTAG

TGGACGAAAG GTGGCTCTTC TACCACGGGA TGGACACTGC
GGAGTTGGCG

GCTGCATTGA GGAACAATTT GGGGGACATC CGGCAATACT
ACACCTATGA

ACTGGATATC AGTAAGTACG ACAAATCTCA GAGTGCTCTC
ATGAAGCAGG

TGGAGGAGTT GATACTCTTG ACACTTGGTG TTGATAGAGA
AGTTTTGTCT

ACTTTCTTTT GTGGTGAGTA TGATAGCGTC GTGAGAACGA
TGACGAAGGA

ATTGGTGTTG TCTGTCGGCT CTCAGAGGCG CAGTGGTGGT
GCTAACACGT

GGTTGGGAAA TAGTTTAGTC TTGTGCACCT TGTTGTCCGT
AGTACTTAGG

GGATTAGATT ATAGTTATAT TGTAGTTAGC GGTGATGATA
GCCTTATATT

TAGTCGGCAG CCGTTGGATA TTGATACGTC GGTTCTGAGC
GATAATTTTG

GTTTTGACGT AAAGATTTTT AACCAAGCTG CTCCATATTT
TTGTTCTAAG

TTTTTAGTTC AAGTCGAGGA TAGTCTCTTT TTTGTTCCCG
ATCCACTTAA

ACTCTTCGTT AAGTTTGGAG CTTCCAAAAC TTCAGATATC
GACCTTTTAC

ATGAGATTTT TCAATCTTTC GTCGATCTTT CGAAGGGTTT
CAATAGAGAG

GACGTCATCC AGGAATTAGC TAAGCTGGTG ACGCGGAAAT
ATAAGCATTC

GGGATGGACC TACTCGGCTT TGTGTGTCTT GCACGTTTTA
AGTGCAAATT

TTTCGCAGTT CTGTAGGTTA TATTACCACA ATAGCGTGAA
TCTCGATGTG

CGCCCTATTC AGAGGACCGA GTCGCTTTCC TTGCTGGCCT
TGAAGGCAAG

AATTTTAAGG TGGAAAGCTT CTCGTTTTGC CTTTTCGATA
AAGAGGGGTT

AA.
```

The RNA-dependent RNA polymerase has an amino acid sequence corresponding to SEQ. ID. NO: 4 as follows:

```
MNFGPTFEGE LVRKIPTSHF VAVNGFLEDL LDGCPAFDYD
FFEDDFETSD

QSFLIEDVRI SESFSHFASK IEDRFYSFIR SSVGLPKRNT
LKCNLVTFEN

RNSNADRGCN VGCDDSVAHE SKEIFFEEVV NKARLAEVTE
SHLSSNTMLL

SDWLDKRAPN AYKSLKRALG SVVFHPSMLT SYTLMVKADV
KPKLDNTPLS

KYVTGQNIVY HDRCVTALFS CIFTACVERL KYVVDERWLF
YHGMDTAELA

AALRNNLGDI RQYYTYELDI SKYDKSQSAL MKQVEELILL
TLGVDREVLS

TFFCGEYDSV VRTMTKELVL SVGSQRRSGG ANTWLGNSLV
LCTLLSVVLR

GLDYSYIVVS GDDSLIFSRQ PLDIDTSVLS DNFGFDVKIF
NQAAPYFCSK

FLVQVEDSLF FVPDPLKLFV KFGASKTSDI SLLHEIFQSF
VDLSKGFNRE

DCIQELAKLV TRKYKHSGWT YSALCVLHVL SANFSQFCRL
YYHNSVNLDV

RPIQRTESLS LLALKARILR WKASRFAFSI KRG
``` and a molecular weight from about 59 to about 63 kDa, preferably about 61 kDa.

Another such DNA molecule constitutes an open reading frame which codes for a grapevine leafroll virus hsp70-related protein or polypeptide and comprises the nucleotide sequence corresponding to SEQ. ID. NO: 5 as follows:

ATGGAAGTAG GTATAGATTT TGGAACCACT TTCAGCACAA TCTGCTTTTC

CCCATCTGGG GTCAGCGGTT GTACTCCTGT GGCCGGTAGT GTTTACGTTG

-continued

```
AAACCCAAAT TTTTATACCT GAAGGTAGCA GTACTTACTT
AATTGGTAAA

GCTGCGGGGA AAGCTTATCG TGACGGTGTA GAGGGAAGGT
TGTATGTTAA

CCCGAAAAGG TGGGCAGGTG TGACGAGGGA TAACGTCGAA
CGCTACGTCG

AGAAATTAAA ACCTACATAC ACCGTGAAGA TAGACAGCGG
AGGCGCCTTA

TTAATTGGAG GTTTAGGTTC CGGACCAGAC ACCTTATTGA
GGGTCGTTGA

CGTAATATGT TTATTCTTGA GAGCCTTGAT ACTGGAGTGC
GAAAGGTATA

CGTCTACGAC GGTTACAGCA GCTGTTGTAA CGGTACCGGC
TGACTATAAC

TCCTTTAAAC GAAGCTTCGT TGTTGAGGCG CTAAAAGGTC
TTGGTATACC

GGTTAGAGGT GTTGTTAACG AACCGACGGC CGCAGCCCTC
TATTCCTTAG

CTAAGTCGCG AGTAGAAGAC CTATTATTAG CGGTTTTTGA
TTTTGGGGGA

GGGACTTTCG ACGTCTCATT CGTTAAGAAG AAGGGAAATA
TACTATGCGT

CATCTTTTCA GTGGGTGATA ATTTCTTGGG TGGTAGAGAT
ATTGATAGAG

CTATCGTGGA AGTTATCAAA CAAAAGATCA AAGGAAAGGC
GTCTGATGCC

AAGTTAGGGA TATTCGTATC CTCGATGAAG GAAGACTTGT
CTAACAATAA

CGCTATAACG CAACACCTTA TCCCCGTAGA AGGGGGTGTG
GAGGTTGTGG

ATTTGACTAG CGACGAACTG GACGCAATCG TTGCACCATT
CAGCGCTAGG

GCTGTGGAAG TATTCAAAAC TGGTCTTGAC AACTTTTACC
CAGACCCGGT

TATTGCCGTT ATGACTGGGG GGTCAAGTGC TCTAGTTAAG
GTCAGGAGTG

ATGTGGCTAA TTTGCCGCAG ATATCTAAAG TCGTGTTCGA
CAGTACCGAT

TTTAGATGTT CGGTGGCTTG TGGGGCTAAG GTTTACTGCG
ATACTTTGGC

AGGTAATAGC GGACTGAGAC TGGTGGACAC TTTAACGAAT
ACGCTAACGG

ACGAGGTAGT GGGTCTTCAG CCGGTGGTAA TTTTCCCGAA
AGGTAGTCCA

ATACCCTGTT CATATACTCA TAGATACACA GTGGGTGGTG
GAGATGTGGT

ATACGGTATA TTTGAAGGGG AGAATAACAG AGCTTTTCTA
AATGAGCCGA

CGTTCCGGGG CGTATCGAAA CGTAGGGGAG ACCCAGTAGA
GACCGACGTG

GCGCAGTTTA ATCTCTCCAC GGACGGAACG GTGTCTGTTA
TCGTTAATGG

TGAGGAAGTA AAGAATGAAT ATCTGGTACC CGGGACAACA
AACGTACTGG
```

-continued

```
ATTCATTGGT CTATAAATCT GGGAGAGAAG ATTTAGAGGC
TAAGGCAATA

CCAGAGTACT TGACCACACT GAATATTTTG CACGATAAGG
CTTTCACGAG

GAGAAACCTG GGTAACAAAG ATAAGGGGTT CTCGGATTTA
AGGATAGAAG

AAAATTTTTT AAAATCCGCC GTAGATACAG ACACGATTTT
GAATGGATAA.
```

The hsp70-related protein or polypeptide has an amino acid sequence corresponding to SEQ. ID. NO: 6 as follows:

```
MEVGIDFGTT FSTICFSPSG VSGCTPVAGS VYVETQIFIP
EGSSTYLIGK

AAGKAYRDGV EGRLYVNPKR WAGVTRDNVE RYVEKLKPTY
TVKIDSGGAL

LIGGLGSGPD TLLRVVDVIC LFLRALILEC ERYTSTTVTA
AVVTVTADYN

SKKRSFVVEA LKGLGIPVRG VVNEPTAAAL YSLAKSRVED
LLLAVFDFGG

GTFDVSFVKK KGNILCVIFS VGDNFLGGRD IDRAIVEVIK
QKIKGKASDA

KLGIFVSSMK EDLSNNNAIT QHLIPVEGGV EVVDLTSDEL
DAIVAPFSAR

AVEVFKTGLD NFYPDPVIAV MTGGSSALVK VRSDVANLPQ
ISKVVFDSTD

FRCSVACGAK VYCDTLAGNS GLRLVDTLTN TLTDEVVGLQ
PVVIFPKGSP

IPCSYTHRYT VGGGDVVYGI FEGENNRAFL NEPTFRGVSK
RRGDPVETDV

AQFNLSTDGT VSVIVNGEEV KNEYLVPGTT NVLDSLVYKS
GREDLEAKAI

PEYLTTLNIL HDKAFTRRNL GNKDKGFSDL RIEENFLKSA
VDTDTILNG
``` and a molecular weight from about 57 to about 61 kDa, preferably about 59 kDa.

Another such DNA molecule constitutes an open reading frame which codes for a grapevine leafroll virus hsp90-related protein or polypeptide and comprises the nucleotide sequence corresponding to SEQ. ID. NO: 7 as follows:

```
ATGGATAAAT ATATTTATGT AACGGGGATA TTAAACCCTA
ACGAGGCTAG

AGACGAGGTA TTCTCGGTAG TGAATAAGGG ATATATTGGA
CCGGGAGGGC

GCTCCTTTTC GAATCGTGGT AGTAAGTACA CCGTCGTCTG
GGAAAACTCT

GCTGCGAGGA TTAGTGGATT TACGTCGACT TCGCAATCTA
CGATAGATGC

TTTCGCGTAT TTCTTGTTGA AAGGCGGATT GACTACCACG
CTCTCTAACC

CAATAAACTG TGAGAATTGG GTCAGGTCAT CTAAGGATTT
AAGCGCGTTT
```

-continued

```
TTCAGGACCC TAATTAAAGG TAAGATTTAT GCATCGCGTT
CTGTGGACAG

CAATCTTCCA AAGAAAGACA GGGATGACAT CATGGAAGCG
AGTCGACGAC

TATCGCCATC GGACGCCGCC TTTTGCAGAG CAGTGTCGGT
TCAGGTAGGG

AAGTATGTGG ACGTAACGCA GAATTTAGAA AGTACGATCG
TGCCGTTAAG

AGTTATGGAA ATAAAGAAAA GACGAGGATC AGCACATGTT
AGTTTACCGA

AGGTGGTATC CGCTTACGTA GATTTTTATA CGAACTTGCA
GGAATTGCTG

TCGGATGAAG TAACTAGGGC CAGAACCGAT ACAGTTTCGG
CATACGCTAC

CGACTCTATG GCTTTCTTAG TTAAGATGTT ACCCCTGACT
GCTCGTGAGC

AGTGGTTAAA AGACGTGCTA GGATATCTGC TGGTACGGAG
ACGACCAGCA

AATTTTTCCT ACGACGTAAG AGTAGCTTGG GTATATGACG
TGATCGCTAC

GCTCAAGATG GTCATAAGAT TGTTTTTCAA CAAGGACACA
CCCGGGGTA

TTAAAGACTT AAAACCGTGT GTGCCTATAG AGTCATTCGA
CCCCTTTCAC

GAGCTTTCGT AAAACCGTGT GTGCCTATAG AGTCATTCGA
CCCCTTTCAC

GAGCTTTCGT CCTATTTCTC TAGGTTAAGT TACGAGATGA
CGACAGGTAA

AGGGGGAAAG ATATGCCCGG AGATCGCCGA GAAGTTGGTG
CGCCGTCTAA

TGGAGGAAAA CTATAAGTTA AGATTGACCC CAGTGATGGC
CTTAATAATT

ATACTGGTAT ACTACTCCAT TTACGGCACA AACGCTACCA
GGATTAAAAG

ACGCCCGGAT TTCCTCAATG TGAGGATAAA GGGAAGAGTC
GAGAAGGTTT

CGTTACGGGG GGTAGAAGAT CGTGCCTTTA GAATATCAGA
AAAGCGCGGG

ATAAACGCTC AACGTGTATT ATGTAGGTAC TATAGCGATC
TCACATGTCT

GGCTAGGCGA CATTACGGCA TTCGCAGGAA CAATTGGAAG
ACGCTGAGTT

ATGTAGACGG GACGTTAGCG TATGACACGG CTGATTGTAT
AACTTCTAAG

GTGAGAAATA CGATCAACAC CGCAGATCAC GCTAGCATTA
TACACTATAT

CAAGACGAAC GAAAACCAGG TTACCGGAAC TACTCTACCA
CACCAGCTTT

AA.
```

The hsp90-related protein or polypeptide has an amino acid sequence corresponding to SEQ. ID. NO: 8 as follows:

```
MDKYIYVTGI LNPNEARDEV FSVVNKGYIG PGGRSFSNRG
SKYTVVWENS

AARISGFTST SQSTIDAFAY FLLKGGLTTT LSNPINCENW
VRSSKDLSAF

FRTLIKGKIY ASRSVDSNLP KKDRDDIMEA SRRLSPSDAA
FCRAVSVQVG

KYVDVTQNLE STIVPLRVME IKKRRGSAHV SLPKVVSAYV
DFYTNLQELL

SDEVTRARTD TVSAYATDSM AFLVKMLPLT AREQWLKDVL
GYLLVRRRPA

NFSYDVRVAW VYDVIATLKL VIRLFFNKDT PGGIKDLKPC
VPIESFDPFH

ELSSYFSRLS YEMTTGKGGK ICPEIAEKLV RRLMEENYKL
RLTPVMALII

ILVYYSIYGT NATRIKRRPD FLNVRIKGRV SKVSLRGVED
RAFRISEKRG

INAQRVLCRY YSDLTCLARR GYGIRRNNWK TLSYVDGTLA
YDTADCITSK

VRNTINTADH ASIIHYIKTN ENQVTGTTLP HQL
``` and a molecular weight from about 53 to about 57 kDa, preferably about 55 kDa.

Another such DNA molecule constitutes an open reading frame which codes for a grapevine leafroll virus coat protein or polypeptide. The DNA molecule comprises the nucleotide sequence corresponding to SEQ. ID. NO: 9 as follows:

```
ATGGCATTTG AACTGAAATT AGGGCAGATA TATGAAGTCG
TCCCCGAAAA

TAATTTGAGA GTTAGAGTGG GGGATGCGGC ACAAGGAAAA
TTTAGTAAGG

CGAGTTTCTT AAAGTACGTT AAGGACGGGA CACAGGCGGA
ATTAACGGGA

ATCGCCGTAG TGCCCGAAAA ATACGTATTC GCCACAGCAG
CTTTGGCTAC

AGCGGCGCAG GAGCCACCTA GGCAGCCACC AGCGCAAGTG
GCGGAACCAC

AGGAAACCGA TATAGGGGTA GTGCCGGAAT CTGAGACTCT
CACACCAAAT

AAGTTGGTTT TCGAGAAAGA TCCAGACAAG TTCTTGAAGA
CTATGGGCAA

GGGAATAGCT TTGGACTTGG CGGGAGTTAC CCACAAACCG
AAAGTTATTA

ACGAGCCAGG GAAAGTATCA GTAGAGGTGG CAATGAAGAT
TAATGCCGCA

TTGATGGAGC TGTGTAAGAA GGTTATGGGC GCCGATGACG
CAGCAACTAA

GACAGAATTC TTCTTGTACG TGATGCAGAT TGCTTGCACG
TTCTTTACAT

CGTCTTCGAC GGAGTTCAAA GAGTTTGACT ACATAGAAAC
CGATGATGGA

AAGAAGATAT ATGCGGTGTG GGTATATGAT TGCATTAAAC
AAGCTGCTGC
```

-continued

```
TTCGACGGGT TATGAAAACC CGGTAAGGCA GTATCTAGCG
TACTTCACAC

CAACCTTCAT CACGGCGACC CTGAATGGTA AACTAGTGAT
GAACGAGAAG

GTTATGGCAC AGCATGGAGT ACCACCGAAA TTCTTTCCGT
ACACGATAGA

CTGCGTTCGT CCGACGTACG ATCTGTTCAA CAACGACGCA
ATATTAGCAT

GGAATTTAGC TAGACAGCAG GCGTTTAGAA ACAAGACGGT
AACGGCCGAT

AACACCTTAC ACAACGTCTT CCAACTATTG CAAAAGAAGT
AG.
```

The coat protein or polypeptide has an amino acid sequence corresponding to SEQ. ID. NO: 10 as follows:

```
MAFELKLGQI YEVVPENNLR VRVGDAAQGK FSKASFLKYV
KDGTQAELTG

IAVVPEKYVF ATAALATAAQ EPPRQPPAQV AEPQETDIGV
VPESETLTPN

KLVFEKDPDK FLKTMGKGIA LDLAGVTHKP KVINEPGKVS
VEVAMKINAA

LMELCKKVMG ADDAATKTEF FLYVMQIACT FFTSSSTEFK
EFDYIETDDG

KKIYAVWVYD CIKQAAASTG YENPVRQYLA YFTPTFITAT
LNGKLVMNEK

VMAQHGVPPK FFPYTIDCVR PTYDLFNNDA ILAWNLARQQ
AFRNKTVTAD

NTLHNVFQLL QKK
``` and a molecular weight from about 33 to about 43 kDa, preferably about 35 kDa.

Alternatively, the DNA molecule of the present invention can constitute an open reading frame which codes for a first undefined protein or polypeptide. This DNA molecule comprises the nucleotide sequence corresponding to SEQ. ID. NO: 11 as follows:

```
ATGTACAGTA GAGGGTCTTT CTTTAAGTCT CGGGTTACCC
TTCCTACTCT

TGTCGGAGCA TACATGTGGG AGTTTGAACT CCCGTATCTT
ACGGACAAGA

CACACATCAG CTATAGCGCG CCAAGTGTCG CGACTTTTAG
CCTTGTGTCG

AGGTAG.
```

The first undefined protein or polypeptide has an amino acid sequence corresponding to SEQ. ID. NO: 12 as follows:

MYSRGSFFKS RVTLPTLVGA YMWEFELPYL TDKRHISYSA PSVATFSLVSR and a molecular weight from about 5 to about 7 kDa, preferably about 6 kDa.

Another such DNA molecule constitutes an open reading frame which codes for a second undefined grapevine leafroll virus protein or polypeptide and comprises the nucleotide sequence corresponding to SEQ. ID. NO: 13 as follows:

```
ATGGATGATT TTAAACAGGC AATACTGTTG CTAGTAGTCG
ATTTTGTCTT

CGTGATAATT CTGCTGCTGG TTCTTACGTT CGTCGTCCCG
AGGTTACAGC

AAAGCTCCAC CATTAATACA GGTCTTAGGA CAGTGTGA.
```

The second undefined protein or polypeptide has an amino acid sequence corresponding to SEQ. ID. NO: 14 as follows:

MDDFKQAILL LVVDFVFVII LLLVLTFVVP RLQQSSTINT GLRTV and a molecular weight from about 4 to about 6 kDa, preferably about 5 kDa.

Another such DNA molecule constitutes an open reading frame which codes for a grapevine leafroll virus coat protein or polypeptide repeat and comprises the nucleotide sequence corresponding to SEQ. ID. NO: 15 as follows:

```
ATGGGAGCTT ATACACATGT AGACTTTCAT GAGTCGCGGT
TGCTGAAAGA

CAAACAAGAC TATCTTTCTT TCAAGTCAGC GGATGAAGCT
CCTCCTGATC

CTCCCGGATA CGTTCGCCCA GATAGTTATG TGAGGGCTTA
TTTGATACAA

AGAGCAGACT TTCCCAATAC TCAAAGCTTA TCAGTTACGT
TATCGATAGC

CAGTAATAAG TTAGCTTCAG GTCTTATGGG AAGCGACGCA
GTATCATCGT

CGTTTATGCT GATGAACGAC GTGGGAGATT ACTTCGAGTG
CGGCGTGTGT

CACAACAAAC CCTACTTAGG ACGGGAAGTT ATCTTCTGTA
GGAAATACAT

AGGTGGGAGA GGAGTGGAGA TCACCACTGG TAAGAACTAC
ACGTCGAACA

ATTGGAACGA GGCGTCGTAC GTAATACAAG TGAACGTAGT
CGATGGGTTA

GCACAGACCA CTGTTAATTC TACTTATACG CAAACGGACG
TTAGTGGTCT

ACCCAAAAAT TGGACGCGTA TCTACAAAAT AACAAAGATA
GTGTCCGTAG

ATCAGAACCT CTACCCTGGT TGTTTCTCAG ACTCGAAACT
GGGTGTAATG

CGTATAAGGT CACTGTTAGT TTCCCCAGTG CGCATCTTCT
TTAGGGATAT

CTTATTGAAA CCTTTGAAGA AATCGTTCAA CGCAAGAATC
GAGGATGTGC

TGAATATTGA CGACACGTCG TTGTTAGTAC CGAGTCCTGT
CGTACCAGAG

TCTACGGGAG GTGTAGGTCC ATCAGAGCAG CTGGATGTAG
TGGCTTTAAC

GTCCGACGTA ACGGAATTGA TCAACACTAG GGGGCAAGGT
AAGATATGTT

TTCCAGACTC AGTGTTATCG ATCAATGAAG CGGATATCTA
CGATGAGCGG
```

-continued
```
TATTTGCCGA TAACGGAAGC TCTACAGATA AACGCAAGAC
TACGCAGACT

CGTTCTTTCG AAAGGCGGGA GTCAAACACC ACGAGATATG
GGGAATATGA

TAGTGGCCAT GATACAACTT TTCGTACTCT ACTCTACTGT
AAAGAATATA

AGCGTCAAAG ACGGGTATAG GGTGGAGACC GAATTAGGTC
AAAAGAGAGT

CTACTTAAGT TATTCGGAAG TAAGGGAAGC TATATTAGGA
GGGAAATACG

GTGCGTCTCC AACCAACACT GTGCGATCCT TCATGAGGTA
TTTTGCTCAC

ACCACTATTA CTCTACTTAT AGAGAAGAAA ATTCAGCCAG
CGTGTACTGC

CCTAGCTAAG CACGGCGTCC CGAAGAGGTT CACTCCGTAC
TGCTTCGACT

TCGCACTACT GGATAACAGA TATTACCCGG CGGACGTGTT
GAAGGCTAAC

GCAATGGCTT GCGCTATAGC GATTAAATCA GCTAATTTAA
GGCGTAAAGG

TTCGGAGACG TATAACATCT TAGAAAGCAT TTGA.
```

The grapevine leafroll virus coat protein or polypeptide repeat has an amino acid sequence corresponding to SEQ. ID. NO: 16 as follows:

```
MGAYTHVDFH ESRLLKDKQD YLSFKSADEA PPDPPGYVRP
DSYVRAYLIQ

RADFPNTQSL SVTLSIASNK LASGLMGSDA VSSSFMLMND
VGDYFECGVC

HNKPYLGREV IFCRKYIGGR GVEITTGKNY TSNNWNEASY
VIQVNVVDGL

AQTTVNSTYT QTDVSGLPKN WTRIYKITKI SVSDQNLYPG
CFSDSKLGVM

RIRSLLVSPV RIFFRDILLK PLKKSFNARI EDVLNIDDTS
LLVPSPVVPE

STGGVGPSEQ LDVVALTSDV TELINTRGQG KICFRDSVLS
INEADIYDER

YLPITEALQI NARLRRLVLS KGGSQTPRDM GNMIVAMIQL
FVLYSTVKNI

SVKDGYRVET ELGQKRVYLS YSEVREAILG GKYGASPTNT
VRSFMRYFAH

TTITLLIEKK IQPACTALAK HGVPKRFTPY CFDFALLDNR
YYPADVLKAN

AMACAIAIKS ANLRRKGSET YNILESI
``` and a molecular weight from about 51 to about 55 kDa, preferably about 53 kDa.

Yet another such DNA molecule constitutes an open reading frame which codes for a third undefined grapevine leafroll virus protein or polypeptide and comprises the nucleotide sequence corresponding to SEQ. ID. NO: 17 as follows:

```
ATGGAATTCA GACCAGTTTT AATTACAGTT CGCCGTGATC
CCGGCGTAAA
```

-continued
```
CACTGGTAGT TTGAAAGTGA TAGCTTATGA CTTACACTAC
GACAATATAT

TCGATAACTG CGCGGTAAAG TCGTTTCGAG ACACCGACAC
TGGATTCACT

GTTATGAAAG AATACTCGAC GAATTCAGCG TTCATACTAA
GTCCTTATAA

ACTGTTTTCC GCGGTCTTTA ATAAGGAAGG TGAGATGATA
AGTAACGATG

TAGGATCGAG TTTCAGGGTT TACAATATCT TTTCGCAAAT
GTGTAAAGAT

ATCAACGAGA TCAGCGAGAT ACAACGCGCC GGTTACCTAG
AAACATATTT

AGGAGACGGG CAGGCTGACA CTGATATATT TTTTGATGTC
TTAACCAACA

ACAAAGCAAA GGTAAGGTGG TTAGTTAATA AAGACCATAG
CGCGTGGTGT

GGGATATTGA ATGATTTGAA GTGGGAAGAG AGCAACAAGG
AGAAATTTAA

GGGGAGAGAC ATACTAGATA CTTACGTTTT ATCGTCTGAT
TATCCAGGGT

TTAAATGA.
```

The third undefined protein or polypeptide has an amino acid sequence corresponding to SEQ. ID. NO: 18 as follows:

```
MEFRPVLITV RRDPGVNTGS LKVIAYDLHY DNIFDNCAVK
SFRDTDTGFT

VMKEYSTNSA FILSPYKLFS AVFNKEGEMI SNDVGSSFRV
YNIFSQMCKD

INEISEIQRA GYLETYLGDG QADTDIFFDV LTNNKAKVRW
LVNKDHSAWC

GILNDLKWEE SNKEKFKGRD ILDTYVLSSD YPGFK
``` and a molecular weight from about 33 to about 39 kDa, preferably about 36 kDa.

Yet another such DNA molecule constitutes an open reading frame which codes for a fourth undefined grapevine leafroll virus protein or polypeptide and comprises the nucleotide sequence corresponding to SEQ. ID. NO: 19 as follows:

```
ATGAAGTTGC TTTCGCTCCG CTATCTTATC TTAAGGTTGT
CAAAGTCGCT

TAGAACGAAC GATCACTTGG TTTTAATACT TATAAAGGAG
GCGCTTATAA

ACTATTACAA CGCCTCTTTC ACCGATGAGG GTGCCGTATT
AAGAGACTCT

CGCGAAAGTA TAGAGAATTT TCTCGTAGCC AGGTGCGGTT
CGCAAAATTC

CTGCCGAGTC ATGAAGGCTT TGATCACTAA CACAGTCTGT
AAGATGTCGA

TAGAAACAGC CAGAAGTTTT ATCGGAGACT TAATACTCGT
CGCCGACTCC

TCTGTTTCAG CGTTGGAAGA AGCGAAATCA ATTAAAGATA
ATTTCCGCTT
```

```
AAGAAAAAGG AGAGGCAAGT ATTATTATAG TGGTCATTGT
GGATCCGACG

TTGCGAAAGT TAAGTATATT TTGTCTGGGG AGAATCGAGG
ATTGGGGTGC

GTAGATTCCT TGAAGCTAGT TTGCGTAGGT AGACAAGGAG
GTGGAAACGT

ACTACAGCAC CTACTAATCT CATCTCTGGG TTAA.
```

The fourth undefined protein or polypeptide has an amino acid sequence corresponding to SEQ. ID. NO: 20 as follows:

```
MKLLSLRYLI LRLSKSLRTN DHLVLILIKE ALINYYNASF
TDEGAVLRDS

RESIENFLVA RCGSQNSCRV MKALITNTVC KMSIETARSF
IGDLILVADS

SVSALEEAKS IKDNFRLRKR RGKYYYSGDC GSDVAKVKYI
LSGENRGLGC

VDSLKLVCVG RQGGGNVLQH LLISSLG
``` and a molecular weight from about 17 to about 23 kDa, preferably about 20 kDa.

Yet another such DNA molecule constitutes an open reading frame which codes for a fifth undefined grapevine leafroll virus protein or polypeptide and comprises the nucleotide sequence corresponding to SEQ. ID. NO: 21 as follows:

```
ATGGACCTAT CGTTTATTAT TGTGCAGATC CTTTCCGCCT
CGTACAATAA

TGACGTGACA GCACTTTACA CTTTGATTAA CGCGTATAAT
AGCGTTGATG

ATACGACGCG CTGGGCAGCG ATAAACGATC CGCAAGCTGA
GGTTAACGTC

GTGAAGGCTT ACGTAGCTAC TACAGCGACG ACTGAGCTGC
ATAGAACAAT

TCTCATTGAC AGTATAGACT CCGCCTTCGC TTATGACCAA
GTGGGGTGTT

TGGTGGGCAT AGCTAGAGGT TTGCTTAGAC ATTCGAAGA
TGTTCTGGAG

GTCATCAAGT CGATGGAGTT ATTCGAAGTG TGTCGTGGAA
AGAGGGGAAG

CAAAAGATAT CTTGGATACT TAAGTGATCA ATGCACTAAC
AAATACATGA

TGCTAACTCA GGCCGGACTG GCCGCAGTTG AAGGAGCAGA
CATACTACGA

ACGAATCATC TAGTCAGTGG TAATAAGTTC TCTCCAAATT
TCGGGATCGC

TAGGATGTTG CTCTTGACGC TTTGTTGCGG AGCACTATAA.
```

The fifth undefined protein or polypeptide has an amino acid sequence corresponding to SEQ. ID. NO: 22 as follows:

```
MDLSFIIVQI LSASYNNDVT ALYTLINAYN SVDDTTRWAA
INDPQAEVNV

VKAYVATTAT TELHRTILID SIDSAFAYDQ VGCLVGIARG
LLRHSEDVLE

VIKSMELFEV CRGKRGSKRY LGYLSDQCTN KYMMLTQAGL
AAVEGADILR

TNHLVSGNKF SPNFGIARML LLTLCCGAL
``` and a molecular weight from about 17 to about 23 kDa, preferably about 20 kDa.

Yet another such DNA molecule constitutes an open reading frame which codes for a sixth undefined grapevine leafroll virus protein or polypeptide and comprises the nucleotide sequence corresponding to SEQ. ID. NO: 23 as follows:

```
ATGAGGCACT TAGAAAAACC CATCAGAGTA GCGGTACACT
ATTGCGTCGT

GCGAAGTGAC GTTTGTGACG GGTGGGATGT ATTTATAGGC
GTAACGTTAA

TCGGTATGTT TATTAGTTAC TATTTATATG CTCTAATTAG
CATATGTAGA

AAAGGAGAAG GTTTAACAAC CAGTAATGGG TAA.
```

The sixth undefined protein or polypeptide has an amino acid sequence corresponding to SEQ. ID. NO: 24 as follows:

```
MRHLEKPIRV AVHYCVVRSD VCDGWDVFIG VTLIGMFISY
YLYALISICR

KGEGLTTSNG
``` and a molecular weight from about 5 to about 9 kDa, preferably about 7 kDa.

Also encompassed by the present invention are fragments of the DNA molecules of the present invention. Suitable fragments capable of imparting grapevine leafroll resistance to grape plants are constructed by using appropriate restriction sites, revealed by inspection of the DNA molecule's sequence, to: (i) insert an interposon (Felley et al., "Interposon Mutagenesis of Soil and Water Bacteria: a Family of DNA Fragments Designed for in vitro Insertion Mutagenesis of Gram-negative Bacteria," Gene, 52:147–15 (1987), which is hereby incorporated by reference) such that truncated forms of the grapevine leafroll virus coat polypeptide or protein, that lack various amounts of the C-terminus, can be produced or (ii) delete various internal portions of the protein. Alternatively, the sequence can be used to amplify any portion of the coding region, such that it can be cloned into a vector supplying both transcription and translation start signals.

Variants may also (or alternatively) be modified by, for example, the deletion or addition of nucleotides that have minimal influence on the properties, secondary structure and hydropathic nature of the encoded polypeptide. For example, the nucleotides encoding a polypeptide may be conjugated to a signal (or leader) sequence at the N-terminal end of the protein which co-translationally or post-translationally directs transfer of the protein. The nucleotide sequence may also be altered so that the encoded polypeptide is conjugated to a linker or other sequence for ease of synthesis, purification, or identification of the polypeptide.

The protein or polypeptide of the present invention is preferably produced in purified form (preferably, at least about 80%, more preferably 90%, pure) by conventional techniques. Typically, the protein or polypeptide of the present invention is isolated by lysing and sonication. After washing, the lysate pellet is resuspended in buffer containing Tris-HCl. During dialysis, a precipitate forms from this protein solution. The solution is centrifuged, and the pellet is washed and resuspended in the buffer containing Tris-HCl. Proteins are. resolved by electrophoresis through an SDS 12% polyacrylamide gel.

The DNA molecule encoding the grapevine leafroll virus protein or polypeptide of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No: 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gtll, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/- or KS +/- (see "Stratagene Cloning Systems" Catalog (1993) from Stratagene, La Jolla, Calif., which is hereby incorporated by reference), pQE, pIH821, PGEX, pET series (see Studier et. al., "Use of T7 RNA Polymerase to Direct Expression of Cloned Genes," *Gene Expression Technology*, vol. 185 (1990), which is hereby incorporated by reference), and any derivatives thereof. Recombinant molecules can be introduced into cells via transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s) Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus; any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecules encoding the various grapevine leafroll virus proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention also relates to RNA molecules which encode the various grapevine leafroll virus proteins or polypeptides described above. The transcripts can be synthesized using the host cells of the present invention by any of the conventional techniques. The mRNA can be translated either in vitro or in vivo. Cell-free systems typically include wheat-germ or reticulocyte extracts. In vivo translation can be effected, for example, by microinjection into frog oocytes.

One aspect of the present invention involves using one or more of the above DNA molecules encoding the various proteins or polypeptides of a grapevine leafroll virus to transform grape plants in order to impart grapevine leafroll resistance to the plants. The mechanism by which resistance is imparted in not known. In one hypothetical mechanism, the transformed plant can express the coat protein or polypeptide, and, when the transformed plant is inoculated by a grapevine leafroll virus, such as GLRaV-1, GLRaV-2, GLRav-3, GLRaV-4, GLRaV-5, or GLRaV-6, or combinations of these, the expressed coat protein or polypeptide surrounds the virus, thereby preventing translation of the viral DNA.

In this aspect of the present invention the subject DNA molecule incorporated in the plant can be constitutively expressed. Alternatively, expression can be regulated by a promoter which is activated by the presence of grapevine leafroll virus. Suitable promoters for these purposes include those from genes expressed in response to grapevine leafroll virus infiltration.

The isolated DNA molecules of the present invention can be utilized to impart grapevine leafroll resistance for a wide variety of grapevine plants. The DNA molecules are particularly well suited to imparting resistance to Vitis scion or rootstock cultivars. Scion cultivars which can be protected include those commonly referred to as Table on Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars which can be protected include Couderc 1202, Couderc 1613, Couderc 1616, Couderc 3309, Dog Ridge, Foex 33 EM, Freedom, Ganzin 1 (A×R #1), Harmony, Kober 5BB, LN33, Millardet & de Grasset 41B, Millardet & de Grasset 420A, Millardet & de Grasset 101–14, Oppenheim 4 (S04) Paulsen 775, Paulsen 1045, Paulsen 1103, Richter 99, Richter 110, Riparia Gloire, Ruggeri 225, Saint-George, Salt Creek, Teleki 5A, *Vitis rupestris Constantia, Vitis california*, and *Vitis girdiana.*

There exists an extensive similarity in the hsp70-related sequence regions of GLRaV-3 and other closteroviruses, such as tristeza virus. Consequently, the GLRaV-3 hsp70-related gene can also be used to produce transgenic cultivars other than grape, such as citrus, which are resistant to closteroviruses other than grapevine leafroll, such as tristeza virus. These include cultivars of lemon, lime, orange, grapefruit, pineapple, tangerine, and the like, such as Joppa, Maltaise Ovale, Parson (Parson Brown), Pera, Pineapple, Queen, Shamouti, Valencia, Tenerife, Imperial Doblefina, Washington Sanguine, Moro, Sanguinello Moscato, Spanish Sanguinelli, Tarocco, Atwood, Australian, Bahia, Baiana, Cram, Dalmau, Eddy, Fisher, Frost Washington, Gillette, LengNavelina, Washington, Satsuma Mandarin, Dancy, Robinson, Ponkan, Duncan, Marsh, Pink Marsh, Ruby Red, Red Seedless, Smooth Seville, Orlando Tangelo, Eureka, Lisbon, Meyer Lemon', Rough Lemon, Sour Orange, Persian Lime, West Indian Lime, Bearss, Sweet Lime, Troyer Citrange, and Citrus trifoliata.

Plant tissue suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to impart grapevine leafroll virus resistance. Transformed cells can be regenerated into whole plants such that the protein or polypeptide imparts resistance to grapevine leafroll virus in the intact transgenic plants. In either case, the plant cells transformed with the recombinant DNA expression system of the present invention are grown and caused to express that DNA molecule to produce one of the above-described grapevine leafroll virus proteins or polypeptides and, thus, to impart grapevine leafroll resistance.

One technique of transforming plants with the DNA molecules in accordance with the present invention is by contacting the tissue of such plants with an inoculum of a bacteria transformed with a vector comprising a gene in accordance with the present invention which imparts grapevine leafroll resistance. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains C58, LBA4404, or EHA105) is particularly useful due to its well-known ability to transform plants.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports*, 14:6–12 (1995) ("Emerschad (1995)"), which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Once a grape plant tissue is transformed in accordance with the present invention, it is regenerated to form a transgenic grape plant. Generally, regeneration is accomplished by culturing transformed tissue on medium containing the appropriate growth regulators and nutrients to allow for the initiation of shoot meristems. Appropriate antibiotics are added to the regeneration medium to inhibit the growth of Agrobacterium and to select for the development of transformed cells. Following shoot initiation, shoots are allowed to develop tissue culture and are screened for marker gene activity.

The DNA molecules of the present invention can be made capable of transcription to a messenger RNA, which, although encoding for a grapevine leafroll virus protein or polypeptide, does not translate to the protein. This is known as RNA-mediated resistance. When a Vitis scion or rootstock cultivar is transformed with such a DNA molecule, the DNA molecule can be transcribed under conditions effective to maintain the messenger RNA in the plant cell at low level density readings. Density readings of between 15 and 50 using a Hewlet ScanJet and Image Analysis Program are preferred.

The grapevine leafroll virus protein or polypeptide can also be used to raise antibodies or binding portions thereof or probes. The antibodies can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature*, 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.*, 6:511 (1976), which is hereby incorporated by reference.) This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow et. al., editors, *Antibodies: A Laboratory Manual* (1988), which is hereby incorporated by reference.

In addition to utilizing whole antibodies, binding portions of such antibodies can be used. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, New York: Academic Press, pp. 98–118 (1983), which is hereby incorporated by reference.

The present invention also relates to probes found either in nature or prepared synthetically by recombinant DNA procedures or other biological procedures. Suitable probes are molecules which bind to grapevine leafroll viral antigens identified by the monoclonal antibodies of the present invention. Such probes can be, for example, proteins, peptides, lectins, or nucleic acid probes.

The antibodies or binding portions thereof or probes can be administered to grapevine leafroll virus infected scion cultivars or rootstock cultivars. Alternatively, at least the binding portions of these antibodies can be sequenced, and the encoding DNA synthesized. The encoding DNA molecule can be used to transform plants together with a promoter which causes expression of the encoded antibody when the plant is infected by grapevine leafroll virus. In either case, the antibody or binding portion thereof or probe will bind to the virus and help prevent the usual leafroll response.

Antibodies raised against the proteins or polypeptides of the present invention or binding portions of these antibodies can be utilized in a method for detection of grapevine leafroll virus in a sample of tissue, such as tissue from a grape scion or rootstock. Antibodies or binding portions thereof suitable for use in the detection method include those raised against a helicase, an RNA-dependent RNA polymerase, an hsp70-related, an hsp90-related, or a coat protein or polypeptide in accordance with the present invention Any reaction of the sample with the antibody is detected using an assay system which indicates the presence of grapevine leafroll virus in the sample. A variety of assay systems can be employed, such as enzyme-linked immunosorbent assays, radioimmunoassays, gel diffusion precipitin reaction assays, immunodiffusion assays, agglutination assays, fluorescent immunoassays, protein A immunoassays, or immunoelectrophoresis assays.

Alternatively, grapevine leafroll virus can be detected in such a sample using a nucleotide sequence of the DNA molecule, or a fragment thereof, encoding for a protein or polypeptide of the present invention. The nucleotide sequence is provided as a probe in a nucleic acid hybridization assay or a gene amplification detection procedure (e.g., using a polymerase chain reaction procedure). Any reaction with the probe is detected so that the presence of grapevine leafroll virus in the sample is indicated.

The following examples are provided to illustrate embodiments of the present invention but are by no means intended to limit its scope.

EXAMPLES

Example 1

Materials and Methods

Virus purification and dsRNA isolation. The NY1 isolate, which is also referred to as isolate GLRaV 109 by Golino, "The Davis Grapevine Virus Collection," *Amer. J. Enol. Vitic*, 43:200–205 (1992), a member of GLRaV-3 (Hu et al., "Characterization of Closterovirus-like Particles Associated with Grapevine Leafroll Disease," *J. Phytopathol. (Berl.)*, 128:1–14 (1990) ("Hu (1990)") and Zee et al., "Cytopathology of Leafroll-Diseased Grapevines and the Purification and Serology of Associated Closteroviruslike Particles," *Phytopathology*, 77:1427–1434 (1987) ("Zee (1987)"), which are hereby incorporated by reference) was used throughout this work. Leafroll-diseased canes and mature leaves were collected from a vineyard in central New York State, and kept at −20° C until used. GLRaV-3 virus particles were purified according to the method described by Zee (1987), which is hereby incorporated by reference, and modified later by Hu (1990), which is incorporated by reference. After two cycles of $Cs_2SO_4$ gradient purification, virus particles were observable from virus-enriched fractions by negative staining on an electron microscope.

The dsRNA was extracted from scraped bark/phloem tissue of canes as described in Hu (1990), which is hereby incorporated by reference. Briefly, total nucleic acid was extracted with phenol/chloroform; dsRNA was absorbed on a CF-11 cellulose column under 17% ethanol and eluted without ethanol. After two cycles of ethanol precipitation, dsRNA was analyzed by electrophoresis on a 6% polyacrylamide or 1% agarose gel. A high Mr dsRNA (~16 kb) along with several smaller Mr dsRNAs was consistently identified in leafroll diseased but not in healthy samples (Hu (1990), which is hereby incorporated by reference). The 16 kb dsRNA, which was presumably a replicative form of the virus, was purified further following separation on a low melting temperature-agarose gel (Sambrook et al., *Molecular Cloning, A Laboratory Manual*, 2nd Ed., Cold Spring Harbor Laboratory Press (1989) ("Sambrook (1989)"), which is hereby incorporated by reference). The double-stranded nature of the dsRNA was confirmed after it was demonstrated to be resistant to DNase and RNase in high salt but sensitive to RNase in water (Hu (1990), which is hereby incorporated by reference)

cDNA synthesis and molecular cloning. Complementary DNA (cDNA) was prepared by the procedure of Gubler et al., "A Simple and Very Efficient Method for Generating cDNA Libraries," *Gene*, 25:263 (1983), which is hereby incorporated by reference, and modified for dsRNA by Jelkmann et al., "Cloning of Four Plant Viruses from Small Quantities of Double-Stranded RNA," *Phytopathology*, 79:1250–1253 (1989), which is hereby incorporated by reference. Briefly, following denaturation of about 2 µg of dsRNA in 20 mM methylmercuric hydroxide (MeHg) for 10 min, the first-strand cDNA was synthesized by avian myeloblastosis virus ("AMV")-reverse transcriptase using random primers (Boehringer Mannheim, Indianapolis, Ind.). The second-strand cDNA was synthesized with DNA polymerase I while RNA templates were treated with RNase H. The cDNA was size-fractionated on a CL-4B Sepharose column and peak fractions, which contained larger molecular weight cDNA, were pooled and used for cloning. Complimentary DNA ends were blunted with T4 DNA polymerase, and Eco RI adapters were ligated onto a portion of the blunt-ended cDNA. After treatment with T4 polynucleotide kinase and removal of unligated adapters by spin column chromatography, the cDNA was ligated with lambda ZAPII/EcoR I prepared arms (Stratagene, La Jolla, Calif.). These recombinant DNAs were packaged in vitro with GIGAPACK II GOLD™ packaging extract according to the manufacturer's instruction (Stratagene). The packaged phage particles were used to infect bacteria, XL1-blue cells.

Screening the cDNA library. To select GLRaV-3 dsRNA specific cDNA clones, probes were prepared from UNI-AMP™ (Clontech, Palo Alto, Calif.) PCR-amplified cDNA. PCR-amplified GLRaV-3 cDNA was labeled with $^{32}P$ [a-dATP] by Klenow fragment of *E. coli* DNA polymerase I with random primers and used as a probe for screening the library (Feinberg et al., "A Technique for Radiolabeling DNA Restriction Endonuclease Fragments to High Specific Activity," *Analytic Biochem.*, 132:6–13 (1983) ("Feinberg (1983)"), which is hereby incorporated by reference). Library screening was carried out by transferring plaques grown overnight onto GENESCREEN PLUS™ filters, following the manufacturer's instructions for denaturation, prehybridization, and hybridization (Dupont, Boston, Mass.). After washing, an autoradiograph was developed after exposing Kodak X-OMAT film to the washed filters overnight at −80° C. Bacteriophage recombinants were converted into plasmids (in vivo excision) following the manufacturer's instruction (Stratagene).

Identification of the coat protein gene was done by immunoscreening the cDNA library with GLRaV-3 specific polyclonal (Zee (1987), which is hereby incorporated by reference) and monoclonal (Hu (1990), which is hereby incorporated by reference) antibodies. Degenerate primer (5'GGNGGNGGNACNTTYGAYGTNTCN (SEQ. ID. NO: 25), I=inosine, Y=T or C) generated from a conserved amino acid sequence in Motif -C of the BYV HSP70 gene (p65) was used to select HSP70 positive clones. Further sequence extension was made possible by the clone walking strategy, which used sequences that flanked the sequence contig to probe the library for a clone that might contain an insert extending farther in either 5' or 3' direction.

Northern blot hybridization. Inserts from selected clones were labeled with $^{32}$P[a-dATP] by Klenow fragment of *E. coli* DNA polymerase I (Feinberg (1983), which is hereby incorporated by reference) and used as probes to test their specific reactions to dsRNAs isolated from leafroll infected tissues. Double-stranded RNA isolated from GLRaV-3 infected vines was separated by electrophoresis on a 1% agarose gel (nondenatured condition), denatured with 50 mM NaOH, 0.6 M NaCl for 30 min at room temperature, and neutralized with 1.5 M NaCl, 0.5 M Tris-HCl, pH 7.5 for another 30 min. Denatured dsRNA was sandwich-blotted onto a GENESCREEN PLUS™ membrane. Prehybridization and hybridization were carried out in a manner similar to that described above. The membrane was washed and exposed to Kodak X-OMAT film, and an autoradiograph was developed.

Identification of inmunopositive clones. For immunoscreening, plates with plaques appearing after 8–12 h incubation at 37° C. were overlaid with a 10 mM isopropyl-β-D-thio-galactopyranoside ("IPTG") impregnated Nylon filters (GENESCREEN PLUS™) and incubated for an additional 3–4 h. After blocking with 3% bovine serum albumin ("BSA"), the blotted filter was incubated in a 1:1000 dilution of alkaline phosphatase-conjugated GLRaV-3 polyclonal antibody for 3 h at 37° C. Positive signals (purple dots) were developed by incubation of washed filters in a freshly prepared nitroblue tetrazolium ("NBT") and 5-bromo-4-chloro-3-indolyl phosphate ("BCIP") solution. To further confirm whether or not a true GLRaV-3 coat protein expression plaque was selected, a secondary immunoscreening was carried out by reinfection of bacterial XL1Blue cells with an earlier selected plaque.

Western blot analysis. After secondary immunoscreening, GLRaV-3 antibody positive plaques were converted into plasmid, the pBluescript, by in vivo excision. Single colonies were picked up and cultured in LB medium with 100 μg/ml of ampicillin until mid-log growth. Fusion protein expression was induced by addition of 10 mM IPTG with an additional 3 h of incubation at 37° C. Bacteria was pelleted and denatured by boiling in protein denaturation buffer (Sambrook (1989), which is hereby incorporated by reference). An aliquot of 5 μl denatured sample was loaded and separated by electrophoresis on a 12% SDS-polyacrylamide gel along with a prestained protein molecular weight marker (Bio-Rad, Hercules, Calif.). The separated proteins were transferred onto an Immobulon membrane (Millipore) with an electroblotting apparatus (Bio-Rad). After blocking with 3% BSA, the transferred membrane was incubated with 1:1,000 dilution of either GLRaV-3 polyclonal or monoclonal antibody alkaline phosphatase conjugate. A positive signal was developed after incubation of the washed membrane in NBT and BCIP.

PCR analysis. To analyze a cloned insert, an aliquot of a bacterial culture was used directly in PCR amplification with common vector primers (SK and KS). PCR-amplif ied product was analyzed by electrophoresis on an agarose gel.

Nucleotide sequencing and computer sequence analysis. Plasmid DNA, purified by either a CsCl method (Sambrook (1989), which is hereby incorporated by reference) or a modified mini alkaline-lysis/PEG precipitation procedure (Applied Biosystems' Instruction), was sequenced either with Sequenase version 2 kit following the manufacturer's instruction (US Biochemical, Cleveland, Ohio) or with Taq DYEDEOXY™ terminator cycle sequencing kit (Applied Biosystems, Inc.). Automated sequencing was conducted on an ABI373 automated sequencer at the New York State Agricultural Experiment Station in Geneva, N.Y.

Nucleotide sequences were analyzed using a Genetics Computer Group (GCG) sequence analysis software package (Madison, Wis.). Sequence fragments were assembled using Newgelstart to initiate the GCG fragment assembly system and to support automated fragment assembly in GCG Version 7.2.

Computer-assisted analysis of phylogenetic relationship. Amino acid sequences were either obtained from database Swiss-Prot or translated from nucleotide sequences obtained from GenBank. A phylogenetic tree depicting a relationship in the evolution of the GLRaV-3 coat protein sequence with respect to those of other filamentous plant viruses was generated using the Clustal Method of the DNASTAR's MegAlign program (Madison, Wis.). With the Clustal method, a preliminary phylogeny is derived from the distances between pairs of input sequences and the application of the UPGMA algorithm (Sneath et al., *Numerical Taxonomy—The Principles and Practice of Numerical Taxonomy*, Freeman Press (1973), which is hereby incorporated by reference) which guides the alignment of ancestral sequences. The final phylogeny is produced by applying the neighborhood joining method of Saitou et al., "The Neighbor Joining Method: A New Method for Reconstructing Phylogenetic Trees," *Mol. Biol. Evol.*, 4:406–425 (1987), which is hereby incorporated by reference, to the distance and alignment data.

Nucleotide sequence and primer selection. The sequence fragment (FIG. 2) selected for PCR has now been identified to be from nucleotides 9,364 to 10,011 of the incomplete GLRaV-3 genome (FIG. 18). This sequence region encodes a short peptide which shares sequence similarity to HSP90 homologues of other closteroviruses (FIG. 3). Selected primers and their designations are shown in FIG. 2.

Sample preparation. These include 1) dsRNA, 2) purified virus, 3) partially purified virus, 4) proteinase K treated crude extract, and 5) immuno-capture preparation.

Isolation of dsRNA from leafroll infected rapevine tissues followed the procedure developed by Hu (1990), which is hereby incorporated by reference.

Virus purification was effected by the following procedure. An aliquot of 500 μl GLRaV-3-enriched fractions after two cycles of $Cs_2SO_4$ gradient was diluted with two volumes of TE buffer (10 mM Tris, 1 mM EDTA, pH 8.0) and incubated on ice for 5 min. The reaction was then adjusted to a final concentration of 200 mM NaAc, pH 5.0, 0.5% SDS, and 200 μg/ml proteinase K and incubated at 37° C. for 3 h. Viral RNA was extracted with phenol and chloroform, ethanol-precipitated, and resuspended in 50 μl of diethyl pyrocarbonate ("DEPC")-treated $H_2O$. For each 100 μl PCR reaction mixture, 1 μl of purified viral RNA was used as template.

Partially purified virus was prepared according to the virus purification procedure described in Hu (1990), which is hereby incorporated by reference, but only to the high speed centrifugation (27,000 rpm, 2 h) step without further $Cs_2SO_4$ gradient centrifugation. The pellet was resuspended in TE buffer and subjected to proteinase K treatment as described above. Viral RNA was extracted with phenol/chloroform and precipitated by ethanol. From 10 g of starting material, the pellet was resuspended in 200 µl of DEPC treated H₂O. A 1 µl aliquot of extracted RNA or its 10-fold dilution series (up to 10⁻⁵) was used for reverse transcription-PCR ("RT-PCR").

Crude extract was treated with Proteinase K using the following procedure. Liquid nitrogen powdered grapevine bark/phloem tissue (100 mg) was macerated in 1 ml of virus extraction buffer (0.5 M Tris-HCl, pH 9.0, 0.01 M MgSO₄, 4% water insoluble polyvinyl pyrrolidone ("PVP40"), 0.5% bentonite, 0.2% 2-mercaptoethanol, and 5% Triton X-100) (Zee (1987), which is hereby incorporated by reference). After a brief centrifugation (5,000 rpm, 2 min), 500 µl of supernatant was transferred into a new tube, adjusted to 100 µg/ml proteinase K, and incubated for 1 h at 55° C. (Kawasaki, "Sample Preparation from Blood, Cells, and Other Fluids," in Innis et al., eds, *PCR Protocols: A Guide to Methods and Applications*, Academic Press, Inc. (1990), which is hereby incorporated by reference). Following incubation, the preparation was boiled for 10 min to inactivate proteinase K and to denature the viral RNA. The upper clear phase was transferred into a new tube after a brief centrifugation. The viral RNA was precipitated with ethanol and resuspended in 100 µl of DEPC-treated H₂O. An aliquot of 1 µl proteinase K-treated crude extract or its 10-fold dilution series (up to 10⁻⁶) was used.

The immuno-capture procedure was adapted from the method described by Wetzel et al., "A Highly Sensitive Immunocapture Polymerase Chain Reaction Method for Plum Pox Potyvirus Detection," *J. Virol. Meth.* 39:27–37 (1992) ("Wetzel (1992)"), which is hereby incorporated by reference. A 0.5 ml thin wall PCR tube was coated directly with 100 µl of 10 µg/ml purified gamma-globulin from GLRaV-3 antiserum (Zee (1987), which is hereby incorporated by reference) in ELISA coating buffer (15 mM Na₂CO₃, 35 mM NaHCO₃, pH 9.6, and 0.02% NaN₃) and incubated for 4 h at 30° C. After washing 3 times with PBS-Tween-20, the antibody coated tube was loaded with 100 µl of crude extract (1:10 or its 10-fold dilution series, up to 10⁻⁸) prepared in ELISA extraction buffer (50 mM sodium citrate, pH 8.3, 20 mM sodium diethyldithiocarbonate ("DIECA"), 2% PVP 40K) and incubated at 30° C. for 4 h. After washing, a 25 µl aliquot of transfer buffer (10 mM Tris, pH 8.0, 1% Triton X-100) was added to the tube and vortexed thoroughly to release viral RNA.

RT-PCR. Initially, reverse transcription ("RT") and polymerase chain reaction ("PCR") were performed in two separate reactions. An aliquot of 20 µl of reverse transcription reaction mixture was prepared to contain 2 µl of 10×PCR buffer (Promega) (10 mM Tris-HCl, pH 8.3, 500 mM KCl, and 0.01% gelatin), 50 mM MgCl₂, 2 µl of 10 mM dNTP, 150 ng of 5' and 3' primers, 16 units of RNasin, 25 units of avian myeloblastosis virus ("AMV") reverse transcriptase, and 1 µl of a denatured sample preparation. The reverse transcription reaction was carried out at 37° C. for 30 min. After denaturation by heating at 95° C. for 5 min, an aliquot of PCR reaction mixture was added. This PCR reaction mixture (80 µl) contained 8 µl of 10×PCR buffer (Promega), 150 mM MgCl₂, 250 ng of each S' and 3' primer, 1 µl of 10 mM dNTP, and 2.5 units of Taq DNA polymerase. The thermal cycling program was set as follows: a precycle at 92° C. for 3 min; followed by 35 cycles of denaturation at 92° C., 1 min; annealing at 50° C., 1 min; and extension at 72° C., 2.5 min. The final extension cycle was set at 72° C. for 5 min.

Because reverse transcriptase can work under the PCR buffer system, combination of RT and PCR would make RT-PCR in a single reaction (Ali et al., "Direct Detection of Hepatitis C Virus RNA in Serum by Reverse Transcription PCR," *Biotechniques*, 15:40–42 (1993) and Goblet et al., "One-Step Amplification of Transcripts in Total RNA Using the Polymerase Chain Reaction," *Nucleic Acids Research*, 17:2144 (1989), which are hereby incorporated by reference). The RT-PCR reaction mixture of 100 µl contains 10 µl of 10×PCR amplification buffer (Promega), 200 mM MgCl₂, 250 ng each of primers, 3 µl of 10 mM dNTPs, 40 units of RNasin, 25 units of AMV or moloney-murine leukemia virus ("M-MLV") reverse transcriptase, 2.5 units of Taq DNA polymerase, and 1 µl of denatured sample preparation. The thermal cycling program was set as follows: one cycle of cDNA synthesis step at 37° C. for 30 min, immediately followed by the PCR cycling parameters described above.

Nested PCR. Inconsistent results obtained from a single round of PCR amplification prompted an investigation into the feasibility of Nested PCR. Initial PCR amplification was performed with an external primer set (93-110 & 92-98) (FIG. 2). A PCR product of 648 bp was consistently observed from dsRNA as template, but the expected PCR product was not consistently observed in samples prepared from proteinase K-treated crude extract or immuno-capture sample preparation. Consequently, additional PCR amplification with an internal primer set (93-25 & 93-40) was carried out by adding 5 µl of the first external primer-amplified PCR product into a freshly prepared 100 µl PCR reaction mixture. The PCR cycling parameters were the same as described above.

Example 2

Virus Purification and dsRNA Isolation

Figure 5:
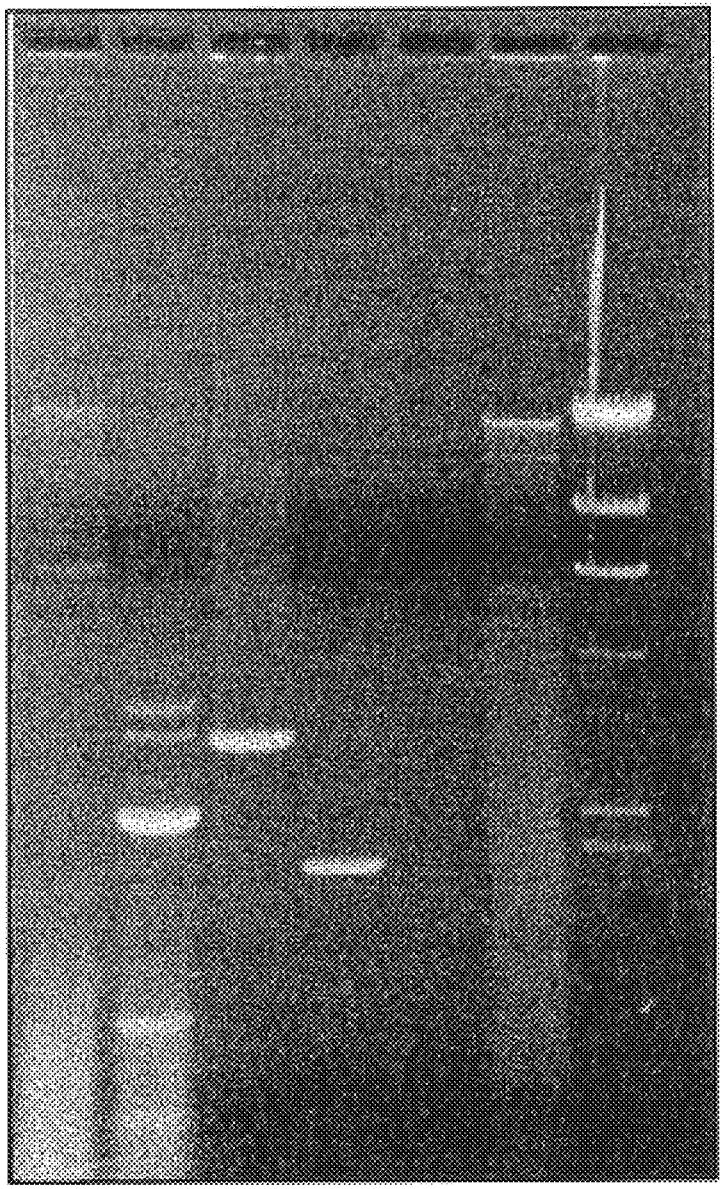

GLRaV-3 virus particles were purified directly from field collected samples of infected grapevines. Attempts to use genomic RNA for cDNA cloning failed due to low yield of virus particles with only partial purity (FIG. 1). However, under an electron microscope, virus particles were shown to be decorated by GLRaV-3 antibody. The estimated coat protein molecular weight of 41K agreed with an earlier study (Hu (1990), which is hereby incorporated by reference). Because of low yield in virus purification, dsRNA isolation was further pursued. Based on the assumption that high Mr dsRNA (16 kb) is the replicative form of the GLRaV-3 genomic RNA, this high Mr dsRNA was separated from other smaller ones by electrophoresis (FIG. 5), purified from a low melting temperature agarose gel, and used for cDNA synthesis.

Example 3 cDNA Synthesis, Molecular Cloning, and Analysis of cDNA Clones

First-strand cDNA was synthesized with AMV reverse transcriptase from purified 16 kb dsRNA which had been denatured with 10 mM MeHg. Only random primers were used to prime the denatured dsRNA because several other closteroviruses (BYV, CTV, and LIYV) have been shown to have no polyadenylated tail on the 3' end (Agranovsky et al., "Nucleotide Sequence of the 3'-Terminal Half of Beet Yellows Closterovirus RNA Genome Unique Arrangement of Eight Virus Genes," *Journal of General Virology*, 72:15–24 (1991) ("Agranovsky (1991)"), Agranovsky et al., "Beet Yellows Closterovirus: Complete Genome Structure and Identification of a Papain-like Thiol Protease," *Virology*, 198:311–324 (1994) ("Agranovsky (1994)"), Karasev et al., "Complete Sequence of the Citrus Tristeza Virus RNA Genome," *Virology*, 208:511–520 (1995) ("Karasev (1995)"), Klaassen et al., "Genome Structure and Phylogenetic Analysis of Lettuce Infectious Yellows Virus, A Whitefly-Transmitted, Bipartite Closterovirus," *Virology*, 208:99–110 (1995) ("Klaassen (1995)"), and Pappu et al., "Nucleotide Sequence and Organization of Eight 3' Open Reading Frames of the Citrus Tristeza Closterovirus Genome," *Virology*, 199:35–46 (1994) ("Pappu (1994)"), which are hereby incorporated by reference). After second-strand cDNA synthesis, the cDNA was size-fractionated on a CL-4B Sepharose column and peak fractions which contained larger molecular weight cDNA were pooled and used for cloning. An autoradiograph of this pooled cDNA revealed cDNA of up to 4 kb in size. A bacteriophage cDNA library was prepared after cloning of the synthesized cDNA into the cloning vector, lambda ZAPII.

Figure 4A:
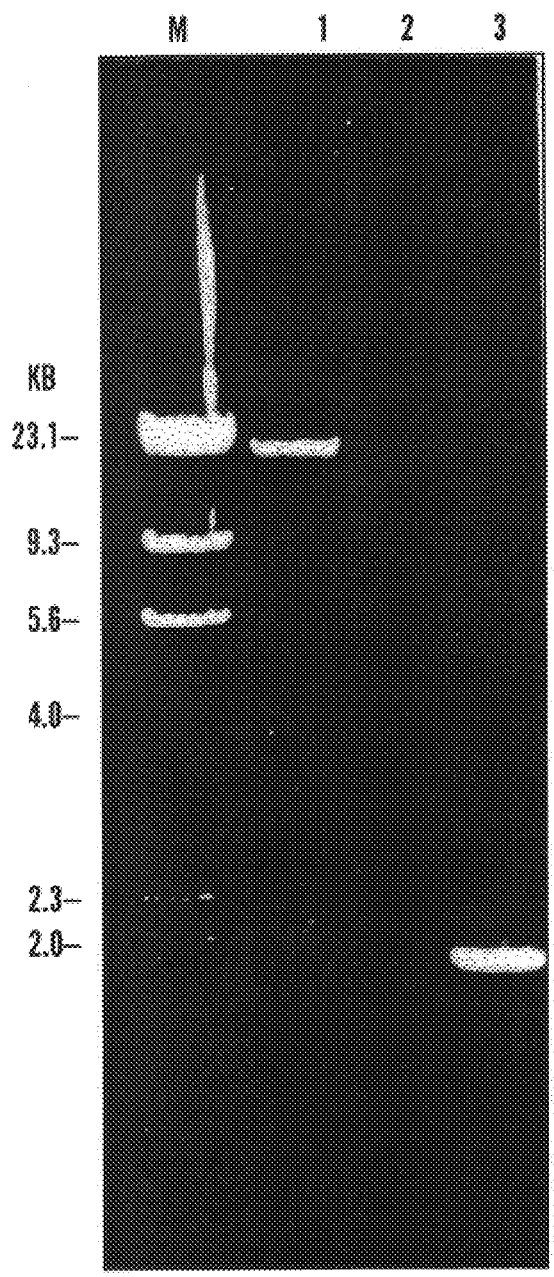
Figure 4B:
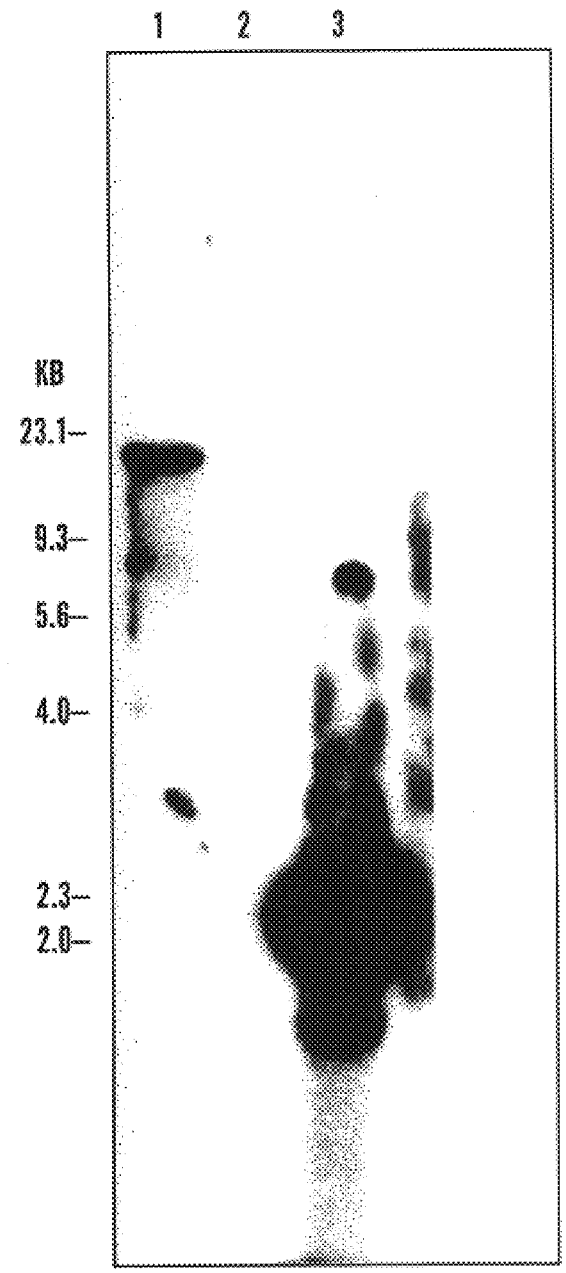

A lambda ZAPII library was prepared from cDNA that was synthesized with random primed, reverse transcription of GLRaV-3 specific dsRNA. Initially, white/blue color selection in IPTG/X-gal containing hplates was used to estimate the ratio of recombination. There were 15.70 white plaques or an estimate of 7×10$^4$ GLRaV-3 specific recombinants in this cDNA library. The library was screened with probes prepared from UNI-AMP™ PCR-amplified GLRaV-3 cDNA. More than 300 clones with inserts of up to 3 kb were selected after screening the cDNA library with probe prepared from UNI-AMP™ PCR-amplified GLRaV-3 cDNA. In Northern blot hybridization, a probe prepared from a clone insert, pC4, reacted strongly to the 16 kb dsRNA as well as to several other smaller Mr dsRNAs. Such a reaction was not observed with nucleic acids from healthy grape nor to dsRNA of CTV (FIG. 4).

Example 4

Selection and Characterization of Immunopositive Clones

Figure 6:
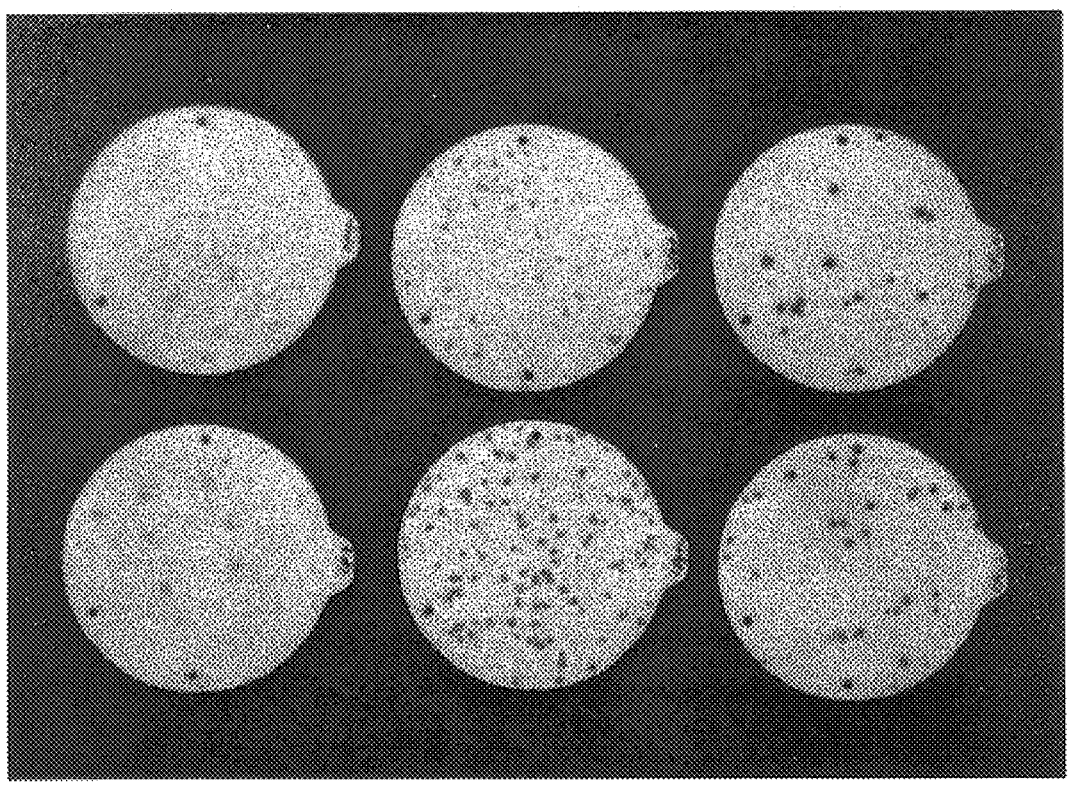
Figure 7:
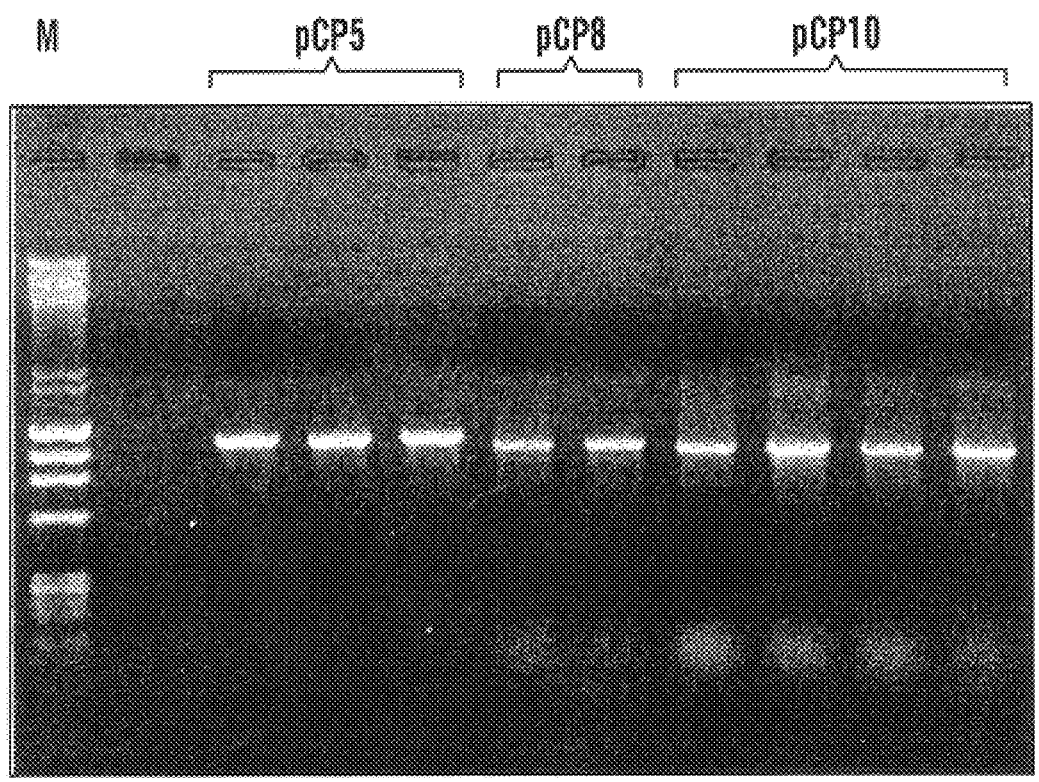

A total of 6×10$^4$ plaques were immunoscreened with GLRaV-3 specific polyclonal antibody. Three cDNA clones, designated pCP5, pCP8-4, and pCP10-1, produced proteins that reacted to the polyclonal antibody to GLRaV-3 (FIG. 6). GLRaV-3 antibody specificity of the clones was further confirmed by their reaction to GLRaV-3 monoclonal antibody. PCR analysis of cloned inserts showed that a similar size of PCR product (1.0–1.1 kb) was cloned in each immunopositive clone (FIG. 7). However, various sizes of antibody-reacting protein were produced from each clone, which suggested that individual clones were independent and contained different segments of the coat protein gene (FIG. 8). The Mr of immunopositive fusion protein from clone pCP10-1 was estimated to be 50K in SDS-PAGE, which was greater than the native coat protein of 41K (compare lanes 1 to 4 in FIG. 8). Immunopositive proteins produced in clone pCP5 (FIG. 8, lane 2) and pCP8 (FIG. 8, lane 3) were different in size and smaller than the native coat protein. Clone pCP5 produced a GLRaV-3 antibody-reacting protein of 29K. Clone pCP8-4, however, produced an antibody-reacted protein of 27K. Similar banding patterns were observed when either polyclonal (FIG. 8A) or monoclonal (FIG. 8B) antibodies were used in Western blots. These results further substantiated the proposition that these cDNA clones contained coding sequences of the GLRaV-3 coat protein,gene.

Example 5

Nucleotide Sequencing and Identification of the Coat Protein Gene

Figure 9:
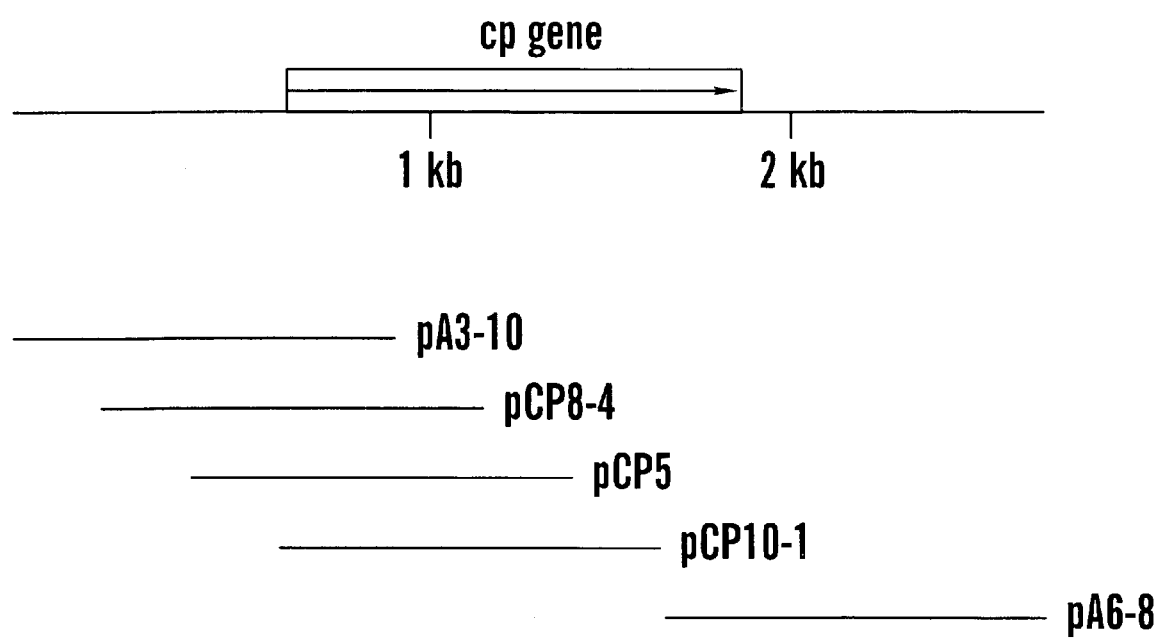
Figure 12:
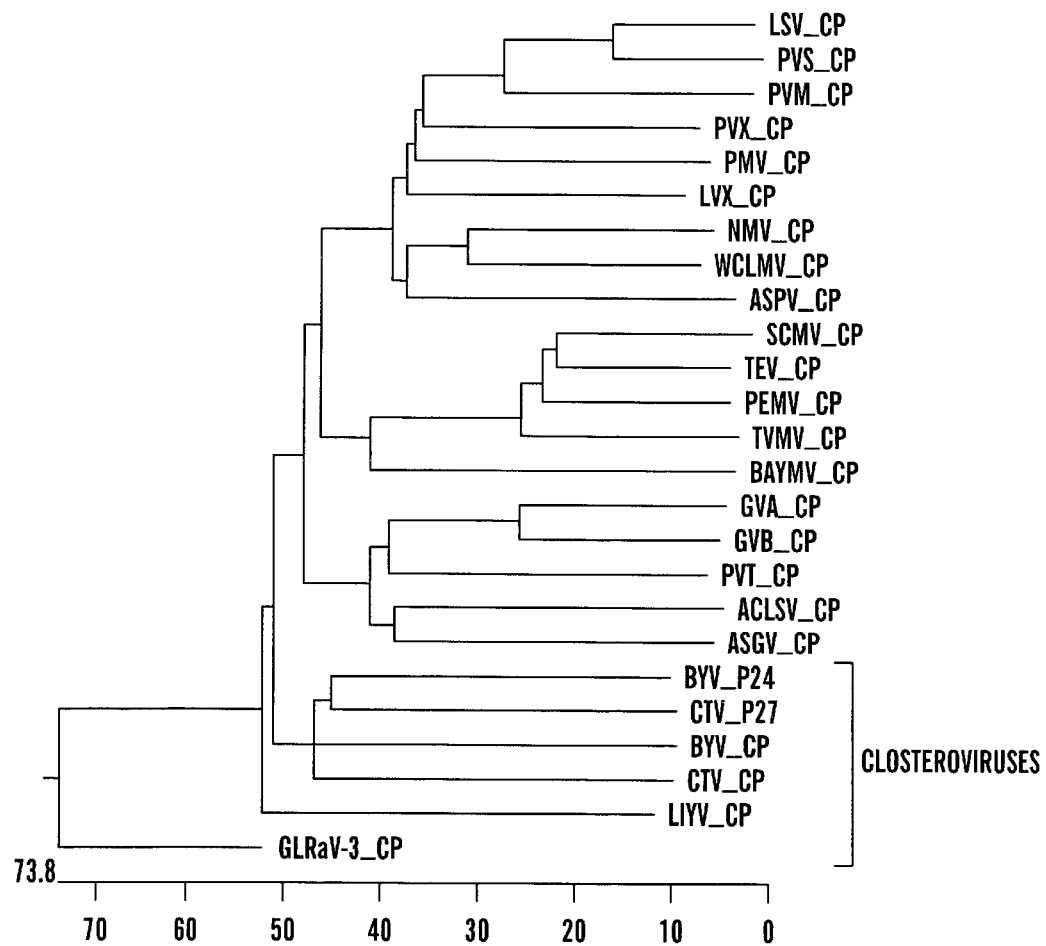

Both strands of the three immunopositive clones were sequenced at least twice. A multiple sequence alignment of these three clones overlapped and contained an incomplete ORF lacking the 3' terminal sequence region. The complete sequence of this ORF was obtained by sequencing an additional clone, pA6-8, which was selected by using the clone walking strategy. The complete ORF potentially encoded a protein of 313 amino acids with a calculated Mr of 34,866 (p35) (FIGS. 9 and 10). Because this ORF was derived from three independent clones after screening with GLRaV-3 coat protein specific antibody, it was identified as the coat protein gene of GLRaV-3. A:multiple amino acid sequence alignment of p35 with the coat proteins of other closteroviruses, including BYV, CTV, and LIYV, is presented in FIG. 11. The typical consensus amino acid residues (S, R, and D) of the coat proteins of the filamentous plant viruses (Dolja et al., "Phylogeny of Capsid Proteins of Rod-Shaped and Filamentous RNA Plant Viruses Two Families with Distinct Patterns of Sequence and Probably Structure Conservation," *Virology*, 184:79–86 (1991) ("Dolja (1991)"), which is hereby incorporated by reference), which may be involved in salt bridge formation and the proper folding of the most conserved core region (Boyko et al., "Coat Protein Gene Duplication in a Filamentous RNA Virus of Plants," *Proc. Natl. Acad. Sci. U.S.A.*, 89:9156–9160 (1992) ("Boyko (1992)"), which is hereby incorporated by reference), were also preserved in the p35. Phylogenetic analysis of the GLRaV-3 coat protein amino acid sequence with respect to the other filamentous plant viruses placed GLRaV-3 into a separate but closely related branch of. the closterovirus (FIG. 12). Direct sequence comparison of GLRaV-3 coat protein with respect to other closterovirus coat proteins or their diverged copies by the GCG Pileup program demonstrated that at the nucleotide level, GLRaV-3 had its highest homology to BYV (41.5%) and CTV (40.3%). At the amino acid level, however, the highest percentage similarity were to the diverged copies of coat protein, with 23.5% identity (46.5% similarity) to CTV p26 and 22.6% (44.3% similarity) to BYV p24.

Example 6

Identification of a Possible Coat Protein Translation Initiation Site

Various sizes of GLRaV-3 specific antibody-reacted proteins were produced by three immunopositive clones in *E. coli* (FIG. 8). Sequences of these clones overlapped and encoded a common ORF that was identified as the coat protein gene (FIG. 9). In searching for possible translation regulatory elements, sequence analysis beyond the coat protein coding region revealed a purine rich sequence, -uGAGuGAAcgcgAUG-(SEQ. ID. NO: 26), which was similar to the Shine-Dalgarno sequence (uppercase letters) (Shine et al., "The 3'-Terminal Sequence of *Escherichia Coli* 16S Ribosomal RNA: Complementarity to Nonsense Triplets and Ribosome Binding Sites," *Proc. Nat. Acad. Sci. U.S.A.*, 71:1342–1346 (1974), which is hereby incorporated by reference), upstream from the coat protein initiation site (AUG). This purine rich sequence may serve as an alternative ribosome entry site for the translation of the GLRaV-3 coat protein gene in *E. coli*. If this first AUG in the ORF was to serve for the actual coat protein translation, the ribosomal entry site must be located in this purine rich region because an in-frame translation stop codon (UGA) was only nine nucleotides upstream from the coat protein gene translation initiation site (AUG). Analysis of nucleotide sequence beyond the cloned insert into the vector sequence of clone pCP8-4 and pCP10-1 provided direct evidence that the fusion protein was made from the N-terminal portion of coat protein and C-terminal portion of β-galactosidase (16.5K). Further analysis of sequence around the selected AUG initiation codon of the coat protein gene revealed a consensus sequence (-GnnAUGG-) that favored the expression of eucaryotic mRNAs (Kozak, "Comparison of Initiation of Protein Synthesis in Procaryotes, Eucaryotes, and Organelles," *Microbiological Reviews*, 47:1–45 (1983) and Kozak, "Point Mutations Define a Sequence Flanking the AUG Initiator Codon that Modulates Translation by Eukaryotic Ribosomes," *Cell*, 44:283–292 (1986), which are hereby incorporated by reference).

Nucleotide sequence analysis of three immunopositive clones revealed overlapping sequences and an ORF that covers about 96% of the estimated coat protein gene (FIG. 9). The complete ORF was obtained after sequencing of an additional clone (pA6-8) that was selected by the clone walking strategy. Identification of this ORF as the coat protein gene was based upon its immunoreactivity to GLRaV-3 polyclonal and monoclonal antibodies, the presence of filamentous virus coat protein consensus amino acid residues (S, R, and D), and the identification of a potential translation initiation site. The calculated coat protein molecular weight (35K) is smaller than what was estimated on SDS-PAGE (41K). This discrepancy in molecular weight between computer-calculated and SDS-PAGE estimated falls in the expected range. However, direct evidence by micro-sequencing of the N-terminal coat protein sequence was not possible due to the difficulties in obtaining sufficient amounts of purified virus.

The estimated coat protein Mr of GLRaV-3 and another grape closterovirus-like designated GLRaV-1 are larger than the 22–28K coat protein range reported for other well characterized closteroviruses, such as BYV, CTV, and LIYV (Agranovsky (1991); Bar-Joseph et al., "Closteroviruses," *CMI/AAB*, NO: 260 (1982), Klaassen. et al., "Partial Characterization of the Lettuce Infectious Yellows Virus Genomic RNAs, Identification of the Coat Protein Gene and Comparison of its Amino Acid Sequence with Those of Other Filamentous-RNA Plant Viruses," *Journal of General Virology*, 75:1525–1533 (1994); (Martelli et al., "Closterovirus, Classification and Nomenclature of Viruses, Fifth Report of the International Committee on Taxonomy of Viruses," in *Archieves of Virology Supplementum* 2, Martelli et al., eds., New York: Springer-Verlag Wein, pp. 345–347 (1991) ("Martelli (1991)"); and Sekiya et al., "Molecular Cloning and Nucleotide Sequencing of the Coat Protein Gene of Citrus Tristeza Virus," *Journal of General Virology*, 72:1013–1020 (1991), which are hereby incorporated by reference). Hu (1990), which is hereby incorporated by reference, suggested a possible coat protein dimer. Our sequence data, however, do not support this suggestion. First, the size of the coat protein is only 35K, which is smaller than what would be expected as a coat protein dimer. Second, a multiple sequence alignment of N-terminal half and C-terminal half of GLRaV-3 coat protein with the coat proteins of other closteroviruses showed that the filamentous virus coat protein consensus amino acid residues (S, R, and D) are only present in the C-terminal portion, but not in the N-terminal portion of the coat protein.

Example 7

Primer Selection

Primers were selected based on the nucleotide sequence of clone pC4 that had been shown to hybridize to GLRaV-3 dsRNAs on a Northern hybridization (FIG. 4). The 648 bp sequence amplified by PCR was identified as nucleotides 9,364 to 10,011 of the incomplete GLRaV-3 genome (FIG. 18). This sequence fragment encodes a short peptide which shows some degree of amino acid sequence similarity to heat shock protein 90 (HSP90) homologues of other closteroviruses, BYV, CTV, and LIYV (FIG. 3). Two sets of primer sequences and their designations (external, 93-110 & 92-98, and internal, 93-25 & 93-40) are shown in FIG. 2. Effectiveness of synthesized primers to amplify the expected PCR product was first evaluated on its respective cDNA clone, pC4 (FIG. 13, lane 11).

Example 8

Development of a Simple and Effective PCR Sample Preparation

Initially, purified dsRNA was used in a RT-PCR reaction. Expected size of PCR product of 219 bp was consistently observed with the internal set of primers (FIG. 13, lane 10). To test whether or not these primers derived from GLRaV-3 specific dsRNA sequence is in fact the GLRaV-3 genome sequence, RNA extracted from a highly purified virus preparation was included in an assay. As expected, PCR products with similar size (219 bp) were observed in cloned plasmid DNA (pC4) (FIG. 13, lane 11), dsRNA (FIG. 13, lane 10) as well as purified viral RNA (FIG. 13, lane 9). This PCR result was encouraging as it was the first evidence to suggest that dsRNA isolated from leafroll-infected tissue may actually be derived from the GLRaV-3 genome. However, PCR sample preparations from the purified virus procedure are too complicated to be used for leafroll diagnosis. Further simplification of sample preparations was made possible by using viral RNA extracted from a partially purified virus preparation. This partially purified virus preparation was again shown to be effective in RT-PCR (FIG. 13). Sensitivity of RT-PCR was further evaluated with 10-fold serial dilution (up to $10^{-5}$) of a sample. The expected PCR product of 219 bp in a partially purified virus preparation was observable up to the $10^{-3}$ dilution (FIG. 13, lane 4). Although RT-PCR was shown again to work with partially purified virus preparations, this method of sample preparation was still too complicated to be used in a routine disease diagnosis. However, over 10 attempts to directly use crude extract for RT-PCR were unsuccessful. Proteinase K-treated crude extract was by far the most simple and still effective for RT-PCR. Therefore, the proteinase K-treated crude extract was used to evaluate RT-PCR for its ability to detect GLRaV-3.

Example 9

RT-PCR

With proteinase K-treated crude extract prepared from scraped phloem tissue collected from a typical leafroll infected vine (Doolittle's vineyard, New York), a PCR product of 219 bp was readily observable. However, application of this sample preparation method to test other field collected samples (USDA, PGRU, Geneva, N.Y.) was disappointing. With different batches of sample preparations, a range of 3 to 10 out of 12 ELISA positive samples were shown to have the expected PCR products. To determine whether or not these inconsistent results were due to some kinds of enzyme (reverse transcriptase or Taq DNA polymerase) inhibition presented in the proteinase K-treated crude extract, increasing amounts of a sample were added into an aliquot of 100 μl PCR reaction mixture. FIG. 14 shows that PCR products of 219 bp were readily observed from samples of 0.1 μl (lane 1) and 1 μl (lane 2) but not from 10 μl (lane 3).

Presumably, sufficient amount of enzyme inhibitors was present in the 10 μl of this sample.

Example 10

Immuno-capture RT-PCR

The immuno-capture method further simplified sample preparation by directly using crude extracts that were prepared in the standard ELISA extraction buffer. Immuno-capture RT-PCR ("IC RT-PCR") tests were initially performed with the internal primer set, and the expected PCR product of 219 bp was observable from a typical leafroll infected sample. However, using this PCR method to test a range of field collected ELISA positive samples, inconsistent results were again experienced. In a PCR test performed with the external primer set, only five out of seven field collected ELISA positive samples were shown to amplify the expected PCR product (648 bp) (FIG. 15A). Meanwhile, the expected PCR product was consistently observed in dsRNA (FIG. 15A, lane 10), but such product was never observed in the healthy control (FIG. 15A, lane 9). In this case, however, the expected PCR product was not observable in a sample prepared by proteinase K-treated crude extract (FIG. 15A, lane 8).

Example 11

Nested PCR

Figure 16B:
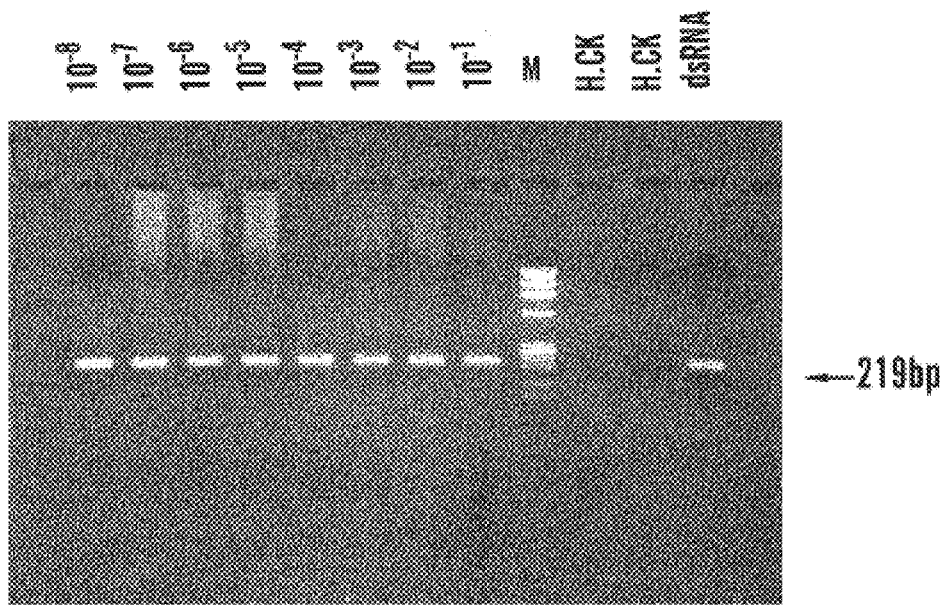

As described above, inconsistency of RT-PCR was experienced with samples prepared either by the proteinase K-treated or by the immuno-capture methods. If this PCR technique is to be used in the practical disease diagnosis, a consistent and repetitive result is desirable. Thus, the Nested PCR method was introduced. Although an expected PCR product of 648 bp from the first PCR amplification with the external primer set was not always observable (FIG. 15A), in a Nested PCR amplification with the internal primer set, the expected 219 bp PCR product was consistently observed from all seven ELISA positive samples (FIG. 15B). These similar products were also observed either in dsRNA (FIG. 15B, lane 10) or in the proteinase K-treated crude extract (FIG. 15B, lane 8) but, again, not in a healthy control (FIG. 15B, lane 9). To determine the sensitivity of Nested PCR with samples prepared either by proteinase K-treated or by immuno-capture methods, Nested PCR and ELISA were performed simultaneously with samples prepared from a 10-fold dilution series. The sensitivity of Nested PCR was shown to be $10^{-5}$ in proteinase K-treated crude extract (FIG. 16A), and was more than $10^{-8}$ (the highest dilution point in this test) in an immuno-capture preparation (FIG. 16B). With similar sample preparations, sensitivity for ELISA was only $10^{-2}$.

Example 12

Validation of PCR with ELISA and Indexing

To determine whether or not the PCR-based GLRaV-3 detection method described in this study has a potential practical implication for grapevine leafroll disease diagnosis, a validation experiment with plants characterized thoroughly by ELISA and indexing is necessary. Several grapevines collected at USDA-PGRU at Geneva, N.Y. that have been well characterized by 3-year biological indexing and by ELISA were selected for validation tests. A perfect correlation was observed between ELISA positive and PCR positive samples, although there was some discrepancy over indexing which suggested that other types of closteroviruses may also be involved in the grapevine leafroll disease (Table 2).

TABLE 2

| Sample # | Accession # | ELISA * | RT-PCR | Indexing |
|---|---|---|---|---|
| 1 | 476.01 | 1.424 (+) | + | + |
| 2 | 447.01 | 0.970 (+) | + | + |
| 3 | 123.01 | 1.101 (+) | + | + |
| 4 | 387.01 | >1.965 (+) | + | + |
| 5 | 80.01 | >2.020 (+) | + | + |
| 6 | 244.01 | >2.000 (+) | + | + |
| 7 | 441.01 | >2.000 (+) | + | + |
| 8 | 510.01 | 0.857 (+) | + | + |
| 9 | 536.01 | 0.561 (+) | + | + |
| 10 | 572.01 | >2.000 (+) | + | + |
| 11 | 468.01 | >2.000 (+) | + | + |
| 12 | 382.01 | >2.000 (+) | + | + |
| 13 | NY1 | 0.656 (+) | + | + |
| 14 | Healthy | 0.002 (−) | − | − |

Plus (+) and Minus (−) represent positive and negative reactions, respectively. For ELISA an $OD_{405\ nm}$ that was at least twice higher than a healthy control, and more than 0.100 was regarded as positive.

PCR technology has been applied to detect viruses, viroids and phytoplasmas in the field of plant pathology (Levy et al., "Simple and Rapid Preparation of Infected Plant Tissue Extracts for PCR Amplification of Virus, Viroid and MLO Nucleic Acids," *Journal of Virological Methods*, 49:295–304 (1994), which is hereby incorporated by reference). However because of the presence of enzyme inhibitors (reverse transcriptase and/or Taq DNA polymerase) in many plant tissues, a lengthy and complicated procedure is usually required to prepare a sample for PCR. In studies of PCR detection of grapevine fanleaf virus, Rowhani et al., "Development of a Polymerase Chain Reaction Technique for the Detection of Grapevine Fanleaf Virus in Grapevine Tissue," *Phytopathology*, 83:749–753 (1993) which is hereby incorporated by reference, have already observed an enzyme inhibitory phenomenon. Substances such as phenolic compounds and polysaccharides in grapevine tissues were suggested to be involved in enzyme inhibition. Present work further confirmed this observation. One of the objectives in the present study was to develop a sound practical procedure of sample preparation to eliminate this inhibitory problem for PCR detection of GLRaV-3 in grapevine tissues. Although the expected PCR product was consistently observed from samples of dsRNA, purified virus and partial purified virus, proteinase K-treated crude extract and immuno-capture methods were the simplest and were still effective. Samples prepared with proteinase K-treated crude extract have an advantage over others in that hazardous organic solvents, such as phenol and chloroform, are avoided. However, care must be taken in the sample concentration because the reaction can be inhibited by adding too much grapevine tissue (see lane 3 in FIG. 14). Minafra et al., "Sensitive Detection of Grapevine Virus A, B, or Leafroll-Associated III from Viruliferous Mealybugs and Infected Tissue by cDNA Amplification," *Journal of Virological Methods*, 47:175–188 (1994) ("Minafra (1994)"), which is hereby incorporated by reference, reported the successful PCR detection of grapevine virus A, grapevine virus B, and GLRaV-3 with crude saps prepared from infected grapevine tissues, this method of sample preparation was, however, not effective in the present study. The similar primers used by Minafra (1994), which is hereby incorporated by reference, were, however, able to amplify the expected size of PCR products from dsRNA of the NY1 isolate of GLRaV-3.

Immuno-capture is another simple and efficient method of sample preparation (Wetzel (1992), which is hereby incorporated by reference). First, crude ELISA extracts can be used directly for RT-PCR. Second, it provides not only a definitive answer, but may also be an indication to a virus serotype. Third, with an immuno-capture step, virus particles are trapped by an antibody, and inhibitory substances may be washed away. Nested PCR with samples prepared by the immuno-capture method is $10^3$ times more sensitive than with samples prepared by proteinase K-treated crude extract. However, this approach requires a virus specific antibody. For some newly discovered or hard to purify viruses, a virus specific antibody might not be always available. More specifically, there are at least six serologically distinctive closteroviruses associated with grapevine leafroll disease (Boscia (1995)), which is hereby incorporated by reference)

Example 13

Nucleotide Sequence and Open Reading Frames

A lambda ZAPII library was prepared from cDNA that was synthesized with random primed, reverse transcription of GLRaV-3 specific dsRNA. Initially, white/blue color selection in IPTG/X-gal containing plates was used to estimate the ratio of recombination. There were 15.7% white plaques or an estimate of $7 \times 10^4$ GLRaV-3 specific recombinants in this cDNA library. The library was screened with probes prepared from UNI-AMP™ PCR-amplified GLRaV-3 cDNA. More than 300 clones with inserts of up to 3 kb were selected after screening the cDNA library with probe prepared from UNI-AMP™ PCR-amplified GLRaV-3 cDNA. In Northern blot hybridization, a probe prepared from a clone insert, pC4, reacted strongly to the 16 kb dsRNA as well as to several other smaller Mr dsRNAs. Such a reaction was not observed with nucleic acids from healthy grape nor to dsRNA of CTV (FIG. 4).

Sequencing work began with clone pB3-1 that was selected after screening the library with HSP70 degenerated primer (5'G-G-I-G-G-I-G-G-I-A-C-I-T-T-Y-G-A-Y-G-T-I-T-C-I (SEQ. ID. NO: 25)). Other clones that were chosen for nucleotide sequencing were selected by the clone walking strategy. The nucleotide sequencing strategy employed was based on terminal sequencing of random selected clones assisted with GCG fragment assembly program to assemble and extend the sequence contig. The step-by-step primer extension method was used to sequence the internal region of a selected clone. A total of 54 clones were selected for sequencing. Among them, 16 clones were completely sequenced on both DNA strands (FIG. 17).

A total of 15,227 nucleotides were sequenced so far (FIG. 18), which potentially encompass nine open reading frames (ORFs) (FIG. 19), designated as ORFs 1a, 1b, and 2 to 8. The sequenced region was estimated to cover about 80% of the complete GLRaV-3 genome. Major genetic components, such as helicase (ORF 1a), RdRp (ORF 1b), HSP70 homologue (ORF 4), HSP90 homologue (ORF 5) and coat protein (ORF 6) were identified.

ORF 1a was an incomplete ORF from which the 5' terminal portion has yet to be cloned and sequenced. The sequenced region presented in FIGS. 18 and 19 represents approximately two-thirds of the expected ORF 1a, as compared to the ORF 1a from BYV, CTV, and LIYV. The partial ORF 1a was terminated by the UGA stop codon at positions 4,165–4,167; the respective product consisted of 1,388 amino acid residues and had a deduced Mr of 148,603. Database searching indicated that the C-terminal portion of this protein shared significant similarity with the Superfamily 1 helicase of positive-strand RNA viruses. Comparison of the conserved domain region (291 amino acids) showed a 38.4% identity with an additional 19.7% similarity between GLRaV-3 and BYV and a 32.4% identity with an additional 21.1% similarity between GLRaV-3 and LIYV (Table 3). Six helicase conserved motifs of Superfamily 1 helicase of positive-strand RNA viruses (Hodgman, "A New Superfamily of Replicative Proteins," *Nature*, 333:22–23 (Erratum 578) (1988) and Koonin et al., "Evolution and Taxonomy of Positive-Strand RNA Viruses: Implications of Comparative Analysis of Amino Acid Sequences," *Critical Reviews in Biochemistry and Molecular Biology*, 28:375–430 (1993), which are hereby incorporated by reference) were also retained in GLRaV-3 (FIG. 20). Analysis of the phylogenetic relationship in helicase domains between GLRaV-3 and the other positive-strand RNA viruses placed GLRaV-3 along with the other closteroviruses, including BYV, CTV, and LIYV, into the "tobamo" branch of the alphavirus-like supergroup (FIG. 21).

TABLE 3

| Virus | Helicase | | RdRp | | p5K | | HSP70 | | HSP90 | | CP | |
| --- | --- | --- | --- | --- | --- | --- | --- | --- | --- | --- | --- | --- |
| | nt | aa | nt | aa | nt | aa | nt | aa | nt | aa | nt | aa |
| BYV | 37.7 | 38.4 (58.1) | 44.5 | 41.2 (61.0) | 42.0 | 30.4 (47.8) | 43.5 | 28.6 (48.0) | 40.5 | 21.7 (51.0) | 41.5 | 20.3 (43.7) |
| CTV | 45.3 | 36.3 (55.2) | 44.0 | 40.1 (62.2) | 42.8 | 20.0 (48.9) | 43.7 | 28.7 (49.3) | 38.6 | 17.5 (43.5) | 40.3 | 20.5 (41.9) |
| LIYV | 44.9 | 32.4 (53.5) | 46.2 | 35.9 (56.4) | 45.8 | 17.9 (46.2) | 43.9 | 28.2 (46.9) | 39.3 | 16.7 (36.8) | 36.3 | 17.8 (41.1) |

Nucleotide ("nt") and amino acid ("aa") sequence similarity was calculated from perfect matches after aligning with the GCG program GAP;
the percentages in parentheses are the percentages calculated by the GAP program, which employs a matching table based on evolutionary conservation of amino acids (Devereux et al., "A Comprehensive Set of Sequence Analysis Programs for the VAX," Nucleic Acids Res., 12: 387–395 (1984), which is hereby incorporated by reference).
The sources for the BYV, CTV, and LIYV sequences were, respectively, Agranovsky (1994), Karasev (1995), and Klaassen (1995), which are hereby incorporated by reference.

ORF 1b overlapped the last 113 nucleotides of ORF 1a and terminated at the UAG codon at positions 5780 to 5782. This ORF encoded a protein of 536 amino acid residues, counting from the first methionine codon and had a calculated Mr of 61,050 (FIGS. 18 and 19). Database screening of this protein revealed a significant similarity to the Supergroup 3 RdRp of the positive-strand RNA viruses. Sequence comparison of GLRaV-3 with BYV, LIYV, and CTV over a 313-amino acid sequence fragment revealed a striking amino acid sequence similarity among eight conserved motifs (FIG. 22). The best alignment was with BYV, with 41.2% identity and 19.8% additional similarity while the least alignment was with LIYV, with 35.9% identity and 20.5% additional similarity (Table 3). Analysis of phylogenetic relationships of the RdRp domains of the alphavirus-like supergroup viruses again placed GLRaV-3 into a "tobamo" branch along with other closteroviruses, BYV, CTV, BYSV, and LIYV (FIG. 23).

Publications on BYV, CTV, and LIYV have proposed that ORF 1b is expressed via a +1 ribosomal frameshift (Agranovsky (1994), Dolja et al., "Molecular Biology and Evolution of Closteroviruses: Sophisticated Build-up of Large RNA Genomes," *Annual Review of Phytopathology*, 32:261–285 (1994) ("Dolja (1994)"), Karasev (1995), and Klaassen (1995), which are hereby incorporated by reference). Direct nucleotide sequence comparison was performed within the ORF1a/1b overlap of GLRaV-3 with respect to BYV, CTV, or LIYV. An apparently significant similarity was observed only to LIYV (FIG. 24), and not to BYV or CTV. The so-called "slippery" GGGUUU sequence and the stem-and-loop structure that were proposed to be involved in the BYV frameshift was absent from the GLRaV-3 ORF1a/1b overlap. The frameshift within the GLRaV-3 ORF 1a/1b overlap was selected based on an inspection of the C-terminal portion of the helicase alignment and the N-terminal portion of the RdRp alignment between GLRaV-3 and LIYV (FIG. 24). The GLRaV-3 ORF 1a/1b frameshift was predicted to occur in the homologous region of the LIYV genome, and was also preceded by a repeat sequence (GCTT) (FIG. 24). Unlike LIYV, this repeat sequence was not a tandem repeat and was separated by one nucleotide (T) in GLRaV-3. The frameshift was predicted to occur at CACA (from His to Thr) in GLRaV-3 rather than slippery sequence AAAG in LIYV. However, additional experiments on in vitro expression of GLRaV-3 genomic RNA are needed in order to determine whether or not a large fusion protein is actually produced.

ORF 2 potentially encoded a small peptide of 51 amino acids with a calculated Mr of 5,927. Database searching did not reveal any obvious protein matches within the existing Genbank (Release 84.0).

Intergenic regions of 220 bp between ORF 1b and ORF 2 and 1,065 bp between ORF 2 and ORF 3 were identified. There is no counterpart in BYV or LIYV genomes; instead, an ORF of 33K in CTV (Karasev et al., "Screening of the Closterovirus Genome by Degenerate Primer-Mediated Polymerase Chain Reaction," *Journal of General Virology*, 75:1415–1422 (1994), which is hereby incorporated by reference) or 32K in LIYV (Klaassen (1995), which is hereby incorporated by reference) is observed over this similar region.

ORF 3 encoded a small peptide of 45 amino acids with a calculated Mr of 5,090 (p5K). Database searching revealed that it was most closely related to the small hydrophobic, transmembrane proteins of BYV (6.4K), CTV (6K), and LIYV (5K) (FIG. 25). Individual comparison (Table 3) showed that LIYV was its most close relative (45.8%) at the nucleotide level and BYV was the most homologous (30.4%) at the amino acid level.

ORF 4 potentially encoded a protein of 549 amino acids with a calculated Mr of 59,113 (p59) (FIGS. 18 and 19). Database screening revealed a significant similarity to the HSP70 family, the p65 protein of BYV, the p65 protein of CTV, and the p62 protein of LIYV. A multiple amino acid sequence alignment of GLRaV-3 p59 with HSP70 analogs of other closteroviruses showed a striking sequence similarity among eight conserved motifs (A–H) (FIG. 26). Functionally important motifs (A–C) that are characteristic of all proteins containing the ATPase domain of the HSP70 type (Bork et al., "An ATPase Domain Common to Prokaryotic Cell Cycle Proteins, Sugar Kinases, Actin, and HSP70 Heat Shock Proteins," *Proc. Natl. Acad. Sci. U.S.A.*, 89:7290–7294 (1992), which is hereby incorporated by reference) were also preserved in GLRaV-3 p59 (FIG. 26), which suggested that this HSP70 chaperon-like protein may also possess ATPase activity on its N-terminal domain and protein-protein interaction on its C-terminal domain (Dolja (1994), which is hereby incorporated by reference). Analysis of the phylogenetic relationship of p59 of GLRaV-3 with HSP70-related proteins of other closteroviruses (BYV, CTV, and BYSV) and cellular HSP70s again placed the four closteroviruses together and the rest of the cellular HSP70s on the other branches (FIG. 27). Although several closterovirus HSP70-related proteins are closely related to each other and distant from other cellular members of this family, inspection of the phylogenetic tree (FIG. 27) suggested that GLRaV-3 may be an ancestral closterovirus relatively early in evolution as predicted by Dolja (1994), which is hereby incorporated by reference, because GLRaV-3 was placed in between closteroviruses and the other cellular HSP70 members.

ORF 5 encoded a protein of 483 amino acids with a calculated Mr of 54,852 (p55) (FIGS. 18 and 19). No significant sequence homology with other proteins was observed in the current database (GenBank, release 84.0). Direct comparison with other counterparts (p61 of CTV, p64 of BYV, and p59 of LIYV) of closteroviruses revealed some degree of amino acid sequence similarity, with 21.7w to BYV, 17.5% to CTV, and 16.7% to LIYV, respectively (Table 3, FIG. 28). Two conserved regions of HSP90 previously described in BYV and CTV (Pappu (1994), which is hereby incorporated by reference) were identified in the p55 of GLRaV-3 (FIG. 28).

The data in this ORF has been extensively described. ORF 6 encoded a protein of 313 amino acids with a calculated Mr of 34,866 (p35) (FIGS. 18 and 19). The fact that this ORF was encoded by three overlapping GLRaV-3 immunpositive clones suggests that it may contain the coat protein gene of GLRaV-3. Alignment of the product of ORF 6 (p35) with respect to BYV, CTV, and LIYV, is presented in FIG. 11. The typical consensus amino acid residues (S, R, and D) of the coat protein of the filamentous plant viruses (Dolja (1991), which is hereby incorporated by reference), which may be involved in salt bridge formation and the proper folding of the most conserved core region (Boyko (1992), which is hereby incorporated by reference), were also retained in the p35 (FIG. 11). Individual sequence comparison showed the highest similarity to CTV (20.5%) and BYV (20.3%), and the lowest similarity to LIYV (17.8%). Analysis of phylogenetic relationships with other filamentous plant viruses placed GLRaV-3 into a separate, but a closely related branch of closteroviruses (FIG. 12).

ORF 7 encoded a protein of 477 amino acids with a calculated Mr of 53,104 (p53) (FIGS. 18 and 19). Based on the presence of conserved amino acid sequences, this protein is designated as grapevine leafroll coat protein repeat (p53).

ORF 8 encoded an unidentified polypeptide having a calculated Mr of 21,148 (p21).

ORF 9 encoded an unidentified polypeptide having a calculated Mr of 19,588 (p20).

ORF 10 encoded an unidentified polypeptide having a calculated Mr of 19,653 (p20).

ORF 11 encoded an unidentified polypeptide having a calculated Mr of 6,963 (p7).

In the present study, many GLRaV-3 dsRNA specific cDNA clones were identified using a probe generated from UNI-AMP™ PCR-amplified cDNA. Using UNI-AMP™ adapters and primers (Clontech) in PCR has several advantages. First, it is not necessary to know the nucleotide sequence of an amplified fragment. Second, cDNA can be amplified in sufficient amounts for specific probe preparation. In general, cDNA amplified by PCR using UNI-AMP™ primers and adapters could be used for cloning as well as a probe for screening of cDNA libraries. However, low abundance of the starting material and many cycles of PCR amplification often incorporate errors into the nucleotide sequence (Keohavong et al., "Fidelity of DNA Polymerases in DNA Amplification," *Proc. Natl. Acad. Sci. U.S.A.*, 86:9253–9257 (1989) and Saiki et al., "Primer-Directed Enzymatic Amplification of DNA with a Thermostable DNA Polymerase," *Science*, 239:487–491 (1988), which are hereby incorporated by reference). In the present study, only UNI-AMP™ PCR amplified cDNA was used as a probe for screening. The cDNA library was generated by direct cloning of the cDNA that was synthesized by AMV reverse transcriptase. Therefore, the cDNA cloned inserts are believed to more accurately reflect the actual sequence of the dsRNA and the genomic RNA of GLRaV-3.

A total of 15,227 nucleotides or about 80% of the estimated 16 kb GLRaV-3 dsRNA was cloned and sequenced. Identification of this sequence fragment as the GLRaV-3 genome was based on its sequence alignment with the coat protein gene of GLRaV-3. This is the first direct evidence showing that high molecular weight dsRNA (~16 kb) isolated from GLRaV-3 infected vines is derived from GLRaV-3 genomic RNA. Based upon the nine ORFs identified, the genome organization of GLRaV-3 bears significant similarity to the other closteroviruses sequenced (BYV, CTV, and LIYV) (FIG. 19).

Dolja (1994), which is hereby incorporated by reference, divided the closterovirus genome into four modules. For GLRaV-3, the 5' accessory module including protease and vector transmission factor is yet to be identified. The core module, including key domains in RNA replication machinery (MET-HEL-RdRp) that is conserved throughout the alphavirus supergroup, has been revealed in parts of the HEL and RdRp domains. The MET domain has not yet been identified for GLRaV-3. The chaperon module, including three ORFs coding for the small transmembrane protein, the HSP70 homologue, and the distantly related HSP90 homologue, has been fully sequenced. The last module includes coat protein and its possible diverged copy and is also preserved in GLRaV-3. Overall similarity of the genome organization of GLRaV-3 with other closteroviruses further support the inclusion of GLRaV-3 as a member of closteroviruses (Hu (1990) and Martelli (1991), which are hereby incorporated by reference). However, observation of a ambisense gene on its 3' terminal region may separate GLRaV-3 from other closteroviruses. Further comparative sequence analysis (Table 3) as well as phylogenetic observation of GLRaV-3 with respect to other closteroviruses over the entire genome sequence region suggested that GLRaV-3 is most closely related to BYV, followed by CTV, and LIYV.

As suggested by others (Agranovsky (1994), Dolja (1994), Karasev (1995), and Klaassen (1995), which are hereby incorporated by reference), expression of ORF 1b in closteroviruses may be via a +1 ribosomal frameshift mechanism. In GLRaV-3, a potential translation frameshift of ORF 1b could make a fusion HEL-RdRp protein of over 1,926 amino acid residues with a capacity to encode a protein of more than 210K Comparative study of GLRaV-3 with respect to other closteroviruses over the ORF 1a/1b overlap revealed a significant sequence similarity to LIYV, but not to BYV or to CTV. The so-called slippery sequence (GGGUUU) and stem-loop and pseudoknot structures identified in BYV (Agranovsky (1994), which is hereby incorporated by reference) is not present in GLRaV-3. Thus, a frameshift mechanism that is similar to LIYV may be employed for GLRaV-3. However, protein analysis is necessary in order to determine the protein encoding capacities of these ORFs.

Differing from BYV, both CTV and LIYV have an extra ORF (ORF 2) in between RdRp (ORF 1b) and the small membrane protein (ORF 3) and potentially encoding a protein of 33K or 32K, respectively. However, in GLRaV-3, there is a much smaller ORF 2 (7K) followed by a long intergenic region of 1,065 bp. Thus, nucleotide sequencing of additional clones around this region may be necessary to resolve this discrepancy.

So far, among all plant viruses described, the HSP70 related gene is present only in the closteroviruses (Dolja (1994), which is hereby incorporated by reference). Identification of the GLRaV-3 HSP70 gene was based on an assumption that this gene should also be present in the closterovirus associated with grapevine leafroll disease, specifically GLRaV-3. Thus, cDNA clones that reacted with HSP70-degenerated primers were identified for sequence analysis. The identification of subsequent clones for sequencing was based on the gene-walking methodology. However, identification of immunopositive clones enabled identification of the coat protein gene of GLRaV-3 and proved that the HSP70-containing sequence fragment is present in the GLRaV-3 RNA genome.

The 16 kb dsRNA used for cDNA synthesis was assumed to be a virus replicative form (Hu (1990), which is hereby incorporated by reference). Identification of the virus coat protein from this study further supports this assumption. Several lines of evidence show that the partial genome of GLRaV-3 has been cloned and sequenced. First, selected clones have been shown by Northern hybridization to hybridize to the 16 kb dsRNA and several smaller RNAs (presumably subgenomic RNAs) (FIG. 4). Second, three GLRaV-3 antibody-reacting clones were identified after immuno-screening of the protein expressive library with both GLRaV-3 polyclonal (Zee (1987), which is hereby incorporated by reference) and monoclonal (Hu (1990), which is hereby incorporated by reference) antibodies. After nucleotide sequencing, these three antibody-reacting clones were shown to overlap one another and contain a common ORF which potentially encodes a protein with calculated Mr of 35K. This is in general agreement with the Mr estimated on SDS-PAGE (41K). Third, analysis of the partial genome sequence of GLRaV-3 suggested a close similarity in genome organization and gene sequences to the other closteroviruses (Dolja (1994), which is hereby incorporated by reference).

Information regarding the genome of GLRaV-3 provides a better understanding of this and related viruses and adds to the fundamental knowledge of closteroviruses. Present work on the nucleotide sequence and genome organization (about 80% of the estimated genome sequence) has provided direct evidence of a close relationship between GLRaV-3 and other closteroviruses. It has also made it possible, for the first time, to thoroughly evaluate a phylogenetic relationship of GLRaV-3 based on a wide range of genes and gene products (helicase, polymerase, HSP70 homologue, HSP90 homologue, and coat protein). Based upon major differences in genome format and organization between BYV, CTV, and LIYV, along with phylogenetic analysis, Dolja (1994), which is hereby incorporated by reference, proposed the establishment of the new family Closteroviridae with three new genera of Closterovirus (BYV), Citrivirus (CTV), and Biclovirus (LIYV). This work on genome organization and phylogenetic analysis, along with evidence that this virus is transmitted by mealybugs (Engelbrecht et al., "Association of a Closterovirus with Grapevines Indexing Positive for Grapevine Leafroll Disease and Evidence for its Natural Spread in Grapevines," *Phytopathol. Mediter.*, 24:101–105 (1990), Engelbrecht et al., "Field Spread of Corky Bark Fleck Leafroll and Shiraz Decline Diseases and Associated Viruses in South African Grapevines," *Phytophylactica*, 22:347–354 (1990), Engelbrecht et al., "Transmission of Grapevine Leafroll Disease and Associated Closteroviruses by the Vine Mealybug Planococcus-Ficus," *Phytophylactica*, 22:341–346 (1990), Rosciglione et al., "Transmission of Grapevine Leafroll Disease and an Associated Closterovirus to Healthy Grapevine by the Mealybug Planococcus Ficus (Abstract)," *Phytoparasitica*, 17:63–63 (1989), and Tanne et al., "Transmission of Closterolike Particles Associated with Grapevine Leafroll by Mealybugs (Abstract)," *Phytoparasitica*, 17:55 (1989), which are hereby incorporated by reference), suggest that a new genus under Closteroviridae family should be established. Thus, GLRaV-3 (the NY1 isolate) is proposed to be the type representative of the new genus, Graclovirus (grapevine clo-sterovirus). Further sequencing of other grapevine leafroll associated closteroviruses may add more members to this genus.

Another cDNA library of GLRaV-3 has been established recently from dsRNA of an Italian isolate of GLRaV-3 (Saldarelli et al., "Detection of Grapevine Leafroll-Associated Closterovirus III by Molecular Hybridization," *Plant Pathology (Oxford)*, 43:91–96 (1994), which is hereby incorporated by reference). Selected clones react specifically to GLRaV-3 dsRNA on a Northern blot; however, no direct evidence was provided to suggest that those clones were indeed from GLRaV-3 genomic RNA. Meanwhile, a small piece of sequence information from one of those cDNA clones was used to synthesize primers for the development of a PCR detection method (Minafra (1994), which is hereby incorporated by reference). Direct sequence comparison of these primer sequences to GLRaV-3 genome sequence obtained in the present study, showed that one of the primers (H229, 5' A-T-A-A-G-C-A-T-T-C-g-G-G-A-T-G-G-A-C-C (SEQ. ID. NO: 27)) is located at nucleotides 5562–5581 and the other (C547, 5'A-T-T-A-A-C-t-T-g-A-C-G-G-A-T-G-G-C-A-C-G-C (SEQ. ID. NO: 28)) is in reverse direction and is the complement of nucleotides 5880–5901. Mismatching nucleotides between the primers and GLRaV-3 sequence are shown in lowercase letters. Sequence comparison over these short primer regions to GLRaV-3 (isolate NY1) genome sequence showed a 90–95% identity, which suggested that these two isolates belong to the same virus (GLRaV-3). Moreover, the primers prepared by Minafra (1994), which is hereby incorporated by reference, from the Italian isolate of GLRaV-3 produced an expected size of PCR product with templates prepared from the NY1 isolate of GLRaV-3.

The reminder of the GLRaV-3 genome can be sequenced using the methods described herein.

Example 14

Identification and Characterization of the 43 K ORF

The complete nucleotide sequence of the GLRaV-3 HSP90 gene is given in FIG. 18. Initial sequencing work indicated that a open reading frame ("ORF") potentially encoding for a protein with a calculated Mr of 43K (FIG. 29) was downstream of the HSP70-related gene. This gene was selected for engineering because the size of its encoded product is similar to the GLRaV-3 coat protein gene. However, after sequence editing, this incomplete ORF was proven to be located in the 3' terminal region of the HSP90-related gene. It is referred to herein as the incomplete GLRaV-3 HSP90 gene or as the 43K ORF.

Example 15

Custom-PCR Engineering the Incomplete GLRaV-3 HSP90 Gene for Expression in Plant Tissues Two custom synthesized oligonucleotide primers, 5' primer (93–224, t-a-c-t-t-a-t-c-t-a-g-a-a-c-c-A-T-G-G-A-A-G-C-G-A-G-T-C-G-A-C-G-A-C-T-A (SEQ. ID. NO: 29)) and 3' complimentary primer (93–225, t-c-t-t-c-a-g-g-a-t-c-c-a-t-g-g-A-G-A-A-A-C-A-T-C-G-T-C-G-C-A-T-A-C-T-A (SEQ. ID. NO: 30)) that flank the 43K ORF were designed to amplify the incomplete HSP90 gene fragment by polymerase chain reaction ("PCR"). Addition of a restriction enzyme Nco I site in the primer is for the convenience of cloning and for protein expression (FIG. 29) (Slightom, "Custom Polymerase-Chain-Reaction Engineering of a Plant Expression Vector," *Gene*, 100:251–255 (1991), which is hereby incorporated by reference). Using these primers, a product of the proper size (1.2 kb) was amplified by reverse-transcription PCR ("RT-PCR") using GLRaV-3 double-stranded RNA ("dsRNA") as template. The PCR amplified product was treated with Nco I, isolated from a low-melting temperature agarose gel, and cloned into the same restriction enzyme treated binary vector pBI525 (obtained from William Crosby, Plant Biotechnology Institute, Saskatoon, Sask., Canada), resulting in a clone pBI525GLRaV-3hsp90 (FIG. 30). A plant expression cassette, the EcoR I and Hind III fragment of clone pBI525GLRaV-3hsp90, which contains proper engineered CaMV 35S promoters and a Nos 3' untranslated region, was excised and cloned into a similar restriction enzyme digested plant transformation vector, pBin19 (FIG. 30) (Clontech Laboratories, Inc.). Two clones, pBin19GLRaV-3hsp90-12-3 and pBin19GLRaV-3hsp90-12-4 that were shown by PCR to contain the proper size of the incomplete HSP90 gene were used to transform the avirulent *Agrobacterium tumefaciens*, strain LBA4404 via electroporation (Bio-Rad). The potentially transformed Agrobacterium was plated on selective media with 75 μg/ml of kanamycin. Agrobacterium lines which contain the HSP90 gene sequence were used to transform tobacco (*Nicotiana tobaccum* cv.Havana 423) using standard procedures (Horsch et al., "A Simple and General Method for Transferring Genes into Plants," *Science*, 227:1229–1231 (1985) ("Horsch (1985)"), which is hereby incorporated by reference). Kanamycin resistant tobacco plants were analyzed by PCR for the presence of the transgene. Transgenic tobacco plants with the transgene were self pollinated and seed was harvested.

Example 16

Custom-PCR Engineering of the 43K ORF

The complete sequence of the GLRaV-3 hsp90 gene was reported in FIG. 18. However, in the present study, using two custom synthesized oligo primers (93–224, tacttatctagaac-cATGGAAGCGAGTCGACGACTA (SEQ. ID. Nos. 29) and 93–225, tcttgaggatccatggAGAAA-CATCGTCGCATACTA (SEQ. ID. NO: 30)) and GLRaV-3 dsRNA as template, the incomplete HSP90 related gene sequence was amplified by RT-PCR which added an Nco I restriction enzyme recognition sequence (CCATGG) around the potential translation initiation codon (ATG) and another Nco I site, 29 nt downstream from the translation termination codon (TAA) (FIG. 29). The PCR amplified fragment was digested with Nco I, and cloned into the same restriction enzyme treated plant expression vector, pBI525. Under ampicillin selective conditions, hundreds of antibiotic resistant, transformants of E. coli strain DH5a were generated. Clones derived from five colonies were selected for further analysis. Restriction enzyme mapping (Nco I or BamH I and EcoR V) showed that three out of five clones contained the proper size of the incomplete GLRaV-3 HSP90 sequence. Among them, two clones were engineered in the correct 5'-3' orientation with respect to the CaMV-AMV gene regulatory elements in the plant expression vector, pBI525. A graphical structure in the region of the plant expression cassette of clone pBI525GLRaV-3hsp90-12 is presented in FIG. 30.

The GLRaV-3 HSP90 expression cassette was removed from clone pBI525GLRaV-3hsp90-12 by a complete digestion with Hind III and EcoR I and cloned into the similar restriction enzyme treated plant transformation vector pBin19. A clone designated as pBin19GLRaV-3hsp90-12 was then obtained (FIG. 30) and was subsequently mobilized into the avirulent Agrobacterium strain LBA4404 using a standard electroporation protocol (Bio-Rad). Potentially transformed Agrobacteria were then plated on a selective medium (75 µg/ml kanamycin), and antibiotic resistant colonies were analyzed further by PCR with specific synthesized primers (93–224 and 93–225) to see whether or not the incomplete HSP90 gene was still present. After analysis, clone LBA4404/pBin19GLRaV-3hsp90-12 was selected and used to transform tobacco tissues.

Example 17

Transformation and Characterization of Transgenic Plants

The genetically engineered *Agrobacterium tumefaciens* strain, LBA4404/pBin19GLRaV-3hsp90-12, was co-cultivated with tobacco leaf discs as described (Horsch (1985), which is hereby incorporated by reference). Potentially transformed tobacco tissues were selected on MS regeneration medium (Murashige et al., "A Revised Medium for Rapid Growth and Bioassays with Tobacco Tissue Cultures," *Physiologia Plantarum*, 15:473–497 (1962), which is hereby incorporated by reference) containing 300 μg/ml of kanamycin. Numerous shoots developed from kanamycin resistant calli in about 6 weeks. Rooted tobacco plants were obtained following growth of developed shoots on a rooting medium (MS without hormones) containing 300 μg/ml of kanamycin. Eighteen independent, regenerated kanamycin resistant plants were transplanted in a greenhouse and tested for the presence of the HSP90-related gene by PCR. Fourteen out of eighteen selected kanamycin resistant transgenic lines were shown to contain a PCR product with the expected size (FIG. 31).

The genetically engineered *Agrobacterium tumefaciens* strain LBA4404/pBin19GLRaV-3hsp90-12 was also used to transform the grapevines rootstock Couderc 3309 (*Vitis riparia*×*Vitis rupestris*). Embryogenic calli of Couderc 3309 were obtained by culturing anthers on MSE media. (MSE media contained Murashige and Skoog salts plus 0.2% sucrose, 1.1 mg/L 2, -4-D, and 0.2 mg/L BA. The media were adjusted to pH 6.5, and 0.8% Noble agar was added. After autoclaving, 100 ml M-0654, 100 ml M-0529, and 1 ml vitamin M-3900 were added to the media). After 60 days, primary calli were induced and transferred to hormone-free HMG medium (½ Murashige salts with 10 g/L sucrose, 4.6 g/L glycerol and 0.8% Noble agar) for embryogenesis. Calli with globular or heart-shaped embryos were immersed for 15 minutes in *Agrobacterium tumefaciens* LBA4404/pBin19GLRaV-3hsp90-12 that was suspended in MS liquid medium. The embryos were blotted on filter paper to remove excess liquid and transferred to HMG medium with acetosyringone (100 μM) and kept for 48 hours in the dark at 28° C. The calli were then washed 2–3 times in MS liquid medium plus cefotaxime (300 μg/ml) and carbenicillin (200 μg/ml) and transferred to HMG medium with the same antibiotics for 1–2 weeks. Subsequently, the embryogenic calli were transferred to HMG medium containing 20 or 40 mg/L kanamycin and 300 mg/L cefotaxime plus 200 mg/L carbenicillin to select transgenic embryos. After being on selection medium for 3–4 months, growing embryos were transferred to HMG, MGC (full-strength MS salts amended with 20 g/L sucrose, 4.6 g/L glycerol, 1 g/L casein hydrolysate, and 0.8% Noble agar), or MSE medium with kanamycin. After 4 months, germinated embryos were transferred to baby food jars containing rooting medium, such as a woody plant medium described, for example, in Lloyd et al., "Commercially Feasible Micropropogation of Mountain Laurel. *Kalmia latifolia*, By Use of Shoot Tip Culture," *Proc. Intl. Plant Prop. Soc.*, 30:421–427 (1981), which is hereby incorporated by reference, that was supplemented with 0.1 mg/L BA, 3 g/L activated charcoal and 1.5% sucrose. The pH was adjusted to 5.8 and Noble agar was added to 0.7%]. Plantlets with roots were transplanted to pots with artificial soil mix and grown in greenhouses. In this manner, 88 grapevine plants were transferred to the greenhouse. The 43K protein gene has been detected by PCR in a number of them.

Using the methods described above, engineering of the incomplete HSP90 gene of GLRaV-3 into plant expression and transformation vectors has been effected. The targeted gene sequence was shown to be integrated into the plant genome by PCR analysis of the transgenic tobacco plants. The engineered Agrobacterium tumefaciens strain LBA4404/pBin19GLRaV-3hsp90-12 has been used to transform grapes and tobacco. Furthermore, success in the genetic engineering of a plant transformation vector may serve as a model for further construction of other GLRaV-3 genes, such as coat protein, RdRp, and HSP70 that are now available.

Since the first demonstration of transgenic tobacco plants expressing the coat protein gene of TMV resulted in resistance against TMV infection (Powell-Abel et al., "Delay of Disease Development in Transgenic Plants that Express the Tobacco Mosaic Virus Coat Protein Gene," *Science*, 232:738–743 (1986), which is hereby incorporated by reference), the phenomenon of the coat protein-mediated protection has been observed for over 20 viruses in at least 10 different taxonomic groups in a wide variety of dicotyledonous plant species (Beachy et al., "Coat Protein-Mediated Resistance Against Virus Infection,"*Annu. Rev. Phytopathol.*, 28:451–74 (1990) ("Beachy (1990)") and Wilson, "Strategies to Protect Crop Plants Against Viruses: Pathogen-Derived Resistance Blossoms," *Proc. Natl. Acad. Sci., U.S.A.*, 90:3134–3141 (1993) ("Wilson (1993)", which are hereby incorporated by reference). If gene silencing (or co-suppression) (Finnegan et al., "Transgene Inactivation: Plants Fight Back!" *Bio/Technology*, 12:883–888 (1994) and Flavell, "Inactivation of Gene Expression in Plants as a Consequence of Specific Sequence Duplication," *Proc. Natl. Acad. Sci. U.S.A.*, 91:3490–3496 (1994), which are hereby incorporated by reference) is one of the resistance mechanisms (Lindbo et al., "Induction of a Highly Specific Antiviral State in Transgenic Plants: Implications for Regulation of Gene Expression and Virus Resistance," *The Plant Cell*, 5:1749–1759 (1993), Pang et al., "Different Mechanisms Protect Transgenic Tobacco Against Tomato Spotted Wilt and Impatiens Necrotic Spot Tospoviruses," *Bio/Technology*, 11:819–824 (1993) ("Pang (1993)"), and Smith et al., "Transgenic Plant Virus Resistance Mediated by Untranslatable Sense RNAs: Expression, Regulation, and Fate of Nonessential RNAS," *The Plant Cell*, 6:1441–1453 (1994), which are hereby incorporated by reference), then one would expect to generate transgenic plants expressing any part of a viral genome sequence to protect plants from that virus infection. Thus, in the present study, trangenic plants expressing the 43K ORF (or the incomplete hsp90 gene) may be protected from GLRaV-3 infection.

Since tobacco (*Nicotiana tobaccum* cv. Havana 423) is not the host of GLRaV-3, direct evaluation of the virus resistance was not possible. However, recently, after a mechanical inoculation of *N. benthamiana* with grapevine leafroll infected tissue, Boscia (1995), which is hereby incorporated by reference, have recovered a long closterovirus from *N. benthamiana* which is probably GLRaV-2. Thus, it is believed that other types of grapevine leafroll associated closteroviruses can also be mechanically transmitted to *N. benthamiana*. If the 43K ORF from GLRaV-3 can also be transferred to *N. benthamiana*, it might be possible to evaluate the resistance of those plants against GLRaV-2 infection. However, the resistance of the transgenic grape rootstock Couderc 3309 against leafroll infection can be presently evaluated.

Example 18

Coat Protein-mediated Protection and Other Forms of Pathogen-derived Resistance

The successful engineering technique used in the above work could be utilized to engineer other gene sequences of GLRaV-3 which have since been identified. Among these, the coat protein gene of GLRaV-3 is the primary candidate since coat protein-mediated protection (Beachy (1990), Hull et al., "Approaches to Nonconventional Control of Plant Virus Diseases," *Crit. Rev. Plant Sci.*, 11:17–33 (1992), and Wilson (1993), which are hereby incorporated by reference) has been the most successful example in the application of the concept of pathogen-derived resistance (Sanford et al., "The Concept of Parasite-Derived Resistance—Deriving Resistance Genes from the Parasite's Own Genome," *J. Theor. Biol.*, 113:395–405 (1985), which is hereby incorporated by reference). Construction of plant expression vector (pEPT8/cpGLRaV-3) and Agrobacterium binary vector (pGA482pEPT8/cpGLRaV-3) was done following a strategy similar to the above. The GLRaV-3 coat protein gene was PCR amplified with primers (KSL95-5, a-c-t-a-t-t-t-c-t-a-g-,a-a-c-c-A-T-G-G-C-A-T-T-T-G-A-A-C-T-G-A-A-A-T-T (SEQ. ID. NO: 31), and KSL95-6, t-t-c-t-g-a-g-g-a-t-c-c-a-t-g-g-T-A-T-A-A-G-C-T-C-C-C-A-T-G-A-A-T-T-A-T (SEQ. ID. NO: 32)) and cloned into pEPT8 after NcoI treatment. The expression cassette from pEPT8/cpGLRaV-3 (including double CaMV 35S enhancers, 35S promotor, alfalfa mosaic virus leader sequence, GLRaV-3 coat protein gene, and 35S terminator) was digested with HindIII and cloned into pGA482G (FIG. 32). Resulting Agrobacterium binary vector (pGA482GpEPT8/cpGLRaV-3) was mobilized into *Agrobacterium tumerfaciens* strain C58Z707 and used for transformation of grapevines.

Other gene sequence (ORF 1b, the RNA dependent RNA polymerase) may also be used, as replicase-mediated protection has been effectively used to protect plants from virus infection (Carr et al., "Replicase-Mediated Resistance," *Seminars in Virology*, 4:339–347 (1993) and Golemboski et al., "Plants Transformed with a Tobacco Mosaic Virus Nonstructural Gene Sequence are Resistant to the Virus," *Proc. Natl. Acad. Sci. U.S.A.*, 87:6311–6315 (1990), which are hereby incorporated by reference). The HSP70 homologue may also be used to generate transgenic plants that are resistant against all types of grapevine leafroll associated closteroviruses since significant consensus sequences are observed over HSP70 conserved domains. Moreover, the phenomenon of RNA-mediated protection has also been observed (de Haan et al., "Characterization of RNA-Mediated Resistance to Tomato Spotted Wilt Virus in Transgenic Tobacco Plants," *Bio/Technology*, 10:1133–1137 (1992), Farinelli et al., "Coat Protein Gene-Mediated Resistance to Potato Virus Y in Tobacco Examination of the Resistance Mechanisms is the Transgenic Coat Protein Required for Protection?" *Mol. Plant Microbe Interact.*, 6:284–292 (1993) ("Farinelli (1993)"), Kawchuk et al., "Sense and Antisense RNA-Mediated Resistance to Potato Leafroll Virus in Russet Burbank Potato Plants," *Mol. Plant Microbe Interact*, 4:247–253 (1991) ("Kawchuk (1991)"), Lindbo et al., "Untranslatable Transcripts of the Tobacco Etch Virus Coat Protein Gene Sequence Can Interfere with Tobacco Etch Virus Replication in Transgenic Plants and Protoplasts," *Virology*, 189:725–733 (1992), Lindbo et al., "Pathogen-Derived Resistance to a Potyvirus Immune and Resistant Phenotypes in Transgenic Tobacco Expressing Altered Forms of a Potyvirus Coat Protein Nucleotide Sequence," *Mol. Plant Microbe Interact*, 5:144–153 (1992), Lindbo et al., "Pathogen Derived Resistance to Potyviruses: Working, But Why?"*Seminars in Virology*, 4:369–379 (1993), Pang (1993), and Van Der Wilk et al., "Expression of the Potato Leafroll Luteovirus Coat Protein Gene in Transgenic Potato Plants Inhibits Viral Infection," *Plant Mol. Biol.*, 17:431–440 (1991), which are hereby incorporated by reference). Thus, untranslatable transcript versions of the above mentioned GLRaV-3 genes might also produce leafroll resistant transgenic plants.

Another form of pathogen-derived resistance that has also been shown to be effective in control of plant viral disease is through the use of antisense RNA. Transgenic tobacco plants expressing the antisense sequence of the coat protein gene of cucumber mosaic virus ("CMV") showed a delay in symptom expression by CMV infection (Cuozzo et al., "Viral Protection in Transgenic Tobacco Plants Expressing the Cucumber Mosaic Virus Coat Protein or its Antisense RNA," *Bio/Technology*, 6:549–554 (1988), which is hereby incorporated by reference). Transgenic plants expressing either potato virus X ("PVX") coat protein or its antisense transcript were protected from infection by PVX. However, plants expressing antisense RNA were protected only at low inoculum concentration. The extent of this protection mediated by antisense transcript is usually lower than transgenic plants expressing the coat protein (Hemenway et al., "Analysis of the Mechanism of Protection in Transgenic Plants Expressing the Potato Virus X Coat Protein or its Antisense RNA," *Embo. (Eur. Mol. Biol. Organ.) J.*, 7:1273–1280 (1988), which is hereby incorporated by reference). This type of resistance has also been observed in bean yellow mosaic virus (Hammond et al., "Expression of Coat Protein and Antisense RNA of Bean Yellow Mosaic Virus in Transgenic Nicotiana-Benthamiana," *Phytopathology*, 81:1174 (1991), which is hereby incorporated by reference, tobacco etch virus (Lindbo et al., "Untranslatable Transcripts of the Tobacco Etch Virus Coat Protein Gene Sequence Can Interfere with Tobacco Etch Virus Replication in Transgenic Plants and Protoplasts," *Virology*, 189:725–733 (1992), which is hereby incorporated by reference), potato virus Y (Farinelli (1993), which is hereby incorporated by reference), and zucchini yellow mosaic virus (Fang et al., "Genetic Engineering of Potyvirus Resistance Using Constructs Derived from the Zucchini Yellow Mosaic Virus Coat Protein Gene," *Mol. Plant Microbe Interact.*, 6:358–367 (1993), which is hereby incorporated by reference). However, high level of resistance mediated by antisense sequence was observed to be similar to potato plants (Russet Burbank) expressing potato leafroll virus coat protein (Kawchuk (1991), which is hereby incorporated by reference). Besides using antisense transcript of the virus coat protein gene, other virus genome sequences have also been demonstrated to be effective. These included the 51-nucleotide sequences near the 5' end of TMV RNA (Nelson et al., "Tobacco Mosaic Virus Infection of Transgenic Nicotiana-Tabacum Plants is Inhibited by Antisense Constructs Directed at the 5' Region of Viral RNA," *Gene* (Abst), 127:227–232 (1993), which is hereby incorporated by reference) and noncoding region of turnip yellow mosaic virus genome (Zaccomer et al., "Transgenic Plants that Express Genes Including the 3' Untranslated Region of the Turnip Yellow Mosaic Virus (TYMV) Genome are Partially Protected Against TYMV Infection," *Gene*, 87–94 (1993), which is hereby incorporated by reference).

GLRaV-3 has been shown to be transmitted by mealybugs and in some cases it has been shown to spread rapidly in vineyards (Engelbrecht et al., "Field Spread of Corky Bark Fleck Leafroll and Shiraz Decline Diseases and Associated Viruses in South African Grapevines," *Phytophylactica*, 22:347–354 (1990), Engelbrecht et al., "Transmission of Grapevine Leafroll Disease and Associated Closteroviruses by the Vine Mealybug Planococcus-Ficus," *Phytophylactica*, 22:341–346 (1990), and Jordan et al., "Spread of Grapevine Leafroll and its Associated Virus in New Zealand Vineyards," 11*th Meeting of the International Council for the Study of Viruses and Virus Diseases of the Grapevine*, pp. 113–114 (1993) which are hereby incorporated by reference). This disease may become more of a problem if mealybugs become difficult to control due to the lack of insecticides. In this scenario, the development of leafroll resistant grapevines becomes very attractive. Although grapevine is a natural host of Agrobacterium (*A. vitis* is the causal agent of the grapevine crown gall disease), transformation of grapevine has proven to be difficult (Baribault et al., "Transgenic Grapevines: Regeneration of Shoots Expressing β-glucuronidase," *J. Exp. Bot.*, 41:1045–1049 (1990), Baribault et al., "Genetic Transformation of Grapevine Cells," *Plant Cell Reports*, 8:137–140 (1989), Colby et al., "Cellular Differences in Agrobacterium Susceptibility and Regenerative Capacity Restrict the Development of Transgenic Grapevines," *J. Am. Soc. Hort. Sci.*, 116:356–361 (1991), Guellec et al., "Agrobacterium-Rhizogenes Mediated Transformation of Grapevine *Vitis-Vinifera l*, Agrobacterium-Rhizogenes Mediated Transformation of Grapevine *Vitis-Vinifera l*," *Plant Cell Tissue Organ Cult.*, 20:211–216 (1990), Hebert et al., "Optimization of Biolistic Transformation of Embryogenic Grape Cell Suspensions," *Plant Cell Reports*, 12:585–589 (1993), Le Gall et al., "Agrobacterium-Mediated Genetic Transformation of Grapevine Somatic Embryos and Regeneration of Transgenic Plants Expressing the Coat Protein of Grapevine Chrome Mosaic Nepovirus (GCMV)," *Plant Science*, 102:161–170 (1994), Martinelli et al., "Genetic Transformation and Regeneration of Transgenic Plants in Grapevine (*Vitis Rupestris S.*)," *Theoretical and Applied Genetics*, 88:621–628 (1994), and Mullins et al., "Agrobacterium-Mediated Genetic Transformation of Grapevines: Transgenic Plants of *Vitis rupestris* Scheele and Buds of *Vitis vinifera L.*," *Bio/Technology*, 8:1041–1045 (1990), which are hereby incorporated by reference). Recently, an efficient regeneration system using proliferative somatic embryogenesis and subsequent plant development has been developed from zygotic embryos of stenospermic seedless grapes (Mozsar, J. et al., "A Rapid Method for Somatic Embryogenesis and Plant Regeneration from Cultured Anthers of *Vitis Riparia*," *Vitis*, 33:245–246 (1994), and Emerschad (1995), which are hereby incorporated by reference). Using this regeneration system, Scorza et al., "Transformation of Grape (*Vitis vinifera L.*) Zygotic-Derived Somatic Embryos and Regeneration of Transgenic Plants," *Plant Cell Reports*, 14:589–592 (1995) ("Scorza (1995)"), which is hereby incorporated by reference, succeeded in obtaining transgenic grapevines through zygotic-derived somatic embryos after particle-wounding/*A. tumefaciens* treatment. Using a Biolistic device, tiny embryos were shot with gold particles (1.0 µm in diameter). The wounded embryos were then co-cultivated with *A. tumefaciens* containing engineered plasmids carrying the selection marker of kanamycin resistance and P-glucuronidase ("GUS") genes. Selection of transgenic grapevines was carried out with 20 µg/ml kanamycin in the initial stage and then 40 µg/ml for later proliferation. Small rooted seedlings were obtained from embryogenic culture within 5 months of bombardment/*A. tumefaciens* (Scorza (1995), which is hereby incorporated by reference). Transgenic grapevines were analyzed by PCR and Southern hybridization, and shown to carry the transgenes. The above-mentioned grapevine transformation approach has been carried out in the current investigation to generate transgenic grapevines expressing GLRaV-3 genes. Evaluation of any potential leafroll resistance on transgenic grapevines may be carried out by insect vectors or grafting.

Example 19

Production of Antibodies Recognizing GLRaV3

The clone pCP10-1 which was shown to contain the major portion of the coat protein gene of GLRaV3 (FIG. 9) was used to express the coat protein and the β-galactosidase fusion protein. About 500 ml of LB medium containing 50 μg/ml of ampicilian was inoculated with a pCP10-1 single colony and incubated with rigorous shaking for overnight until log-phase growth. Expression of the fusion protein was further induced by the addition of 1 mM IPTG. Bacteria were harvested by centrifugation at 5,000 rpm for 10 min. The bacterial cell wall was broken by sonication. After low speed centrifugation to get rid of cell debris, the fusion protein was precipitated by the addition of saturated ammonium sulfate, then resuspended in PBS buffer and electrophoresced in a SDS-polyacrylamide gel ("SDS-PAGE"). The fusion protein band was excised after soaking the SDS-PAGE gel in 0.25M KCl to locate the protein band. The protein was eluted with buffer (0.05M Tris-HCl, pH7.9, 0.1% SDS, 0.1 mM EDT and 0.15M NaCl) and precipitated by trichoroacetic acid to a final concentration of 20%.

An antiserum was prepared by immunization of a rabbit with 0.5–1 mg of the purified protein emulsified with Freund's completed adjuvant followed by two more weekly injections of 0.5–1 mg protein emulsified with Freund's incomplete adjuvant. After the last injection, antisera were collected from blood taken from the rabbit every week for a period of 4 months.

On Western blot analysis, the antibody gave a specific reaction to the 41K protein from GLRaV3 infected tissue as well as to the fusion protein itself (50K) and generated a pattern similar to the pattern seen in FIG. 8. This antibody was also successfully used as a coating antibody and as an antibody-conjugate in enzyme linked immunosorbent assay ("ELISA").

The above method of producing antibody to GLRaV3 can also be applied to other gene sequences of the present invention. The method affords a large amount of highly purified protein from *E. coli* from which antibodies can be readily obtained. It is particularly useful in the common case where it is rather difficult to obtain sufficient amount of purified virus from GLRaV3 infected grapevine tissues.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of detecting the presence of a grapevine leafroll virus in a sample, said method comprising contacting said sample with a nucleic acid probe consisting essentially of the nucleic acid sequence of SEQ ID NO:9 or a fragment thereof, wherein hybridization of said probe to said sample is taken as an indication of the presence of said grapevine leafroll virus in said sample.

2. The method of claim 1, wherein said probe is a fragment of the nucleic acid sequence of SEQ ID NO:9.

* * * * *

UNITED STATES PATENT AND TRADEMARK OFFICE
CERTIFICATE OF CORRECTION

PATENT NO.    : 6,638,720 B1
DATED         : October 28, 2003
INVENTOR(S)   : Dennis Gonsalves and Kai-Shu Ling It is certified that error appears in the above-identified patent and that said Letters Patent is hereby corrected as shown below:

Column 1,
Line 12, please insert -- This work was supported by U.S. – Israel Binational Agricultural Research and Development Fund Grant No. US-1737-89 and by the U.S. Department of Agriculture Cooperative Agreement No. 58-2349-9-01. The Federal Government may have certain rights in the invention. --

Signed and Sealed this

Thirteenth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,638,720 B1
DATED : October 28, 2003
INVENTOR(S) : Dennis Gonsalves and Kai-Shu Ling It is certified that error appears in the above-identified patent and that said Letters Patent is hereby corrected as shown below:

<u>Title page,</u>
Item [56], References Cited, OTHER PUBLICATIONS, "Wetzel et al." reference, before "A Highly" insert -- " --.

<u>Column 4,</u>
Line 19, replace "at" with -- et --.

<u>Column 7,</u>
Line 59, replace "kilobases (kb)" with -- kilobases (kb) --.

<u>Column 8,</u>
Line 2, replace "("PTOL")" with -- ("PLO3") --.

<u>Column 9,</u>
Line 16, after "et al." insert -- " --.

<u>Column 27,</u>
Line 7, replace "are." with -- are --; and
Line 51, after "sequence (s)" insert -- . --.

<u>Column 33,</u>
Line 14, replace "tion.Any" with -- tion. Any --.

<u>Column 34,</u>
Line 13, after "reference)" insert -- . --.

<u>Column 35,</u>
Line 1, replace "Motif-C" with -- Motif C --; and
Line 62, replace "PCR-amplif ied" with -- PCR-amplified --.

<u>Column 37,</u>
Line 58, replace "S'" with -- 5' --.

<u>Column 39,</u>
Line 20, replace "hplates" with -- plates --; and
Line 21, replace "15.70" with -- 15.7% --; and
Line 61, replace "protein,gene." with -- protein, gene. --.

UNITED STATES PATENT AND TRADEMARK OFFICE
CERTIFICATE OF CORRECTION

PATENT NO. : 6,638,720 B1
DATED : October 28, 2003
INVENTOR(S) : Dennis Gonsalves and Kai-Shu Ling It is certified that error appears in the above-identified patent and that said Letters Patent is hereby corrected as shown below:

Column 40,
Line 10, replace "A:multiple" with -- A multiple --; and
Line 29, replace "of." with -- of --; and
Line 50, replace "-uGAGuGAAcgcgAUG-" with -- -uGAGuGAAcgcgAUG --.

Column 44,
Line 36, after "(1993)" insert -- , --.

Column 45,
Line 16, after "reference)" insert -- . --.

Column 48,
Line 34, replace "21.7w" with -- 21.7% --.

Column 50,
Line 6, after "210K" insert -- . --.

Column 51,
Line 66, replace "reminder" with -- remainder --.

Column 52,
Line 55, replace "cv.Havana 423" with -- cv. Havana 423 --.

Column 54,
Line 67, after "("Wilson (1993)"" insert -- ) --.

Signed and Sealed this

Twenty-second Day of March, 2005

JON W. DUDAS
*Director of the United States Patent and Trademark Office*

SEQUENCE LISTING

<160> NUMBER OF SEQ ID NOS: 67

<210> SEQ ID NO 1
<211> LENGTH: 4173
<212> TYPE: DNA
<213> ORGANISM: Grapevine Leafroll Virus

<400> SEQUENCE: 1

```
gtgtctactt acgcgaagag tgtgatgaac gacaatttca atatccttga gaccctggta      60
actttgccca agtcctttat agtcaaagta cctggttcgg tgctggttag cataaccact     120
tcgggcattt ccgacaaact tgaacttcgg ggcgcgttcg acgtttctaa aaagaatttc     180
tccaggaggt tacgttcgag tcgtttgcgc gtattttcta gggctattgt ggaggatacg     240
atcaaggtta tgaagggcat gaaatcagag gatggtaaac cactccctat agccgaggat     300
tccgtgtacg cgttcatgac aggcaatatg tcaaacgttc attgcactag ggctggtttg     360
ctcggggget caaaggcttg cgcggcttct ttagctgtga agggtgcagc ttcacgcgct     420
actggaacaa aactcttttc aggtctcaca tcctttcttt ccgccggtgg tctgttttac     480
gatgaaggct tgacgcccgg agagaggctt gatgcactaa cgcgccgtga acatgctgtg     540
aattcacctg taggcctctt agaacctgga gcttcggttg cgaagcgggt cgtttccgga     600
acgaaagctt ttctgtcaga attgtcattg gaggacttca ccactttcgt cataaaaaat     660
agggtgctta ttggtgtttt tactctttcc atggctctca ctccggtggt ctggaagtac     720
agaaggaata tcgcgcgaac tggcgtggat gttttccacc gtgctcgttc gggtaccgcg     780
gccatcggtt tacaatgtct tagtggagga aggtcgttag ctggtgacgc tgctcgtggc     840
gcgttaacag tgactcgagg agggctatct tcggcggttg cggtgaccag aaatacagtg     900
gctaggcgtc aggtaccatt ggcgttgctt tcgttttcca cgtcttacgc agtcagtggt     960
tgcactttgt taggtatttg ggctcatgct ctccctaggc atttgatgtt cttctttggc    1020
ctagggacgc tcttcggggt gagtgccagt accaattctt ggtcgcttgg gggctatacg    1080
aacagtctgt tcaccgtacc ggaattaact tgggaaggga ggagttacag atctttattg    1140
ccccaagcag ctttaggtat ttctctcgtt gtgcgcgggt tgttaagtga aactgtgcca    1200
caactaacgt acgtaccgcc gattgaaggt cggaatgttt atgatcaggc actaaatttt    1260
tatcgcgact ttgactatga cgatggtgca ggcccatccg ggacggctgg tcaaagcgat    1320
cctgaaacca atacttcgga tacttcttcg gttttctctg acgatggttt gcccgctagt    1380
ggcggtggct tcgacgcgcg cgttgaggca ggtcccagcc atgctgttga tgaatcacca    1440
```

```
aggggtagtg ttgagttcgt ctacagagaa cgtgtagatg aacatccggc gtgtggtgaa    1500
gctgaagttg aaaaggatct aataacacca cttggtacag ctgtcttaga gtcgcccccc    1560
gtaggtcctg aagctgggag cgcgcccaac gtcgaggacg ttgtccgga ggttgaagct     1620 gagaaatgtt cggaggtcat cgttgacgtt cctagttcag aaccgccggt acaagaagtc    1680
cttgaatcaa ccaatggtgt ccaagctgca agaactgaag aggttgtgca gggcgacaca    1740
tgtggagctg ggtagctaa atcagaagtg agtcaacgtg tgtttcctgc gcaagtaccc     1800
gcacatgaag ctggtcttga ggcatctagt ggcgcggtcg tggagccatt gcaagtttct    1860
gtgccagtag ccgtagagaa aactgttta tctgtcgaga aggcgcgtga gctaaaggcg     1920
gtagataagg gcaaggcggt cgtgcacgca aggaagtca agaatgtacc ggttaagacg      1980
ttaccacgag gggctctaaa aattagtgag gataccgttc gtaaggaatt gtgcatgttt    2040
agaacgtgtt cctgcggcgt gcagttggac gtgtacaatg aagcgaccat cgccactagg    2100
ttctcaaatg cgtttacctt tgtcgatagc ttgaaaggga ggagtgcggt cttttctca     2160 aagctgggtg aggggtatac ctataatggt ggtagccatg tttcatcagg gtggcctcgt    2220
gccctagagg atatcttaac ggcaattaag tacccaagcg tcttcgacca ctgtttagtg    2280
cagaagtaca agatgggtgg aggcgtacca ttccacgctg atgacgagga gtgctatcca    2340
tcagataacc ctatcttgac ggtcaatctc gtggggaagg caaacttctc gactaagtgc    2400
aggaagggtg gtaaggtcat ggtcataaac gtagcttcgg gtgactattt tcttatgcct    2460
tgcggttttc aaaggacgca cttgcattca gtaaactcca tcgacgaagg gcgcatcagt    2520
ttgacgttca gggcaactcg gcgcgtcttt ggtgtaggca ggatgttgca gttagccggc    2580
ggcgtgtcgg atgagaagtc accaggtgtt ccaaaccagc aaccacagag ccaaggtgct    2640
accagaacaa tcacaccaaa atcgggggc aaggctctat ctgagggaag tggtagggaa     2700
gtcaagggga ggtcgacata ctcgatatgg tgcgaacaag attacgttag gaagtgtgag    2760
tggctcaggg ctgataatcc agtgatggct cttaaacctg gctacacccc aatgacattt    2820
gaagtggtta aagccgggac ctctgaagat gccgtcgtgg agtacttgaa gtatctggct    2880
ataggcattg ggaggacata cagggcgttg cttatggcta gaaatattgc cgtcactacc    2940
gccgaaggtg ttctgaaagt acctaatcaa gtttatgaat cactaccggg ctttcacgtt    3000
tacaagtcgg gcacagatct cattttcat tcaacacaag acggcttgcg tgtgagagac     3060
ctaccgtacg tattcatagc tgagaaaggt attttttatca agggcaaaga tgtcgacgcg    3120
gtagtagctt tgggcgacaa tctgtccgta tgtgatgata tattggtttt ccatgatgct    3180
attaatttga tgggtgcact gaaagttgct cgatgtggta tggtgggtga atcatttaag    3240
tcgttcgaat acaaatgcta taatgctccc ccaggtggcg gtaagacgac gatgctagtg    3300
gacgaatttg tcaagtcacc caatagcacg gccaccatta cggctaacgt gggaagttct    3360
gaggacataa atatggcggt gaagaagaga gatccgaatt tggaaggtct caacagtgct    3420
accacagtta actccagggt ggttaacttt attgtcaggg gaatgtataa aagggttttg    3480
gtggatgagg tgtacatgat gcatcaaggc ttactacaac taggcgtctt cgcaaccggc    3540
gcgtcggaag gcctcttttt tggagacata aatcagatac cattcataaa ccgggagaag    3600
gtgtttagga tggattgtgc tgtatttgtt ccaagaaagg aaagcgttgt atacacttct    3660
aaatcataca ggtgtccgtt agatgtttgc tacttgttgt cctcaatgac cgtaaggga     3720 acggaaaagt gttaccctga aaaggtcgtt agcggtaagg acaaaccagt agtaagatcg    3780
ctgtccaaaa ggccaattgg aaccactgat gacgtagctg aaataaacgc tgacgtgtac    3840
```

-continued

```
ttgtgcatga cccagttgga gaagtcggat atgaagaggt cgttgaaggg aaaaggaaaa    3900
gaaacaccag tgatgacagt gcatgaagca cagggaaaaa cattcagtga tgtggtattg    3960
tttaggacga agaaagccga tgactcccta ttcactaaac aaccgcatat acttgttggt    4020
ttgtcgagac acacacgctc actggtttat gccgctctga gctcagagtt ggacgataag    4080
gtcggcacat atattagcga cgcgtcgcct caatcagtat ccgacgcttt gcttcacacg    4140
ttcgccccgg ctggttgctt tcgaggtata tga                                 4173
```

<210> SEQ ID NO 2
<211> LENGTH: 1390
<212> TYPE: PRT
<213> ORGANISM: Grapevine Leafroll Virus

<400> SEQUENCE: 2

```
Val Ser Thr Tyr Ala Lys Ser Val Met Asn Asp Asn Phe Asn Ile Leu
 1               5                  10                  15

Glu Thr Leu Val Thr Leu Pro Lys Ser Phe Ile Val Lys Val Pro Gly
            20                  25                  30

Ser Val Leu Val Ser Ile Thr Thr Ser Gly Ile Ser Asp Lys Leu Glu
        35                  40                  45

Leu Arg Gly Ala Phe Asp Val Ser Lys Lys Asn Phe Ser Arg Arg Leu
    50                  55                  60

Arg Ser Ser Arg Leu Arg Val Phe Ser Arg Ala Ile Val Glu Asp Thr
65                  70                  75                  80

Ile Lys Val Met Lys Gly Met Lys Ser Glu Asp Gly Lys Pro Leu Pro
                85                  90                  95

Ile Ala Glu Asp Ser Val Tyr Ala Phe Met Thr Gly Asn Met Ser Asn
            100                 105                 110

Val His Cys Thr Arg Ala Gly Leu Leu Gly Gly Ser Lys Ala Cys Ala
        115                 120                 125

Ala Ser Leu Ala Val Lys Gly Ala Ala Ser Arg Ala Thr Gly Thr Lys
    130                 135                 140

Leu Phe Ser Gly Leu Thr Ser Phe Leu Ser Ala Gly Gly Leu Phe Tyr
145                 150                 155                 160

Asp Glu Gly Leu Thr Pro Gly Glu Arg Leu Asp Ala Leu Thr Arg Arg
                165                 170                 175

Glu His Ala Val Asn Ser Pro Val Gly Leu Leu Glu Pro Gly Ala Ser
            180                 185                 190

Val Ala Lys Arg Val Val Ser Gly Thr Lys Ala Phe Leu Ser Glu Leu
        195                 200                 205

Ser Leu Glu Asp Phe Thr Thr Phe Val Ile Lys Asn Arg Val Leu Ile
    210                 215                 220

Gly Val Phe Thr Leu Ser Met Ala Leu Thr Pro Val Val Trp Lys Tyr
225                 230                 235                 240

Arg Arg Asn Ile Ala Arg Thr Gly Val Asp Val Phe His Arg Ala Arg
                245                 250                 255

Ser Gly Thr Ala Ala Ile Gly Leu Gln Cys Leu Ser Gly Gly Arg Ser
            260                 265                 270

Leu Ala Gly Asp Ala Ala Arg Gly Ala Leu Thr Val Thr Arg Gly Gly
        275                 280                 285

Leu Ser Ser Ala Val Ala Val Thr Arg Asn Thr Val Ala Arg Arg Gln
    290                 295                 300

Val Pro Leu Ala Leu Leu Ser Phe Ser Thr Ser Tyr Ala Val Ser Gly
```

```
            305                 310                 315                 320
Cys Thr Leu Leu Gly Ile Trp Ala His Ala Leu Pro Arg His Leu Met
            325                 330                 335
Phe Phe Phe Gly Leu Gly Thr Leu Phe Gly Val Ser Ala Ser Thr Asn
            340                 345                 350
Ser Trp Ser Leu Gly Gly Tyr Thr Asn Ser Leu Phe Thr Val Pro Glu
            355                 360                 365
Leu Thr Trp Glu Gly Arg Ser Tyr Arg Ser Leu Leu Pro Gln Ala Ala
            370                 375                 380
Leu Gly Ile Ser Leu Val Val Arg Gly Leu Leu Ser Glu Thr Val Pro
385                 390                 395                 400
Gln Leu Thr Tyr Val Pro Pro Ile Glu Gly Arg Asn Val Tyr Asp Gln
            405                 410                 415
Ala Leu Asn Phe Tyr Arg Asp Phe Asp Tyr Asp Asp Gly Ala Gly Pro
            420                 425                 430
Ser Gly Thr Ala Gly Gln Ser Asp Pro Gly Thr Asn Thr Ser Asp Thr
            435                 440                 445
Ser Ser Val Phe Ser Asp Asp Gly Leu Pro Ala Ser Gly Gly Gly Phe
            450                 455                 460
Asp Ala Arg Val Glu Ala Gly Pro Ser His Ala Val Asp Glu Ser Pro
465                 470                 475                 480
Arg Gly Ser Val Glu Phe Val Tyr Arg Glu Arg Val Asp Glu His Pro
            485                 490                 495
Ala Cys Gly Glu Ala Glu Val Glu Lys Asp Leu Ile Thr Pro Leu Gly
            500                 505                 510
Thr Ala Val Leu Glu Ser Pro Pro Val Gly Pro Glu Ala Gly Ser Ala
            515                 520                 525
Pro Asn Val Glu Asp Gly Cys Pro Glu Val Glu Ala Glu Lys Cys Ser
            530                 535                 540
Glu Val Ile Val Asp Val Pro Ser Ser Glu Pro Pro Val Gln Glu Val
545                 550                 555                 560
Leu Glu Ser Thr Asn Gly Val Gln Ala Ala Arg Thr Glu Glu Val Val
            565                 570                 575
Gln Gly Asp Thr Cys Gly Ala Gly Val Ala Lys Ser Glu Val Ser Gln
            580                 585                 590
Arg Val Phe Pro Ala Gln Val Pro Ala His Glu Ala Gly Leu Glu Ala
            595                 600                 605
Ser Ser Gly Ala Val Val Glu Pro Leu Gln Val Ser Val Pro Val Ala
            610                 615                 620
Val Glu Lys Thr Val Leu Ser Val Glu Lys Ala Arg Glu Leu Lys Ala
625                 630                 635                 640
Val Asp Lys Gly Lys Ala Val Val His Ala Lys Glu Val Lys Asn Val
            645                 650                 655
Pro Val Lys Thr Leu Pro Arg Gly Ala Leu Lys Ile Ser Glu Asp Thr
            660                 665                 670
Val Arg Lys Glu Leu Cys Met Phe Arg Thr Cys Ser Cys Gly Val Gln
            675                 680                 685
Leu Asp Val Tyr Asn Glu Ala Thr Ile Ala Thr Arg Phe Ser Asn Ala
            690                 695                 700
Phe Thr Phe Val Asp Ser Leu Lys Gly Arg Ser Ala Val Phe Phe Ser
705                 710                 715                 720
Lys Leu Gly Glu Gly Tyr Thr Tyr Asn Gly Gly Ser His Val Ser Ser
            725                 730                 735
```

-continued

```
Gly Trp Pro Arg Ala Leu Glu Asp Ile Leu Thr Ala Ile Lys Tyr Pro
        740                 745                 750
Ser Val Phe Asp His Cys Leu Val Gln Lys Tyr Lys Met Gly Gly Gly
        755                 760                 765
Val Pro Phe His Ala Asp Asp Glu Glu Cys Tyr Pro Ser Asp Asn Pro
        770                 775                 780
Ile Leu Thr Val Asn Leu Val Gly Lys Ala Asn Phe Ser Thr Lys Cys
785                 790                 795                 800
Arg Lys Gly Gly Lys Val Met Val Ile Asn Val Ala Ser Gly Asp Tyr
                805                 810                 815
Phe Leu Met Pro Cys Gly Phe Gln Arg Thr His Leu His Ser Val Asn
                820                 825                 830
Ser Ile Asp Glu Gly Arg Ile Ser Leu Thr Phe Arg Ala Thr Arg Arg
                835                 840                 845
Val Phe Gly Val Gly Arg Met Leu Gln Leu Ala Gly Gly Val Ser Asp
        850                 855                 860
Glu Lys Ser Pro Gly Val Pro Asn Gln Gln Pro Gln Ser Gln Gly Ala
865                 870                 875                 880
Thr Arg Thr Ile Thr Pro Lys Ser Gly Gly Lys Ala Leu Ser Glu Gly
                885                 890                 895
Ser Gly Arg Glu Val Lys Gly Arg Ser Thr Tyr Ser Ile Trp Cys Glu
        900                 905                 910
Gln Asp Tyr Val Arg Lys Cys Glu Trp Leu Arg Ala Asp Asn Pro Val
        915                 920                 925
Met Ala Leu Lys Pro Gly Tyr Thr Pro Met Thr Phe Glu Val Val Lys
        930                 935                 940
Ala Gly Thr Ser Glu Asp Ala Val Glu Tyr Leu Lys Tyr Leu Ala
945                 950                 955                 960
Ile Gly Ile Gly Arg Thr Tyr Arg Ala Leu Leu Met Ala Arg Asn Ile
                965                 970                 975
Ala Val Thr Thr Ala Glu Gly Val Leu Lys Val Pro Asn Gln Val Tyr
        980                 985                 990
Glu Ser Leu Pro Gly Phe His Val Tyr Lys Ser Gly Thr Asp Leu Ile
        995                 1000                1005
Phe His Ser Thr Gln Asp Gly Leu Arg Val Arg Asp Leu Pro Tyr Val
        1010                1015                1020
Phe Ile Ala Glu Lys Gly Ile Phe Ile Leu Gly Lys Asp Val Asp Ala
1025                1030                1035                1040
Val Val Ala Leu Gly Asp Asn Leu Ser Val Cys Asp Asp Ile Leu Val
                1045                1050                1055
Phe His Asp Ala Ile Asn Leu Met Gly Ala Leu Lys Val Ala Arg Cys
                1060                1065                1070
Gly Met Val Gly Glu Ser Phe Lys Ser Phe Glu Tyr Lys Cys Tyr Asn
        1075                1080                1085
Ala Pro Pro Gly Gly Lys Thr Thr Met Leu Val Asp Glu Phe Val
        1090                1095                1100
Lys Ser Pro Asn Ser Thr Ala Thr Ile Thr Ala Asn Val Gly Ser Ser
1105                1110                1115                1120
Glu Asp Ile Asn Met Ala Val Lys Lys Arg Asp Pro Asn Leu Glu Gly
                1125                1130                1135
Leu Asn Ser Ala Thr Thr Val Asn Ser Arg Val Val Asn Phe Ile Val
                1140                1145                1150
```

```
Arg Gly Met Tyr Lys Arg Val Leu Val Asp Glu Val Tyr Met Met His
        1155                1160                1165

Gln Gly Leu Leu Gln Leu Gly Val Phe Ala Thr Gly Ala Ser Glu Gly
        1170                1175                1180

Leu Phe Phe Gly Asp Ile Asn Gln Ile Pro Phe Ile Asn Arg Glu Lys
1185                1190                1195                1200

Val Phe Arg Met Asp Cys Ala Val Phe Val Pro Lys Lys Glu Ser Val
                1205                1210                1215

Val Tyr Thr Ser Lys Ser Tyr Arg Cys Pro Leu Asp Val Cys Tyr Leu
        1220                1225                1230

Leu Ser Ser Met Thr Val Arg Gly Thr Glu Lys Cys Tyr Pro Glu Lys
        1235                1240                1245

Val Val Ser Gly Lys Asp Lys Pro Val Val Arg Ser Leu Ser Lys Arg
        1250                1255                1260

Pro Ile Gly Thr Thr Asp Asp Val Ala Glu Ile Asn Ala Asp Val Tyr
1265                1270                1275                1280

Leu Cys Met Thr Gln Leu Glu Lys Ser Asp Met Lys Arg Ser Leu Lys
        1285                1290                1295

Gly Lys Gly Lys Glu Thr Pro Val Met Thr Val His Glu Ala Gln Gly
        1300                1305                1310

Lys Thr Phe Ser Asp Val Val Leu Phe Arg Thr Lys Lys Ala Asp Asp
        1315                1320                1325

Ser Leu Phe Thr Lys Gln Pro His Ile Leu Val Gly Leu Ser Arg His
        1330                1335                1340

Thr Arg Ser Leu Val Tyr Ala Ala Leu Ser Ser Glu Leu Asp Asp Lys
1345                1350                1355                1360

Val Gly Thr Tyr Ile Ser Asp Ala Ser Pro Gln Ser Val Ser Asp Ala
                1365                1370                1375

Leu Leu His Thr Phe Ala Pro Ala Gly Cys Phe Arg Gly Ile
        1380                1385                1390

<210> SEQ ID NO 3
<211> LENGTH: 1602
<212> TYPE: DNA
<213> ORGANISM: Grapevine Leafroll Virus

<400> SEQUENCE: 3
atgaattttg daccgacctt cgaaggggag ttggtacgga agataccaac aagtcatttt      60
gtagccgtga atgggtttct cgaggactta ctcgacggtt gtccggcttt cgactatgac    120
ttctttgagg atgatttcga aacttcagat cagtctttcc tcatagaaga tgtgcgcatt    180
tctgaatctt tttctcattt tgcgtcgaaa atagaggata ggttttacag ttttattagg    240
tctagcgtag gtttaccaaa gcgcaacacc ttgaagtgta acctcgtcac gtttgaaaat    300
aggaattcca acgccgatcg cggttgtaac gtgggttgtg acgactctgt ggcgcatgaa    360
ctgaaggaga tttcttcga ggaggtcgtt aacaaagctc gtttagcaga ggtgacggaa    420
agccatttgt ccagcaacac gatgttgtta tcagattggt tggacaaaag gcacctaac    480 gcttacaagt ctctcaagcg ggctttaggt tcggttgtct ttcatccgtc tatgttgacg    540
tcttatacgc tcatggtgaa agcagacgta aaacccaagt tggacaatac gccattgtcg    600
aagtacgtaa cggggcagaa tatagtctac acgataggt gcgtaactgc gctttttct    660 tgcatttta ctgcgtgcgt agagcgctta aaatacgtag tggacgaaag gtggctcttc    720
taccacggga tggacactgc ggagttggcg gctgcattga ggaacaattt gggggacatc    780
```

-continued

```
cggcaatact acacctatga actggatatc agtaagtacg acaaatctca gagtgctctc    840
atgaagcagg tggaggagtt gatactcttg acacttggtg ttgatagaga agttttgtct    900
actttctttt gtggtgagta tgatagcgtc gtgagaacga tgacgaagga attggtgttg    960
tctgtcggct ctcagaggcg cagtggtggt gctaacacgt ggttgggaaa tagtttagtc   1020
ttgtgcacct tgttgtccgt agtacttagg ggattagatt atagttatat tgtagttagc   1080
ggtgatgata gccttatatt tagtcggcag ccgttggata ttgatacgtc ggttctgagc   1140
gataattttg gttttgacgt aaagattttt aaccaagctg ctccatattt ttgttctaag   1200
tttttagttc aagtcgagga tagtctcttt tttgttcccg atccacttaa actcttcgtt   1260
aagtttggag cttccaaaac ttcagatatc gacctttttac atgagatttt tcaatctttc   1320
gtcgatcttt cgaagggttt caatagagag gacgtcatcc aggaattagc taagctggtg   1380
acgcggaaat ataagcattc gggatggacc tactcggctt tgtgtgtctt gcacgttttta  1440 agtgcaaatt tttcgcagtt ctgtaggtta tattaccaca atagcgtgaa tctcgatgtg   1500
cgccctattc agaggaccga gtcgctttcc ttgctggcct tgaaggcaag aattttaagg   1560
tggaaagctt ctcgttttgc cttttcgata aagagggtt aa                       1602
```

<210> SEQ ID NO 4
<211> LENGTH: 533
<212> TYPE: PRT
<213> ORGANISM: Grapevine Leafroll Virus

<400> SEQUENCE: 4

```
Met Asn Phe Gly Pro Thr Phe Glu Gly Glu Leu Val Arg Lys Ile Pro
  1               5                  10                  15

Thr Ser His Phe Val Ala Val Asn Gly Phe Leu Glu Asp Leu Leu Asp
             20                  25                  30

Gly Cys Pro Ala Phe Asp Tyr Asp Phe Phe Glu Asp Asp Phe Glu Thr
         35                  40                  45

Ser Asp Gln Ser Phe Leu Ile Glu Asp Val Arg Ile Ser Glu Ser Phe
     50                  55                  60

Ser His Phe Ala Ser Lys Ile Glu Asp Arg Phe Tyr Ser Phe Ile Arg
 65                  70                  75                  80

Ser Ser Val Gly Leu Pro Lys Arg Asn Thr Leu Lys Cys Asn Leu Val
                 85                  90                  95

Thr Phe Glu Asn Arg Asn Ser Asn Ala Asp Arg Gly Cys Asn Val Gly
            100                 105                 110

Cys Asp Asp Ser Val Ala His Glu Leu Lys Glu Ile Phe Phe Glu Glu
        115                 120                 125

Val Val Asn Lys Ala Arg Leu Ala Glu Val Thr Glu Ser His Leu Ser
    130                 135                 140

Ser Asn Thr Met Leu Leu Ser Asp Trp Leu Asp Lys Arg Ala Pro Asn
145                 150                 155                 160

Ala Tyr Lys Ser Leu Lys Arg Ala Leu Gly Ser Val Phe His Pro
                165                 170                 175

Ser Met Leu Thr Ser Tyr Thr Leu Met Val Lys Ala Asp Val Lys Pro
            180                 185                 190

Lys Leu Asp Asn Thr Pro Leu Ser Lys Tyr Val Thr Gly Gln Asn Ile
        195                 200                 205

Val Tyr His Asp Arg Cys Val Thr Ala Leu Phe Ser Cys Ile Phe Thr
    210                 215                 220

Ala Cys Val Glu Arg Leu Lys Tyr Val Val Asp Glu Arg Trp Leu Phe
```

```
                   225                 230                 235                 240
        Tyr His Gly Met Asp Thr Ala Glu Leu Ala Ala Leu Arg Asn Asn
                        245                 250                 255
        Leu Gly Asp Ile Arg Gln Tyr Tyr Thr Tyr Glu Leu Asp Ile Ser Lys
                    260                 265                 270
        Tyr Asp Lys Ser Gln Ser Ala Leu Met Lys Gln Val Glu Glu Leu Ile
                    275                 280                 285
        Leu Leu Thr Leu Gly Val Asp Arg Glu Val Leu Ser Thr Phe Phe Cys
            290                 295                 300
        Gly Glu Tyr Asp Ser Val Val Arg Thr Met Thr Lys Glu Leu Val Leu
        305                 310                 315                 320
        Ser Val Gly Ser Gln Arg Arg Ser Gly Gly Ala Asn Thr Trp Leu Gly
                        325                 330                 335
        Asn Ser Leu Val Leu Cys Thr Leu Leu Ser Val Val Leu Arg Gly Leu
                        340                 345                 350
        Asp Tyr Ser Tyr Ile Val Val Ser Gly Asp Ser Leu Ile Phe Ser
                    355                 360                 365
        Arg Gln Pro Leu Asp Ile Asp Thr Ser Val Leu Ser Asp Asn Phe Gly
            370                 375                 380
        Phe Asp Val Lys Ile Phe Asn Gln Ala Ala Pro Tyr Phe Cys Ser Lys
        385                 390                 395                 400
        Phe Leu Val Gln Val Glu Asp Ser Leu Phe Phe Val Pro Asp Pro Leu
                        405                 410                 415
        Lys Leu Phe Val Lys Phe Gly Ala Ser Lys Thr Ser Asp Ile Asp Leu
                        420                 425                 430
        Leu His Glu Ile Phe Gln Ser Phe Val Asp Leu Ser Lys Gly Phe Asn
                    435                 440                 445
        Arg Glu Asp Val Ile Gln Glu Leu Ala Lys Leu Val Thr Arg Lys Tyr
            450                 455                 460
        Lys His Ser Gly Trp Thr Tyr Ser Ala Leu Cys Val Leu His Val Leu
        465                 470                 475                 480
        Ser Ala Asn Phe Ser Gln Phe Cys Arg Leu Tyr Tyr His Asn Ser Val
                        485                 490                 495
        Asn Leu Asp Val Arg Pro Ile Gln Arg Thr Glu Ser Leu Ser Leu Leu
                        500                 505                 510
        Ala Leu Lys Ala Arg Ile Leu Arg Trp Lys Ala Ser Arg Phe Ala Phe
                    515                 520                 525
        Ser Ile Lys Arg Gly
                530

<210> SEQ ID NO 5
<211> LENGTH: 1650
<212> TYPE: DNA
<213> ORGANISM: Grapevine Leafroll Virus

<400> SEQUENCE: 5
atggaagtag gtatagattt tggaaccact ttcagcacaa tctgcttttc cccatctggg       60
gtcagcggtt gtactcctgt ggccggtagt gtttacgttg aaacccaaat ttttataccct     120 gaaggtagca gtacttactt aattggtaaa gctgcgggga aagcttatcg tgacggtgta      180
gagggaaggt tgtatgttaa cccgaaaagg tgggcaggtg tgacgaggga taacgtcgaa      240
cgctacgtcg agaaattaaa acctacatac accgtgaaga tagacagcgg aggcgcctta     300
ttaattggag gtttaggttc cggaccagac accttattga gggtcgttga cgtaatatgt    360
ttattcttga gagccttgat actggagtgc gaaaggtata cgtctacgac ggttacagca    420
```

```
gctgttgtaa cggtaccggc tgactataac tcctttaaac gaagcttcgt tgttgaggcg    480
ctaaaaggtc ttggtatacc ggttagaggt gttgttaacg aaccgacggc cgcagccctc    540
tattccttag ctaagtcgcg agtagaagac ctattattag cggttttttga ttttggggga   600 gggactttcg acgtctcatt cgttaagaag aagggaaata tactatgcgt catcttttca    660
gtgggtgata atttcttggg tggtagagat attgatagag ctatcgtgga agttatcaaa    720
caaaagatca aggaaaggc gtctgatgcc aagttaggga tattcgtatc ctcgatgaag     780
gaagacttgt ctaacaataa cgctataacg caacacctta tccccgtaga aggggtgtg    840 gaggttgtgg atttgactag cgacgaactg gacgcaatcg ttgcaccatt cagcgctagg    900
gctgtggaag tattcaaaac tggtcttgac aactttttacc cagacccggt tattgccgtt   960
atgactgggg ggtcaagtgc tctagttaag gtcaggagtg atgtggctaa tttgccgcag    1020
atatctaaag tcgtgttcga cagtaccgat tttagatgtt cggtggcttg tggggctaag    1080
gtttactgcg atactttggc aggtaatagc ggactgagac tggtggacac tttaacgaat    1140
acgctaacgg acgaggtagt gggtcttcag ccggtggtaa ttttcccgaa aggtagtcca    1200 atacctgtt catatactca tagatacaca gtgggtggtg gagatgtggt atacggtata    1260
tttgaagggg agaataacag agcttttcta aatgagccga cgttccgggg cgtatcgaaa    1320 cgtagggag acccagtaga gaccgacgtg gcgcagttta atctctccac ggacggaacg     1380
gtgtctgtta tcgttaatgg tgaggaagta aagaatgaat atctggtacc cgggacaaca    1440
aacgtactgg attcattggt ctataaatct gggagagaag atttagaggc taaggcaata    1500
ccagagtact tgaccacact gaatattttg cacgataagg ctttcacgag gagaaacctg    1560
ggtaacaaag ataaggggtt ctcggattta aggatagaag aaaattttt aaaatccgcc     1620 gtagatacag acacgatttt gaatggataa                                     1650
```

<210> SEQ ID NO 6
<211> LENGTH: 549
<212> TYPE: PRT
<213> ORGANISM: Grapevine Leafroll Virus

<400> SEQUENCE: 6

```
Met Glu Val Gly Ile Asp Phe Gly Thr Thr Phe Ser Thr Ile Cys Phe
  1               5                  10                  15

Ser Pro Ser Gly Val Ser Gly Cys Thr Pro Val Ala Gly Ser Val Tyr
             20                  25                  30

Val Glu Thr Gln Ile Phe Ile Pro Glu Gly Ser Ser Thr Tyr Leu Ile
         35                  40                  45

Gly Lys Ala Ala Gly Lys Ala Tyr Arg Asp Gly Val Glu Gly Arg Leu
     50                  55                  60

Tyr Val Asn Pro Lys Arg Trp Ala Gly Val Thr Arg Asp Asn Val Glu
 65                  70                  75                  80

Arg Tyr Val Glu Lys Leu Lys Pro Thr Tyr Thr Val Lys Ile Asp Ser
                 85                  90                  95

Gly Gly Ala Leu Leu Ile Gly Gly Leu Gly Ser Gly Pro Asp Thr Leu
            100                 105                 110

Leu Arg Val Val Asp Val Ile Cys Leu Phe Leu Arg Ala Leu Ile Leu
        115                 120                 125

Glu Cys Glu Arg Tyr Thr Ser Thr Thr Val Thr Ala Ala Val Val Thr
    130                 135                 140

Val Pro Ala Asp Tyr Asn Ser Phe Lys Arg Ser Phe Val Val Glu Ala
```

```
                145                 150                 155                 160
Leu Lys Gly Leu Gly Ile Pro Val Arg Gly Val Asn Glu Pro Thr
                165                 170                 175
Ala Ala Ala Leu Tyr Ser Leu Ala Lys Ser Arg Val Glu Asp Leu Leu
                180                 185                 190
Leu Ala Val Phe Asp Phe Gly Gly Thr Phe Asp Val Ser Phe Val
                195                 200                 205
Lys Lys Lys Gly Asn Ile Leu Cys Val Ile Phe Ser Val Gly Asp Asn
                210                 215                 220
Phe Leu Gly Gly Arg Asp Ile Asp Arg Ala Ile Val Glu Val Ile Lys
225                 230                 235                 240
Gln Lys Ile Lys Gly Lys Ala Ser Asp Ala Lys Leu Gly Ile Phe Val
                245                 250                 255
Ser Ser Met Lys Glu Asp Leu Ser Asn Asn Asn Ala Ile Thr Gln His
                260                 265                 270
Leu Ile Pro Val Glu Gly Gly Val Glu Val Val Asp Leu Thr Ser Asp
                275                 280                 285
Glu Leu Asp Ala Ile Val Ala Pro Phe Ser Ala Arg Ala Val Glu Val
                290                 295                 300
Phe Lys Thr Gly Leu Asp Asn Phe Tyr Pro Asp Pro Val Ile Ala Val
305                 310                 315                 320
Met Thr Gly Gly Ser Ser Ala Leu Val Lys Val Arg Ser Asp Val Ala
                325                 330                 335
Asn Leu Pro Gln Ile Ser Lys Val Val Phe Asp Ser Thr Asp Phe Arg
                340                 345                 350
Cys Ser Val Ala Cys Gly Ala Lys Val Tyr Cys Asp Thr Leu Ala Gly
                355                 360                 365
Asn Ser Gly Leu Arg Leu Val Asp Thr Leu Thr Asn Thr Leu Thr Asp
                370                 375                 380
Glu Val Val Gly Leu Gln Pro Val Val Ile Phe Pro Lys Gly Ser Pro
385                 390                 395                 400
Ile Pro Cys Ser Tyr Thr His Arg Tyr Thr Val Gly Gly Gly Asp Val
                405                 410                 415
Val Tyr Gly Ile Phe Glu Gly Glu Asn Asn Arg Ala Phe Leu Asn Glu
                420                 425                 430
Pro Thr Phe Arg Gly Val Ser Lys Arg Arg Gly Asp Pro Val Glu Thr
                435                 440                 445
Asp Val Ala Gln Phe Asn Leu Ser Thr Asp Gly Thr Val Ser Val Ile
                450                 455                 460
Val Asn Gly Glu Glu Val Lys Asn Glu Tyr Leu Val Pro Gly Thr Thr
465                 470                 475                 480
Asn Val Leu Asp Ser Leu Val Tyr Lys Ser Gly Arg Glu Asp Leu Glu
                485                 490                 495
Ala Lys Ala Ile Pro Glu Tyr Leu Thr Thr Leu Asn Ile Leu His Asp
                500                 505                 510
Lys Ala Phe Thr Arg Arg Asn Leu Gly Asn Lys Asp Lys Gly Phe Ser
                515                 520                 525
Asp Leu Arg Ile Glu Glu Asn Phe Leu Lys Ser Ala Val Asp Thr Asp
                530                 535                 540
Thr Ile Leu Asn Gly
545

<210> SEQ ID NO 7
```

<211> LENGTH: 1452
<212> TYPE: DNA
<213> ORGANISM: Grapevine Leafroll Virus

<400> SEQUENCE: 7

| | | | | | |
|---|---|---|---|---|---|
| atggataaat | atatttatgt | aacggggata | ttaaaccctta | acgaggctag | agacgaggta | 60 |
| ttctcggtag | tgaataaggg | atatattgga | ccgggagggc | gctccttttc | gaatcgtggt | 120 |
| agtaagtaca | ccgtcgtctg | ggaaaactct | gctgcgagga | ttagtggatt | tacgtcgact | 180 |
| tcgcaatcta | cgatagatgc | tttcgcgtat | ttcttgttga | aaggcggatt | gactaccacg | 240 |
| ctctctaacc | caataaactg | tgagaattgg | gtcaggtcat | ctaaggattt | aagcgcgttt | 300 |
| ttcaggaccc | taattaaagg | taagatttat | gcatcgcgtt | ctgtggacag | caatcttcca | 360 |
| aagaaagaca | gggatgacat | catggaagcg | agtcgacgac | tatcgccatc | ggacgccgcc | 420 |
| ttttgcagag | cagtgtcggt | tcaggtaggg | aagtatgtgg | acgtaacgca | gaatttagaa | 480 |
| agtacgatcg | tgccgttaag | agttatggaa | ataaagaaaa | gacgaggatc | agcacatgtt | 540 |
| agtttaccga | aggtggtatc | cgcttacgta | gattttttata | cgaacttgca | ggaattgctg | 600 |
| tcggatgaag | taactagggc | cagaaccgat | acagtttcgg | catacgctac | cgactctatg | 660 |
| gctttcttag | ttaagatgtt | acccctgact | gctcgtgagc | agtggttaaa | agacgtgcta | 720 |
| ggatatctgc | tggtacggag | acgaccagca | aatttttcct | acgacgtaag | agtagcttgg | 780 |
| gtatatgacg | tgatcgctac | gctcaagctg | gtcataagat | tgttttttcaa | caaggacaca | 840 |
| cccgggggta | ttaaagactt | aaaaccgtgt | gtgcctatag | agtcattcga | ccccttttcac | 900 |
| gagctttcgt | cctatttctc | taggttaagt | tacgagatga | cgacaggtaa | aggggggaaag | 960 |
| atatgcccgg | agatcgccga | gaagttggtg | cgccgtctaa | tggaggaaaa | ctataagtta | 1020 |
| agattgaccc | cagtgatggc | cttaataatt | atactggtat | actactccat | ttacggcaca | 1080 |
| aacgctacca | ggattaaaag | acgcccggat | ttcctcaatg | tgaggataaa | gggaagagtc | 1140 |
| gagaaggttt | cgttacgggg | ggtagaagat | cgtgccttta | gaatatcaga | aaagcgcggg | 1200 |
| ataaacgctc | aacgtgtatt | atgtaggtac | tatagcgatc | tcacatgtct | ggctaggcga | 1260 |
| cattacggca | ttcgcaggaa | caattggaag | acgctgagtt | atgtagacgg | gacgttagcg | 1320 |
| tatgacacgc | tgattgtat | aacttctaag | gtgagaaata | cgatcaacac | cgcagatcac | 1380 |
| gctagcatta | tacactatat | caagacgaac | gaaaaccagg | ttaccggaac | tactctacca | 1440 |
| caccagcttt | aa | | | | | 1452 |

<210> SEQ ID NO 8
<211> LENGTH: 483
<212> TYPE: PRT
<213> ORGANISM: Grapevine Leafroll Virus

<400> SEQUENCE: 8

Met Asp Lys Tyr Ile Tyr Val Thr Gly Ile Leu Asn Pro Asn Glu Ala
1               5                   10                  15

Arg Asp Glu Val Phe Ser Val Val Asn Lys Gly Tyr Ile Gly Pro Gly
            20                  25                  30

Gly Arg Ser Phe Ser Asn Arg Gly Ser Lys Tyr Thr Val Val Trp Glu
        35                  40                  45

Asn Ser Ala Ala Arg Ile Ser Gly Phe Thr Ser Thr Ser Gln Ser Thr
    50                  55                  60

Ile Asp Ala Phe Ala Tyr Phe Leu Leu Lys Gly Gly Leu Thr Thr Thr
65                  70                  75                  80

```
Leu Ser Asn Pro Ile Asn Cys Glu Asn Trp Val Arg Ser Ser Lys Asp
                85                  90                  95
Leu Ser Ala Phe Phe Arg Thr Leu Ile Lys Gly Lys Ile Tyr Ala Ser
            100                 105                 110
Arg Ser Val Asp Ser Asn Leu Pro Lys Lys Asp Arg Asp Asp Ile Met
        115                 120                 125
Glu Ala Ser Arg Arg Leu Ser Pro Ser Asp Ala Ala Phe Cys Arg Ala
    130                 135                 140
Val Ser Val Gln Val Gly Lys Tyr Val Asp Val Thr Gln Asn Leu Glu
145                 150                 155                 160
Ser Thr Ile Val Pro Leu Arg Val Met Glu Ile Lys Lys Arg Arg Gly
                165                 170                 175
Ser Ala His Val Ser Leu Pro Lys Val Val Ser Ala Tyr Val Asp Phe
            180                 185                 190
Tyr Thr Asn Leu Gln Glu Leu Leu Ser Asp Glu Val Thr Arg Ala Arg
        195                 200                 205
Thr Asp Thr Val Ser Ala Tyr Ala Thr Asp Ser Met Ala Phe Leu Val
    210                 215                 220
Lys Met Leu Pro Leu Thr Ala Arg Glu Gln Trp Leu Lys Asp Val Leu
225                 230                 235                 240
Gly Tyr Leu Leu Val Arg Arg Pro Ala Asn Phe Ser Tyr Asp Val
                245                 250                 255
Arg Val Ala Trp Val Tyr Asp Val Ile Ala Thr Leu Lys Leu Val Ile
            260                 265                 270
Arg Leu Phe Phe Asn Lys Asp Thr Pro Gly Gly Ile Lys Asp Leu Lys
        275                 280                 285
Pro Cys Val Pro Ile Glu Ser Phe Asp Pro Phe His Glu Leu Ser Ser
    290                 295                 300
Tyr Phe Ser Arg Leu Ser Tyr Glu Met Thr Thr Gly Lys Gly Gly Lys
305                 310                 315                 320
Ile Cys Pro Glu Ile Ala Glu Lys Leu Val Arg Arg Leu Met Glu Glu
                325                 330                 335
Asn Tyr Lys Leu Arg Leu Thr Pro Val Met Ala Leu Ile Ile Ile Leu
            340                 345                 350
Val Tyr Tyr Ser Ile Tyr Gly Thr Asn Ala Thr Arg Ile Lys Arg Arg
        355                 360                 365
Pro Asp Phe Leu Asn Val Arg Ile Lys Gly Arg Val Glu Lys Val Ser
    370                 375                 380
Leu Arg Gly Val Glu Asp Arg Ala Phe Arg Ile Ser Glu Lys Arg Gly
385                 390                 395                 400
Ile Asn Ala Gln Arg Val Leu Cys Arg Tyr Tyr Ser Asp Leu Thr Cys
                405                 410                 415
Leu Ala Arg Arg His Tyr Gly Ile Arg Arg Asn Asn Trp Lys Thr Leu
            420                 425                 430
Ser Tyr Val Asp Gly Thr Leu Ala Tyr Asp Thr Ala Asp Cys Ile Thr
        435                 440                 445
Ser Lys Val Arg Asn Thr Ile Asn Thr Ala Asp His Ala Ser Ile Ile
    450                 455                 460
His Tyr Ile Lys Thr Asn Glu Asn Gln Val Thr Gly Thr Thr Leu Pro
465                 470                 475                 480
His Gln Leu

<210> SEQ ID NO 9
```

```
<211> LENGTH: 942
<212> TYPE: DNA
<213> ORGANISM: Grapevine Leafroll Virus

<400> SEQUENCE: 9
atggcatttg aactgaaatt agggcagata tatgaagtcg tccccgaaaa taatttgaga      60
gttagagtgg gggatgcggc acaaggaaaa tttagtaagg cgagtttctt aaagtacgtt     120
aaggacggga cacaggcgga attaacggga atcgccgtag tgcccgaaaa atacgtattc     180
gccacagcag ctttggctac agcggcgcag gagccaccta gcagccacc agcgcaagtg      240
gcggaaccac aggaaaccga tagggggta gtgccggaat ctgagactct cacaccaaat      300
aagttggttt tcgagaaaga tccagacaag ttcttgaaga ctatgggcaa gggaatagct     360
ttggacttgg cgggagttac ccacaaaccg aaagttatta acgagccagg aaagtatca     420
gtagaggtgg caatgaagat taatgccgca ttgatggagc tgtgtaagaa ggttatgggc     480
gccgatgacg cagcaactaa gacagaattc ttcttgtacg tgatgcagat tgcttgcacg     540
ttctttacat cgtcttcgac ggagttcaaa gagtttgact acatagaaac cgatgatgga     600
aagaagatat atgcggtgtg gtatatgat tgcattaaac aagctgctgc ttcgacgggt      660
tatgaaaacc cggtaaggca gtatctagcg tacttcacac caaccttcat cacggcgacc     720
ctgaatggta aactagtgat gaacgagaag gttatggcac agcatggagt accaccgaaa     780
ttctttccgt acacgataga ctgcgttcgt ccgacgtacg atctgttcaa caacgacgca     840
atattagcat ggaatttagc tagacagcag gcgtttagaa acaagacggt aacggccgat     900
aacaccttac acaacgtctt ccaactattg caaagaagt ag                         942

<210> SEQ ID NO 10
<211> LENGTH: 313
<212> TYPE: PRT
<213> ORGANISM: Grapevine Leafroll Virus

<400> SEQUENCE: 10

Met Ala Phe Glu Leu Lys Leu Gly Gln Ile Tyr Glu Val Val Pro Glu
 1               5                  10                  15

Asn Asn Leu Arg Val Arg Val Gly Asp Ala Ala Gln Gly Lys Phe Ser
            20                  25                  30

Lys Ala Ser Phe Leu Lys Tyr Val Lys Asp Gly Thr Gln Ala Glu Leu
        35                  40                  45

Thr Gly Ile Ala Val Val Pro Glu Lys Tyr Val Phe Ala Thr Ala Ala
    50                  55                  60

Leu Ala Thr Ala Ala Gln Glu Pro Pro Arg Gln Pro Pro Ala Gln Val
65                  70                  75                  80

Ala Glu Pro Gln Glu Thr Asp Ile Gly Val Val Pro Glu Ser Glu Thr
                85                  90                  95

Leu Thr Pro Asn Lys Leu Val Phe Glu Lys Asp Pro Asp Lys Phe Leu
            100                 105                 110

Lys Thr Met Gly Lys Gly Ile Ala Leu Asp Leu Ala Gly Val Thr His
        115                 120                 125

Lys Pro Lys Val Ile Asn Glu Pro Gly Lys Val Ser Val Glu Val Ala
    130                 135                 140

Met Lys Ile Asn Ala Ala Leu Met Glu Leu Cys Lys Lys Val Met Gly
145                 150                 155                 160

Ala Asp Asp Ala Ala Thr Lys Thr Glu Phe Phe Leu Tyr Val Met Gln
                165                 170                 175
```

```
Ile Ala Cys Thr Phe Phe Thr Ser Ser Ser Thr Glu Phe Lys Glu Phe
            180                 185                 190

Asp Tyr Ile Glu Thr Asp Asp Gly Lys Lys Ile Tyr Ala Val Trp Val
            195                 200                 205

Tyr Asp Cys Ile Lys Gln Ala Ala Ser Thr Gly Tyr Glu Asn Pro
            210                 215                 220

Val Arg Gln Tyr Leu Ala Tyr Phe Thr Pro Thr Phe Ile Thr Ala Thr
225                 230                 235                 240

Leu Asn Gly Lys Leu Val Met Asn Glu Lys Val Met Ala Gln His Gly
                245                 250                 255

Val Pro Pro Lys Phe Phe Pro Tyr Thr Ile Asp Cys Val Arg Pro Thr
                260                 265                 270

Tyr Asp Leu Phe Asn Asn Asp Ala Ile Leu Ala Trp Asn Leu Ala Arg
            275                 280                 285

Gln Gln Ala Phe Arg Asn Lys Thr Val Thr Ala Asp Asn Thr Leu His
            290                 295                 300

Asn Val Phe Gln Leu Leu Gln Lys Lys
305                 310

<210> SEQ ID NO 11
<211> LENGTH: 156
<212> TYPE: DNA
<213> ORGANISM: Grapevine Leafroll Virus

<400> SEQUENCE: 11
atgtacagta gagggtcttt ctttaagtct cgggttaccc ttcctactct tgtcggagca      60
tacatgtggg agtttgaact cccgtatctt acggacaaga gacacatcag ctatagcgcg     120
ccaagtgtcg cgacttttag ccttgtgtcg aggtag                               156

<210> SEQ ID NO 12
<211> LENGTH: 51
<212> TYPE: PRT
<213> ORGANISM: Grapevine Leafroll Virus

<400> SEQUENCE: 12

Met Tyr Ser Arg Gly Ser Phe Phe Lys Ser Arg Val Thr Leu Pro Thr
1               5                   10                  15

Leu Val Gly Ala Tyr Met Trp Glu Phe Glu Leu Pro Tyr Leu Thr Asp
            20                  25                  30

Lys Arg His Ile Ser Tyr Ser Ala Pro Ser Val Ala Thr Phe Ser Leu
        35                  40                  45

Val Ser Arg
    50

<210> SEQ ID NO 13
<211> LENGTH: 138
<212> TYPE: DNA
<213> ORGANISM: Grapevine Leafroll Virus

<400> SEQUENCE: 13
atggatgatt ttaaacaggc aatactgttg ctagtagtcg attttgtctt cgtgataatt      60
ctgctgctgg ttcttacgtt cgtcgtcccg aggttacagc aaagctccac cattaataca    120
ggtcttagga cagtgtga                                                   138

<210> SEQ ID NO 14
<211> LENGTH: 45
<212> TYPE: PRT
```

<213> ORGANISM: Grapevine Leafroll Virus

<400> SEQUENCE: 14

```
Met Asp Asp Phe Lys Gln Ala Ile Leu Leu Val Val Asp Phe Val
1               5                  10                  15

Phe Val Ile Ile Leu Leu Val Leu Thr Phe Val Val Pro Arg Leu
            20                  25                  30

Gln Gln Ser Ser Thr Ile Asn Thr Gly Leu Arg Thr Val
        35                  40                  45
```

<210> SEQ ID NO 15
<211> LENGTH: 1434
<212> TYPE: DNA
<213> ORGANISM: Grapevine Leafroll Virus

<400> SEQUENCE: 15

| | | | | | |
|---|---|---|---|---|---|
| atgggagctt | atacacatgt | agactttcat | gagtcgcggt | tgctgaaaga | caaacaagac |       60 |
| tatctttctt | tcaagtcagc | ggatgaagct | cctcctgatc | ctcccggata | cgttcgccca |      120 |
| gatagttatg | tgagggctta | tttgatacaa | agagcagact | ttcccaatac | tcaaagctta |      180 |
| tcagttacgt | tatcgatagc | cagtaataag | ttagcttcag | gtcttatggg | aagcgacgca |      240 |
| gtatcatcgt | cgtttatgct | gatgaacgac | gtgggagatt | acttcgagtg | cggcgtgtgt |      300 |
| cacaacaaac | cctacttagg | acgggaagtt | atcttctgta | ggaaatacat | aggtgggaga |      360 |
| ggagtggaga | tcaccactgg | taagaactac | acgtcgaaca | attggaacga | ggcgtcgtac |      420 |
| gtaatacaag | tgaacgtagt | cgatgggtta | gcacagacca | ctgttaattc | tacttatacg |      480 |
| caaacggacg | ttagtggtct | acccaaaaat | tggacgcgta | tctacaaaat | aacaaagata |      540 |
| gtgtccgtag | atcagaacct | ctaccctggt | tgtttctcag | actcgaaact | gggtgtaatg |      600 |
| cgtataaggt | cactgttagt | ttccccagtg | cgcatcttct | ttagggatat | cttattgaaa |      660 |
| cctttgaaga | aatcgttcaa | cgcaagaatc | gaggatgtgc | tgaatattga | cgacacgtcg |      720 |
| ttgttagtac | cgagtcctgt | cgtaccagag | tctacgggag | gtgtaggtcc | atcagagcag |      780 |
| ctggatgtag | tggctttaac | gtccgacgta | acggaattga | tcaacactag | ggggcaaggt |      840 |
| aagatatgtt | ttccagactc | agtgttatcg | atcaatgaag | cggatatcta | cgatgagcgg |      900 |
| tatttgccga | taacggaagc | tctacagata | aacgcaagac | tacgcagact | cgttctttcg |      960 |
| aaaggcggga | gtcaaacacc | acgagatatg | gggaatatga | tagtggccat | gatacaactt |     1020 |
| ttcgtactct | actctactgt | aaagaatata | agcgtcaaag | acgggtatag | ggtggagacc |     1080 |
| gaattaggtc | aaaagagagt | ctacttaagt | tattcggaag | taagggaagc | tatattagga |     1140 |
| gggaaatacg | gtgcgtctcc | aaccaacact | gtgcgatcct | tcatgaggta | ttttgctcac |     1200 |
| accactatta | ctctacttat | agagaagaaa | attcagccag | cgtgtactgc | cctagctaag |     1260 |
| cacggcgtcc | cgaagaggtt | cactccgtac | tgcttcgact | tcgcactact | ggataacaga |     1320 |
| tattacccgg | cggacgtgtt | gaaggctaac | gcaatggctt | gcgctatagc | gattaaatca |     1380 |
| gctaatttaa | ggcgtaaagg | ttcggagacg | tataacatct | agaaagcat | ttga       |     1434 |

<210> SEQ ID NO 16
<211> LENGTH: 477
<212> TYPE: PRT
<213> ORGANISM: Grapevine Leafroll Virus

<400> SEQUENCE: 16

```
Met Gly Ala Tyr Thr His Val Asp Phe His Glu Ser Arg Leu Leu Lys
1               5                  10                  15
```

-continued

```
Asp Lys Gln Asp Tyr Leu Ser Phe Lys Ser Ala Asp Glu Ala Pro Pro
             20                  25                  30
Asp Pro Pro Gly Tyr Val Arg Pro Asp Ser Tyr Val Arg Ala Tyr Leu
         35                  40                  45
Ile Gln Arg Ala Asp Phe Pro Asn Thr Gln Ser Leu Ser Val Thr Leu
 50                  55                  60
Ser Ile Ala Ser Asn Lys Leu Ala Ser Gly Leu Met Gly Ser Asp Ala
 65                  70                  75                  80
Val Ser Ser Ser Phe Met Leu Met Asn Asp Val Gly Asp Tyr Phe Glu
                 85                  90                  95
Cys Gly Val Cys His Asn Lys Pro Tyr Leu Gly Arg Glu Val Ile Phe
            100                 105                 110
Cys Arg Lys Tyr Ile Gly Gly Arg Gly Val Glu Ile Thr Thr Gly Lys
            115                 120                 125
Asn Tyr Thr Ser Asn Asn Trp Asn Glu Ala Ser Tyr Val Ile Gln Val
        130                 135                 140
Asn Val Val Asp Gly Leu Ala Gln Thr Thr Val Asn Ser Thr Tyr Thr
145                 150                 155                 160
Gln Thr Asp Val Ser Gly Leu Pro Lys Asn Trp Thr Arg Ile Tyr Lys
            165                 170                 175
Ile Thr Lys Ile Val Ser Val Asp Gln Asn Leu Tyr Pro Gly Cys Phe
            180                 185                 190
Ser Asp Ser Lys Leu Gly Val Met Arg Ile Arg Ser Leu Leu Val Ser
        195                 200                 205
Pro Val Arg Ile Phe Phe Arg Asp Ile Leu Leu Lys Pro Leu Lys Lys
210                 215                 220
Ser Phe Asn Ala Arg Ile Glu Asp Val Leu Asn Ile Asp Asp Thr Ser
225                 230                 235                 240
Leu Leu Val Pro Ser Pro Val Val Pro Glu Ser Thr Gly Gly Val Gly
            245                 250                 255
Pro Ser Glu Gln Leu Asp Val Val Ala Leu Thr Ser Asp Val Thr Glu
        260                 265                 270
Leu Ile Asn Thr Arg Gly Gln Gly Lys Ile Cys Phe Pro Asp Ser Val
        275                 280                 285
Leu Ser Ile Asn Glu Ala Asp Ile Tyr Asp Glu Arg Tyr Leu Pro Ile
290                 295                 300
Thr Glu Ala Leu Gln Ile Asn Ala Arg Leu Arg Arg Leu Val Leu Ser
305                 310                 315                 320
Lys Gly Gly Ser Gln Thr Pro Arg Asp Met Gly Asn Met Ile Val Ala
            325                 330                 335
Met Ile Gln Leu Phe Val Leu Tyr Ser Thr Val Lys Asn Ile Ser Val
        340                 345                 350
Lys Asp Gly Tyr Arg Val Glu Thr Glu Leu Gly Gln Lys Arg Val Tyr
        355                 360                 365
Leu Ser Tyr Ser Glu Val Arg Glu Ala Ile Leu Gly Gly Lys Tyr Gly
        370                 375                 380
Ala Ser Pro Thr Asn Thr Val Arg Ser Phe Met Arg Tyr Phe Ala His
385                 390                 395                 400
Thr Thr Ile Thr Leu Leu Ile Glu Lys Lys Ile Gln Pro Ala Cys Thr
            405                 410                 415
Ala Leu Ala Lys His Gly Val Pro Lys Arg Phe Thr Pro Tyr Cys Phe
            420                 425                 430
```

```
Asp Phe Ala Leu Leu Asp Asn Arg Tyr Tyr Pro Ala Asp Val Leu Lys
            435                 440                 445
Ala Asn Ala Met Ala Cys Ala Ile Ala Ile Lys Ser Ala Asn Leu Arg
    450                 455                 460
Arg Lys Gly Ser Glu Thr Tyr Asn Ile Leu Glu Ser Ile
465                 470                 475
```

<210> SEQ ID NO 17
<211> LENGTH: 558
<212> TYPE: DNA
<213> ORGANISM: Grapevine Leafroll Virus

<400> SEQUENCE: 17

```
atggaattca gaccagtttt aattacagtt cgccgtgatc ccggcgtaaa cactggtagt      60
ttgaaagtga tagcttatga cttacactac gacaatatat tcgataactg cgcggtaaag     120
tcgtttcgag acaccgacac tggattcact gttatgaaag aatactcgac gaattcagcg     180
ttcatactaa gtccttataa actgttttcc gcggtcttta ataaggaagg tgagatgata     240
agtaacgatg taggatcgag tttcagggtt tacaatatct tttcgcaaat gtgtaaagat     300
atcaacgaga tcagcgagat acaacgcgcc ggttacctag aaacatattt aggagacggg     360
caggctgaca ctgatatatt ttttgatgtc ttaaccaaca caaagcaaa ggtaaggtgg      420
ttagttaata aagaccatag cgcgtggtgt gggatattga atgatttgaa gtgggaagag     480
agcaacaagg agaaatttaa ggggagagac atactagata cttacgtttt atcgtctgat     540
tatccagggt ttaaatga                                                    558
```

<210> SEQ ID NO 18
<211> LENGTH: 185
<212> TYPE: PRT
<213> ORGANISM: Grapevine Leafroll Virus

<400> SEQUENCE: 18

```
Met Glu Phe Arg Pro Val Leu Ile Thr Val Arg Arg Asp Pro Gly Val
 1               5                  10                  15
Asn Thr Gly Ser Leu Lys Val Ile Ala Tyr Asp Leu His Tyr Asp Asn
            20                  25                  30
Ile Phe Asp Asn Cys Ala Val Lys Ser Phe Arg Asp Thr Asp Thr Gly
        35                  40                  45
Phe Thr Val Met Lys Glu Tyr Ser Thr Asn Ser Ala Phe Ile Leu Ser
    50                  55                  60
Pro Tyr Lys Leu Phe Ser Ala Val Phe Asn Lys Glu Gly Glu Met Ile
65                  70                  75                  80
Ser Asn Asp Val Gly Ser Ser Phe Arg Val Tyr Asn Ile Phe Ser Gln
                85                  90                  95
Met Cys Lys Asp Ile Asn Glu Ile Ser Glu Ile Gln Arg Ala Gly Tyr
            100                 105                 110
Leu Glu Thr Tyr Leu Gly Asp Gly Gln Ala Asp Thr Asp Ile Phe Phe
        115                 120                 125
Asp Val Leu Thr Asn Asn Lys Ala Lys Val Arg Trp Leu Val Asn Lys
    130                 135                 140
Asp His Ser Ala Trp Cys Gly Ile Leu Asn Asp Leu Lys Trp Glu Glu
145                 150                 155                 160
Ser Asn Lys Glu Lys Phe Lys Gly Arg Asp Ile Leu Asp Thr Tyr Val
                165                 170                 175
Leu Ser Ser Asp Tyr Pro Gly Phe Lys
```

```
                180              185
```

<210> SEQ ID NO 19
<211> LENGTH: 534
<212> TYPE: DNA
<213> ORGANISM: Grapevine Leafroll Virus

<400> SEQUENCE: 19

```
atgaagttgc tttcgctccg ctatcttatc ttaaggttgt caaagtcgct tagaacgaac    60
gatcacttgg ttttaatact tataaaggag gcgcttataa actattacaa cgcctctttc   120
accgatgagg gtgccgtatt aagagactct cgcgaaagta tagagaattt tctcgtagcc   180
aggtgcggtt cgcaaaattc ctgccgagtc atgaaggctt tgatcactaa cacagtctgt   240
aagatgtcga tagaaacagc cagaagtttt atcggagact aatactcgt cgccgactcc    300
tctgtttcag cgttggaaga agcgaaatca attaaagata atttccgctt aagaaaaagg   360
agaggcaagt attattatag tggtgattgt ggatccgacg ttgcgaaagt taagtatatt   420
ttgtctgggg agaatcgagg attggggtgc gtagattcct tgaagctagt ttgcgtaggt   480
agacaaggag gtggaaacgt actacagcac ctactaatct catctctggg ttaa          534
```

<210> SEQ ID NO 20
<211> LENGTH: 177
<212> TYPE: PRT
<213> ORGANISM: Grapevine Leafroll Virus

<400> SEQUENCE: 20

```
Met Lys Leu Leu Ser Leu Arg Tyr Leu Ile Leu Arg Leu Ser Lys Ser
 1               5                  10                  15

Leu Arg Thr Asn Asp His Leu Val Leu Ile Leu Ile Lys Glu Ala Leu
            20                  25                  30

Ile Asn Tyr Tyr Asn Ala Ser Phe Thr Asp Glu Gly Ala Val Leu Arg
        35                  40                  45

Asp Ser Arg Glu Ser Ile Glu Asn Phe Leu Val Ala Arg Cys Gly Ser
    50                  55                  60

Gln Asn Ser Cys Arg Val Met Lys Ala Leu Ile Thr Asn Thr Val Cys
65                  70                  75                  80

Lys Met Ser Ile Glu Thr Ala Arg Ser Phe Ile Gly Asp Leu Ile Leu
                85                  90                  95

Val Ala Asp Ser Ser Val Ser Ala Leu Glu Glu Ala Lys Ser Ile Lys
            100                 105                 110

Asp Asn Phe Arg Leu Arg Lys Arg Gly Lys Tyr Tyr Tyr Ser Gly
        115                 120                 125

Asp Cys Gly Ser Asp Val Ala Lys Val Lys Tyr Ile Leu Ser Gly Glu
    130                 135                 140

Asn Arg Gly Leu Gly Cys Val Asp Ser Leu Lys Leu Val Cys Val Gly
145                 150                 155                 160

Arg Gln Gly Gly Gly Asn Val Leu Gln His Leu Leu Ile Ser Ser Leu
                165                 170                 175

Gly
```

<210> SEQ ID NO 21
<211> LENGTH: 540
<212> TYPE: DNA
<213> ORGANISM: Grapevine Leafroll Virus

<400> SEQUENCE: 21

```
atggaccta t cgtttattat tgtgcagatc ctttccgcct cgtacaataa tgacgtgaca    60
gcactttaca ctttgattaa cgcgtataat agcgttgatg atacgacgcg ctgggcagcg   120
ataaacgatc cgcaagctga ggttaacgtc gtgaaggctt acgtagctac tacagcgacg   180
actgagctgc atagaacaat tctcattgac agtatagact ccgccttcgc ttatgaccaa   240
gtggggtgtt tggtgggcat agctagaggt ttgcttagac attcggaaga tgttctggag   300
gtcatcaagt cgatggagtt attcgaagtg tgtcgtggaa agaggggaag caaaagatat   360
cttggatact taagtgatca atgcactaac aaatacatga tgctaactca ggccggactg   420
gccgcagttg aaggagcaga catactacga acgaatcatc tagtcagtgg taataagttc   480
tctccaaatt tcgggatcgc taggatgttg ctcttgacgc tttgttgcgg agcactataa   540
```

<210> SEQ ID NO 22
<211> LENGTH: 179
<212> TYPE: PRT
<213> ORGANISM: Grapevine Leafroll Virus

<400> SEQUENCE: 22

```
Met Asp Leu Ser Phe Ile Ile Val Gln Ile Leu Ser Ala Ser Tyr Asn
 1               5                  10                  15

Asn Asp Val Thr Ala Leu Tyr Thr Leu Ile Asn Ala Tyr Asn Ser Val
            20                  25                  30

Asp Asp Thr Thr Arg Trp Ala Ala Ile Asn Asp Pro Gln Ala Glu Val
        35                  40                  45

Asn Val Val Lys Ala Tyr Val Ala Thr Thr Ala Thr Thr Glu Leu His
    50                  55                  60

Arg Thr Ile Leu Ile Asp Ser Ile Asp Ser Ala Phe Ala Tyr Asp Gln
65                  70                  75                  80

Val Gly Cys Leu Val Gly Ile Ala Arg Gly Leu Leu Arg His Ser Glu
                85                  90                  95

Asp Val Leu Glu Val Ile Lys Ser Met Glu Leu Phe Glu Val Cys Arg
            100                 105                 110

Gly Lys Arg Gly Ser Lys Arg Tyr Leu Gly Tyr Leu Ser Asp Gln Cys
        115                 120                 125

Thr Asn Lys Tyr Met Met Leu Thr Gln Ala Gly Leu Ala Ala Val Glu
    130                 135                 140

Gly Ala Asp Ile Leu Arg Thr Asn His Leu Val Ser Gly Asn Lys Phe
145                 150                 155                 160

Ser Pro Asn Phe Gly Ile Ala Arg Met Leu Leu Leu Thr Leu Cys Cys
                165                 170                 175

Gly Ala Leu
```

<210> SEQ ID NO 23
<211> LENGTH: 183
<212> TYPE: DNA
<213> ORGANISM: Grapevine Leafroll Virus

<400> SEQUENCE: 23

```
atgaggcact tagaaaaacc catcagagta gcggtacact attgcgtcgt gcgaagtgac    60
gtttgtgacg ggtgggatgt atttataggc gtaacgttaa tcggtatgtt tattagttac   120
tatttatatg ctctaattag catatgtaga aaaggagaag gtttaacaac cagtaatggg   180
taa                                                                  183
```

<210> SEQ ID NO 24

```
<211> LENGTH: 60
<212> TYPE: PRT
<213> ORGANISM: Grapevine Leafroll Virus

<400> SEQUENCE: 24

Met Arg His Leu Glu Lys Pro Ile Arg Val Ala Val His Tyr Cys Val
  1               5                  10                  15

Val Arg Ser Asp Val Cys Asp Gly Trp Asp Val Phe Ile Gly Val Thr
             20                  25                  30

Leu Ile Gly Met Phe Ile Ser Tyr Tyr Leu Tyr Ala Leu Ile Ser Ile
         35                  40                  45

Cys Arg Lys Gly Glu Gly Leu Thr Thr Ser Asn Gly
     50                  55                  60

<210> SEQ ID NO 25
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3, 6, 9, 12, 21, 24
<223> OTHER INFORMATION: n = A,T,C or G

<400> SEQUENCE: 25
ggnggnggna cnttygaygt ntcn                                           24

<210> SEQ ID NO 26
<211> LENGTH: 15
<212> TYPE: RNA
<213> ORGANISM: Grapevine Leafroll Virus

<400> SEQUENCE: 26
ugagugaacg cgaug                                                     15

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ataagcattc gggatggacc                                                20

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
attaacttga cggatggcac gc                                             22

<210> SEQ ID NO 29
<211> LENGTH: 36
<212> TYPE: DNA
<213> ORGANISM: Artificial Sequence
<220> FEATURE:
<223> OTHER INFORMATION: Synthetic

<400> SEQUENCE: 29
tacttatcta gaaccatgga agcgagtcga cgacta                              36
```

-continued

<210> SEQ ID NO 30
<211> LENGTH: 36
<212> TYPE: DNA
<213> ORGANISM: Artificial Sequence
<220> FEATURE:
<223> OTHER INFORMATION: Synthetic

<400> SEQUENCE: 30
tcttgaggat ccatggagaa acatcgtcgc atacta 36

<210> SEQ ID NO 31
<211> LENGTH: 35
<212> TYPE: DNA
<213> ORGANISM: Artificial Sequence
<220> FEATURE:
<223> OTHER INFORMATION: Synthetic

<400> SEQUENCE: 31
actatttcta gaaccatggc atttgaactg aaatt 35

<210> SEQ ID NO 32
<211> LENGTH: 36
<212> TYPE: DNA
<213> ORGANISM: Artificial Sequence
<220> FEATURE:
<223> OTHER INFORMATION: Synthetic

<400> SEQUENCE: 32
ttctgaggat ccatggtata agctcccatg aattat 36

<210> SEQ ID NO 33
<211> LENGTH: 230
<212> TYPE: PRT
<213> ORGANISM: Beet Yellow Virus
<220> FEATURE:
<223> OTHER INFORMATION: Synthetic

<400> SEQUENCE: 33

```
Val Gly Cys Lys Phe Asn Ile Gln Ser Val Thr Glu Phe Val Lys Lys
 1               5                  10                  15

Ile Asn Gly Asn Val Ala Glu Pro Ser Leu Val Glu His Cys Trp Ser
            20                  25                  30

Leu Ser Asn Ser Cys Gly Glu Leu Ile Asn Pro Lys Asp Thr Lys Arg
        35                  40                  45

Phe Val Ser Leu Ile Phe Lys Gly Lys Asp Leu Ala Glu Ser Thr Asp
    50                  55                  60

Glu Ala Ile Val Ser Ser Ser Tyr Leu Asp Tyr Leu Ser His Cys Leu
65                  70                  75                  80

Asn Leu Tyr Glu Thr Cys Asn Leu Ser Ser Asn Ser Gly Lys Lys Ser
                85                  90                  95

Leu Tyr Asp Glu Phe Leu Lys His Val Ile Asp Tyr Leu Glu Asn Ser
            100                 105                 110

Asp Leu Glu Tyr Arg Ser Pro Ser Asp Asn Pro Leu Val Ala Gly Ile
        115                 120                 125

Leu Tyr Asp Met Cys Phe Glu Tyr Asn Thr Leu Lys Ser Thr Tyr Leu
    130                 135                 140

Lys Asn Ile Glu Ser Phe Asp Cys Phe Leu Ser Leu Tyr Leu Pro Leu
145                 150                 155                 160

Leu Ser Glu Val Phe Ser Met Asn Trp Glu Arg Pro Ala Pro Asp Val
                165                 170                 175
```

-continued

```
Arg Leu Leu Phe Glu Leu Asp Ala Ala Glu Leu Leu Lys Val Pro
            180                 185                 190

Thr Ile Asn Met His Asp Ser Thr Phe Leu Tyr Lys Asn Lys Leu Arg
            195                 200                 205

Tyr Leu Glu Ser Tyr Phe Glu Asp Asp Ser Asn Glu Leu Ile Lys Val
            210                 215                 220

Lys Val Asp Ser Leu Leu
225                 230

<210> SEQ ID NO 34
<211> LENGTH: 226
<212> TYPE: PRT
<213> ORGANISM: Citrus Tristeza Virus

<400> SEQUENCE: 34

Val Gly Cys Arg Phe Thr Leu Asn Asp Val Glu Ser Tyr Leu Met Ser
  1               5                  10                  15

Arg Gly Glu Asp Phe Ala Asp Leu Ala Ala Val Glu His Ser Trp Cys
             20                  25                  30

Leu Ser Asn Ser Cys Ser Arg Leu Leu Ser Ser Thr Glu Ile Asp Ala
         35                  40                  45

Asn Lys Thr Leu Val Phe Thr Lys Asn Phe Asp Ser Asn Ile Ser Gly
     50                  55                  60

Val Thr Thr Lys Leu Glu Thr Tyr Leu Ser Tyr Cys Ile Ser Leu Tyr
 65                  70                  75                  80

Lys Lys His Cys Met Lys Asp Asp Tyr Phe Asn Leu Ile Leu Pro
                 85                  90                  95

Met Phe Asn Cys Leu Met Lys Val Leu Ala Ser Leu Gly Leu Phe Tyr
                100                 105                 110

Glu Lys His Ala Asp Asn Pro Leu Leu Thr Gly Met Leu Ile Glu Phe
            115                 120                 125

Cys Leu Glu Asn Lys Val Tyr Tyr Ser Thr Phe Lys Val Asn Leu Asp
130                 135                 140

Asn Val Arg Leu Phe Lys Ser Lys Val Leu Pro Val Val Leu Thr Val
145                 150                 155                 160

Trp Asp Ile Ser Glu Pro Asp Asp Pro Val Asp Glu Arg Val Leu Ile
                165                 170                 175

Pro Phe Asp Pro Thr Asp Phe Val Leu Asp Leu Pro Lys Leu Asn Ile
            180                 185                 190

His Asp Thr Met Val Val Val Gly Asn Gln Ile Arg Gln Leu Glu Tyr
            195                 200                 205

Val Val Glu Ser Asp Ala Leu Asp Asp Leu Ser Gln His Val Asp Leu
            210                 215                 220

Arg Leu
225

<210> SEQ ID NO 35
<211> LENGTH: 219
<212> TYPE: PRT
<213> ORGANISM: Lettuce Infectious Yellow Virus

<400> SEQUENCE: 35

Glu Gly Cys Ser Phe Thr Glu Gln Gln Val Val Glu Lys Tyr Pro Gln
  1               5                  10                  15

Val Asp Ser Leu Val Ala Lys Ile Leu Tyr Arg Val Cys Asn Ser Leu
             20                  25                  30
```

-continued

```
Gly Lys Leu Leu Asp Leu Lys Asp Phe Glu Asn Lys Asn Ile Ser Gly
         35                  40                  45

Phe Glu Ile Asn Thr Ala Gln Asp Ser Pro Thr Val Ala Asp Asp Asn
     50                  55                  60

Glu Ser Asn Asp Phe Phe Arg Glu Cys Val Asn Asp Gln Arg Tyr Tyr
 65                  70                  75                  80

Ser Ser Leu Ser Gly Ser Lys Leu Gly Lys Ala Lys Leu Glu Ala Asn
                 85                  90                  95

Ala Tyr Ile Phe Lys Ile Leu Lys Ser Ala Ser Gly Glu Phe Asp
                100                 105                 110

Ile Asp Arg Leu Ser Arg Asn Pro Leu Ala Ile Ser Lys Phe Met Asn
                115                 120                 125

Leu Tyr Thr Asn His Val Thr Asp Ser Glu Thr Phe Lys Ser Lys Phe
        130                 135                 140

Glu Ala Leu Lys Ser Ile Lys Thr Pro Phe Ala Ser Phe Ile Lys Lys
145                 150                 155                 160

Ala Phe Gly Ile Arg Leu Asn Phe Glu Asp Ser Lys Ile Phe Tyr Ala
                165                 170                 175

Leu Pro Lys Glu Arg Gln Ser Asp Val Leu Ser Asp Asp Met Met Val
                180                 185                 190

Glu Ser Ile Val Arg Asp Ala Ala Ser Phe Thr Val Val Ser Asp Asn
                195                 200                 205

Asn Tyr Leu Pro Glu Arg Val Asp Arg Phe Val
        210                 215

<210> SEQ ID NO 36
<211> LENGTH: 204
<212> TYPE: PRT
<213> ORGANISM: Beet Yellow Virus

<400> SEQUENCE: 36

Met Gly Ser Ala Glu Pro Ile Ser Ala Ile Ala Thr Phe Glu Asn Val
 1               5                  10                  15

Ser Leu Ala Asp Gln Thr Cys Leu His Gly Glu Asp Cys Asp Lys Leu
             20                  25                  30

Arg Lys Asn Phe Glu Glu Cys Leu Lys Leu Lys Gly Val Pro Glu Asp
         35                  40                  45

Asn Leu Gly Ile Ala Leu Gly Leu Cys Leu Tyr Ser Cys Ala Thr Ile
     50                  55                  60

Gly Thr Ser Asn Lys Val Asn Val Gln Pro Thr Ser Thr Phe Ile Lys
 65                  70                  75                  80

Ala Ser Phe Gly Gly Lys Glu Leu Tyr Leu Thr His Gly Glu Leu
                 85                  90                  95

Asn Ser Phe Leu Gly Ser Gln Lys Leu Leu Glu Gly Lys Pro Asn Lys
                100                 105                 110

Leu Arg Cys Phe Cys Arg Thr Phe Gln Lys Asp Tyr Ile Ser Leu Arg
                115                 120                 125

Lys Glu Tyr Arg Gly Lys Leu Pro Pro Ile Ala Arg Ala Asn Arg His
        130                 135                 140

Gly Leu Pro Ala Glu Asp His Tyr Leu Ala Ala Asp Phe Ile Ser Thr
145                 150                 155                 160

Ser Thr Glu Leu Thr Asp Leu Gln Gln Ser Arg Leu Leu Leu Ala Arg
                165                 170                 175

Glu Asn Ala Thr His Thr Glu Phe Ser Ser Glu Ser Pro Val Thr Ser
```

-continued

```
                180                 185                 190
Leu Lys Gln Leu Gly Arg Gly Leu Gly Thr Gly Arg
            195                 200
```

<210> SEQ ID NO 37
<211> LENGTH: 223
<212> TYPE: PRT
<213> ORGANISM: Citrus Tristeza Virus

<400> SEQUENCE: 37

```
Met Asp Asp Glu Thr Lys Lys Leu Lys Asn Lys Asn Lys Glu Thr Lys
 1               5                  10                  15
Glu Gly Asp Asp Val Val Ala Ala Glu Ser Ser Phe Gly Ser Val Asn
             20                  25                  30
Leu His Ile Asp Pro Thr Leu Ile Thr Met Asn Asp Val Arg Gln Leu
         35                  40                  45
Ser Thr Gln Gln Asn Ala Ala Leu Asn Arg Asp Leu Phe Leu Ala Leu
     50                  55                  60
Lys Gly Lys Tyr Pro Asn Leu Pro Asp Lys Asp Lys Asp Phe His Ile
 65                  70                  75                  80
Ala Met Met Leu Tyr Arg Leu Ala Val Lys Ser Ser Ser Leu Gln Ser
                 85                  90                  95
Asp Asp Asp Thr Thr Gly Ile Thr Tyr Thr Arg Glu Gly Val Glu Val
            100                 105                 110
Asp Leu Ser Asp Lys Leu Trp Thr Asp Ile Val Tyr Asn Ser Lys Gly
        115                 120                 125
Ile Gly Asn Arg Thr Asn Ala Leu Arg Val Trp Gly Arg Thr Asn Asp
130                 135                 140
Ala Leu Tyr Leu Ala Phe Cys Arg Gln Asn Arg Asn Leu Ser Tyr Gly
145                 150                 155                 160
Gly Arg Pro Leu Asp Ala Gly Ile Pro Ala Gly Tyr His Tyr Leu Cys
                165                 170                 175
Ala Asp Phe Leu Thr Gly Ala Gly Leu Thr Asp Leu Glu Cys Ala Val
            180                 185                 190
Tyr Ile Gln Ala Lys Glu Gln Leu Leu Lys Lys Arg Gly Ala Asp Glu
        195                 200                 205
Val Val Val Thr Asn Val Arg Gln Leu Gly Lys Phe Asn Thr Arg
    210                 215                 220
```

<210> SEQ ID NO 38
<211> LENGTH: 249
<212> TYPE: PRT
<213> ORGANISM: Lettuce  Infectious Yellow Virus

<400> SEQUENCE: 38

```
Met Asp Thr Asp Gly Asp Asn Asp Val Phe Gly Ser Gly Asn Asp Thr
 1               5                  10                  15
Arg Asn Asn Asp Asp Lys Lys Lys Glu Glu Met Lys Gln Asn Ile Ser
             20                  25                  30
Asp Asn Ser Gln Ile Ile Ser Thr Arg Asp His Glu Ala Asp Ile Ile
         35                  40                  45
Gly Ser Ile Ser Lys Glu Asp Leu Ser Lys Ile Val Val Arg Val Asp
     50                  55                  60
Arg His Asp Ala Leu Ser Ala Asn Asp Val Gln Ser Phe Arg Glu Ala
 65                  70                  75                  80
Met Ile Asn Phe Met Arg Asp Lys Asp Pro Asn Arg Asn Gln Pro Ser
```

-continued

```
                85                  90                  95

Asp Lys Leu Ile Ile Ala Met Glu Val Gly Val Tyr Gln Met Val Ile
            100                 105                 110
Asn Leu Gly Thr Ser Ala Lys Leu Gly Asn Ala Asn Asn Leu Glu Phe
        115                 120                 125
Thr Ile Ala Tyr Asp Gln Glu Thr Arg Thr Tyr Lys Val Ala Asp Phe
    130                 135                 140
Val Asn Tyr Met Gln Ser Arg Met Arg Asn Ser Pro Asn Val Val Arg
145                 150                 155                 160
Gln Tyr Ala Arg Ala Met Glu Lys Thr Ile Asn Asn Ile Arg Ser Ala
                165                 170                 175
Gly Ile Ile Asn Ser Asn Gly Val Leu Ala Ala Lys His Gly Val Leu
            180                 185                 190
Ala Ser Tyr Arg Asn Ser Tyr Ser Asp Phe Ala Val Gly Phe Gly Asn
        195                 200                 205
Asp Thr Thr Asp Ala Gln Leu Thr Ser Leu Met Leu Ala Arg Lys Gln
    210                 215                 220
Ala Leu Cys Lys Gly Glu Gly Gly Ser Val Glu His Tyr Asn Thr Met
225                 230                 235                 240
Gln Leu Ala Asn Leu Lys His Pro Cys
                245

<210> SEQ ID NO 39
<211> LENGTH: 39
<212> TYPE: PRT
<213> ORGANISM: Grapevine Leafroll VIrus

<400> SEQUENCE: 39

Ala Gln Ser Trp Thr Ile Arg Ser Ala His Ile Leu Ala Thr Arg His
 1               5                  10                  15

Leu Asn Gln Tyr Pro Thr Leu Cys Phe Thr Arg Ser Pro Arg Leu Val
            20                  25                  30
Ala Phe Glu Val Tyr Glu Arg
        35

<210> SEQ ID NO 40
<211> LENGTH: 229
<212> TYPE: DNA
<213> ORGANISM: Grapevine Leafroll Virus

<400> SEQUENCE: 40
tcgcgttggc cacgctatag tgtttctgtg cctcggttct tcgtgaggtt aataccgaag     60
ggtcgtcgta cttatctcag ttatttattt tttcgtcttc tcttaggcgt gccatccgtg    120
aagttaatac cggtggcact ccttctcgaa gtgggtatta aagaccaaaa ttttttattt    180
gtgtgtactt tttgttttgt tcacaccgtg aggacaagac cggtggaac               229

<210> SEQ ID NO 41
<211> LENGTH: 1066
<212> TYPE: DNA
<213> ORGANISM: Grapevine Leafroll Virus

<400> SEQUENCE: 41
gataggggcc aacaggtgac caacagcctg cacttaaggt gcgctggaag tgttggattt     60
ggtctcagtg tgccaaatat ccttttaggc gatgtacagg agtctagttt agtgtgtctt    120
tgggggatga cgggagcgac taggtttagg actgtagctg ctatgtaagt cgtgcatgcg    180
```

-continued

```
gcattgtgcg taagacgtgc atgcatttgg gcgagtgccc tagggcagcg tcggtcaggt    240
gactagcagc cggctctacg gagcgctgaa agtgctaggt cctgaaggta cagttgggct    300
gaggcaggac atggttgaac gagttgaccg tggggaccag cggcggtgac tcgggccgta    360
gccacgcgcg gggcggcagg gcgtctcgtg gtgtatctgg gcaagatacg gctttattag    420
gcaccataat atggagccca aagcgtcggg gtcgggaaac atctccatag cttagtggca    480
gcagcctaag ataggctggg aggcccgttc cctgtagtag tggtgggtta gcatgccact    540
aagcggtgcg gcgtgataag gcgccaccgt ccgtagttag gcgacccgtg ttttaatagg    600
gtctctttag ttaagtttag gcatgtcgta cagttaggat ttctttttag atattctttt    660
attttttatt gtttgttagt ttagatgtac attattacgt aggttacttt ggcgctacgc    720
cagaggtttt tcctctttgt gtgtagcctt taatgtaggt ttctttgttt tatttttgcc    780
tttcaggcgg cgcgtttctt ttcttctatt taggtttatc ttctttcctt agtgttgtcg    840
tatatgacgc tacgtccaaa ttatgaattt tccttcgtgt aggcgtcgtt gagtgcgttc    900
atcggcgcta gacgaggttt agtggcgaca taaataggtt tttgcgcgag attgggatag    960
aacgagttcg ccttaaaaga gaaatcgggg aaggcgccac gcgaatgacc ttcgtgctga   1020
gcgaaggtag tatcgtgatt ttatattgaa gtaggcgtat ttgttt                  1066
```

```
<210> SEQ ID NO 42
<211> LENGTH: 18
<212> TYPE: DNA
<213> ORGANISM: Grapevine Leafroll Virus

<400> SEQUENCE: 42
ttcctccttt agttagat                                                    18

<210> SEQ ID NO 43
<211> LENGTH: 89
<212> TYPE: DNA
<213> ORGANISM: Grapevine Leafroll Virus

<400> SEQUENCE: 43
agctgcgtgt agtatgcgac gatgtttctc gtattagttt tataaaaatt tttaattgct     60
ctgtgtgtgg ttttttgttga gtgaacgcg                                       89

<210> SEQ ID NO 44
<211> LENGTH: 62
<212> TYPE: DNA
<213> ORGANISM: Grapevine Leafroll Virus

<400> SEQUENCE: 44
ctacgatcga tgtctataaa ttggtgaaaa atttagaaat atttacctttt tattgataat     60 tc                                                                     62

<210> SEQ ID NO 45
<211> LENGTH: 5
<212> TYPE: PRT
<213> ORGANISM: Grapevine Leafroll Virus

<400> SEQUENCE: 45

Met Ser Ile Asn Trp
 1               5

<210> SEQ ID NO 46
<211> LENGTH: 10
<212> TYPE: DNA
```

<213> ORGANISM: Grapevine Leafroll Virus

<400> SEQUENCE: 46

```
ttatctaaag                                                          10
```

<210> SEQ ID NO 47
<211> LENGTH: 109
<212> TYPE: DNA
<213> ORGANISM: Grapevine Leafroll Virus

<400> SEQUENCE: 47

```
aaatgttatg ttgttcagcc agtgtcaaat tttcaaacgg gttacaatta tcgctactta   60
tttgcgcatg tttgttagcg gtgctaattg ttagcttttg tagaaggcg              109
```

<210> SEQ ID NO 48
<211> LENGTH: 284
<212> TYPE: DNA
<213> ORGANISM: Grapevine Leafroll Virus

<400> SEQUENCE: 48

```
aaatccttca ataaatttga ataaacaaa agtaagaaaa atgaaataat taggctagtc    60
tttttgttcg tctttcgctt ttgtagaata ggttttattt cgaggtaaga tgactaaact  120
ctacctcacg gtttaatact ctgatatttg taaaattagt ccgtaaagtc agatagtgat  180
attatattag tatagtataa taaacgccaa aatccaatca agtttggga cctaggcggg    240 cctcttatga ggctaactta tcgacaataa gttaggtccg ccac                   284
```

<210> SEQ ID NO 49
<211> LENGTH: 296
<212> TYPE: PRT
<213> ORGANISM: Beet Yellow Virus

<400> SEQUENCE: 49

Phe Thr Phe Thr Asn Leu Ser Ala Asn Val Leu Leu Tyr Glu Ala Pro
1               5                   10                  15

Pro Gly Gly Gly Lys Thr Thr Thr Leu Ile Lys Val Phe Cys Glu Thr
            20                  25                  30

Phe Ser Lys Val Asn Ser Leu Ile Leu Thr Ala Asn Lys Ser Ser Arg
        35                  40                  45

Glu Glu Ile Leu Ala Lys Val Asn Arg Ile Val Leu Asp Glu Gly Asp
    50                  55                  60

Thr Pro Leu Gln Thr Arg Asp Arg Ile Leu Thr Ile Asp Ser Tyr Leu
65                  70                  75                  80

Met Asn Asn Arg Gly Leu Thr Cys Lys Val Leu Tyr Leu Asp Glu Cys
                85                  90                  95

Phe Met Val His Ala Gly Ala Ala Val Ala Cys Ile Glu Phe Thr Lys
            100                 105                 110

Cys Asp Ser Ala Ile Leu Phe Gly Asp Ser Arg Gln Ile Arg Tyr Gly
        115                 120                 125

Arg Cys Ser Glu Leu Asp Thr Ala Val Leu Ser Asp Leu Asn Arg Phe
    130                 135                 140

Val Asp Asp Glu Ser Arg Val Tyr Gly Glu Val Ser Tyr Arg Cys Pro
145                 150                 155                 160

Trp Asp Val Cys Ala Trp Leu Ser Thr Phe Tyr Pro Lys Thr Val Ala
                165                 170                 175

Thr Thr Asn Leu Val Ser Ala Gly Gln Ser Ser Met Gln Val Arg Glu
            180                 185                 190

-continued

```
Ile Glu Ser Val Asp Asp Val Glu Tyr Ser Ser Glu Phe Val Tyr Leu
        195                 200                 205
Thr Met Leu Gln Ser Glu Lys Lys Asp Leu Leu Lys Ser Phe Gly Lys
    210                 215                 220
Arg Ser Arg Ser Ser Val Glu Lys Pro Thr Val Leu Thr Val His Glu
225                 230                 235                 240
Ala Gln Gly Glu Thr Tyr Arg Lys Val Asn Leu Val Arg Thr Lys Phe
                245                 250                 255
Gln Glu Asp Asp Pro Phe Arg Ser Glu Asn His Ile Thr Val Ala Leu
            260                 265                 270
Ser Arg His Val Glu Ser Leu Thr Tyr Ser Val Leu Ser Ser Lys Arg
        275                 280                 285
Asp Asp Ala Ile Ala Gln Ala Ile
    290                 295
```

<210> SEQ ID NO 50
<211> LENGTH: 300
<212> TYPE: PRT
<213> ORGANISM: Citrus Tristeza Virus

<400> SEQUENCE: 50

```
Leu Thr Phe Thr Asn Glu Glu His Ser Leu Ile Val Tyr Glu Ala Pro
1               5                   10                  15
Pro Gly Gly Lys Thr His Ser Leu Val Asn Ser Tyr Ala Asp Tyr
            20                  25                  30
Cys Val Lys Val Ser Cys Leu Val Thr Ala Asn Lys Asn Ser Gln
        35                  40                  45
Thr Glu Ile Ser Gln Arg Ile Ser Asn Glu Leu Met Gly Arg Lys Leu
    50                  55                  60
Ala Ala Lys Tyr Val Thr Asp Ala Ala Ser Arg Val Phe Thr Val Asp
65                  70                  75                  80
Ser Tyr Leu Met Asn His Leu Arg Leu Thr Thr Gln Leu Leu Phe Ile
                85                  90                  95
Asp Glu Cys Phe Met Val His Ala Gly Ala Ile Gly Ala Val Val Glu
            100                 105                 110
Phe Thr Ser Cys Lys Ala Val Val Phe Phe Gly Asp Ser Lys Gln Ile
        115                 120                 125
His Tyr Ile His Arg Asn Asp Leu Gly Val Ser Phe Val Ala Asp Ile
    130                 135                 140
Asp Ala Phe Ile Gln Pro Glu His Arg Ile Tyr Gly Glu Val Ser Tyr
145                 150                 155                 160
Arg Cys Pro Trp Asp Ile Cys Glu Trp Leu Ser Glu Phe Tyr Pro Arg
                165                 170                 175
His Val Ala Thr Ala Asn Val Gly Ser Ile Gly Lys Ser Ser Val Ser
            180                 185                 190
Ile Glu Glu Ile Asn Gly Cys Asp Asp Val Pro Tyr Asp Lys Ala Ala
        195                 200                 205
Lys Tyr Ile Val Tyr Thr Gln Ala Glu Lys Asn Asp Leu Gln Lys His
    210                 215                 220
Leu Gly Arg Leu Thr Val Gly Arg Asn Lys Val Val Pro Ile Val Asn
225                 230                 235                 240
Thr Val His Glu Val Gln Gly Glu Thr Tyr Lys Arg Val Arg Leu Val
                245                 250                 255
Arg Phe Lys Tyr Gln Glu Asp Thr Pro Phe Ser Ser Lys Asn His Ile
```

260                 265                 270
Val Val Ala Leu Thr Arg His Val Asp Ser Leu Val Tyr Ser Val Leu
                275                 280                 285
Thr Ser Arg Arg Tyr Asp Asp Thr Ala Thr Asn Ile
        290                 295                 300

<210> SEQ ID NO 51
<211> LENGTH: 295
<212> TYPE: PRT
<213> ORGANISM: Lettuce Infectious Yellow Virus

<400> SEQUENCE: 51

Met Val Arg Arg Pro Asp Val Asn Gly Leu Lys Phe Tyr Asn Lys Pro
1               5                   10                  15

Pro Gly Ala Gly Lys Thr Thr Ile Ala Lys Leu Met Ser Lys Asp
            20                  25                  30

Leu Lys Asn Lys Val Lys Cys Leu Ala Leu Ser Tyr Thr Lys Val Gly
        35                  40                  45

Arg Leu Glu Leu Ile Asp Lys Leu Lys Lys Asp Gly Ile Glu Lys Pro
    50                  55                  60

Glu Lys Tyr Val Lys Thr Tyr Asp Ser Phe Leu Met Asn Asn Asp Asn
65                  70                  75                  80

Ile Leu Glu Ile Val Asn Leu Tyr Cys Asp Glu Val Phe Met Met His
                85                  90                  95

Ala Gly His Phe Leu Thr Leu Leu Thr Lys Ile Ala Tyr Gln Asn Gly
            100                 105                 110

Tyr Cys Tyr Gly Asp Val Asn Gln Ile Pro Phe Ile Asn Arg Asp Pro
        115                 120                 125

Tyr Thr Pro Ala Tyr Leu Ser Arg Glu Phe Phe Arg Lys Gln Asp Leu
    130                 135                 140

Asn Tyr Asp Thr Tyr Thr Tyr Arg Cys Pro Leu Asp Thr Cys Tyr Leu
145                 150                 155                 160

Leu Ser Asn Leu Lys Asp Glu Met Gly Asn Ile Ile Tyr Ala Gly Gly
                165                 170                 175

Val Lys Asn Val Asn Glu Val Tyr Pro Thr Ile Arg Ser Leu Asn Leu
            180                 185                 190

Phe Gly Ile Asn Val Val Gly Glu Val Pro Val Glu Tyr Asn Ala Lys
        195                 200                 205

Tyr Leu Thr Phe Thr Gln Asp Glu Lys Leu Asn Leu Gln Arg His Ile
    210                 215                 220

Asp Ser Gln Gly Gly Cys Arg Asn Ala Val Ser Thr Val Asn Glu Ala
225                 230                 235                 240

Gln Gly Cys Thr Phe Ser Glu Val Asn Leu Val Arg Leu Val Gln Phe
                245                 250                 255

Asp Asn Pro Val Met Ser Asp Ile Asn Gln Phe Val Val Ala Ile Ser
            260                 265                 270

Arg His Thr Thr Thr Phe Lys Tyr Phe Thr Pro His Ser Arg Leu Asn
        275                 280                 285

Asp Arg Val Ser Asn Ala Ile
    290                 295

<210> SEQ ID NO 52
<211> LENGTH: 315
<212> TYPE: PRT
<213> ORGANISM: Beet Yellow Virus

```
<400> SEQUENCE: 52

Ile Thr Thr Phe Lys Leu Met Val Lys Arg Asp Ala Lys Val Lys Leu
  1               5                  10                  15

Asp Ser Ser Cys Leu Val Lys His Pro Pro Ala Gln Asn Ile Met Phe
             20                  25                  30

His Arg Lys Ala Val Asn Ala Ile Phe Ser Pro Cys Phe Asp Glu Phe
         35                  40                  45

Lys Asn Arg Val Ile Thr Cys Thr Asn Ser Asn Ile Val Phe Phe Thr
 50                  55                  60

Glu Met Thr Asn Ser Thr Leu Ala Ser Ile Ala Lys Glu Met Leu Gly
 65                  70                  75                  80

Ser Glu His Val Tyr Asn Val Gly Glu Ile Asp Phe Ser Lys Phe Asp
                 85                  90                  95

Lys Ser Gln Asp Ala Phe Ile Lys Ser Phe Glu Arg Thr Leu Tyr Ser
            100                 105                 110

Ala Phe Gly Phe Asp Glu Asp Leu Leu Asp Val Trp Met Gln Gly Glu
        115                 120                 125

Tyr Thr Ser Asn Ala Thr Thr Leu Asp Gly Gln Leu Ser Phe Ser Val
    130                 135                 140

Asp Asn Gln Arg Lys Ser Gly Ala Ser Asn Thr Trp Ile Gly Asn Ser
145                 150                 155                 160

Ile Glu Thr Leu Gly Ile Leu Ser Met Phe Tyr Tyr Thr Asn Arg Phe
                165                 170                 175

Lys Ala Leu Phe Val Ser Gly Asp Asp Ser Leu Ile Phe Ser Glu Ser
            180                 185                 190

Pro Ile Arg Asn Ser Ala Asp Ala Met Cys Thr Glu Leu Gly Phe Glu
        195                 200                 205

Thr Lys Phe Leu Thr Pro Ser Val Pro Tyr Phe Cys Ser Lys Phe Phe
    210                 215                 220

Val Met Thr Gly His Asp Val Phe Phe Val Pro Asp Pro Tyr Lys Leu
225                 230                 235                 240

Leu Val Lys Leu Gly Ala Ser Lys Asp Glu Val Asp Asp Glu Phe Leu
                245                 250                 255

Phe Glu Val Phe Thr Ser Phe Arg Asp Leu Thr Lys Asp Leu Val Asp
            260                 265                 270

Glu Arg Val Ile Glu Leu Leu Thr His Leu Val His Ser Lys Tyr Gly
        275                 280                 285

Tyr Glu Ser Gly Asp Thr Tyr Ala Ala Leu Cys Ala Ile His Cys Ile
    290                 295                 300

Arg Ser Asn Phe Ser Ser Phe Lys Lys Leu Tyr
305                 310                 315

<210> SEQ ID NO 53
<211> LENGTH: 315
<212> TYPE: PRT
<213> ORGANISM: Citrus Tristeza Virus

<400> SEQUENCE: 53

Ile Ser Asn Phe Lys Leu Met Val Lys Arg Asp Ala Lys Val Lys Leu
  1               5                  10                  15

Asp Asp Ser Ser Leu Ser Lys His Pro Ala Ala Gln Asn Ile Met Phe
             20                  25                  30

His Lys Lys Phe Ile Asn Ala Ile Phe Ser Pro Cys Phe Asp Glu Phe
         35                  40                  45
```

```
Lys Asn Arg Val Leu Ser Ser Leu Asn Asp Asn Ile Val Phe Phe Thr
    50                  55                  60

Glu Met Thr Asn Ala Gly Leu Ala Glu Ile Ile Arg Arg Ile Ile Gly
 65              70                  75                  80

Asp Asp Asp Asn Leu Phe Val Gly Glu Val Asp Phe Ser Lys Phe Asp
                85                  90                  95

Lys Ser Gln Asp Leu Phe Ile Lys Glu Tyr Glu Arg Thr Leu Tyr Ser
            100                 105                 110

Glu Phe Gly Phe Asp Thr Glu Leu Leu Asp Val Trp Met Glu Gly Glu
        115                 120                 125

Tyr Arg Ala Arg Ala Thr Thr Leu Asp Gly Gln Leu Ser Phe Ser Val
    130                 135                 140

Asp Gly Gln Arg Arg Ser Gly Gly Ser Asn Thr Trp Ile Gly Asn Ser
145                 150                 155                 160

Leu Val Thr Leu Gly Ile Leu Ser Leu Tyr Tyr Asp Val Ser Lys Phe
                165                 170                 175

Asp Leu Leu Val Ser Gly Asp Ser Leu Ile Tyr Ser Ser Glu
            180                 185                 190

Lys Ile Ser Asn Phe Ser Ser Glu Ile Cys Leu Glu Thr Gly Phe Glu
        195                 200                 205

Thr Lys Phe Met Ser Pro Ser Val Pro Tyr Phe Cys Ser Lys Phe Val
    210                 215                 220

Val Gln Thr Gly Asn Lys Thr Cys Phe Val Pro Asp Pro Tyr Lys Leu
225                 230                 235                 240

Leu Val Lys Leu Gly Ala Pro Gln Asn Lys Leu Thr Asp Val Glu Leu
                245                 250                 255

Phe Glu Leu Phe Thr Ser Phe Lys Asp Met Thr Gln Asp Phe Gly Asp
            260                 265                 270

Gln Val Val Leu Glu Lys Leu Lys Leu Val Glu Ala Lys Tyr Gly
        275                 280                 285

Phe Ala Ser Gly Thr Thr Met Pro Ala Leu Cys Ala Ile His Cys Val
    290                 295                 300

Arg Ser Asn Phe Leu Ser Phe Glu Arg Leu Phe
305                 310                 315

<210> SEQ ID NO 54
<211> LENGTH: 319
<212> TYPE: PRT
<213> ORGANISM: Lettuce Infectious Yellow Virus

<400> SEQUENCE: 54

Phe Lys Thr Leu Asn Leu Met Val Lys Gly Glu Thr Lys Pro Lys Met
 1               5                  10                  15

Asp Leu Ser Thr Tyr Asp Ser Tyr Asn Ala Pro Ala Asn Ile Val Tyr
                20                  25                  30

Tyr Gln Gln Ile Val Asn Leu Tyr Phe Ser Pro Ile Phe Leu Glu Cys
            35                  40                  45

Phe Ala Arg Leu Thr Tyr Cys Leu Ser Asp Lys Ile Val Leu Tyr Ser
    50                  55                  60

Gly Met Asn Thr Asp Val Leu Ala Glu Leu Ile Glu Ser Lys Leu Pro
 65              70                  75                  80

Leu Gly Leu Asn Ala Tyr His Thr Leu Glu Ile Asp Phe Ser Lys Phe
                85                  90                  95

Asp Lys Ser Gln Gly Thr Cys Phe Lys Leu Tyr Glu Glu Met Met Tyr
            100                 105                 110
```

```
Lys Met Phe Gly Phe Ser Pro Glu Leu Tyr Asp Arg Asp Phe Lys Tyr
        115                 120                 125

Thr Glu Tyr Phe Cys Arg Ala Lys Ala Thr Cys Gly Val Asp Leu Glu
        130                 135                 140

Leu Gly Thr Gln Arg Arg Thr Gly Ser Pro Asn Thr Trp Leu Ser Asn
145                 150                 155                 160

Thr Leu Val Thr Leu Gly Met Met Leu Ser Ser Tyr Asp Ile Asp Asp
                165                 170                 175

Ile Asp Leu Leu Leu Val Ser Gly Asp Asp Ser Leu Ile Phe Ser Arg
                180                 185                 190

Lys His Leu Pro Asn Lys Thr Gln Glu Ile Asn Lys Asn Phe Gly Met
        195                 200                 205

Glu Ala Lys Tyr Ile Glu Lys Ser Ser Pro Tyr Phe Cys Ser Lys Phe
        210                 215                 220

Ile Val Glu Leu Asn Gly Lys Leu Lys Val Ile Pro Asp Pro Ile Arg
225                 230                 235                 240

Phe Phe Glu Lys Leu Ser Ile Pro Ile Arg Gln Glu Asp Phe Val Asn
                245                 250                 255

Gly Ser Val Val Lys Glu Arg Phe Ile Ser Phe Lys Asp Leu Met Lys
                260                 265                 270

Glu Tyr Asp Asn Asp Val Ala Val Ile Arg Ile Asp Glu Ala Val Cys
        275                 280                 285

Tyr Arg Tyr Ser Ile Pro Val Gly Cys Ser Tyr Ala Ala Leu Cys Tyr
        290                 295                 300

Ile His Cys Cys Met Ser Asn Phe Val Ser Phe Arg Arg Ile Tyr
305                 310                 315

<210> SEQ ID NO 55
<211> LENGTH: 54
<212> TYPE: PRT
<213> ORGANISM: Beet Yellow Virus

<400> SEQUENCE: 55

Met Asp Cys Val Leu Arg Ser Tyr Leu Leu Leu Ala Phe Gly Phe Leu
1               5                   10                  15

Ile Cys Leu Phe Leu Phe Cys Leu Val Val Phe Ile Trp Phe Val Tyr
                20                  25                  30

Lys Gln Ile Leu Phe Arg Thr Thr Ala Gln Ser Asn Glu Ala Arg His
            35                  40                  45

Asn His Ser Thr Val Val
        50

<210> SEQ ID NO 56
<211> LENGTH: 39
<212> TYPE: PRT
<213> ORGANISM: Lettuce Infectious Yellow Virus

<400> SEQUENCE: 56

Met Ser Ile Leu Leu Phe Phe Leu Met Ser Ile Leu Val Trp Phe Ile
1               5                   10                  15

Phe Thr Ile Leu Lys Leu Leu Phe Val Asn Thr Asp Ser Glu Val Asn
                20                  25                  30

Ile Pro Asn Lys Ser Arg Phe
            35

<210> SEQ ID NO 57
```

-continued

<211> LENGTH: 51
<212> TYPE: PRT
<213> ORGANISM: Citrus Tristeza Virus

<400> SEQUENCE: 57

```
Met Asp Cys Val Ile Gln Gly Phe Leu Thr Phe Leu Val Gly Ile Ala
 1               5                  10                  15

Val Phe Cys Ala Phe Ala Gly Leu Ile Ile Ile Val Ile Thr Ile Tyr
            20                  25                  30

Arg Cys Thr Ile Lys Pro Val Arg Ser Ala Ser Pro Tyr Gly Thr His
        35                  40                  45

Ala Thr Val
    50
```

<210> SEQ ID NO 58
<211> LENGTH: 598
<212> TYPE: PRT
<213> ORGANISM: Beet Yellow Virus

<400> SEQUENCE: 58

```
Met Val Val Phe Gly Leu Asp Phe Gly Thr Thr Phe Ser Ser Val Cys
 1               5                  10                  15

Ala Tyr Val Gly Glu Glu Leu Tyr Leu Phe Lys Gln Arg Asp Ser Ala
            20                  25                  30

Tyr Ile Pro Thr Tyr Val Phe Leu His Ser Asp Thr Gln Glu Val Ala
        35                  40                  45

Phe Gly Tyr Asp Ala Glu Val Leu Ser Asn Asp Leu Ser Val Arg Gly
    50                  55                  60

Gly Phe Tyr Arg Asp Leu Lys Arg Trp Ile Gly Cys Asp Glu Glu Asn
65                  70                  75                  80

Tyr Arg Asp Tyr Leu Glu Lys Leu Lys Pro His Tyr Lys Thr Glu Leu
                85                  90                  95

Leu Lys Val Ala Gln Ser Ser Lys Ser Thr Val Lys Leu Asp Cys Tyr
            100                 105                 110

Ser Gly Thr Val Pro Gln Asn Ala Thr Leu Pro Gly Leu Ile Ala Thr
        115                 120                 125

Phe Val Lys Ala Leu Ile Ser Thr Ala Ser Glu Ala Phe Lys Cys Gln
    130                 135                 140

Cys Thr Gly Val Ile Cys Ser Val Pro Ala Asn Tyr Asn Cys Leu Gln
145                 150                 155                 160

Arg Ser Phe Thr Glu Ser Cys Val Asn Leu Ser Gly Tyr Pro Cys Val
                165                 170                 175

Tyr Met Val Asn Glu Pro Ser Ala Ala Ala Leu Ser Ala Cys Ser Arg
            180                 185                 190

Ile Lys Gly Ala Thr Ser Pro Val Leu Val Tyr Asp Phe Gly Gly Gly
        195                 200                 205

Thr Phe Asp Val Ser Val Ile Ser Ala Leu Asn Asn Thr Phe Val Val
    210                 215                 220

Arg Ala Ser Gly Gly Asp Met Asn Leu Gly Gly Arg Asp Ile Asp Lys
225                 230                 235                 240

Ala Phe Val Glu His Leu Tyr Asn Lys Ala Gln Leu Pro Val Asn Tyr
                245                 250                 255

Lys Ile Asp Ile Ser Phe Leu Lys Glu Ser Leu Ser Lys Lys Val Ser
            260                 265                 270

Phe Leu Asn Phe Pro Val Val Ser Glu Gln Gly Val Arg Val Asp Val
        275                 280                 285
```

```
Leu Val Asn Val Ser Glu Leu Ala Glu Val Ala Ala Pro Phe Val Glu
        290                 295                 300

Arg Thr Ile Lys Ile Val Lys Glu Val Tyr Glu Lys Tyr Cys Ser Ser
305                 310                 315                 320

Met Arg Leu Glu Pro Asn Val Lys Ala Lys Leu Leu Met Val Gly Gly
                325                 330                 335

Ser Ser Tyr Leu Pro Gly Leu Leu Ser Arg Leu Ser Ser Ile Pro Phe
                340                 345                 350

Val Asp Glu Cys Leu Val Leu Pro Asp Ala Arg Ala Ala Val Ala Gly
                355                 360                 365

Gly Cys Ala Leu Tyr Ser Ala Cys Leu Arg Asn Asp Ser Pro Met Leu
        370                 375                 380

Leu Val Asp Cys Ala Ala His Asn Leu Ser Ile Ser Ser Lys Tyr Cys
385                 390                 395                 400

Glu Ser Ile Val Cys Val Pro Ala Gly Ser Pro Ile Pro Phe Thr Gly
                405                 410                 415

Val Arg Thr Val Asn Met Thr Gly Ser Asn Ala Ser Ala Val Tyr Ser
                420                 425                 430

Ala Ala Leu Phe Glu Gly Asp Phe Val Lys Cys Arg Leu Asn Lys Arg
        435                 440                 445

Ile Phe Phe Gly Asp Val Val Leu Gly Asn Val Gly Val Thr Gly Ser
        450                 455                 460

Ala Thr Arg Thr Val Pro Leu Thr Leu Glu Ile Asn Val Ser Ser Val
465                 470                 475                 480

Gly Thr Ile Ser Phe Ser Leu Val Gly Pro Thr Gly Val Lys Lys Leu
                485                 490                 495

Ile Gly Gly Asn Ala Ala Tyr Asp Phe Ser Ser Tyr Gln Leu Gly Glu
                500                 505                 510

Arg Val Val Ala Asp Leu His Lys His Asn Ser Asp Lys Val Lys Leu
        515                 520                 525

Ile His Ala Leu Thr Tyr Gln Pro Phe Gln Arg Lys Lys Leu Thr Asp
        530                 535                 540

Gly Asp Lys Ala Leu Phe Leu Lys Arg Leu Thr Ala Asp Tyr Arg Arg
545                 550                 555                 560

Glu Ala Arg Lys Phe Ser Ser Tyr Asp Asp Ala Val Leu Asn Ser Ser
                565                 570                 575

Glu Leu Leu Leu Gly Arg Ile Ile Pro Lys Ile Leu Arg Gly Ser Arg
                580                 585                 590

Val Glu Lys Leu Asp Val
                595

<210> SEQ ID NO 59
<211> LENGTH: 594
<212> TYPE: PRT
<213> ORGANISM: Citrus Tristeza Virus

<400> SEQUENCE: 59

Met Val Leu Leu Gly Leu Asp Phe Gly Thr Thr Phe Ser Thr Val Ala
1                5                  10                  15

Met Ala Thr Pro Ser Glu Leu Val Ile Leu Lys Gln Ser Asn Ser Ser
                20                  25                  30

Tyr Ile Pro Thr Cys Leu Leu Leu His Ala Glu Pro Asn Ser Val Ser
            35                  40                  45

Tyr Gly Tyr Asp Ala Glu Tyr Leu Ala Ala Ser Gly Glu Ser Gly Ser
```

```
            50                  55                  60
Phe Tyr Lys Asp Leu Lys Arg Trp Val Gly Cys Thr Ala Lys Asn Tyr
 65                  70                  75                  80

Gln Thr Tyr Leu His Lys Leu Ser Pro Ser Tyr Lys Val Ile Val Lys
                 85                  90                  95

Glu Phe Gly Thr Lys Ser Val Pro Val Pro Tyr Leu Ser Pro Leu Asn
                100                 105                 110

Asn Asp Leu Gly Leu Ser Val Ala Leu Pro Ser Leu Ile Ala Ser Tyr
                115                 120                 125

Ala Lys Ser Ile Leu Ser Asp Ala Glu Arg Val Phe Asn Val Ser Cys
130                 135                 140

Thr Gly Val Ile Cys Ser Val Pro Ala Gly Tyr Asn Thr Leu Gln Arg
145                 150                 155                 160

Ala Phe Thr Gln Gln Ser Ile Ser Met Ser Gly Tyr Ser Cys Val Tyr
                165                 170                 175

Ile Ile Asn Glu Pro Ser Ala Ala Tyr Ser Thr Leu Pro Lys Leu
                180                 185                 190

Asn Ser Ala Asp Lys Tyr Leu Ala Val Tyr Asp Phe Gly Gly Gly Thr
                195                 200                 205

Phe Asp Val Ser Ile Val Ser Val Arg Leu Pro Thr Phe Ala Val Arg
210                 215                 220

Ser Ser Gly Asp Met Asn Leu Gly Gly Arg Asp Ile Asp Lys Lys
225                 230                 235                 240

Leu Ser Asp Lys Ile Tyr Glu Met Ala Asp Phe Val Pro Gln Lys Glu
                245                 250                 255

Leu Asn Val Ser Ser Leu Lys Glu Ala Leu Ser Leu Gln Thr Asp Pro
                260                 265                 270

Val Lys Tyr Thr Val Asn His Tyr Gly Met Ser Glu Thr Val Ser Ile
                275                 280                 285

Asp Gln Thr Val Leu Arg Glu Ile Ala Ser Val Phe Ile Asn Arg Thr
290                 295                 300

Ile Asp Ile Leu Thr Gln Val Lys Val Lys Ser Met Pro Glu Ser
305                 310                 315                 320

Gln Ser Leu Lys Leu Val Val Val Gly Gly Ser Ser Tyr Leu Pro Gly
                325                 330                 335

Leu Leu Asp Ala Leu Ala Thr Val Pro Phe Val Ser Gly Ile Val Pro
                340                 345                 350

Val Glu Asp Ala Arg Thr Ala Val Ala Arg Gly Cys Ala Leu Tyr Ser
                355                 360                 365

Glu Cys Leu Asp Gly Arg Ser Lys Ala Leu Leu Ile Asp Cys Ile Thr
                370                 375                 380

His His Leu Ser Val Thr Thr Phe Ser Ala Asp Ser Val Val Val Ala
385                 390                 395                 400

Ala Ala Gly Ser Pro Ile Pro Phe Glu Gly Glu Arg Lys Leu Thr Leu
                405                 410                 415

Arg Lys Cys Val Ser Thr Ser Asn Tyr Gln Ala Arg Met Phe Glu Gly
                420                 425                 430

Asp Tyr Glu Lys Val Phe Arg Asn Glu Arg Ile Tyr Ala Ala Ser Val
                435                 440                 445

Ser Leu Phe Thr Leu Gly Val Asn Trp Ser Val Pro Asn Asp Val Glu
                450                 455                 460

Met Thr Leu Val Thr Lys Val Asp Ser Met Gly Lys Val Glu Phe Tyr
465                 470                 475                 480
```

```
Leu Lys Gly Pro Ser Gly Glu Leu Val Asn Val Gln Gly Thr Ser His
                485                 490                 495

Tyr Asp Tyr Ala Gly Met Pro His Pro Thr Arg Lys Leu Val Arg Leu
            500                 505                 510

Ser Asp Tyr Asn Val Asn Ser Ala Ala Leu Val Leu Ala Leu Thr Leu
            515                 520                 525

Thr Arg Glu Lys Arg Glu Lys Phe Leu Leu Arg Thr Leu Phe Asp Thr
        530                 535                 540

Leu Leu Ala Asp Leu Arg Lys Thr Ala Ser Leu Ser Glu Tyr Ser Lys
545                 550                 555                 560

Lys Tyr Pro Ile Thr Arg Asn Asp Ile Asp Val Val Ser Ser Arg Met
                565                 570                 575

Gly Ile Val Val Ser Lys Val Leu Arg Gly Ser Asp Leu Glu Arg Ile
                580                 585                 590

Pro Leu

<210> SEQ ID NO 60
<211> LENGTH: 554
<212> TYPE: PRT
<213> ORGANISM: Lettuce Infectious Yellow Virus

<400> SEQUENCE: 60

Met Arg Asp Cys Lys Val Gly Leu Asp Phe Gly Thr Thr Phe Ser Thr
1               5                   10                  15

Val Ser Thr Leu Val Asn Asn Ser Met Tyr Val Leu Arg Leu Gly Asp
                20                  25                  30

Ser Ala Tyr Ile Pro Thr Cys Ile Ala Ile Thr Pro Gly Gly Glu Ala
            35                  40                  45

Ile Ile Gly Gly Ala Ala Glu Val Leu Ser Gly Asp Asp Thr Pro His
        50                  55                  60

Cys Phe Phe Tyr Asp Leu Lys Arg Trp Val Gly Val Asp Asp Asn Thr
65                  70                  75                  80

Phe Lys Phe Ala Met Asn Lys Ile Arg Pro Lys Tyr Val Ala Glu Leu
                85                  90                  95

Val Glu Gly Glu Val Tyr Leu Thr Gly Ile Asn Lys Gly Phe Ser Ile
                100                 105                 110

Lys Leu Ser Val Lys Gln Leu Ile Lys Ala Tyr Ile Glu Thr Ile Val
            115                 120                 125

Arg Leu Leu Ala Ser Ser Tyr Ser Leu Arg Val Ile Asp Leu Asn Gln
        130                 135                 140

Ser Val Pro Ala Asp Tyr Lys Asn Ala Gln Arg Leu Ala Ala Arg Ser
145                 150                 155                 160

Val Leu Lys Ala Leu Ser Phe Pro Cys Arg Arg Ile Ile Asn Glu Pro
                165                 170                 175

Ser Ala Ala Val Tyr Cys Val Ser Arg Tyr Pro Asn Tyr Asn Tyr
            180                 185                 190

Phe Leu Val Tyr Asp Phe Gly Gly Thr Phe Asp Val Ser Leu Ile
        195                 200                 205

Gly Lys Tyr Lys Ser Tyr Val Thr Val Ile Asp Thr Glu Gly Asp Ser
    210                 215                 220

Phe Leu Gly Gly Arg Asp Ile Asp Lys Ser Ile Glu Asp Tyr Leu Val
225                 230                 235                 240

Gly Lys Tyr Asn Ile Lys Lys Val Ile Pro Ala Thr Tyr Leu Ala Leu
                245                 250                 255
```

-continued

```
Ile Lys Glu Glu Cys Asn Asn Thr Asn Lys Ser Ile Phe Thr Ile Leu
            260                 265                 270

Phe Asp Asp Gly Ser Val Gln Val Val Glu Phe Ser Lys Ser Glu Leu
            275                 280                 285

Glu Lys Cys Val Arg Pro Phe Val Glu Arg Ser Ile Lys Leu Ile Asn
            290                 295                 300

Asp Val Val Arg Asn Lys Leu Thr Ser Gly Val Ile Tyr Met Val
305                 310                 315                 320

Gly Gly Ser Ser Leu Leu Gln Pro Val Gln Asp Met Val Arg Ser Tyr
            325                 330                 335

Ala Ser Thr Lys Gly Leu Thr Leu Val Ala Asp Gln Asp Met Arg Ser
            340                 345                 350

Ala Val Ser Tyr Gly Cys Ser Val Leu His Lys Leu Glu Asp Asn Lys
            355                 360                 365

Glu Ile Val Tyr Ile Asp Cys Asn Ser His Pro Leu Ser Asp Ile Ser
            370                 375                 380

Phe Asn Cys Asp Pro Glu Pro Ile Ile Arg Lys Pro Met Ser Ile Pro
385                 390                 395                 400

Tyr Thr His Thr Val Lys Met Arg His Asp Arg Pro Leu Lys Thr Ile
            405                 410                 415

Val Asn Ile Tyr Glu Gly Ser Asn Leu Phe Met Pro Glu Asn Asp Trp
            420                 425                 430

Leu Ile Ser Ser Asn Ile Asn Thr Thr Asp Phe Ala Lys Val Gly Glu
            435                 440                 445

Glu Tyr Ser Lys Val Tyr Glu Tyr Asp Ile Asp Gly Ile Ile Thr Leu
            450                 455                 460

Lys Ile Arg Asn Glu Val Thr Gly Lys Met Phe Thr Leu Pro Asn Ser
465                 470                 475                 480

Phe Thr Lys Ser Asp Asn Ile Lys Pro Ile Thr Phe Lys Leu Thr Gln
            485                 490                 495

Leu Ser Asn Thr Asp Asp Leu Ala Thr Leu Thr Ser Leu Leu Gly Tyr
            500                 505                 510

His Asp Lys Asn Phe Glu Arg Phe Tyr Gly Leu Phe Asn Val Pro Thr
            515                 520                 525

Ile Leu Ile Lys Glu Ile Asp Lys Leu Gly Gly Phe Lys Thr Leu Tyr
            530                 535                 540

Arg Arg Leu Lys Ser Met Asn Ala Asn Phe
545                 550

<210> SEQ ID NO 61
<211> LENGTH: 553
<212> TYPE: PRT
<213> ORGANISM: Beet Yellow Virus

<400> SEQUENCE: 61

Met Thr Thr Arg Phe Ser Thr Pro Ala Asn Tyr Tyr Trp Gly Glu Leu
1               5                   10                  15

Phe Arg Arg Phe Phe Gly Gly Gln Glu Trp Lys Asn Leu Met Ser Glu
            20                  25                  30

Ala Ala Ser Val Ser Arg Pro Tyr Ser Ser Asp Phe Arg Phe Ser
            35                  40                  45

Asp Gly Val Ile Leu Ser Arg Lys Thr Phe Gly Glu Ser Thr Gly Glu
            50                  55                  60

Ser Phe Val Arg Glu Phe Ser Leu Leu Leu Thr Phe Pro Lys Thr Tyr
```

-continued

```
 65                  70                  75                  80
Glu Val Cys Lys Leu Cys Gly Val Ala Met Glu Leu Ala Leu Asn Gly
                85                  90                  95
Met Asn Arg Leu Ser Asp Tyr Asn Val Ser Glu Phe Asn Ile Val Asp
            100                 105                 110
Val Lys Thr Val Gly Cys Lys Phe Asn Ile Gln Ser Val Thr Glu Phe
        115                 120                 125
Val Lys Lys Ile Asn Gly Asn Val Ala Glu Pro Ser Leu Val Glu His
    130                 135                 140
Cys Trp Ser Leu Ser Asn Ser Cys Gly Glu Leu Ile Asn Pro Lys Asp
145                 150                 155                 160
Thr Lys Arg Phe Val Ser Leu Ile Phe Lys Gly Lys Asp Leu Ala Glu
                165                 170                 175
Ser Thr Asp Glu Ala Ile Val Ser Ser Ser Tyr Leu Asp Tyr Leu Ser
            180                 185                 190
His Cys Leu Asn Leu Tyr Glu Thr Cys Asn Leu Ser Ser Asn Ser Gly
        195                 200                 205
Lys Lys Ser Leu Tyr Asp Glu Phe Leu Lys His Val Ile Asp Tyr Leu
    210                 215                 220
Glu Asn Ser Asp Leu Glu Tyr Arg Ser Pro Ser Asp Asn Pro Leu Val
225                 230                 235                 240
Ala Gly Ile Leu Tyr Asp Met Cys Phe Glu Tyr Asn Thr Leu Lys Ser
                245                 250                 255
Thr Tyr Leu Lys Asn Ile Glu Ser Phe Asp Cys Phe Leu Ser Leu Tyr
            260                 265                 270
Leu Pro Leu Leu Ser Glu Val Phe Ser Met Asn Trp Glu Arg Pro Ala
        275                 280                 285
Pro Asp Val Arg Leu Leu Phe Glu Leu Asp Ala Ala Glu Leu Leu Leu
    290                 295                 300
Lys Val Pro Thr Ile Asn Met His Asp Ser Thr Phe Leu Tyr Lys Asn
305                 310                 315                 320
Lys Leu Arg Tyr Leu Glu Ser Tyr Phe Glu Asp Ser Asn Glu Leu
                325                 330                 335
Ile Lys Val Lys Val Asp Ser Leu Leu Thr Arg Asp Asn Pro Glu Leu
            340                 345                 350
Lys Leu Ala Gln Arg Trp Val Gly Phe His Cys Tyr Tyr Gly Val Phe
        355                 360                 365
Arg Thr Ala Gln Thr Arg Lys Val Arg Asp Ala Glu Tyr Lys Leu
    370                 375                 380
Pro Pro Ala Leu Gly Glu Phe Val Ile Asn Met Ser Gly Val Glu Glu
385                 390                 395                 400
Phe Phe Glu Glu Leu Gln Lys Lys Met Pro Ser Ile Ser Val Arg Arg
                405                 410                 415
Arg Phe Cys Gly Ser Leu Ser His Glu Ala Phe Ser Val Phe Lys Arg
            420                 425                 430
Phe Gly Val Gly Phe Pro Pro Ile Thr Arg Leu Asn Val Pro Val Lys
        435                 440                 445
Tyr Ser Tyr Leu Asn Val Asp Tyr Tyr Arg His Val Lys Arg Val Gly
    450                 455                 460
Leu Thr Gln Asp Glu Leu Thr Ile Leu Ser Asn Ile Glu Phe Asp Val
465                 470                 475                 480
Ala Glu Met Cys Cys Glu Arg Glu Val Ala Leu Gln Ala Arg Arg Ala
                485                 490                 495
```

-continued

Gln Arg Gly Glu Lys Pro Phe Gln Gly Trp Lys Gly Thr Lys Asn Glu
            500                 505                 510

Ile Ser Pro His Ala Arg Ser Ser Ile Arg Val Lys Lys Asn Asn Asp
            515                 520                 525

Ser Leu Leu Asn Ile Leu Trp Lys Asp Val Gly Ala Arg Ser Gln Arg
            530                 535                 540

Arg Leu Asn Pro Leu His Arg Lys His
545             550

<210> SEQ ID NO 62
<211> LENGTH: 535
<212> TYPE: PRT
<213> ORGANISM: Citrus Tristeza Virus

<400> SEQUENCE: 62

Met Ser Ser His His Val Trp Gly Ser Leu Phe Arg Lys Phe Tyr Gly
  1               5                  10                  15

Glu Ala Ile Trp Lys Glu Tyr Leu Ser Glu Ser Thr Arg Asn Phe Asp
            20                  25                  30

Glu Arg Asn Val Ser Leu Asp His Thr Leu Ser Ser Gly Val Val Val
            35                  40                  45

Arg Arg Gln Ser Leu Leu Asn Ala Pro Gln Gly Thr Phe Glu Asn Glu
     50                  55                  60

Leu Ala Leu Leu Tyr Asn Ser Val Ile Asn Asp Phe Val Glu Leu
65                   70                  75                  80

Thr Gly Met Pro Leu Lys Ser Leu Met Thr Gly Ile Glu Asp Arg Lys
                 85                  90                  95

Val Pro Asp Glu Leu Ile Ser Val Asp Pro His Glu Val Gly Cys Arg
            100                 105                 110

Phe Thr Leu Asn Asp Val Glu Ser Tyr Leu Met Ser Arg Gly Glu Asp
            115                 120                 125

Phe Ala Asp Leu Ala Ala Val Glu His Ser Trp Cys Leu Ser Asn Ser
     130                 135                 140

Cys Ser Arg Leu Leu Ser Ser Thr Glu Ile Asp Ala Asn Lys Thr Leu
145                 150                 155                 160

Val Phe Thr Lys Asn Phe Asp Ser Asn Ile Ser Gly Val Thr Thr Lys
                165                 170                 175

Leu Glu Thr Tyr Leu Ser Tyr Cys Ile Ser Leu Tyr Lys Lys His Cys
            180                 185                 190

Met Lys Asp Asp Asp Tyr Phe Asn Leu Ile Leu Pro Met Phe Asn Cys
            195                 200                 205

Leu Met Lys Val Leu Ala Ser Leu Gly Leu Phe Tyr Glu Lys His Ala
     210                 215                 220

Asp Asn Pro Leu Leu Thr Gly Met Leu Ile Glu Phe Cys Leu Glu Asn
225                 230                 235                 240

Lys Val Tyr Tyr Ser Thr Phe Lys Val Asn Leu Asp Asn Val Arg Leu
                245                 250                 255

Phe Lys Ser Lys Val Leu Pro Val Val Leu Thr Val Trp Asp Ile Ser
            260                 265                 270

Glu Pro Asp Asp Pro Val Asp Arg Val Leu Ile Pro Phe Asp Pro
            275                 280                 285

Thr Asp Phe Val Leu Asp Leu Pro Lys Leu Asn Ile His Asp Thr Met
     290                 295                 300

Val Val Val Gly Asn Gln Ile Arg Gln Leu Glu Tyr Val Val Glu Ser

```
305                 310                 315                 320
Asp Ala Leu Asp Asp Leu Ser Gln His Val Asp Leu Arg Leu Ala Ala
                325                 330                 335
Asp Asn Pro Asp Leu Arg Val Gly Leu Arg Trp Ala Gly Met Phe Val
                340                 345                 350
Tyr Tyr Gly Val Tyr Arg Cys Val Val Asp Arg Ala Val Glu Arg Pro
                355                 360                 365
Thr Leu Phe Arg Leu Pro Gln Lys Leu Leu Ser Gln Asp Asp Gly Glu
            370                 375                 380
Ser Cys Ser Leu His Met Gly Ser Val Glu Ala Leu Phe Asn Leu Val
385                 390                 395                 400
Gln Lys Val Asn Lys Asp Ile Asn Val Arg Arg Gln Phe Met Gly Arg
                405                 410                 415
His Ser Glu Val Ala Leu Arg Leu Tyr Arg Asn Leu Gly Leu Arg Phe
                420                 425                 430
Pro Pro Ile Ser Ser Val Arg Leu Pro Ala His His Gly Tyr Leu Tyr
            435                 440                 445
Val Asp Phe Tyr Lys Arg Val Pro Asp Gly Ala Val Thr Ala Asp Glu
    450                 455                 460
Leu Glu Ser Leu Arg Gln Leu Arg Ser Ser Val Asp Val Met Cys Lys
465                 470                 475                 480
Asp Arg Val Ser Ile Thr Pro Pro Phe Asn Arg Leu Arg Arg Gly
                485                 490                 495
Ser Ser Arg Thr Phe Arg Gly Arg Gly Ala Arg Gly Ala Ser Ser Arg
            500                 505                 510
His Met Ser Arg Asp Val Ala Thr Ser Gly Phe Asn Leu Pro Tyr His
            515                 520                 525
Gly Arg Leu Tyr Ser Thr Ser
    530                 535

<210> SEQ ID NO 63
<211> LENGTH: 514
<212> TYPE: PRT
<213> ORGANISM: Lettuce Infectious Yellow Virus

<400> SEQUENCE: 63

Met Leu Asn Asp Arg Ile Ala Val Thr Cys Phe Gln Thr Leu Leu Lys
1               5                   10                  15
Lys Ser Asn Val Lys His Glu Met Glu Gln Thr Asn Asn Tyr Ile Val
            20                  25                  30
Asn Asn Leu Ala Asp Ile Asn Arg Asn Thr Phe Pro Ala Leu Ala Gly
        35                  40                  45
Ser Val Arg Ile Asp Phe Asn Ser Asp Tyr Tyr Ile Ser Gly Gly Gln
    50                  55                  60
Ile Val Val Ser Pro Lys Asp Ser Asn Ala Tyr Val Lys Leu Leu Ile
65                  70                  75                  80
Val Tyr Leu Lys Tyr Cys Tyr Ile Asn Tyr Ser Ala Lys Thr Lys Tyr
                85                  90                  95
Pro Pro Gln Ser Leu Leu Ala Val Leu Asp Tyr Asp Ser Phe Lys Ala
            100                 105                 110
Lys Trp Val Lys Tyr Leu Asp Lys Ser Leu Thr Asp Tyr Leu Asp Asp
            115                 120                 125
Asn Lys Thr Glu Gly Cys Ser Phe Thr Glu Gln Gln Val Val Glu Lys
        130                 135                 140
```

-continued

Tyr Pro Gln Val Asp Ser Leu Val Ala Lys Ile Leu Tyr Arg Val Cys
145                 150                 155                 160

Asn Ser Leu Gly Lys Leu Leu Asp Leu Lys Asp Phe Glu Asn Lys Asn
                165                 170                 175

Ile Ser Gly Phe Glu Ile Asn Thr Ala Gln Asp Ser Pro Thr Val Ala
            180                 185                 190

Asp Asp Asn Glu Ser Asn Asp Phe Phe Arg Glu Cys Val Asn Asp Gln
                195                 200                 205

Arg Tyr Tyr Ser Ser Leu Ser Gly Ser Lys Leu Gly Lys Ala Lys Leu
            210                 215                 220

Glu Ala Asn Ala Tyr Ile Phe Lys Ile Leu Lys Ser Ala Ser Gly
225                 230                 235                 240

Glu Phe Asp Ile Asp Arg Leu Ser Arg Asn Pro Leu Ala Ile Ser Lys
                245                 250                 255

Phe Met Asn Leu Tyr Thr Asn His Val Thr Asp Ser Glu Thr Phe Lys
                260                 265                 270

Ser Lys Phe Glu Ala Leu Lys Ser Ile Lys Thr Pro Phe Ala Ser Phe
            275                 280                 285

Ile Lys Lys Ala Phe Gly Ile Arg Leu Asn Phe Glu Asp Ser Lys Ile
290                 295                 300

Phe Tyr Ala Leu Pro Lys Glu Arg Gln Ser Asp Val Leu Ser Asp Asp
305                 310                 315                 320

Met Met Val Glu Ser Ile Val Arg Asp Ala Ala Ser Phe Thr Val Val
            325                 330                 335

Ser Asp Asn Asn Tyr Leu Pro Glu Arg Val Asp Arg Phe Val Thr Gln
            340                 345                 350

Leu Leu Leu Glu Leu Phe Pro Lys Thr Lys Ala Ser Phe Pro Asn Lys
            355                 360                 365

Ile Met Phe Gly Phe Leu His Tyr Phe Ala Leu Ser Thr Thr Asn Ser
            370                 375                 380

Lys Arg Phe Asn Asp Thr Gln Glu Ser Thr Ile Glu Ile Gly Glu
385                 390                 395                 400

Thr Leu Lys Ile Ser Leu Lys Phe Ile Thr Ser Tyr Leu Arg Asn Ala
                405                 410                 415

Ile Gln Ser Gln His Pro Asp Tyr Ala Asp Ser Asn Ile Val Arg Leu
            420                 425                 430

Trp Cys Asn Lys Arg Ser Asn Leu Ala Leu Gly Tyr Phe Lys Ser Arg
            435                 440                 445

Asn Ile Gln Leu Tyr Leu Tyr Ser Lys Tyr Pro Arg Leu Leu Asn Tyr
450                 455                 460

Met Arg Phe Asp Tyr Phe Lys Gly Leu Asp Met Gly Lys Leu Thr Asp
465                 470                 475                 480

Glu Glu Arg Leu Ser Ile Gln Thr Leu Arg Cys Ile Thr Glu Asp Arg
            485                 490                 495

Ser Glu Gly Thr Leu Ala Thr His Asn Asp Leu Asn Ser Trp Ile Leu
            500                 505                 510

Arg Pro

<210> SEQ ID NO 64
<211> LENGTH: 67
<212> TYPE: DNA
<213> ORGANISM: Lettuce Infectious Yellow Virus

<400> SEQUENCE: 64

-continued

```
tcactacaat ctgttagtga ttttgttttg aaagactatc attttagaca gtgcctttga    60
cgtgtat                                                              67
```

<210> SEQ ID NO 65
<211> LENGTH: 10
<212> TYPE: PRT
<213> ORGANISM: Lettuce Infectious Yellow Virus

<400> SEQUENCE: 65

```
Ser Leu Gln Ser Val Ser Asp Phe Val Leu
 1               5                  10
```

<210> SEQ ID NO 66
<211> LENGTH: 12
<212> TYPE: PRT
<213> ORGANISM: Lettuce Infectious Yellow Virus

<400> SEQUENCE: 66

```
Lys Thr Ile Ile Leu Asp Ser Ala Phe Asp Val Tyr
 1               5                  10
```

<210> SEQ ID NO 67
<211> LENGTH: 16
<212> TYPE: DNA
<213> ORGANISM: Artificial Sequence
<220> FEATURE:
<223> OTHER INFORMATION: Synthetic

<400> SEQUENCE: 67

```
ggtacctagg agttct                                                    16
```